US008435495B2

(12) United States Patent
Murphy et al.

(10) Patent No.: US 8,435,495 B2
(45) Date of Patent: *May 7, 2013

(54) CHARACTERIZATION OF GRANULOCYTIC EHRLICHIA AND METHODS OF USE

(75) Inventors: Cheryl Murphy, Hopkinton, MA (US); James Storey, Lynwood, MA (US); Gerald A. Beltz, Lexington, MA (US); Richard T. Coughlin, Portland, ME (US)

(73) Assignee: Antigenics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/532,222

(22) Filed: Jun. 25, 2012

(65) Prior Publication Data

US 2012/0270232 A1 Oct. 25, 2012

Related U.S. Application Data

(60) Continuation of application No. 13/346,088, filed on Jan. 9, 2012, which is a continuation of application No. 12/859,236, filed on Aug. 18, 2010, now Pat. No. 8,093,008, which is a division of application No. 09/792,957, filed on Feb. 26, 2001, now Pat. No. 7,863,434, which is a division of application No. 09/066,046, filed on Apr. 24, 1998, now Pat. No. 6,204,252.

(60) Provisional application No. 60/044,933, filed on Apr. 25, 1997.

(51) Int. Cl.
*A61K 49/00* (2006.01)

(52) U.S. Cl.
USPC .......... 424/9.1; 424/9.2; 424/184.1; 435/243; 435/252.1; 530/300; 530/350

(58) Field of Classification Search ............... 424/9.1, 424/9.2, 184.1; 435/243, 252.1; 530/300, 530/350
See application file for complete search history.

(56) References Cited

U.S. PATENT DOCUMENTS

| 5,976,860 | A | 11/1999 | Coughlin et al. | |
|---|---|---|---|---|
| 6,204,252 | B1 * | 3/2001 | Murphy et al. | 514/44 R |
| 6,207,169 | B1 | 3/2001 | Reed et al. | |
| 6,231,869 | B1 | 5/2001 | Reed et al. | |
| 6,277,381 | B1 | 8/2001 | Reed et al. | |
| 6,284,238 | B1 | 9/2001 | Coughlin et al. | |
| 6,306,394 | B1 | 10/2001 | Murphy et al. | |
| 6,306,402 | B1 | 10/2001 | Reed et al. | |
| 7,863,434 | B2 | 1/2011 | Murphy et al. | |
| 8,093,008 | B2 * | 1/2012 | Murphy et al. | 435/7.1 |
| 2012/0178102 | A1 | 7/2012 | Murphy et al. | |

FOREIGN PATENT DOCUMENTS

| CA | 2284251 A1 | 10/1998 |
|---|---|---|
| WO | WO 96/39484 | 12/1996 |
| WO | WO 97/45540 | 12/1997 |
| WO | WO 98/14584 | 4/1998 |
| WO | WO 98/42740 | 10/1998 |
| WO | WO 98/49312 | 11/1998 |
| WO | WO 99/52370 | 4/1999 |
| WO | WO 00/06744 | 2/2000 |
| WO | WO 00/00615 | 10/2000 |

OTHER PUBLICATIONS

Alleman et al., 1997, Anaplasma marginale Major Surface Protein 3 Is Encoded by a Polymorphic, Multigene Family, Infection and Immunity, 65(1): 156-163.

Anacker et al., 1987, "Neutralizing Activity of Monoclonal Antibodies to Heat-Sensitive and Heat-Resistant Epitopes of *Rickettsia rickettsia* Surface Proteins," Infect. Immun. 55:825-827.

Anderson et al., 1991, *Ehrlichia chaffeensis*, a New Species Associated with Human Ehrlichiosis, Journal of Clinical Microbiology, 29(12): 2838-2842.

Asanovich et al., 1997, Antigenic Diversity of Granulocytic *Ehrlichia* Isolates from Humans in Wisconsin and New York and a Horse in California, The Journal of Infectious Diseases, 176:1029-1034.

Asanovich et al., 1996, "Partial characterization of cloned genes encoding immunoreactive proteins of *Ehrlichia equi* and the agent of human granulocytic ehrlichiosis (HGE)," 96th General Meeting of the America Society for Microbiology, New Orleans, LA; May 19-23, p. 22.

Caturegli et al., 1998, "Cloning and characterization of an ankyrin-like protein antigen gene from the agent of human granulocytic ehrlichiosis," Database Genbank; Accession No. AF047896, Mar. 31.

Chen et al., 1994, Identification of a Granulocytotropic *Ehrlichia* Species as the Etiologic Agent of Human Disease, Journal of Clinical Microbiology, 32(3):589-595.

Coughlin et al., 1995, "Protection of Dogs from Lyme Disease with a Vaccine Containing Outer Surface Protein (Osp) A, OspB, and the Saponin Adjuvant QS21," J. Infect. Dis. 171:1049-1052.

Dasch et al, 1984, "1984, Approaches to Subunit Vaccines Against the Typhus Rickettsiae *Rickettsia typhii* and *Rickettsia prowazekii*," In: Microbiology, D. Schlessinger, ed., American Society of Microbiology, Washington, D.C., 251-256.

Dumler et al., 1995, "Serologic Cross-Reactions Among *Ehrlichia equi*, *Ehrlichia phagocytophaila*, and Human Granulocytic *Ehrlichia*," J. Clin. Microbiol. 33:1098-1103.

Dumler et al., 1991, "Identification of *Ehrlichia* in Human Tissue," N. Engl. J. Med. 325:1109-1110.

Eid et al., 1996, Expression of Major Surface Protein 2 Antigenic Variants during Acute Anaplasma marginale Rickettsemia, Infection and Immunity, 64(3): 836-841.

(Continued)

*Primary Examiner* — Rodney P. Swartz

(74) *Attorney, Agent, or Firm* — Wolf, Greenfield & Sacks, P.C.

(57) ABSTRACT

The present invention relates, in general, to methods of screening a sample obtained from a subject for antibodies relating to granulocytic ehrlichia (GE) infection.

15 Claims, 72 Drawing Sheets

OTHER PUBLICATIONS

Eremeeva et al., 1994, "Differentiation Among Spotted Fever Group Rickettsiae Species by Analysis of Restriction Fragment Length Polymorphism of PCR-Amplified DNA," J. Clin. Microbiol. 32:803-810.

Goodman et al., 1996, "Direct Cultivation of the Causative Agent of Human Granulocytic Ehrlichiosis," N. Engl. J. Med. 334:209-215.

International Search Report for International Application No. PCT/US98/08265.

Kolbert et al., 1997, Characterization of an Immunoreactive Protein from the Agent of Human Granulocytic Ehrlichiosis, Journal of Clinical Microbiology, 35(5):1172-1178.

Magnarelli et al., 1995, Coexistence of Antibodies to Tick-Borne Pathogens of Babesiosis, Ehrlichiosis, and Lyme Borreliosis in Human Sera, Journal of Clinical Microbiology, 33(11): 3054-3057.

Mahan et al., 1994, "Molecular Cloning of a Gene Encoding the Immunogenic 21 kDa Protein of *Cowdria ruminantium*," Microbiol. 140:2135-2142.

Murphy et al., 1998, Major Antigenic Proteins of the Agent of Human Granulocytic Ehrlichiosis Are Encoded by Members of a Multigene Family, Infection and Immunity, 66(8):3711-3718.

Nicholson et al., 1997, An Indirect Immunofluorescence Assay Using a Cell Culture-Derived Antigen for Detection of Antibodies to the Agent of Human Granulocytic Ehrlichiosis, 35(6):1510-1516.

Office Action mailed Nov. 2, 1999 in U.S. Appl. No. 09/066,046.
Office Action mailed Nov. 3, 1999 in U.S. Appl. No. 09/066,047.
Office Action mailed Sep. 21, 2000 in U.S. Appl. No. 09/066,047.
Office Action mailed Aug. 30, 1996 in U.S. Appl. No. 08/470,358.
Office Action mailed May 28, 1997 in U.S. Appl. No. 08/470,358.
Office Action mailed Dec. 8, 1999 in U.S. Appl. No. 08/470,358.
Office Action mailed Aug. 20, 2000 in U.S. Appl. No. 08/470,358.
Office Action mailed Jul. 14, 2006 in U.S. Appl. No. 09/792,957.
Office Action mailed Jan. 25, 2007 in U.S. Appl. No. 09/792,957.
Office Action mailed Sep. 11, 2007 in U.S. Appl. No. 09/792,957.
Office Action mailed Sep. 28, 2007 in U.S. Appl. No. 09/792,957.
Office Action mailed Mar. 24, 2008 in U.S. Appl. No. 09/792,957.
Office Action mailed Sep. 25, 2008 in U.S. Appl. No. 09/792,957.
Office Action mailed Mar. 17, 2009 in U.S. Appl. No. 09/792,957.

Ohashi et al., 1998, Immunodominant Major Outer Membrane Proteins of *Ehrlichia chaffeensis* Are Encoded by a Polymorphic Multigene Family, Infection and Immunity, 66(1):132-139.

Palmer et al., 1994, The Immunoprotective *Anaplasma marginale* Major Surface Protein 2 Is Encoded by a Polymorphic Multigene Family, Infection and Immunity, 62(9):3808-3816.

Rikihisa Y., 1991, "Protection against murine Potomac horse fever by an inactivated *Ehrlichia risticli* vaccine," Vet Microbiol., 27(3-4):339-350.

Rikihisa Y. et al., 1992, "Analyses of *Ehrlichia canis* and a canine granulocytic *Ehrlichia* infection," J Clin Microbiol., 30(1):143-148.

Ristic and Huxsoll, 1984, "Tribe II. *Ehrlichieae* Philip 1957, 948$^{AL}$," Bergey's Manual of Systemic Bacteriology, vol. 1, Krieg et al., Eds., Williams & Wilkins, pp. 704-709.

Spencer et al., 1984, "Nucleoside Sequence of the *sucB* Gene Encoding the Dihydrolipoamide Succinyltransferase of *Escherichia coli* K12 and Homology with the Corresponding Acetyltransferase," Eur. J. Biochem. 141:361-374.

Storey et al., 1998, Molecular Cloning and Sequencing of Three Granulocytic *Ehrlichia* Genes Enclding High-Molecular-Weight Immunoreactive Proteins, 66(4):1356-1363.

Sumner et al., 1997, PRC Amplification and Comparison of Nucleotide Sequences from the groESL Heat Shock Operon of *Ehrlichia* Species, Journal of Clinical Microbiology, 35(8):2087-2092.

Sumner et al., 1995, "Protection of Guinea-Pigs form Experimental Rocky Mountain Spotted Fever by Immunization with Baculovirus-Expressed *Rickettsia rickettsia* rOmpA Protein," Vaccine 13:29-35.

Sutcliffe, J. et al., 1983, "Antibodies that React with Predetermined Sites on Proteins," Science, 219:660-666.

Tebele et al., 1991, "Induction of Protective Immunity by Using *Anaplasma marginale* Initial Body Membranes," Infect. Immun. 59:3199-3204.

Yeh et al., 1997, Serologic and Molecular Detection of Granulocytic Ehrlichiosis in Rhode Island, Journal of Clinical Microbiology, 35(4):944-947.

Yu et al., 1996, The Recombinant 120-Kilodalton Protein of *Ehrlichia chaffeensis*, a Potential Diagnostic Tool, Journal of Clinical Microbiology, 34(11):2853-2855.

Yu et al., 1997, Cloning and sequencing of the gene for a 120-kDa immunodominant protein of *Ehrlichia chaffeensis*, Gene, 184:149-154.

VanVliet et al, 1994, "Molecular Cloning, Sequence Analysis, and Expression of the Gene Encoding the Immunodominant 32-Kilodalton Protein of *Cowdria ruminantium*", Infect. Immun. 62:1451-1456.

Wren, 1991 "A Family of Clostridial and Streptococcal Ligand-Binding Proteins with Conserved C-Terminal Repeat Sequencies," Mol. Microbiol. 5:797-803.

Wong et al., 1997, Serological Responses to *Ehrlichia equi, Ehrlichia chaffeensis,* and *Borrelia burgdorferi* in Patients from New York State, Journal of Clinical Microbiology, 35(9):2198-2205.

Zhi et al., 1997, Comparison of Major Antigenic Proteins of Six Strains of the Human Granulocytic Ehrlichiosis Agent by Western Immunoblot Analysis, Journal of Clinical Microbiology, 35(10):2606-2611.

BLAST comparison of SEQ ID Nos. 4, 6, 2, 8, 21, 22, 39, 27, 29 and 30 in U.S. Appl. No. 09/792,957 with SEQ ID No. 8 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 9 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 10 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 11 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 12 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 13 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 14 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 23 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 24 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 25 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 26 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 27 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 28 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 29 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 30 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 32 in U.S. Patent No. 6,231,869, 2007.

BLAST comparison of SEQ ID Nos. 4, 6, 2, 8, 21, 22, 39, 27, 29 and 30 in U.S. Appl. No. 09/792,957 with SEQ ID No. 33 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 35 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 37 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 38 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 50 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 51 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 52 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 53 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 54 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 55 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 56 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 57 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 58 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 59 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 60 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 61 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 62 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 63 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 64 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 65 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 66 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 67 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 68 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 69 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 70 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 71 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 72 in U.S. Patent No. 6,231,869, 2007.
BLAST comparison of SEQ ID Nos. 4, 6, 2, 8, 21, 22, 39, 27, 29 and 30 in U.S. Appl. No. 09/792,957 with SEQ ID No. 73 in U.S. Patent No. 6,231,869, 2007.
Laing et al., Diversity in CD8(+) T cell function and epitope breadth among persons with genital herpes. J Clin Immunol. Sep. 2010;30(5):703-22. Epub Jul. 16, 2010.
Mo et al., A heat shock protein based polyvalent vaccine targeting HSV-2: CD4(+) and CD8(+) cellular immunity and protective efficacy. Vaccine. Nov. 3, 2011;29(47):8530-41. Epub Jul. 19, 2011.
Sutcliffe et al., Antibodies that react with predetermined sites on proteins. Science. Feb. 11, 1983;219(4585):660-6.
Wald et al., Safety and immunogenicity of long HSV-2 peptides complexed with rbHsc70 in HSV-2 seropositive persons. Vaccine. Nov. 3, 2011;29(47):8520-9. Epub Sep. 21, 2011.

* cited by examiner

```
   1 GAATTCCTTA CCTCCCTATA TTTCGTACAG GTTATTCGCA AGTCTAGCTA TGATGCTTTA
  61 CCAGGATACG TTAAACGTTG ACGTTCTACG CTGTCATAGC CTTTTATTCT GCAAAAATAG
 121 CTTAACTGTG TCACTTCCTG AGAAAGTAAG ATACATATTT AGTTTTTGCA CAGCCAAAAA
 181 ACTTCTAGTG AACTGTGGTT TCTCTGGAAT CAATAACCTG TTTTATATTC GTGCGTTCTA
 241 TAACAATCTA CAGCTGTGGT TATTAGGCGT GGTTTCGCCT GATAATAAAG ATACTTTAGA
 301 GGGTATAAAC TTGGAAAAAA TAATGAAAAA CCCTCCTTAG TGCCTCCCCG TTTTTGACAA
 361 CATACTCTTA TGGGGAGTT TTAGGGAGTT GCTTCGCTTG TCACGCGTGC GTTAGTTTT
 421 ACGTATACGT GTCTGGGACT TCACGAAAAC TCGACGCAGG CGGATTTTGT ACTATGTTTC
 481 ACTTAACAAG GTATTATAAA TGTTTGAACA CAATATTCCT GATACATACA CAGGAACAAC
 541 TGCAGAAGGT TCTCCTGGCT TAGCAGGCGG GGATTTTAGC TTAAGTTCTA TTGACTTTAC
 601 AAGGGACTTT ACAATTGAAT CACATAGAGG AAGCTCAGCT GATGACCCAG GTTACATCAG
 661 CTTTAGGGAT CAAGACGGAA ACGTCATGTC ACGTTTTCTT GATGTGTACG TAGCTAATTT
 721 CAGCTTGCGA TGCAAGCATT CTCCCTATAA CAACGACAGA ATGGAAACAG CTGCGTTCTC
 781 TCTAACTCCC GACATAATAG AGCCTTCTGC TTTATTGCAA GAATCACATA GTACACAAAA
 841 CAATGTAGAA GAGGCAGTAC AAGTTACAGC TCTTGAGTGC CCTCCATGTA ATCCAGTCCC
 901 TGCCGAGGAA GTAGCTCCTC AACCGTCTTT TCTAAGCAGA ATAATTCAGG CGTTCTTGTG
 961 GTTATTCACG CCTTTCTTCTA CTACCGACAC TGCTGAAGAC AGCAAGTGTA ATAGTAGCGA
1021 TACTTCAAAA TGTACCTCTG CTAGCAGTGA GTCATTAGAG CAGCAACAAG AATCAGTGGA
1081 AGTGCAACCA TCTGTACTTA TGTCTACTGC CCCTATAGCA ACAGAGCCTC AAAAATGCGGT
1141 TGTTAACCAA GTAAACACTA CTGCAGTACA AGTAGAATCA TCCATTATTG TGCCAGAATC
1201 GCAACACACT GACGTTACCG TGCTCGAAGA TACTACTGAG ACGATAACTG TTGATGGGGA
1261 ATATGGACAT TTTAGTGACA TTGCTTCAGG TGAACACAAT AACGATCTGC CTGCCATGTT
1321 GTTAGATGAA GCAGACTTCA CTATGTTATT AGCCGAACGAG GAGTCAAAGA CCCTGGAGTC
1381 TATGCCTTCT GATAGCCTAG AAGACAATGT TCAGGAACTA GGTACATTGC CTTTACAAGA
1441 AGTGAAACA GTTTCTGAGG GCAACACACG AGAGTCACTA CCCACTGACG TTTCACAAGA
1501 CTCAGTTGGT GTAAGTACAG ATCTTGAAGC TCATTCTCAA GAAGTTGAAA CAGTTCTGA
1561 GGTCAGCACA CAAGATTCAC TATCCACTAA CATTTCACAA GACTCAGTTG GTGTAAGTAC
```

FIG. 4A

```
1621  AGATCTTGAA GCTCATTCTA AAGGAGTTGA AATAGTTTCT GAGGGCGGCA CACAAGATTC
1681  ACTATCCGCT GATTTTCCAA TAAACACAGT TGAAAGTGAA AGTACAGATC TTGAAGCTCA
1741  TTCTCAAGAA GTTGAAACTG TTTCTGAATT CACACAAGAT TCACTATCCA CTAACATTTC
1801  ACAAGACTCA GTTGGTGTAA GTACAGATCT TGAAGTTCAT TCTCAAGAAG TTGAAATAGT
1861  TTCTGAGGGC GGCACACAAG ATTCACTATC CACTAACATT TCACAAGACT CAGTTGGTGT
1921  AAGTACAGAT CTTGAAGCTC ATTCTCAAGA AGTTGAAACT GTTTCTGAAT TCACACAAGA
1981  TTCACTATCC ACTAACATTT CACAAGACTC AGTTGGTGTA AGTACAGATC TTGAAGTTCA
2041  TTCTCAAGAA GTTGAAATAG TTTCTGAGGG CGGCACACAA GATTCACTAT CCACTAACAT
2101  TTCACAAGAC TCAGTTGGTG TAAGTACAGA TCTTGAAGCT CATTCTAAAG GAGTTGAAAT
2161  AGTTTCTGAG GGCGGCACAC AAGATTCCAT ATCCGCTGAT TTTCCAATAA ACACAGTTGA
2221  AAGTGAAAGT ACAGATCTTG AAGCTCATTC CCCAGAAGGT GAAATAGTTT CTGAGGTCAG
2281  CACACAAGAT GCGCCATCCA CTGGAGTAGA GATCAGATTT ATGGATCGTG ATTCTGATGA
2341  TGACGTGCTC GCGTTGTGAA GTGATCATGG TAGGGGAAAC AGTTATGGCG TAAAGACATC
2401  TTTGATGACT TGTCTTGCGT GAATAAGTAG TGCAAGTTTT TTATGCATTG ATGTGCATGA
2461  TCATTGCCCC TAAGGAAAGC AGTACTAATG GTAGTCTAAG ATCTTATACA GGGTTTCGGA
2521  CTACCACTTT TGGTGTTTTA AAACGTCTTA TTCGCGTTGG GTGCTTGCTT ACAATGTACC
2581  TGTACGTGCC CAACACTAAA AATGGTCAGT ATTACTTAGG GGAGTTCGTA GACGAGGCAT
2641  CTCGATTTAC TCTAAGTAAG CTACAAATAA CTCAGTCATA TCAAGGTAGT TCAAGATGAA
2701  AGCAGTGCTA TGCTTATCAT GGAGAATTCC TGCCGTTCTC TTCAAAATTC TCTTTTCCCG
2761  CAAGGGCAGA CTCTTATTTG TTAAAATAAC AAAATTTCTC TACAGGAAGC GACATTTCAT
2821  ATCAAAGCTG ATTGTGAAAT AATGGCATTG AGTATTTTTC TCGCCCTAGA AGATAATCAT
2881  TTCGGCACTA TCAAAGCATT TACGATATTC TCCATTATCT TGTAATCAGA TGGCTATCTT
2941  GAAAGCAACC AAGGATATCC GTACATGGTA GCTTACATAC TGCTATCAAT CTCCTATACG
3001  ACCTTCAATG AAACGGTAAC TGTTGCTGAC AGTTGCACA TGCTGTGATT CAATTCCTGG
3061  TTCCTAGATG TTCTACTACG TTTATCCGGT ACTAATATTA TTCTTTGGCG CTCTATTATC
3121  TAGCAACTCA GAGTCCATTA GGAATTC  (SEQ ID NO:1)
```

FIG. 4B

```
  1  MFEHNIPDTY TGTTAEGSPG LAGGDFSLSS IDFTRDFTIE SHRGSSADDP GYISFRDQDG
 61  NVMSRFLDVY VANFSLRCKH SPYNNDRMET AAFSLTPDII EPSALLQESH STQNNVEEAV
121  QVTALECPPC NPVPAEEVAP QPSFLSRIIQ AFLWLFTPSS TTDTAEDSKC NSSDTSKCTS
181  ASSESLEQQQ ESVEVQPSVL MSTAPIATEP QNAVVNQVNT TAVQVESSII VPESQHTDVT
241  VLEDTTETIT VDGEYGHFSD IASGEHNNDL PAMLLDEADF TMLLANEESK TLESMPSDSL
301  EDNVQELGTL PLQEGETVSE GNTRESLPTD VSQDSVGVST DLEAHSQEVE TVSEVSTQDS
361  LSTNISQDSV GVSTDLEAHS KGVEIVSEGG TQDSLSADFP INTVESESTD LEAHSQEVET
421  VSEFTQDSLS TNISQDSVGV STDLEVHSQE VEIVSEGGTQ DSLSTNISQD SVGVSTDLEA
481  HSQEVETVSE FTQDSLSTNI SQDSVGVSTD LEVHSQEVEI VSEGGTQDSL STNISQDSVG
541  VSTDLEAHSK GVEIVSEGGT QDSLSADFPI NTVESESTDL EAHSPEGEIV SEVSTQDAPS
601  TGVEIRFMDR DSDDDVLAL (SEQ ID NO:2)
```

FIG. 5A

```
  1   TCGACGCAGGCGGATTTGTACTATGTTCACTTAACAAGTATTATAAATGTTTGAACA
                                                              M  F  E  H
 61   CAATATTCCTGATACATCAGGAACAACTGCAGAAGTTCTCCTGGCTTAGCAGGCGG
       N  I  P  D  T  Y  T  G  T  T  A  E  G  S  P  G  L  A  G  G
121   GGATTTAGCTTAAGTTCTATTGACTTTACAAGGGACTTTACAATTGAATCACATAGAGG
       D  F  S  L  S  S  I  D  F  T  R  D  F  T  I  E  S  H  R  G
181   AAGCTCAGCTGATGACCCAGGTTACATCAGCTTTAGGGATCAAGACGGAAACGTCATGTC
       S  S  A  D  D  P  G  Y  I  S  F  R  D  Q  D  G  N  V  M  S
241   ACGTTTCTTGATGTGTACGTAGCTAATTTCAGCTTGCGATGCAAGCATTCTCCCTATAA
       R  F  L  D  V  Y  V  A  N  F  S  L  R  C  K  H  S  P  Y  N
301   CAACGACAGAATGGAAACAGCTGCGTTCTCTCTAACTCCCGACATAATAGAGCCTTCGC
       N  D  R  M  E  T  A  A  F  S  L  T  P  D  I  I  E  P  S  A
361   TTTATTGCAAGAATCACATAGTACACAAAACATGTAGAAGAGGCAGTAGCAAGTACAGC
       L  L  Q  E  S  H  S  T  Q  N  N  V  E  E  A  V  Q  V  T  A
421   TCTTGAGTGCCCTCCATGTAATCCAGTCCCTGCCGAGGAAGTAGCTCCTCAACCGTCTTT
       L  E  C  P  P  C  N  P  V  P  A  E  E  V  A  P  Q  P  S  F
481   TCTAAGCAGAATAATTCAGGGCGTTCTTGTTATTCACGCCCTTCTTCTACTACCGACAC
       L  S  R  I  I  Q  A  F  L  W  L  F  T  P  S  S  T  T  D  T
541   TGCTGAAGACAGCAAGTGTAATAGTAGCGATACTTCAAAATGTACCTCTGCTAGCAGTGA
       A  E  D  S  K  C  N  S  S  D  T  S  K  C  T  S  A  S  S  E
601   GTCATTAGAGCAGCAACAAGAATCAGTGGAAGTGCAACCATCTGTACTTATGTCTACTGC
       S  L  E  Q  Q  Q  E  S  V  E  V  Q  P  S  V  L  M  S  T  A
661   CCCTATAGCAACAGAGCCTCAAAATGCGGTTGTTAACCAAGTAAACACTACTGCAGTACA
       P  I  A  T  E  P  Q  N  A  V  V  N  Q  V  N  T  T  A  V  Q
721   AGTAGAATCATCCATTATTGTTCCAGAATCGCAACACACTGACGTTACCGTGCTCGAAGA
       V  E  S  S  I  I  V  P  E  S  Q  H  T  D  V  T  V  L  E  D
781   TACTACTGAGACGATAACTGTTGATGGGGAATATGGACATTTAGTGACATTGCTTCAGG
       T  T  E  T  I  T  V  D  G  E  Y  G  H  F  S  D  I  A  S  G
```

FIG. 5B-1

```
841   TGAACACAATAACGATCTGCCTGCCATGTTGTTAGATGAAGCAGACTTCACTATGTTATT
       E  H  N  D  L  P  A  M  L  L  D  E  A  D  F  T  M  L  L
901   AGCGAACGAGGAGTCAAAGACCCTGAGTCTATGCCTTCTGATAGCCTAGAAGACAATGT
       A  N  E  E  S  K  T  L  E  S  M  P  S  D  S  L  E  D  N  V
961   TCAGGAACTAGTACATTGCCTTTACAAGAAGGTGAAACAGTTTCTGAGGGCAACACACG
       Q  E  L  G  T  L  P  L  Q  E  G  E  T  V  S  E  G  N  T  R
1021  AGAGTCACTACCACTGACGTTTCACAAGACTCAGTTGGTGTAAGTACAGATCTTGAAGC
       E  S  L  P  T  D  V  S  Q  D  S  V  G  V  S  T  D  L  E  A
1081  TCATTCTCAAGAAGTTGAAACAGTTTCTGAGGTCAGCACACAAGATTCACTATCCACTAA
       H  S  Q  E  V  E  T  V  S  E  V  S  T  Q  D  S  L  S  T  N
1141  CATTCACAAGACTCAGTTGGTGTAAGTACAGATCTTGAAGCTCATTCTAAGGAGTTGA
       I  H  K  T  Q  L  V  *  V  Q  T  L  K  L  I  L  K  E  L  ...
1201  AATAGTTTCTGAGGGCACACAAGACTCACTATCCGCTGATTTCCAATAAACACAGT
       I  V  S  E  G  T  Q  D  S  L  S  A  D  F  P  I  N  T  V
1261  TGAAAGTGAAAGTACAGAAGTACAGATCTTGAAGCTCAGTGAAACTGTTTCTGAATT
       E  K  V  K  V  Q  I  L  K  L  S  *  K  L  F  L  N  ...
1321  CACACAAGATTCACTACTAACATTCACAAGACTCAGTTGGTGTAAGTACAGATCT
       T  Q  D  S  L  S  T  N  I  S  Q  D  S  V  G  V  S  T  D  L
1381  TGAAGTTCATTCTCAAGAAGTTGAAATAGTTTCTGAAGTTGAAGCTTGAAGCTCAAGA
       E  V  H  S  Q  E  V  E  I  V  S  E  G  T  Q  D  S  L  S  E
1441  CACTAACATTTCACAAGACTCAGTTGGTGTAAGTACAGATCTTGAAGCTCATTCTCAAGA
       T  N  I  S  Q  D  S  V  G  V  S  T  D  L  E  A  H  S  Q  E
1501  AGTTGAAACTGTTTCTGAATTCACAAGATTCATTCTCAAGAAGTTGAAATAGTTTCTGAGG
       V  E  T  V  S  E  F  T  Q  D  S  L  S  T  N  I  S  Q  D  S
1561  AGTTGGTGTAAGTACAGATCTTGAAGTTCACATTCACAAGACTTCACAAGACTC
       V  G  V  S  T  D  L  E  V  H  S  Q  E  V  I  V  S  E  G
1621  CGGCACACAAGATTCACTACTAACATTCACAAGACTCAGTTGGTGTAAGTACAGA
       G  T  Q  D  S  L  S  T  N  I  S  Q  D  S  V  G  V  S  T  D
```

FIG. 5B-2

```
1681  TCTTGAAGCTCATTCTAAAGGAGTTGAAATAGTTTCTGAGGCGGCACACAAGATTCACT
       L  E  A  H  S  K  G  V  E  I  V  S  E  G  G  T  Q  D  S  L
1741  ATCCGCTGATTTCCAATAAACACAGTTGAAAGTGAAGTACAGATCTTGAAGCTCATTC
       S  A  D  F  P  I  N  T  V  E  S  E  V  Q  I  L  K  L  I  H
1801  CCAGAAGGTGAAATAGTTTCTGAGGTCAGTACACAAGATGCCCATCCACTGGAGTAGA
       P  E  G  E  I  V  S  E  V  S  T  Q  D  A  P  S  T  G  V  E
1861  GATCAGATTATGATGATCGTGATTCTGATGATGACGTGCTCGCGTTGTGAAGTGATCATGG
       I  R  F  M  D  R  D  S  D  D  D  V  L  A  L
1921  TAGGGAAA
```

FIG. 5B-3

```
   1 GGATCCCCCG GGCTGCAGGA ATTCCTAAAA AGATCTGGCG CCTGAGCCGTC TGCTACAGGC
  61 AGATTGTGCG CGCTAAGATA GGTTTAGTAA GACGTGTTTT TTATTGAATA AAGGCCCCAA
 121 CAATGTTGAC AGAAGAAGAA AAGAAAAAGA GCGCCGGTGC TCTGCAAGCC ATTATCACAG
 181 GAGATTACGA GAGTGTTCAG GCGTCCCGTTC AGGGAATTTC TTCCGAAGAC TTAATACTCC
 241 CGTTGATTAT GAGGGGAGAA CACTACTGCA CTATGCAGCT TCATCCCGTA ATGGTAATTT
 301 CTATGGCATT CTGGTTGAAA GAGGATGTGT TACTAATATC AGAGATGCTT ATGGATTAC
 361 TCCAGAACAA GCACGTGAGA AGGCAGGGTA TGCACGCACA CAGTGGTATG GAGCAGATGT
 421 AAATGACCCT GGTGTATCTA GGCAGTTAAT GACGCAAGCT GTTCAGCAGT CTGCGAAAGG
 481 TAACATGTAT GCTGCTCTCG CTATATTAGA CCTTGTGCGT AATGACGATG CAAAACATTC
 541 AGTCAATGA GGAAAGGGGC ATAGTGTTTT GCATCTAGCA TGTATTGAAG GCAGTAATCC
 601 ATCTTTCACT TCATCCCTCA TGCTAAAGGG TTGTTCTTTA AACATTAAGG ATGTAGATGG
 661 TAATACGCCA TTACATACAG CTGCGTTTTC AGTAGGCAAA AATGCTTTAG GCAATCTTGA
 721 TGTACTATGC GACAAGCTCT TATAGCAGAT GTTAATGCTA AGGGACCGGG TGGAAACACT
 781 CCGCTTCATA TTGCTACGGA GCGTATGGCT CACCAGAAAG TAGAGCATCT TCTCTCAAGG
 841 TTAAGTGATA TTAGCGTTGC AAATCGATGC TGGTGAAACC GTTTGCCACA TTGTTGCAAA
 901 GCAATGGCCA AGGCGGGATG TTTTACCATA CATTGACAAG ATGCAAGAAG CGGTGTCGTC
 961 AAATATTGAG GGCAATCGCG AGTGTGCAGA GGCACTAATA TTCCCGGATA AAAAAGGGAT
1021 GAGTGCAGTA CAGTATGCTA TTAGAAGGCA TATACCGGAG CTGAGAAGAT CTTCGAGAAG
1081 GCCATTAACA TTGCAGATAA AGTGTATGGC TTAGCTTCTT CAGAAGTAGA ATCTCTCTTT
1141 ACATGTCCTA ATCCAGAGGA CGCATCAACG CTGGTGCATT TTGTATCTTC TAATGGGACC
1201 CCAAATTTTG ATTCTCTTGC GAAAAGGGTA TTGTTGCAGG CATATCATAG GTATGGAGAG
1261 AAACCTTTTA CTAATTTAGA TGTTGCAGGT AATGCACCTA TACATGCTGC AGCACAAAAA
1321 TCAACAGTGG GGGTTTTTGA GCAGGTGGTA AGATACACTC CTGAGTCTGT TGTAAACTCA
1381 ATTAGCACCG AATGGCAAAG CGCCTATTCA AGATGATAGTT CATGATAGTG GAGGATGAGC TGTAAACTCA
1441 AAGCGTAAGC ATTAAATTGC AGATGTTGAT TGGGAATGTG CGTAATATTC CATCAATCAA
1501 TGTACCATCC CCAGTGACAG GTGAAACGCT GCGGTAGCTG CGTATAAAGG GGGCAACACT
```

FIG. 6A

```
1561 GAGGATGTTA AGACTATGTT ACGCTGTAAT AGCATGGACG TAGATGCTCG GTCACATGAT
1621 GGTAGAACTA TAATACATTA CGCAGCAAAG GATGGAAATT TAGAGATATT GCAGCAGGCT
1681 CTTGGAAGGA AGAGTAGTTA TTCTAAGTTT CCTGTAAAGG ATGGTGTTCC TACTCCAGGT
1741 GTATATGCGA TTCGTGAAGC AAGTGGTGGA AAAGTATCGC TACAAGCACT TGACATGTTA
1801 ATGAGATATG AGCCTCACCC GCAGCATGTT GCTGTCGAGG CAGTAAGAAC AGGTGCAGTA
1861 GGTGTATTGG AGCACCCTAT TACCACTGAA GTGATTAGTG TAAATGAAGA AATTACAACT
1921 CCTGAAGGAA AAAGACAAC TTTGACCGCT GAAGCACTAA CTAGTGGTAA ATATGGTGTA
1981 GTGAAGGCGT TAATTAAAAA CAGTGCTGAT GTAAATGCGT CTCCAGAACC AGCTATTACT
2041 TTGGGTATAC AAGGAAGGTG CTTTCAGGGG GTAAAAGCTA TAAAGCATTT AAAGCGTGTT
2101 GTAGAAGCTG GGGCACATAT AAATACTCCT ACCGGATCTA TGAGCCCTTT AGCTGCTGCA
2161 GTTCAAGCGG CAAATGAGGC AAGTAACCTT AAAGAGGCTA ATAAGATTGT AAATTTCCTT
2221 TTACATAGGG GTGCAGATCT TTCGTCTACG GAACACACTG CTTGCATTTA
2281 GCAACAGCTG CTGGCAACCA TAGGACTGCT ATGTTGCTCT TGGATAAAGG GGCTCCAGCA
2341 ACGCAGAGAG ATGCTAGGGG TAGGACGGCT TTACATATAG CAGCTGCTAA TGGTGACGGT
2401 AAGCTATATA GGATGATTGC CCAGATAGCT GTCAACCACT CTGTTCTGAT
2461 ATGGGAGATA CAGCGTTACA TGAGGCTTTA TATTCTGATA ATGTTACAGA AAAATGCTTT
2521 TTAAAGATGC TTAAAGAGTC TCGAAAGCAT TTGTCAAACT CATCTTTTTT CGGAGACTTG
2581 CTTAATACTC CTCAAGAAGC AAATGGTGAC ACGTTACTGC ATCTGGCTGC ATCGCGTGGT
2641 TTCGGTAAAG CATGTAAAAT ACTACTAAAG GCTGGGGCGT CAGTATCAGT CGTGAATGTA
2701 GAGGGAAAAA CACCGGTAGA TGTTGCGGAT CCATCATTGA AAACTCGTCC GTGGTTTTT
2761 GGAAAGTCCG TTGTCACAAT GATGGCTGAA CGTGTTCAAG TTCCTGAAGG GGGATTCCCA
2821 CCATATACTC CGCCTGAAAG TCCAACTCCT TCTTTAGGAT CTATTTCAAG TTTTGAGAGT
2881 GTCTCTGCGC TATCATCCTT GGGTAGTGGC CTAGATACTG CAGGAGCTGA GGAGTCTATC
2941 TACGAAGAAA TTAAGGATAC AGCAAAAGGT ACAACGGAAG TTGAAAGCAC ATATACAACT
3001 GTAGGAGCTG AGGAGTCTAT CTACGAAGAA ATTAAGGATA CAGCAAAAGG TACAACGGAA
```

FIG. 6B

```
3061 GTTGAAAGCA CATATACAAC TGTAGGAGCT GAAGGTCCGA GAACACCAGA AGGTGAAGAT
3121 CTGTATGCTA CTGTGGGAGC TGCAATTACT TCCGAGGCGC AAGCATCAGA TGCGGCGTCA
3181 TCTAAGGGAG AAAGCCGGAA ATCCATTTAT GCTGATCCAT TTGATATAGT GAAACCTAGG
3241 CAGGAAAGGC CTGAATCTAT CTATGCTGAC CCATTTGCTG CGGAACGAAC ATCTTCTGGA
3301 GTAACGACAT TTGGCCCTAA GGAAGAGCCG ATTTATGCAA CAGTGAAAAA GGGTCCTAAG
3361 AAGAGTGATA CTTCTCAAAA AGAAGGAACA GCTTCTGAAA AAGTCTGCTC AACAATAACT
3421 GTGATTAAGA AGAAAGTGAA ACCTCAGGTT CCAGCTAGGA CAAGTAGTTT GCCTACTAAA
3481 GAAGGTATAG GTTCTGATAA AGACCTGAGT TCAGGAACTA GTAGCTCTTT TGCAGCTGAG
3541 CTGCAAGCAC AAAGGGGTAA ATTGCGTCCT GTGAAGGGAG GTGCTCCGGA TTCTACCAAA
3601 GACAAAAACAG CTACTTCTAT ATTCTCCAGT AAAGAGTTCA AAAAGGAACT AACAAAAGCT
3661 GCCGAAGGAT TACAGGGAGC AGTTGAAGAA GCTCAGAAGG GTGATGGAGG AGCTGCAAAG
3721 GCAAAGCAAG ATCTGGGCAT GGAATCTGGT GCCCCAGGAT CTCAACCAGA AGCTCCTCAA
3781 AGTGAAGGCC CTAAGTCTGT AAAAGGAGGT CGGGGTAGGT AGAATTATAC CGAAAAATCG
3841 CTGAGGTACT TTGATCAATA TAATTCGCGC TTCTGAGTAT TTAGGCGATG ATCTCGCCAC
3901 TTTAATAATA CCCCTTTTAG AGTACATAAC GCTCTAAAGG GGGCAGATTA TTTTAAGTAG
3961 TAGGGTTTTG ATTCTGAGAT CTTTTGAGTA CAACTATTCC TTAGTGTTTT TTTGGAATGC
4021 TATGTGCTTG ATAAAGAAAA AACTTGCTCT GGGGTGGGAT GCACTCTTGA GTACTTTCCG
4081 CGCTCTGTAT ATTCCTTTTT TTGCATCTGC ATAATCTGCT GCATATGTGA TTATGTGATA
4141 ATGACGGAAT TACCCAGAAA AGCCTTAGCG TGTGAGGCCT ATCATTCTCA GAAAGTCACA
4201 GTAGGAAAACT TGCATTTTCA TCTTGTATTT TTGTAAGTTG GCTAAGAGCA CTAGCTATAA
4261 CAAATGCATC TATGGCATTT TTTGAGAGTT ATAATAATGA GAGCAACAAA GGGTGGTACT
4321 ATTGTTCAAA ATTTGTTTAT GTGCTTTGTC TCACAATGGA GTTAAAGTC ATCTCCGAGT
4381 AGTACTACGA CTTTAAGTAG AGAATACTTT GTATTTTCTT TATAGAGCTC AGAGATATAC
4441 TTCAGTATGT GTCGGAGGTT GTTCCCTTGG GAAAAAGGGC ATTTTATCAA CTGTGAACTA
4501 TCGCTACTAT GGCTGAGGAA AAGTAGATAG CAACAAAGAT AGTATTCTGG TTTTATAATC
4561 AAACCGTAAT CTTTCAACAT GTTCGAAGAT CGCTTTCACT TATCCTCGCT TTTTGACTGC
4621 CCTGCTGAAA GGGCTTTTT GTTATGAAAC TATCCTCGCT CGATTTTCTT ATCTTTGGAT
4681 TCTATTACCA CGGATAAATGT TGTTGGAAT TATTTAGAA GAAG    (SEQ ID NO:3)
```

FIG. 6C

```
  1  MLRCNSMDVD  ARSHDGRTII  HYAAKDGNLE  ILQQALGRKS  SYSKFPVKDG  VPTPGVYAIR
 61  EASGGKVSLQ  ALDMLMRYEP  HPQHVAVEAV  RTGAVGVLEH  LITTEVISVN  EEITTPEGKK
121  TTLTAEALTS  GKYGVVKALI  KNSADVNASP  EPAITLGIQG  RCFQGSKAIK  HLKRVVEAGA
181  HINTPTGSMS  PLAAAVQAAN  EASNLKEANK  IVNFLLHRGA  DLSSTEHTGT  PALHLATAAG
241  NHRTAMLLLD  KGAPATQRDA  RGRTALHIAA  ANGDGKLYRM  IAKKCPDSCQ  PLCSDMGDTA
301  LHEALYSDNV  TEKCFLKMLK  ESRKHLSNSS  FFGDLLNTPQ  EANGDTLLHL  AASRGFGKAC
361  KILLKAGASV  SVVNVEGKTP  VDVADPSLKT  RPWFFGKSVV  TMMAERVQVP  EGGFPPYLPP
421  ESPTPSLGSI  SSFESVSALS  SLGSGLDTAG  AEESIYEEIK  DTAKGTTEVE  STYTTVGAEE
481  SIYEEIKDTA  KGTTEVESTY  TTVGAEGPRT  PEGEDLYATV  GAAITSEAQA  SDAASSKGER
541  PESIYADPFD  IVKPRQERPE  SIYADPFAAE  RTSSGVTTFG  PKEEPIYATV  KKGPKKSDTS
601  QKEGTASEKV  CSTITVIKKK  VKPQVPARTS  SLPTKEGIGS  DKDLSSGTSS  SFAAELQAQR
661  GKLRPVKGGA  PDSTKDKTAT  SIFSSKEFKK  ELTKAAEGLQ  GAVEEAQKGD  GGAAKAKQDL
721  GMESGAPGSQ  PEAPQSEGPK  SVKGGRGR (SEQ ID NO:4)
```

FIG. 7A

```
  1  TGTACCATCCCAGTGACAGTGAAACGCTGCGTAGCTGCGTATAAAGGGGCAACACT
 61  GAGGATGTTAAGACTATGCGTTACGCAGCGTGTAATAGCATGGACGTAGATGTCGGTCGGTCACATGAT
         M  L  R  C  N  S  M  D  V  D  A  R  S  H  D
121  GGTAGAACTATAATACATTACGCCAGCAAGGATGGAAATTTAGAGATATTGCAGCAGGCT
         G  R  T  I  I  H  Y  A  K  D  G  N  L  E  I  L  Q  Q  A
181  CTTGGAAGGAAGAGTAGTTATTCTAAGTTCCTGTAAAGGATGGTGTTCCTACTCCAGGT
         L  G  R  K  S  Y  S  K  F  P  V  K  D  G  V  P  T  P  G
241  GTATATGCGATTCGTGAAGCAAGTGGTGGAAAACTATCGCTACAAGCACTTGACATGTTA
         V  Y  A  I  R  E  A  S  G  G  K  V  S  L  Q  A  L  D  M  L
301  ATGAGATATGAGCCTCACCCGCAGCATGTTGCTGTCGAGCAGCAGTAAGAACAGGTCCAGTA
         M  R  Y  E  P  H  P  Q  H  V  A  V  E  A  V  R  T  G  A  V
361  GGTGTATTGGAGCACCTTATTACCACTGAAGTGATTAGTGTAAATGAAGAATTACAACT
         G  V  L  E  H  L  I  T  T  E  V  I  S  V  N  E  I  T  T
421  CCTGAAGGAAAAAGACACTTTGAAACAGTGCTGATGCTAATGCCTCCAGAACCAGCTATTACT
         P  E  G  K  K  T  L  T  A  E  A  L  T  S  G  K  Y  G  V
481  GTGAAGGCGTTAATTAAAAACAGTGCTGATGTAATGCCTCCAGAACCAGCTATTACT
         V  K  A  L  I  K  N  S  A  D  V  N  A  S  P  E  A  I  T
541  TTGGGTATACAAGGAAGGTGCTTTCAGGAGTACTCCTACGGATCTATGAGCCCTTAGCTGCTGCA
         L  G  I  Q  G  R  C  F  Q  G  S  K  A  I  K  H  L  K  R  V
601  GTAGAAGCTGGGGCACATAAATACTCCTACGGATCTATGAGCCCTTAGCTGCTGCA
         V  E  A  G  A  H  I  N  T  P  T  G  S  M  S  P  L  A  A
661  GTTCAAGCGGCAAATGAGGCAAGTAACCTTAAAGAGGCTAATAGATTGTAAATTCCTT
         V  Q  A  N  E  A  S  N  L  K  E  A  N  K  I  V  N  F  L
721  TTACATAGGGGTGCAGATCTTTCGTCTACGGAACACTGAACTCCAGCCTTGCATTTA
         L  H  R  G  A  D  L  S  T  E  H  T  G  T  P  A  L  H  L
781  GCAACAGCTGCTGGCAACATAGGACTGCTATTGCTCTTGGATAAAGGGCCTCCAGCA
         A  T  A  G  N  H  R  T  A  M  L  L  D  K  G  A  P  A
```

FIG. 7B-1

```
841   ACGCAGAGAGATGCTAGGGGTAGGACGGCTTTACATATAGCACTGCTAATGTGACGGT
       T  Q  R  D  A  R  G  R  T  A  L  H  I  A  A  H  N  G  D  G
901   AAGCTATATAGGATGATTGGCAAAAATGCCAAGATAGTGTCACCACTGTGTTCTGAT
       K  L  Y  R  H  I  A  K  K  C  P  D  S  Q  P  L  C  S  D
961   ATGGGAGATACAGGCTTACATGAGGCTTTATATTCTGATAATGTTACAGAAATGCTTT
       M  G  D  T  A  L  H  E  A  L  Y  S  D  N  V  T  E  K  C  F
1021  TTAAGATGCTTAAGCAGTCTCGAAGCATTGTCAACTCATCTTTTTGGAGACTTG
       L  K  M  L  K  E  S  R  R  K  L  S  N  S  S  F  F  G  D  L
1081  CTTAATACTCCTCAAGAAGCAAATGGTGACACTTACTGCATCTGGCTGCATCGGCTGGT
       L  N  T  P  Q  E  A  N  G  D  T  L  H  L  A  A  S  R  G
1141  TTCGGTAAGCATGTAAAATACTACTAAGGCTGGGCGTCAGTATGAGTGTGAAGTA
       F  G  K  A  C  K  I  L  L  K  A  G  A  S  V  S  V  V  N  V
1201  GAGGGAAAACACCGGTAGATGTTGCAATGATGGCTGAACGTGTTCAAGTCTGAAGTT
       E  G  K  T  P  V  D  Y  A  D  P  S  L  K  T  R  P  W  F  F
1261  GGAAAGTCCGTGTGTCACAATGATGGCTGAACTCCCTTCTTTAGGATCTATTCAAGTTTGAGT
       G  K  S  V  V  T  M  M  A  E  R  V  Q  V  P  E  G  G  F  P
1321  CCATATCTGCCGCCTATCATCCTGAAAGTCCAACTCCTTCTTTAGGATCTATTCAAGTTTGAGT
       P  Y  L  P  P  E  S  P  T  P  S  L  G  S  I  S  F  E  S
1381  GTCTCGGCTATCATCCTGGTAGGCAAAGTACAACGGAGTGAAAGCACATATACAACT
       V  S  A  L  S  S  L  G  S  L  G  D  T  A  G  A  E  E  S  I
1441  TACGAAGAAATTAAGGATACAGCTAAGGGTACTACGAAGTTGAGTACCAACATATACAACT
       Y  E  E  I  K  D  T  A  K  G  T  T  E  V  E  S  T  Y  T
1501  GTAGGAGCTGAGGAGTCTATCTACGAAGAAATTAAGGATACAGCTAAAGGTACAACGGAA
       V  G  A  E  E  S  I  Y  E  E  I  K  D  T  A  K  G  T  T  E
1561  GTTGAAAGCACATATATACAACTGTAGGAGTCGAAGGTCCGAGAACCAGTAAGGTGAAGAT
       V  E  S  T  Y  T  T  V  G  A  E  G  P  R  T  P  E  G  E  D
```

FIG. 7B-2

```
1621  CTGTATGCTACTGTGGGAGCTGCAATTACTTCCGAGGCGAAGCATCAGATGCGGGCGTCA
       L  Y  A  T  V  G  A  A  I  T  S  E  A  Q  A  S  D  A  A  S
1681  TCTAAGGGAGAAAGGCCGGAATCCGAATCCATTTATGCTGATGCGACCCATTTGATATAGTGAAACCTAGG
       S  K  G  E  R  P  E  S  I  Y  A  D  P  F  D  I  V  K  P  R
1741  CAGGAAAGGCCTGAATCTATCTATGCTGACCATTGCTGGGAACGAACATCTCTGAA
       Q  E  R  P  E  S  I  Y  A  D  P  F  A  E  R  T  S  G
1801  GTAAGGACACATTGGCCCTAAGGAAGAGCCGATTTATGCAACAGTGAAAAGGGTCCTAAG
       V  T  T  F  G  P  K  E  E  P  I  Y  A  T  V  K  K  G  P  K
1861  AAGAGTGATACTTCTCAAAAGAAGGAACAGTTCTGAAAAGTGCTCAACAATAACT
       K  S  D  T  S  Q  K  E  G  T  A  S  E  K  V  C  S  T  I  T
1921  GTGATTAAGAAAGTGAAAAGTGCTAGGACCTCAGTTGCTAGTAGCTAGTCTTTTGCAGCTGAG
       V  I  K  K  V  K  P  Q  V  P  A  R  T  S  S  L  P  T  K
1981  GAAGGTATAGGTTCTGATAAGACCTAGTCAGGAACTAGTAGCTCTCTTTTGCAGCTGAG
       E  G  I  G  S  D  K  D  L  S  S  G  T  S  S  F  A  A  E
2041  CTGCAAGCACAAGGGTAATTGCCTCGTGAAGGAGGTGCTCCGGATTCTACCAAA
       L  Q  A  Q  R  G  K  L  R  P  V  K  G  A  P  D  S  T  K
2101  GACAAACAGAGCTACTTCTCTATATTCTCCAGTAAGAGTTCAAAAGAACTAACAAAGCT
       D  K  T  A  T  S  I  F  S  S  K  E  F  K  K  E  L  T  K  A
2161  GCCGAAGGATTACAGGAGCAGTTGAGAAGCAGAAGCAGAAGGGTGATGGAGGAGCTGCAAAG
       A  E  G  L  Q  G  A  V  E  E  A  Q  K  G  D  G  G  A  K
2221  GCAAAGCAAGATCTTGGCATGGAATCGTGTGCCCCCAGAGTCTCAACCAGAAGCTCCTCAA
       A  K  Q  D  L  G  M  E  S  G  A  P  G  S  Q  P  E  A  P  Q
2281  AGTGAAGGCCCTAAGTCTGTAAAGGAGGTGCGGTAGGTAGGAATTATACCGAAAATCG
       S  E  G  P  K  S  V  K  G  G  R  G  R
2341  CTGAGGTACT
```

FIG. 7B-3

```
   1 GAATTCCTGA TAGTATTTTA GAGGATAGTA GGCAATATGG TTTAGGGGAT TTCTTCGCAT
  61 ACTTGTTATC ATCGTCCTTA TTTGTGCTTA GTTGGTCGGA TATTTGTGCA AGTTGTTGTA
 121 AAATATGCAT ATTGTATGTA TAGGTGTGCA AGATATCATC TCTTTAGGTG TATCGTGTAG
 181 CACTTAAACA AATGCTGGTG AACGTAGAGG GATTAAAGGA GGATTGCGT ATATGTATGG
 241 TATAGATATA GAGCTAAGTG ATTACAGAAT TGGTAGTGAA ACCATTTCCA GTGGAGATGA
 301 TGGCTACTAC GAAGGATGTG CTGTGACAA AGATGCCAGC ACTAATGCGT ACTCGTATGA
 361 CAAGTGTAGG GTAGTACGGG GAACGTGGAG ACCGAGCGAA CTGGTTTTAT ATGTTGGTGA
 421 TGAGCATGTG GCATTGCTTC GGGTATGCAT CATGGTAATT TGCCAGGGAA
 481 GGTGTATTTT ATAGAGGCAG AAGCGGGCAG AGCTGCTACT GCTGAAGGTG GTGTTTATAC
 541 TACCGTTGTG GAGGCATTAT CGCTGGTGCA AGAGGAAGAG GGTACAGGTA TGTACTTGAT
 601 AAACGCACCA GAAAAAGCGG TCGTAAGGTT TTTCAAGATA GAAAAGAGTG CAGCAGAGGA
 661 ACCTCAAACA GTAGATCCTA GTCAGTTGA GTCAGCAACA GGGTCGGGTG TAGATACGCA
 721 AGAAGAACAA GAAATAGATC AAGAAGCACC AGCAATTGAA GAAGTTGAGA CAGAAGAGCA
 781 AGAAGTTATT CTGGAAGAAG GTACTTTGAT AGATCTTGAG CAACCTGTAG CGCAAGTACC
 841 TGTAGTAGCT GAAGCAGAAT TACCTGGTGT TGAAGCTGCA GAAGCGATTG TACCATCACT
 901 AGAAGAAAAT AAGCTTCAAG AAGTGGTAGT TGCTCCAGAA GCGCAACAAC TAGAATCAGC
 961 TCCTGAAGTT TCTGCGCCAG CACAACCTGA GTCTACAGTT CTTGGTGTTG CTGAAGGTGA
1021 TCTAAAGTCT GAAGTATCTG TAGAAGCTAA TGCTGATGTA CCGCAAAAAG AAGTAATCTC
1081 TGGTCAACAA GAGCAAGAAA TTGCAGAAGC ACTAGAGGGA ACTGAAGCTC CTGTAGAAGT
1141 AAAAGAAGAA ACAGAAGTTC TTCTAAAGGA AGATACTTTG ATAGATCTTG AGCAACCTGT
1201 AGCACAAGTA CCTGTAGTAG CTGAAGCAGA ATTACCTGGT GTTGAAGCTG CAGAAGCGAT
1261 TGTACCATCA CTAGAAGAAA ATAAGCTTCA AGAAGTGGTA GTTGCTCCAG AAGCGCAACA
1321 ACTAGAATCA GCTCCTGAAG TTTCTGCGCC AGCACAACCT GAGTCTACAG TTCTTGGTGT
```

FIG. 8A

```
1381  TACTGAAGGT GATCTGAAGT TGTAGAAGCT CTGAAGTATC GATGCTGGTA TGCAGCAAGA
1441  AGCAGGAATC TCTGATCAAG AAACACAAGC AGACACAAGG GTTGAAAAGG TTGAAGTATC
1501  TGTAGAAACA AAAACGAAGG AGCCAGAAGT TATTCTAGAA GAAGGTACTT TGATAGATCT
1561  TGAGCAACCT GTAGCGCAAG TACCTGTAGT AGCTGAAGCA GAATTACCTG GTGTTGAAGC
1621  TGCAGAAGCG ATTGTACCAT CACTAGAAGA AAATAAGCTT CAAGAAGTGG TAGTTGCTCC
1681  AGAAGCGCAA CAACTAGAAT CAGCTCCTGA AGTTTCTGCG CCAGTACAAC CTGAGTCTAC
1741  AGTTCTTGGT GTTACTGAAG GTCTGAAGTA TCTGAAGTA TCTGTAGAAG CTGATGCTGG
1801  TATGCAGCAA GAAGCAGGAA TCTCTGATCA AGAGACACAA GCAACTGAAG AAGTTGAGAA
1861  GGTTGAAGTA TCTGTAGAAG CTGATGCTGG TATGCAGCAA GAGTTAGTAG ATGTTCCGAC
1921  TGCTTTGCCG TTAAAGGATC CTGACGATGA AGATGTTCTA AGTTATTAGG ATATCTTTCT
1981  CGTGAAAAGT ATGGGGAAGG TTCGATGTGT TGAACCGTGC CCCATGCTTT TTCTTTAAGA
2041  TTTCTTCAAA AAGAGGTAAA ACTCTCCTAT GTTTTTTGTG AGCAGTAATT TCTTGCAGTT
2101  TTGCGACTGA GTTGTGTGTT ATTGCGAAGT TTTTCTTCTG ATTATTGGAC GAAGGTGGTG
2161  CTTGTCATGT CTGTGGTGCG TGCTTTCCAT GCTTGATAGA GCTCCTGATT ATTTTCTTTA
2221  TACGCAAGCC AGTAAAATCG TGTATGTGGC GACTTTTCGA ATCAGTGTTT AGATTACATA
2281  GAAGTAATTG TGGCTTATAC GCTGTTAATT GCGCTGCAAT CTGTCAAAAG TGATGCAGTA
2341  ACTTCCTCTA TATGTCCTAA TGCTGTTACA TGCACATGGGT GTTTATATA AATGCATAGC ATTATCAATG
2401  GTCATGGTGT CTTAGTAGG CATACCAGCG GTTTATATA AGATATTGG TATACCTAGC GCGAGCCTTG
2461  TTCTCCGCTT TCATAAAGA TTTATTACTC AAGATATTGG TATACCTAGC GATTCACGTG
2521  TAATTTGAGT ACTTACCTGC GTATTTCGAA GGTAACGTAC TAATAGCGTA TGGTAAAACT
2581  AACTATTATC CCAATCCCTA AGAATAACTA TGCTGTTTTG GAGCTGTTGC ATGCTGAAAG
2641  ATGTCTTATA GCATCGCGGT TATATATTTT CACATTTAG AGATTTAAG AGTATAACTT
2701  TCTAGCATCT TAGAGAACTA TAAACACAAT AAAAACATGA AGCATTAAAA
2761  CTCAAGTATA CTAAACCAGC CTTAGACCTT AAAGGAAAGT AAGGAATGCT TATCTATGTT
```

FIG. 8B

```
2821  CAATTGTGCC ATTACTTAAA AAGCGAACCT AACACCGAAT TCCCCACCGA CATAAGCCAT
2881  GGAGAAATTA GCAATAGCAG TATCCTTAGT ACGACCCGCC GACTAGTAT  CATCTACAAG
2941  ACGTTGAGCC GGCAGATCAT CATAAACGCC ATCTCCAACA ACGCGATGAT AGAATCCACC
3001  CGCAAAAGCG GAGATTTCAG GTGAGAGCTG ATAACTCAAG CCAGCCTTTA ACCTCAAGCT
3061  TAGGAGTGAT GTTCTAGACA CCATCCGTAT TAGTCACAGA TTAGCTTCCT CTCGAAGTAC
3121  AGATAACCTC TGGAAAGTTT TAGAAAGGAC GGAATGTGTA ACGCCGCTCC GTGCCATCAA
3181  CCACGCCAAC GAAGTTACCG CCTAAACCAA CACAAGCATA AGGAACAACA CCTAAACCTT
3241  CACTAAGAAG ATCATAACAA GCATTAACCA TTACAGATGT AGAAGAAACA GCTCTGATCT
3301  CAACAACCTC TCCCCCTTCA ATAGTTTTAG CAAGTAATCC TGCTACTATG GTTTTTTCAT
3361  CACGATTAAG ACCTAATAGG TCTTTAGCCA TAGCGTTTGC ATTACTATTA GGTTCTCCCT
3421  CGACGTTTTG ACTGCTGCCA TTACTCCCTC GTCCCCTAGG CCAGTTTTTA CCTTCACCGA
3481  CTTTCACAGT ATTAACAAAA CCACTCAAGG TCTTTGGTCC TGTCGCCCCC GTCGTATTTC
3541  CCAAACCGCT ACACTGTGTT GTCTCCTCGT TGCCGTGTGT CGTCGACAAC TCCGCAACAT
3601  ACTTCTTCCC CTTAGCCTTA GTTATAGCAG CATGATCCCC ACTACAAACC TTCCCATCAA
3661  TTTCAGGGCT GGAAATTTTC ACAGCATTGG CAAACTGAAC GATGTCTTTC CCAGAGGTTT
3721  TGGCAAGAGC AGCGGCAAGG TTATCAGTCT GCCCAGTAAC AACATCATAA GCTAACTCCT
3781  TAGCTAGTAG ATATACTGTA TCAGCTTCAT CTTCCTTACT ACCACTATCT CTAATACCCT
3841  TGGTCTTCCT TTTAATAATA AGAGTTATTG CATAGGATAT TGATATACCT ATCGATTTAT
3901  AGGCAGTTGA GCCGAAGAT  CATCTTAAAC ACCATCTCCC ACAACACGAT GGTAAAAGCC
3961  ACCCGCAGGA ATTCCGGAAT TCCGGAATTC
                    (SEQ ID NO:5)
```

FIG. 8C

```
  1  MYGIDIELSD YRIGSETISS GDDGYYEGCA CDKDASTNAY SYDKCRVVRG TWRPSELVLY
 61  VGDEHVACRD VASGMHHGNL PGKVYFIEAE AGRAATAEGG VYTTVVEALS LVQEEGTGM
121  YLINAPEKAV VRFFKIEKSA AEEPQTVDPS VVESATGSGV DTQEEQEIDQ EAPAIEEVET
181  EEQEVILEEG TLIDLEQPVA QVPVVAAEL  PGVEAAEAIV PSLEENKLQE VVVAPEAQQL
241  ESAPEVSAPA QPESTVLGVA EGDLKSEVSV EANADVPQKE VISGQQEQEI AEALEGTEAP
301  VEVKEETEVL LKEDTLIDLE QPVAQVPVVA EAELPGVEAA EAIVPSLEEN KLQEVVVAPE
361  AQQLESAPEV SAPAQPESTV LGVTEGDLKS EVSVEADAGM QQEAGISDQE TQATEEVEKV
421  EVSVETKTEE PEVILEEGTL IDLEQPVAQV PVVAEAELPG VEAAEAIVPS LEENKLQEVV
481  VAPEAQQLES APEVSAPVQP ESTVLGVTEG DLKSEVSVEA DAGMQQEAGI SDQETQATEE
541  VEKVEVSVEA DAGMQQELVD VPTALPLKDP DDEDVLSY  (SEQ ID NO:6)
```

FIG. 9A

```
  1   ATCGTGTAGCACTTAAACAAATGCTGGTGAACGTAGAGGGATTAAAGGAGGATTTGCGTA
 61   TATGTATGGTATAGATATAGAGCTAAGTGATTACAGAATTGGTAGTGAAACCATTTCCAG
        M  Y  G  I  D  I  E  L  S  D  Y  R  I  G  S  E  T  I  S  S
121   TGGAGATGATGGCTACTACGAAGGATGTGCTTGTGACAAAGATGCCAGCACTAATGCGTA
        G  D  D  G  Y  Y  E  G  C  A  C  D  K  D  A  S  T  N  A  Y
181   CTCGTATGACAAGTGTAGGGTAGTACGCGTGGTACGAGCGTGGAACTGGTTTTATA
        S  Y  D  K  C  R  V  V  R  G  T  W  R  P  S  E  L  V  L  Y
241   TGTTGGTGATGAGCATGTGGCATGCAGAGATGTTGCTTCGGGTATGCATGGTAATTT
        V  G  D  E  H  V  A  C  R  D  V  A  S  G  M  H  H  G  N  L
301   GCCAGGGAAGTGTATTTTATAGAGGCAGAGGCGGCAGAGCTGCTACTGCTGAAGGTGG
        P  G  K  V  Y  F  I  E  A  E  G  R  A  A  T  A  E  G  G
361   TGTTTATACCGTTGTGGAGGCATTATCGCTGTGCAAGAGGTACAGTAT
        V  Y  T  T  V  V  E  A  L  S  L  V  Q  E  E  G  T  G  M
421   GTACTTGATAACGCACCAGAAAAAGCGGTCGTAAGTTTTCAAGATAGAAAAGAGTGC
        Y  L  I  N  A  P  E  K  A  V  R  F  F  K  I  E  K  S  A
481   AGCAGGAACCTCAAACAGTAGATCCAGTTGAGTGTAGTGAGTTGAGCAACAGGGTCGGGTGT
        A  E  P  Q  T  V  D  P  S  V  V  E  S  A  T  G  S  G  V
541   AGATACGCAGAAGAACAAGAATAGAAACAAGCCACCAGCATTGAAGAAGTTGAGAC
        D  T  Q  E  E  Q  E  I  D  Q  E  A  P  A  I  E  E  V  E  T
601   AGAAGAGCAAGAAGTTATTCTGGAAGGTACTTTGATATCTTGACCAACCTGTAGC
        E  E  Q  E  V  I  L  E  E  G  T  L  I  D  L  E  Q  P  V  A
661   GCAAGTACCTGTAGTAGCTGAAGCAGAATTACCTGGTGTTGAAGCTGCAGAAGCGATTGT
        Q  V  P  V  V  A  E  A  E  L  P  G  V  E  A  A  E  A  I  V
721   ACCATCACTAGTAGAAAATAAGCTTCAAGAAGTGGTAGTTGCTCCAGAAGCGCAACAACT
        P  S  L  E  E  N  K  L  Q  E  V  V  A  P  E  A  Q  Q  L
781   AGAATCAGCTCCTGAAGTTTCTGCCCAGCACAACCTGAGTCTACAGTTCTTGGTGTTGC
        E  S  A  P  E  V  S  A  P  A  Q  P  E  S  T  V  L  G  V  A
```

FIG. 9B-1

```
 841  TGAAGGTGATCTAAAGTCTGAAGTATCTGTAGAAGCTAATGCTGATGTACCGCAAAAGA
        E  G  D  L  K  S  E  V  S  V  E  A  N  A  D  V  P  Q  K  E
 901  AGTAATCTCTGGTCAACAAGAGCAAGAAATTGCAGAACTAGAGGAACTGGAACTGAAGCTCC
        V  I  S  G  Q  Q  E  Q  E  I  A  E  L  E  G  T  E  A  P
 961  TGTAGAAGTAAAGAAGAAGAAACAGAAGAGTTCTTCTAAAGGAAGATACTTTGATAGATCTTGA
        V  E  V  K  E  E  T  E  V  L  K  E  D  T  L  I  D  L  E
1021  GCAACCTGTAGCACAAGTACCTGTAGTAGCTGAAGCAGAATTACCTGGTGTTGAAGCTGC
        Q  P  V  A  Q  V  P  V  V  A  E  L  P  G  V  E  A  A
1081  AGAAGCGATTGTACCATCACTAGAAGAAGAAATAAGCTTCAAGAAGTGGTAGTTGCTCCAGA
        E  A  I  V  P  S  L  E  E  N  K  L  Q  E  V  V  A  P  E
1141  AGCGCAACAACTAGAATCAGCTCCTGAAGTTTCTGCGCCAGCACAACCTGAGTCTACAGT
        A  Q  L  E  S  A  P  E  V  S  A  P  A  Q  P  E  S  T  V
1201  TCTTGGTGTTACTGAAGGTGATCTGAAGTCTGAAGTATCTGTAGAAGCTGATGCTGTAT
        L  G  V  T  E  G  D  L  K  S  E  V  S  V  E  A  D  A  M
1261  GCAGCAAGAAGCAGAAATCTCTGATCAAGAGACAAGCCAGAGTTATTCTAGAAGAAGGTACTTT
        Q  Q  E  A  G  I  S  D  Q  E  T  Q  A  T  E  E  V  E  K  V
1321  TGAAGTATCTGTAGAAACAAAACGAAGAGCCAGAAGTACCTGTAGCTGAAGCAGAATTACCTGG
        E  V  S  V  E  T  K  T  E  E  P  E  V  I  L  E  G  T  L
1381  GATAGATCTTGAGCAACCTGTAGCACAAGTACCTGTAGTAGCTGAAGAAAATAAGCTTCAAGAAGTGGT
        I  D  L  E  Q  P  V  A  Q  V  P  V  V  A  E  E  L  P  G
1441  TGTTGAAGCTGCAGAAGCGATTGTACCATCACTAGAAGAAAATAAGCTTCAAGAAGTGGT
        V  E  A  A  E  A  I  V  P  S  L  E  E  N  K  L  Q  E  V  V
1501  AGTTGCTCCAGAAGCCAACAACTAGAATCAGCTCCTGAAGTTCTGCGCCAGTACAAC
        V  A  P  E  A  Q  L  E  S  A  P  E  V  S  A  P  V  Q  P
1561  TGAGTCTACAGTTCTTGGTGTTACTGAAGGTGATCTGAAGTCTGAAGTATCTGTAGAAGC
        E  S  T  V  L  G  V  T  E  G  D  L  K  S  E  V  S  V  E  A
```

FIG. 9B-2

1621 TGATGCTGGTATGCAGCAAGAAGCAGGAATCTCTGATCAAGACACAAGCAACTGAAGA
     D  A  G  M  Q  Q  E  A  G  I  S  D  Q  E  T  Q  A  T  E  E

1681 AGTTGAGAAGGTTGAAGTATCTGTAGAAGCTGATGCTGGTATGCAGCAAGAGTTAGTAGA
     V  E  K  V  E  V  S  V  E  A  D  A  G  M  Q  Q  E  L  V  D

1741 TGTTCCGACTGCTTTGCCGTTAAAGGATCCTGACGATGAAGATGTTCTAAGTTATTAGGA
     V  P  T  A  L  P  L  K  D  P  D  D  E  D  V  L  S  Y

1801 TATCTTTCTCGTGAAAAGTATGGGAAGGT

FIG. 9B-3

```
   1 GAATTCCCTG TGGTTATTAG GCGTGGTTTC GCCTGATAAT AAGATACTT TAGAGGGTAT
  61 AAACTGGAA AAATAATGA AAAACCCTCC TTAGTGCCTC CCCGTTTTG ACAACATACT
 121 CTTATGAAA AGCGTTAGGG AGTTGCTTCG CTTGCTCACGC GTGCGTTAGG TTTTACGTAT
 181 ACGTGTCTGG GACTTCACGA AAACTCGACG CAGGCGGATT TTGTACTATG TTTCACTTAA
 241 CAAGTATTA TAAATGTTTG AACACAATAT TCCTGATACA TACACAGGAA CAACTGCAGA
 301 AGGTTCTCCT GGCTTAGCAG GCGGGGATTT TAGCTTAAGT TCTATTGACT TTACAAGGGA
 361 CTTTACAATT GAATCACATA GAGGAAGCTC AGCTGATGAC CCAGGTTACA TCAGCTTTAG
 421 GGATCAAGAC GGAAACGTCA TGTCACGTTT TCTTGATGTG TACGTAGCTA ATTTCAGCTT
 481 GCGATGCAAG CATTCTCCCT ATAACAACGA CAGAATGGAA ACAGCTGCGT TCTCTCTAAC
 541 TCCCGACATA ATAGAGCCTT CTGCTTTATT GCAAGAATCA CATAGTACAC AAAACAATGT
 601 AGAAGAGGCA GTACAAGTTA CAGCTCTTGA GTGCCCTCCA TGTAATCCAG TCCCTGCCGA
 661 GGAAGTAGCT CCCTCAACCGT CTTTCTAAG CAGAATAATT CAGGCCGTTCT TGTGGTTATT
 721 CACGCCTTCT TCTACTACCG ACACTGCTGA AGACACCAAG TGTAATAGTA GCGATACTTC
 781 AAAATGTACC TCTGCTAGCA GTGAGTCATT CAGAATCAG CAAGAATCAG TGGAAGTGCA
 841 ACCATCTGTA CTTATGTCTA CTGCCCCTAT AGCAACAGAG CCTCAAAAATG CGGTTGTTAA
 901 CCAAGTAAAC ACTACTGCAG TACAAGTAGA ATCATCCATT ATTGTGCCAG AATCGCAACA
 961 CACTGACGTT ACCGTGCTCG AAGATACTAC TGAGACGATA ACTGTTGATG GGAATATGG
1021 ACATTTAGT GACATTGCTT CAGGTGAACA CAATAACGAT CTGCCTGCCA TGTTGTTAGA
1081 TGAAGCAGAC TTCACTATGT TATTAGCGAA CGAGGAGTCA AAGACCCTGG AGTCTATGCC
1141 TTCTGATAGC CTAGAAGACA ATGTTCAGGA ACTAGGTACA TTGCCTTTAC AAGAAGGTGA
1201 AACAGTTTCT GAGGGCCAACA CACGAGAGTC ACTACCCACT ACTACCCACT AAGACTCAGT
1261 TGGTGTAAGT ACAGATCTTG AAGCTCATTC TCAAGAAGTT GAAACAGTTT CTGAGGTCAG
1321 CACACAAGAT TCACTATCCA CTAACATTTC ACAAGACTCA GTTGGTGTAA GTACAGATCT
1381 TGAAGTTCAT TCTCAAGAAG TTGAAATAGT TTCTGAGGGC GGCACACAAG ATTCACTATC
1441 CACTAACATT TCACAAGACT CAGTTGGTGT AAGTACAGAT CTTGAAGCTC ATTCTAAAGG
```

FIG. 10A

```
1501  AGTTGAAATA GTTTCTGAGG GCGGCACACA AGATTCACTA TCCGCTGATT TTCCAATAAA
1561  CACAGTTGAA AGTGAAAGTA CAGATCTTGA AGCTCATTCC CCAGAAGGTG AAATAGTTTC
1621  TGAGGTCAGC ACACAAGATG CGCCATCCAC TGGAGTAGAG ATCAGATTTA TGGATCGTGA
1681  TTCTGATGAT GACGTGCTCG CGTTGTGAAG TGATCATGGT AGGGAAACA GTTATGGCGT
1741  AAAGACATCT TTGATGACTT GTCTTGCGTG AATAAGTAGT GCAAGTTTTT TATGCATTGA
1801  TGTGCATGAT CATTGCCCCT AAGGAAAGCA GTACTAATGG TAGTCTAAGA TCTTATACAG
1861  GGTTCGGAC TACCACTTTT GGTGTTTTAA AACGTCTTAT TCGCGTTGGG TGCTTGCTTA
1921  CAATGTACCT GTACGTGCCC AACACTAAAA ATGGTCAGTA TTACTTAGGG GAGTTCGTAG
1981  ACGAGGCATC TCGATTACT CTAAGTAAGC TACAAATAAC TCAGTCATAT CAAGTAGTT
2041  CAAGATGAAA GCAGTGCAGAC GCTTATCATG GAGAATTCCT GCGGTTCTCT ACAGGAAGCG
2101  CTTTTCCCGC AAGGGCAGAC TTGTGAAATA TAAAATAACA AAATTTCTCT CGCCCTAGAA
2161  ACATTCATA TCAAAGCTGA TTGTCACTAT ATGGCATTGA GTATTTTCT GTAATCAGAT
2221  GATAATCATT TCGGCACTAT CAAAGCATTT ACGATATATCC CCATTATCTT GCTATCAATC
2281  GGCTATCGTTG AAAGCAACCA AGGATATCCG TACATGGTAG CTTACATACT AGATCGATAA
2341  TCCTATACGA CCTTCAATGA ACGGTAACT GTTGCTGACA GCTTGCACAT AGTACCTCGA
2401  AATTCCTGGT TCCTAGATGT TCTACTACGT TTATCCGGTA CTAATATTAT GCTGTGATTC
2461  TCTATTATCT AGCAACTCAG AGTCCATTAT TGGATCTCTA ATACCAAGGG TATAAGGGAA
2521  AGTGGAAGAG TATTATTAGA GAGAAGAAGC AAATACAGTA TATCTACTAG CTAAGGAGTT
2581  AGCTTATGAT GTTGTTACTG GACAGACTTGA TAAGCTTGCT GCTGCTCTTG CCAAGACCTC
2641  CGGGAAAGAT ATCGTTCAGT TTGCTAAGGC AGTTGAGATT TCGGCTCCTA AGATCGATAA
2701  GCAAGTTTGT GTGACTAATA AGAATGGGGA TAGCGGAACA AGATATGCTA AGTACCTCGA
2761  AGAAGCTGAA ACGTCTAGCA GTCGTTGTGT TAGCCTAAAA GGTGGTAAAA ACCTAAAGAC
2821  GACTGACTCC AACACAGGAG TAGAGAAAGG ACAGGTGTTA CATGACTTTG TTTCTGGAAC
2881  GTTGAGTGGG GGTACTAAGA ACTGGCCGAC ATCTACTGAA AGTACTAAAG AAAATAACGA
2941  CAACGCAGGG AAGGTAGCTA AGACCTGAC AAGACCTGAC AAAACTAACC CCTGAAGAAA AAACCATAGT
```

FIG. 10B

```
3001 AGCAGGGTTA CTAGCTAAGA CTATTGAAGG GGGTGAAGTT GTTGAGATCA GGGCGGTTTC
3061 TTCTACTTCT GTGATGGTTA ATGCTTGTTA TGATCTTCTT AGTGAAGGTT TAGGTGTCGT
3121 TCCTTACGCT TGTGTTGGTC TTGGGGGTAA CTTCGTGGGG GGTTGTTGAT GGCACGGCGC
3181 AGCGTTACAC AATCCGTCCT TGACCTGAAT ACTCTAGTTA AGCACTAGGC AAAATTAGTG
3241 CTGGATCACT TACGCAACAT ACTACGGTCA GCGATTTTCC ATACTGAGCA GGTACGTACA
3301 GTGGCTTTAT ACTCTTACCC AGCATGAAAT TACTTGTTAT CTAAGAAATCT CCACAGCTGA
3361 CCTTAGAAAG GTTATCTGTC C-TTCGAGAG AAAGCTAATC TGTGTCTTAT GCGGATGCG
3421 TTGAACGTAT TACAGGTCCC AAGCTGTCTT GCAAGTTTCT AAGGATATTA TAAGGCACA
3481 CCTATAAAAC TGCGCAATAT ATCACCTGCA ATACGGTCCC GATTCGAAAA CACTGGGAAG
3541 TGCGCTCATT ATCTATGAAT CGCTAGCTAG GCATAAATAA GAGTATACGC AATAACGCTT
3601 ATTATTAAAA ACAAGACCAA GGGTATTAGA GATAGTGGTA GTAAGGAAGA TGAAGCTGAT
3661 ACAGTATATC TACTAGCTAA GGAGTTAGCT TATGATGTTG TTACTGGGCA GACTGATAAC
3721 CTTGCTGCTG CTCTTGCCAA GACTTCTGGT AAAGATATTG TTCAGTTTGC TAAGACTCTT
3781 AATATTTCTC ACTCTAATAT CGATGGGAAG GTTTGTAGGA GGGAAAAGCA TGGGAGTCAA
3841 GGTTTGACTG GAACCAAAGC AGGTTCGTGT GATAGTCAGC CACAAACGGC GGGTTTCGAT
3901 TCCATGAAAC AAGGTTTGAT GGCAGTTTA GGCGAACAAG GCGCTGAAAA GTGGCCCAAA
3961 ATTAACAATG GTGGCCACGC AACAATTTAT AGTAGTAGCG CAGGTCCAGG AAATGCGTAT
4021 GCTAGAGATG CATCTACTAC GGTAGCTACA GACCTAACAA AGCTCACTAC TGAAGAAAAA
4081 ACCATAGTAG CAGGGTTACT AGCTAGAACT ATTGAAGGGG GTGAAGTTGT TGAGATTAGG
4141 GCAGTTTCTT CTACTTCTGT GATGGTTAAT GCTTGTTATG ATCTTCTGAA GGGAAACCCA
4201 TCACATTATT TATCTGGTTG CTGTAATCTG ATCTTCCCGT TGCTATGATC GCATCTCCCC
4261 CTCACTTCTC TGCAAACTC TGGATTAACC TCTGGATGCG AATAATGTTT ATCAGCTTTG
4321 AGAAAAACAT ATTAGAGTTT TATACAGCAC CAATGATAAG CGTGGGCACT TAAATAAAGG
4381 TTCATATCCC TAGAAATTTA TCCCACTAGC TAAAACTATT GAAGGGGGTG AGGTCGTTGA
4441 GATAAGGGCA GTTTCTTCTA CTTCTGTGAT GGTTAATGCT TGTTATGATC TTCTTAGTGA
4501 AGGTTTAGGC GTTGTTCCTT ATGCTTGCGT GGGTCTTGGT GGGAACTTCG TGGGCGTGGT
```

FIG. 10C

```
4561  TGATGGGCAT ATCACAAACC ACTCCATCTC TGACCCTGTA TGCACTAGCA AGTAACTAGG
4621  CAAAATTATT GCTGCATCAC TTTGAAACAA ACTACGATCA GCAATGTTCA ATACTTAGCA
4681  GGTCTGTACA GTGGCTTTAC ACTCTTACCC AGCATGAAAT ACTTGCTATC TAAGAATCTC
4741  CTCTAAAACT TTCCAGAGGT TATCTGTACT TTGAGGGAAG CTAATCTGTG GCTAATGAGG
4801  ATGGTGTCTA GAATATCACT CCTAAGCTTG CTTATAGGTT AAAGGCTGGG TTGAGTTATC
4861  AGCTTTCTCC TGAAATCTCT GCTTTTGTAG GTGGTTTCTA TCATTGGTTT GTTGGTTATG
4921  GTGTTTATGA TGATCTTCCG GCTCAACGTC TTGTAGATGA TACTAGTCCG GCGGGTCGTA
4981  CTAAGGATAC TGCTATTGCT AACTTCTCCA TGGCCTATGT TGGTGCATCA TTTCAGCCAT
5041  ATTACGCAGT TCTTCTAGTA GAACTGTATG AGTATCGATA AAAAGATATA CGACGCAGCA
5101  TGCTCTGAAA AAGTGACAGG GTGCAGCATA CATTAGCCTG TCTGTATCAG
5161  TGTGCAATCT GTTACACAGG ATTCTTTTAA CACCTATCGG GTTCATCAAG
5221  AAAATGAGTG CATACGTGAC GGCAAGCGCT AAAACGCTAA AGCTGATGCA TCACATTAAA
5281  AGCTTTCTCC GTTAGACCTT CCAAGCACTG CGATTCCCCC GCATACGTTC
5341  TTATGCGTGA TTTTGAAAAA CCCGGCGTCT TAAAGTGTGG AAGAGAATTG TTTTTGTGTG
5401  GGAAAAGCTC TTATGCTTTC AACTAAGTAG GCAACTTCGG CAATATCCCC GGCTACTATT
5461  TTGCCAATTT TCGGTATAAC AAAGAAAGAA TACAGGTCAT AAGCTGTTTT GAATGCACTG
5521  TCTTCGAGTA TAGGAGAAAA CTCCAAGCAT AAAAACCTAC CACATGGTTT CAGGAATTC (SEQ ID NO:7)
```

FIG. 10D

```
  1  MFEHNIPDTY TGTTAEGSPG LAGGDFSLSS IDFTRDFTIE SHRGSSADDP GYISFRDQDG
 61  NVMSRFLDVY VANFSLRCKH SPYNNDRMET AAFSLTPDII EPSALLQESH STQNNVEEAV
121  QVTALECPPC NPVPAEEVAP QPSFLSRIIQ AFLWLFTPSS TTDTAEDSKC NSSDTSKCTS
181  ASSESLEQQQ ESVEVQPSVL MSTAPIATEP QNAVVNQVNT TAVQVESSII VPESQHTDVT
241  VLEDTTETIT VDGEYGHFSD IASGEHNNDL PAMLLDEADF TMLLANEESK TLESMPSDSL
301  EDNVQELGTL PLQEGETVSE GNTRESLPTD VSQDSVGVST DLEAHSQEVE TVSEVSTQDS
361  LSTNISQDSV GVSTDLEVHS QEVEIVSEGG TQDSLSTNIS QDSVGVSTDL EAHSKGVEIV
421  SEGGTQDSLS ADFPINTVES ESTDLEAHSP EGEIVSEVST QDAPSTGVEI RFMDRDSDDD
481  VLAL   (SEQ ID NO:8)
```

FIG. 11

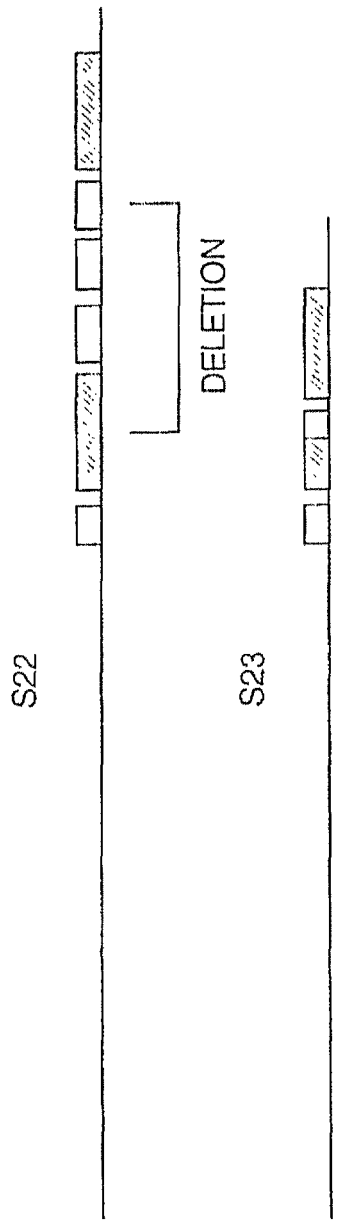

S2
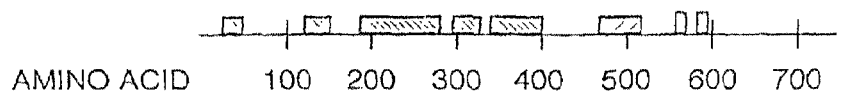
AMINO ACID    100   200   300   400   500   600   700
    ▭    1ST SET REPEATS: 27 AMINO ACIDS
    ▭    2ND SET REPEATS: 11 AMINO ACIDS
    ▭    ANKYRIN-LIKE REPEAT UNITS (8)
             HOMOLOGY TO PROTEINS CONTAINING
             ANKYRIN REPEATS
S7
AMINO ACID    100       200       300       400       500
▭ REPEATS 93, 111, 122 AMINO ACIDS
———————————  93
——————————————  111
————————————————  122
FIG. 13

S2
160 kDa PROTEIN

AMINO ACID  100  200  300  400  500  600  700

☐ ANKYRIN-LIKE REPEAT UNITS (1-8)
☐ 27 AMINO ACIDS REPEATS
☐ 11 AMINO ACIDS REPEATS

S2
160 kDa PROTEIN ANKYRIN REPEATS

```
                    t S/TPLH  Ah      tt  thht  LLt   t  tthht   t (SEQ ID NO:17)
(SEQ ID NO:9) CONSENSUS: DGRTIHYAAKDGNLEILQQALGRKSSYSKFPV
(SEQ ID NO:10) REPEAT 1  KKIKELTAEANEASNLKEANKITVNFLLHRGADLSSREH
(SEQ ID NO:11)        2  AVQAAANEASNLKEANKITVNFLLHRGADLSSREH
(SEQ ID NO:12)        3  TGHPALHLHIAAAANGDGKLYRMIAKKCPDSCQPLC
(SEQ ID NO:13)        4  RGRTAALHEALYSDNBTEKCFLKMLKESRKRLSN
(SEQ ID NO:14)        5  MGDTAALHEALYSDNBTEKCFLKMLKESRKRLSN
(SEQ ID NO:15)        6  NGDRILHLAASRGFGKACKILLKAGASVSVVNV
(SEQ ID NO:16)        7  EGKTPVDADPSLKTRPWFFGKSVVTMMAERVQ
```

FIG. 14

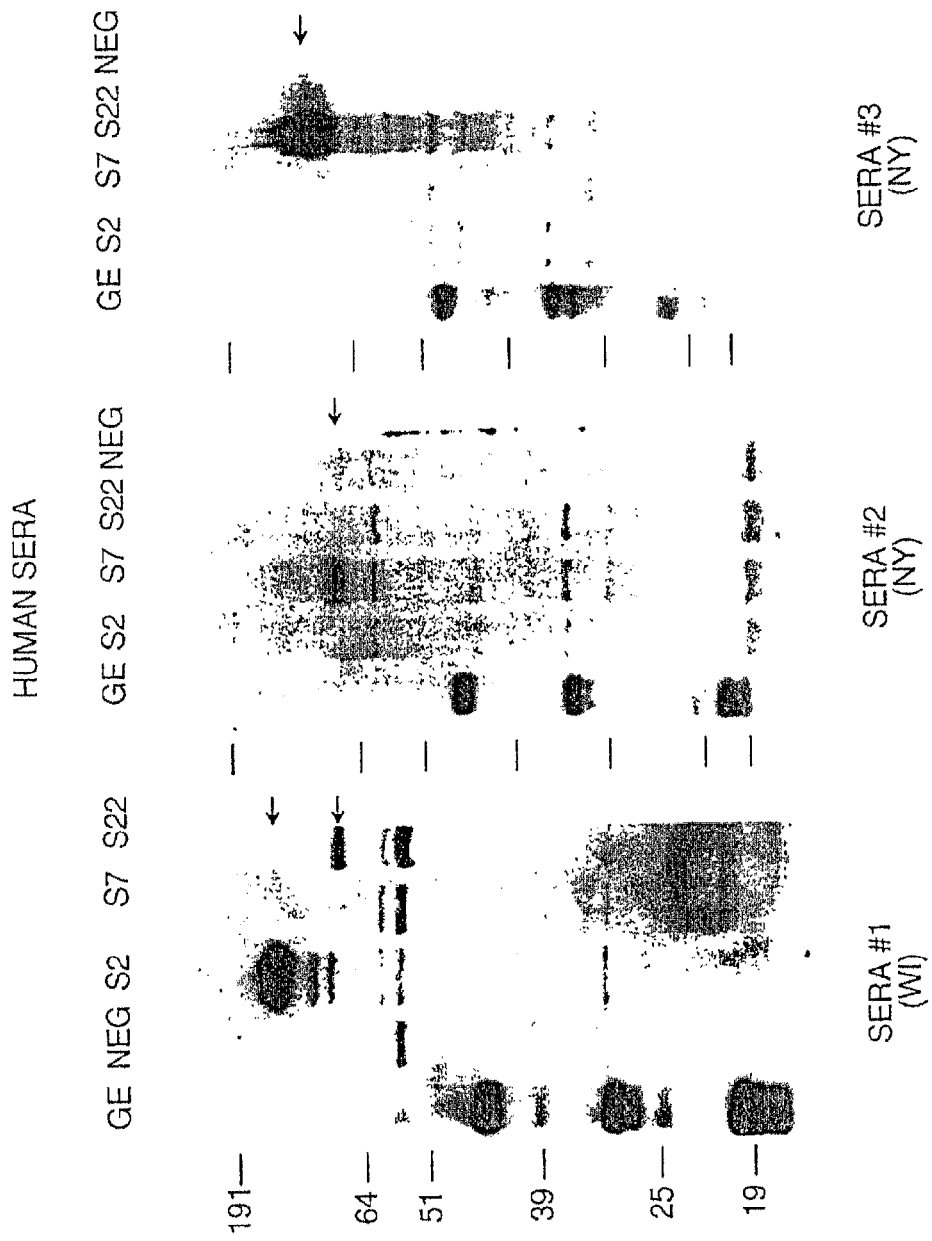

```
  1  MGDAVEVRAE NLGGESILEA PIRVMKKVGD TVSAEDVLFI VETDKTSLEI SAPVAGVLTE
 61  LRVADEEVIT KGQVLAIIRP QGEATAEGVN KEPESKEEVP AQPVVAQAVS TQKPQEKTII
121  EGKGLVTPTV EDFVAGINTT PTSRALGMSA KSEQDKKIVA SQPSKDLMSC HGDVVGERRV
181  KMSKIRQVLA ARLKESQNTS ATLSTENEVD MSKVMELRAK YKDAFVKRYD VKLGFMSFFI
241  RAVVLVLSEI PVLNAEISGD DIVYRDYCNI GVAVGTDKGL VVPVIRRAET MSLAEMEQAL
301  VDLSTKARSG KLSVSDMSGA TFTITNGGVY GSLLSTPIIN PPQSGILGMH AIQQRPVAVD
361  GKVEIRPMMY LALSYDHRIV DGQGAVTFLV RVKQYIEDPN RLALGI        (SEQ ID NO:21)
```

FIG. 21

```
  1  MGRGTITIHS KEDFACMRRA GMLAAKVLDF ITPHVVPGVT TNALNDLCHD FIISAGAIPA
 61  PLGYRGYPKS ICTSKNFVVC HGIPDDIALK NGDIVNIDVT VILDGWHGDT SRMYWGDNV
121  SIKAKRICEA SYKALMAAIG VIQPGKKLNS IGLAIEEEIR GYGYSIVRDY CGHGIGREFH
181  AAPNIVHYYD EEDDVTIQEG MFFTVEPMIN AGKYHTVLDK KDGWTVTTRD FSLSAQFEHT
241  LGVTETGVEI FTMSPKNWHC PPYL      (SEQ ID NO:22)
```

FIG. 22

```
   1 GAATTCCGGA ATTCCGGAAT TCCTATGGAT CGTGCAGTGA TGGAAGAGGG CAGCATGTTA
  61 GCTGCAGGTT CACTGCTCAC TAGGGGTAAG ATTGTAAAAT CTGGAGAGTT ATGGGCAGGT
 121 AGGCCTGCAA AATTTCTACG TATGATGACT GAAGAGGAGA TTTTATACCT ACAAAAATCT
 181 GCTGAAAATT ACATAGCGTT ATCGCGTGGA TACTTATAAC AAGTATTCA TCTATGGTTT
 241 GACATTAGTG TCTTTGGTG ATTACACTGC CTTTCAATCT GTGTTTTTTG TTTTAGTTCT
 301 GGTTTGTATT TATGGGTGAT GCTGTAGAAG TTAGGGCTGA GAATCTTGGT GGCGAATCCA
 361 TTCTAGAAGC TCCGATTCGG GTAATGAAAA AGTGGGAGA TACTGTATCT GCAGAAGATG
 421 TGCTCTTCAT TGTTGAAACA GACAAGACTT CTCTTGAAAT ATCAGCCCCT GTTGCTGGTG
 481 TTCTCACAGA GTTGAGAGTT GCAGATGAAG AAGTGATTAC CAAGGGGCAG GTCTTGGCTA
 541 TCATACGGCC ACAGGGTGAG GCTACTGCAG AGGGTGTTAA TAAGGAGCCA GAGAGCAAGG
 601 AGGAGGTGCC TGCTCAACCC GTTGTTGCAA AGCCAGTGAG CACTCAAAAA CCGCAGGAAA
 661 AGACAATTAT TGAAGGCAAA GGTCTAGTAA CTCCTACTGT AGAAGATTT GTTGCAGGAA
 721 TCAACACAAC TCCTACTTCT AGAGCTTTGG GTATGAGTGC TAAGAGTGAA CAAGACAAGA
 781 AGATAGTTGC TAGCCAGCCG TCTAAGGATC TGATGAGTTG CCATGGCGAC GTGGTGGGTG
 841 AAAGACGCGT GAAGATGAGC AAAATCCGCC AAGTTATAGC TGCTAGGCTT AAGGAGTCAC
 901 AAAATACCTC TGCTACACTC AGCACCTTTA ATGAAGTTGA TATGAGCAAA GTGATGGAGC
 961 TCAGAGCTAA GTACAAAGAT GCCCTTTGTA AGAGGTATGA TGTTAAGCTT GGGTTTATGT
1021 CCTTCTTTAT CAGAGCGGTT GTGCTAGTCC TTTCCGAAAT TCCTGTGCTG AATGCGGAGA
1081 TTTCAGGCGA TGATATAGTC TACAGGGACT ATTGTAACAT TGGAGTCGCG GTAGGTACCG
1141 ATAAGGGGTT AGTGGTGCCT GTTATCAGAA GAGCGGAAAC TATGTCACTT GCTGAAATGC
1201 AGCAAGCACT TGTTGACTTA AGTACAAAAG CAAGAAGTGG CAAGCTCTCT GTTTCTGATA
1261 TGTCTGGTGC AACCTTTACT ATTACCAATG GTGGTGTGTA TGGGTCGCGG TTGTCTACCC
1321 CTATAATCAA CCCTCCCTCAA TCTGGAATCT TGGGTATGCA TGCTATACAG CAGCGTCCTG
1381 TGGCAGTAGA TGGTAAGGTA GAGATAAGGC CTATGATGTA TTTGGCGCTA TCATATGATC
1441 ATAGAATAGT TGACGGGCAA CGTTTTTGT AAGAGTGAAG CAGTACATAG CAGTACATAG
1501 AAGATCCTAA CAGATTGGCT CTAGGAATTT AGGGGGTTTT TATGGGGCGG GGTACAATAA
```

FIG. 23A

```
1561  CCATCCACTC CAAAGAGGAT TTTGCCTGTA TGAGAAGGGC TGGGATGCTT GCAGCTAAGG
1621  TGCTTGATTT TATAACGCCG CATGTTGTTC CTGGTGTGAC TACTAATGCT CTGAATGATC
1681  TATGTCACGA TTTCATCATT TCTGCCGGGG CTATTCCAGC GCCTTTGGGC TATAGAGGGT
1741  ATCCTAAGTC TATTTGTACT TCGAAGAATT TTGTGGTTTG CCATGGCATT CCAGATGATA
1801  TTGCATTAAA AAACGGCGAT ATAGTTAACA TAGACGTTAC TGTGATCCTC GATGGTTGGC
1861  ACGGGGATAC TAGTAGGATG TATTGGGTTG GTGATAACGT CTCTATTAAG GCTAAGCGCA
1921  TTTGTGAGGC AAGTTATAAG GCATTGATGG CGGCGATTGG TGTAATACAG CCAGGTAAGA
1981  AGCTCAATAG CATAGGGTTA GCTATAGAGG AAGAAATCAG AGGTTATGGA TACTCCATTG
2041  TTAGAGATTA CTGCGGACAT GGGATAGGTC GCGAATTTCA TGCTGCTCCT AACATAGTTC
2101  ACTACTATGA CGAAGAGGAT GATGTTACGA TTCAGGAGGG AATGTTTTTC ACTGTTGAGC
2161  CAATGATCAA TGCTGGAAAT TATCATACTG TGCTAGATAA GAAAGACGGA TGGACAGTTA
2221  CAACGAGAGA CTTTTCCCTT TCAGCGCCAGT TTGAACATAC CTTGGGTGTA ACTGAAACTG
2281  GCGTTGAGAT TTTTACTATG TCGCCCAAAA ATTGGCATTG TCCGCCATAC CTTTAAGTAG
2341  GATATTTTTG TTATGTGTAA AGCGTGTGGC AGGGTAATGT TAGGTGCATG TTCTGTTGAC
2401  GATGTGTGCT GATAAGAAAT TGTACAATCA TACTGCGTTG GAAGTTAGGA ATATGTACTT
2461  ATGAGTGCTA ATAAGCTTGC TGTGTTATTA AGCGAAGCCG CTTCAGTTTT GAAAAGAGTA
2521  GGAATAGATA CACCGGGGTT AGACGCTCGA CTAATTGCGG GACATGTTTT GGGTTTAAGT
2581  GAGCATGAGG TGCTAATAAA TCCAGATTTA GTTGTTACTG CTGCTAAAAC AAAAGAATTT
2641  TTTGAAGTTA TTGCAAGACG TTTAGCCGGG GTACCAGTTT CGCATATTTT ACGCAGACGA
2701  GAATTC
      (SEQ ID NO:23)
```

FIG. 23B

```
              10              20
PCR prod  tg GAG y FY V GLDYSPAF sk I RDF sI      (SEQ ID NO:24)
AM MSP-2  ga GAG s FY I GLDYSPAF gs I KDF kV      (SEQ ID NO:25)

30              40              50
PCR prod  RE S N G a TK a VV PY l KD g k - s V k l e s
AM MSP-2  QE A G G i TR g VF PY k RD a a g r V d f k v 60              70
PCR prod  H k FDW a T PD PR I g FKD a ML v AM EGS
AM MSP-2  H a FDW s A PE PK I s FKD s ML t AL EGS 80              90             100
PCR prod  V GY g IGGARVE LE IGYERF k t KG i R
AM MSP-2  I GY s IGGARVE VE VGYERF v i KG g K 110             120
PCR prod  d S G s k ED e A d T VY LL a KELAY d v v t
AM MSP-2  k S N - - ED - T a S VF LL g KELAY h t a r 130             140             150
PCR prod  G Q t D a LAAAL a K t S g k D i v Q f a k A V
AM MSP-2  G Q v D f LATAL g K m T k s E a k K w g a A I 160             170
PCR prod  g - - - - - v S h p g I d KKVC d g G h A r G k
AM MSP-2  e s a t g t t S g d e L s KKVC g k G t T s G s 180
PCR prod  k - - S G d N g S
AM MSP-2  t a q C G t T d S
```

```
Sequence Range: 1 to 3435

10         20         30         40         50         60
             *          *          *          *          *          *
    TTTTTATATC TGGAGCTCTT GTACTGTGTT TACCACGGGA TTTATTATTG GGTAGGCTTG 70         80         90        100        110        120
             *          *          *          *          *          *
    ATATTCAGGC TCTATCAACG CAGCTATTCA TGGCATTATT ACAGATAAAT TTGGCATTTT 130        140        150        160        170        180
             *          *          *          *          *          *
    GGAGATAGGC GATCTAGGGT TCTATTATTA GGAATCTATT ATTAGATAT ATAGGGATAT 190        200        210        220        230        240
             *          *          *          *          *          *
    AAGGGAGAGT AACGGAGAGA CTAAGGCAGT ATATCCATAC TTAAAGGATG GAAAGAGTGT 250        260        270        280        290        300
             *          *          *          *          *          *
    AAAGCTAGAG TCACACAAGT TTGACTGGAA CACTCCTGAT CCTCGGATTG GGTTTAAGGA
```

FIG. 30A

```
          310                320                330                340
           *                  *                  *                  *
CAAC ATG CTT GTA GCT ATG GAA GGC AGT GTT GGT TAT GGT ATT GGT GGT
     Met Leu Val Ala Met Glu Gly Ser Val Gly Tyr Gly Ile Gly Gly>
      a   a   a   a   a   a   a   a   a   a   a   a   a   a   a     ORF 1

350                360                370                380                390
           *                  *                  *                  *                  *
GCC AGG GTT GAG CTT GAG ATT GGT TAC GAG CGC TTC AAG ACC AAG GGT
Ala Arg Val Glu Leu Glu Ile Gly Tyr Glu Arg Phe Lys Thr Lys Gly>
 a   a   a   a   a   a   a   a   a   a   a   a   a   a   a   a     ORF 1

400                410                420                430                440
           *                  *                  *                  *                  *
ATT AGA GAT AGT GGT AGT AAG GAT GAA GCA GAT ACA GTA TAT CTA
Ile Arg Asp Ser Gly Ser Lys Asp Glu Ala Asp Thr Val Tyr Leu>
 a   a   a   a   a   a   a   a   a   a   a   a   a   a   a     ORF 1

450                460                470                480                490
           *                  *                  *                  *                  *
CTA GCT AAG GAG TTA GCT TAT GAT GTT GTT ACT GGA CAG ACT GAT AAC
Leu Ala Lys Glu Leu Ala Tyr Asp Val Val Thr Gly Gln Thr Asp Asn>
 a   a   a   a   a   a   a   a   a   a   a   a   a   a   a   a
```

FIG. 30B

```
        500        510        520        530        540
         *          *          *          *          *
CTT GCC GCT GCT CTT GCC AAA ACC TCG GGG AAG GAC ATC GTT CAG TTT
Leu Ala Ala Ala Leu Ala Lys Thr Ser Gly Lys Asp Ile Val Gln Phe>
 a   a   a   a   a   a   a   a   a   a   a   a   a   a   a   a >
                                   ORF 1

550        560        570        580
         *          *          *          *
GCC AAT GCT GTG AAA ATT TCT TAC CCT AAA ATT GAT GAG CAG GTT TGT
Ala Asn Ala Val Lys Ile Ser Tyr Pro Lys Ile Asp Glu Gln Val Cys>
 a   a   a   a   a   a   a   a   a   a   a   a   a   a   a   a >
                                   ORF 1

590        600        610        620        630
 *          *          *          *          *
AAT AAA AAT CAT ACA GTG TTG AAT ACG GGG AAA GGG ACA ACC TTT AAT
Asn Lys Asn His Thr Val Leu Asn Thr Gly Lys Gly Thr Thr Phe Asn>
```

FIG. 30C

```
                              a   a   a   a   a   ORF 1  a   a   a   a   a   a   a   a   a   >
                                          *                       *                       *
     640         650         660         670         680
      *           *           *           *           *
CCA GAT CCC AAG ACA ACC GAA GAT AAT ACA GCG CAG TGC AGT GGG TTG
Pro Asp Pro Lys Thr Thr Glu Asp Asn Thr Ala Gln Cys Ser Gly Leu>
  a   a   a   a   a   a   ORF 1  a   a   a   a   a   a   a   a   a   >
              *                       *                       *
     690         700         710         720         730
      *           *           *           *           *
AAC ACG AAG GGA ACG AAT AAG TTT AGC GAT TTT GCT GAA GGT GTA GGT
Asn Thr Lys Gly Thr Asn Lys Phe Ser Asp Phe Ala Glu Gly Val Gly>
  a   a   a   a   a   a   ORF 1  a   a   a   a   a   a   a   a   a   >
              *                       *                       *
     740         750         760         770         780
      *           *           *           *           *
TTG AAA GAT AAT AAG AAT TGG CCT ACT GGT CAG GCT GGG AAG AGC AGT
Leu Lys Asp Asn Lys Asn Trp Pro Thr Gly Gln Ala Gly Lys Ser Ser>
  a   a   a   a   a   a   ORF 1  a   a   a   a   a   a   a   a   a   >
              *                       *                       *
     790         800         810         820
      *           *           *           *
GGT GGT CCT GTG GGT GCA TCT AAT AGT AAT GCC AAC GCT ATG GCT
Gly Gly Pro Val Gly Ala Ser Asn Ser Asn Ala Asn Ala Met Ala>
  a   a   a   a   a   a   a   a   a   a   a   a   a   a   a   >
```

FIG. 30D

```
                830       840       850       860       870
                 *         *         *         *         *
              AGA GAC CTA GTA GAT CTT AAT CGA GAC GAA AAA ACC ATA GTA GCA GGG
              Arg Asp Leu Val Asp Leu Asn Arg Asp Glu Lys Thr Ile Val Ala Gly>
                      ORF 1  a   a   a   a   a   a   a   a   a   a   a   >

880       890       900       910       920
                 *         *         *         *         *
              TTA CTA GCT AAA ACT ATT GAA GGT GGT GAG GTT GTT GAG ATT AGG GCG
              Leu Leu Ala Lys Thr Ile Glu Gly Gly Glu Val Val Glu Ile Arg Ala>
                  a   a   a   a   ORF 1  a   a   a   a   a   a   a   a   a   >

930       940       950       960       970
                 *         *         *         *         *
              GTT TCT TCT ACT TCT GTA ATG GTC AAT GCT TGT TAT GAT CTT CTT AGT
              Val Ser Ser Thr Ser Val Met Val Asn Ala Cys Tyr Asp Leu Leu Ser>
                  a   a   a   a   a   a   a   ORF 1  a   a   a   a   a   a   >

980       990      1000      1010      1020
                 *         *         *         *         *
              GAA GGT CTA GGC GTT GTT CCT TAC GCT TGT GTC GGT CTT GGA GGT AAC
              Glu Gly Leu Gly Val Val Pro Tyr Ala Cys Val Gly Leu Gly Gly Asn>
                  a   a   a   a   a   a   a   a   ORF 1  a   a   a   a   a   >

FIG. 30E
```

```
          1030        1040        1050        1060
           *           *           *           *
TTC GTG GGC GTT GTT GAT GGG CAT ATC ACT CCT AAG CTT GCT TAT AGA
Phe Val Gly Val Val Asp Gly His Ile Thr Pro Lys Leu Ala Tyr Arg>
 a   a   a   a   a   a   a   a   ORF 1  a   a   a   a   a   a   a   >

1070        1080        1090        1100        1110
  *           *           *           *           *
TTA AAG GCT GGG TTG AGT TAT CAG CTC TCT CCT GAA ATC TCC GCT TTT
Leu Lys Ala Gly Leu Ser Tyr Gln Leu Ser Pro Glu Ile Ser Ala Phe>
 *   a   a   a   a   a   a   a   a   ORF 1  a   a   a   a   a   a   >
```

FIG. 30F

```
1120        1130        1140        1150        1160
  *           *           *           *           *
GCT GGG GGA TTC TAT CAT CGC GTT GTG GGA GAT GGT GTC TAT GAT GAT
Ala Gly Gly Phe Tyr His Arg Val Val Gly Asp Gly Val Tyr Asp Asp>
 a   a   a   a   a   a   a   a   a   a   a   ORF 1  a   a   a   a   >

1170        1180        1190        1200        1210
  *           *           *           *           *
CTT CCA GCT CAA CGT CTT GTA GAT GAT ACT AGT CCG GCG GGT CGT ACT
Leu Pro Ala Gln Arg Leu Val Asp Asp Thr Ser Pro Ala Gly Arg Thr>
 a   a   a   a   a   a   a   a   a   a   ORF 1   a   a   a   a   a   >

1220        1230        1240        1250        1260
  *           *           *           *           *
AAG GAT ACT GCT ATT ACT AAC TTC TCC ATG GCT TAT GTC GGT GGG GAA
Lys Asp Thr Ala Ile Ala Asn Phe Ser Met Ala Tyr Val Gly Gly Glu>
 a   a   a   a   a   a   a   a   a   a   ORF 1   a   a   a   a   a   >

1270        1280        1290        1300        1310
  *           *           *           *           *
TTT GGT GTT AGG TTT GCT TTT TAAGGTGG TTTGTTGAA GCGGGGTAAG
Phe Gly Val Arg Phe Ala Phe>
 a   *  ORF 1                                         (SEQ ID NO:29)

1320        1330        1340        1350        1360
  *           *           *           *           *
TCAAACTTAC CCCGCTTCTA TTAGGGAGTT AGTAT ATG AGA AGT AAG CTA
                                       Met Arg Ser Arg Ser Lys Leu>
                                        b   b  ORF 2   b   b   >
```

FIG. 30G

```
        1370      1380      1390      1400      1410
          *         *         *         *         *
      TTT TTA GGA AGC GTA ATG ATG TCG TTG GCT ATA GTC ATG GCT GGG AAT
      Phe Leu Gly Ser Val Met Met Ser Leu Ala Ile Val Met Ala Gly Asn>
       b   b   b   b   b  ORF 2  b   b   b   b   b   b   b   b   b  >

1420      1430      1440      1450      1460
          *         *         *         *         *
      GAT GTC AGG GCT CAT GAT GAC GTT AGC GCT TTG GAT ACT GGT GGT GCG
      Asp Val Arg Ala His Asp Asp Val Ser Ala Leu Asp Thr Gly Gly Ala>
       b   b   b   b   b   b   b  ORF 2  b   b   b   b   b   b   b  >

1470      1480      1490      1500      1510
          *         *         *         *         *
      GGA TAT TTC TAT GTT GGT TTG GAT TAC AGT CCA GCG TTT AGC AAG ATA
      Gly Tyr Phe Tyr Val Gly Leu Asp Tyr Ser Pro Ala Phe Ser Lys Ile>
       b   b   b   b   b   b   b   b  ORF 2  b   b   b   b   b   b  >

1520      1530      1540      1550      1560
          *         *         *         *         *
      AGA GAT TTT AGT ATA AGG GAG AGT AAC GGA GAG ACT AAG GCA GTA TAT
      Arg Asp Phe Ser Ile Arg Glu Ser Asn Gly Ser Glu Thr Lys Ala Val Tyr>
       b   b   b   b   b   b   b   b   b  ORF 2  b   b   b   b   b   b >

1560      1570      1580      1590      1600
          *         *         *         *         *
      CCA TAC TTA AAG GAT GGA AAG AGT GTA AAG CTA GAG TCA CAC AAG TTT
      Pro Tyr Leu Lys Asp Gly Lys Ser Val Lys Leu Glu Ser His Lys Phe>
       b   b   b   b   b   b   b   b   b  ORF 2  b   b   b   b   b   b >
```

FIG. 30H

```
1610        1620        1630        1640        1650
  *           *           *           *           *
GAC TGG AAC ACT CCT GAT CCT CGG ATT GGG TTT AAG GAC AAC ATG CTT
Asp Trp Asn Thr Pro Asp Pro Arg Ile Gly Phe Lys Asp Asn Met Leu>
 b   b   b   b   b   b   b  ORF 2  b   b   b   b   b   b   b   b  >

1660        1670        1680        1690        1700
     *           *           *           *           *
GTA GCT ATG GAA GGT AGT GTT GGT TAT GGT ATT GGT GGT GCC AGG GTT
Val Ala Met Glu Gly Ser Val Gly Tyr Gly Ile Gly Gly Ala Arg Val>
 b   b   b   b   b   b   b  ORF 2  b   b   b   b   b   b   b   b  >

1710        1720        1730        1740        1750
     *           *           *           *           *
GAG CTT GAG ATT GGT TAC GAG CGC TTC AAG ACC AAG GGT ATT AGA GAT
Glu Leu Glu Ile Gly Tyr Glu Arg Phe Lys Thr Lys Gly Ile Arg Asp>
 b   b   b   b   b   b   b  ORF 2  b   b   b   b   b   b   b   b  >

1760        1770        1780        1790        1800
     *           *           *           *           *
AGT GGT AGT AAG GAA GAT GAA GCT GAT ACA GTA TAT CTA CTA GCT AAG
Ser Gly Ser Lys Glu Asp Glu Ala Asp Thr Val Tyr Leu Leu Ala Lys>
 b   b   b   b   b   b   b  ORF 2  b   b   b   b   b   b   b   b  >

1800        1810        1820        1830        1840
  *           *           *           *           *
GAG TTA GCT TAT GAT GTT GTT ACT GGG CAG ACT GAT AAC CTT GCC GCT
Glu Leu Ala Tyr Asp Val Val Thr Gly Gln Thr Asp Asn Leu Ala Ala>
 b   b   b   b   b   b   b  ORF 2  b   b   b   b   b   b   b   b  >

FIG. 30I
```

```
      1850        1860        1870        1880        1890
       *           *           *           *           *
GCT CTG GCC AAA ACC TCC GGT AAA GAC TTT GTC CAG TTT GCT AAG GCG
Ala Leu Ala Lys Thr Ser Gly Lys Asp Phe Val Gln Phe Ala Lys Ala>
 b   b   b   b   b   b   b   b  ORF 2  b   b   b   b   b   b   b 1900        1910        1920        1930        1940
       *           *           *           *           *
GTT GGG GTT TCT CAT CCT AGT ATT GAT GGG AAG GTT TGT AAG ACG AAG
Val Gly Val Ser His Pro Ser Ile Asp Gly Lys Val Cys Lys Thr Lys>
 b   b   b   b   b   b   b   b  ORF 2  b   b   b   b   b   b   b
                        <Gly Leu Ile Ser Pro Phe Thr Gln Leu Val Phe
                         <d   d   d   d ORF 4  d   d   d   d   d   d 1950        1960        1970        1980        1990
       *           *           *           *           *
GCG GAT AGC TCG AAG AAA TTT CCG TTA TAT AGT GAC GAA ACG CAC ACG
Ala Asp Ser Ser Lys Lys Phe Pro Leu Tyr Ser Asp Glu Thr His Thr>
 b   b   b   b   b   b   b   b  ORF 2  b   b   b   b   b   b   b
<Ala Ser Leu Glu Phe Phe Asn Gly Asn Tyr Leu Ser Ser Val Cys Val
 <d   d   d   d   d   d   d   d ORF 4  d   d   d   d   d   d   d 2000        2010        2020        2030
       *           *           *           *
AAG GGG GCA AGT GAG GGG AGA ACG TCT TTG TGC GGT GAC AAT GGT AGT
Lys Gly Ala Ser Glu Gly Arg Thr Ser Leu Cys Gly Asp Asn Gly Ser>
 b   b   b   b   b   b   b   b  ORF 2  b   b   b   b   b   b   b
<Phe Pro Ala Leu Ser Pro Leu Val Asp Lys His Pro Ser Leu Pro Leu
 <d   d   d   d   d   d   d   d ORF 4  d   d   d   d   d   d   d
```

FIG. 30J

```
       2040          2050          2060          2070          2080
         *             *             *             *             *
       TCT ACG ATA ACA AAC AGT GGT GCG AAT GTA AGT GAA ACT GGG CAG GTT
       Ser Thr Ile Thr Asn Ser Gly Ala Asn Val Ser Glu Thr Gly Gln Val> b   b   b   b   b   b       ORF 2   b   b   b   b   b   b    >
<Glu Val Ile Val Phe Leu Pro Ala Phe Thr Leu Ser Val Pro Cys Thr
 v   d   d   d   d   d   d       ORF 4   d   d   d   d   d   d 2090          2100          2110          2120          2130
         *             *             *             *             *
       TTT AGG GAT TTT ATC AGG GCA ACG CTG AAA GAG GAT GGT AGT AAA AAC
       Phe Arg Asp Phe Ile Arg Ala Thr Leu Lys Glu Asp Gly Ser Lys Asn> b   b   b   b   b   b       ORF 2   b   b   b   b   b   b    >
<Lys Leu Ser Lys Ile Leu Ala Val Ser Phe Ser Ser Pro Leu Leu Phe
 v   d   d   d   d   d   d       ORF 4   d   d   d   d   d   d 2140          2150          2160          2170          2180
         *             *             *             *             *
       TGG CCA ACT TCA AGC GGC ACG GGA ACT CCA AAA CCT GTC ACG AAC GAC
       Trp Pro Thr Ser Ser Gly Thr Gly Thr Pro Lys Pro Val Thr Asn Asp> b   b   b   b   b   b       ORF 2   b   b   b   b   b   b    >
<Gln Gly Val Glu Leu Pro Val Gly Phe Gly Thr Val Phe Ser
 v   d   d   d   d   d   d       ORF 4   d   d   d   d   d   d 2190          2200          2210          2220          2230
         *             *             *             *             *
       AAC GCC AAA GCC GTA GCT AAA GAC CTA GTA CAG GAG CTA ACC CCT GAA
       Asn Ala Lys Ala Val Ala Lys Asp Leu Val Gln Glu Leu Thr Pro Glu> b   b   b   b   b   b       ORF 2   b   b   b   b   b   b    >
<Leu Ala Leu Ala Thr Ala Leu Ser Arg Thr Cys Ser Ser Val Gly Ser
 v   d   d   d   d   d   d       ORF 4   d   d   d   d   d   d
```

FIG. 30K

```
              2240        2250        2260        2270
                *           *           *           *
GAA AAA ACC ATA GTA GCA GGG TTA CTA GCT AAA ACT ATT GAA GGT GGT
Glu Lys Thr Ile Val Ala Gly Leu Leu Ala Lys Thr Ile Glu Gly Gly>
 b   b   b   b   b   b   b   b   b   b   b   b   b   b   b   b    ORF 2
<Ser Phe Val Met
 d   d   d   d 2280        2290        2300        2310        2320
      *           *           *           *           *
GAG GTT ATT GAA ATC AGG GCG GTT TCT TCT ACT TCT GTG ATG GTC AAT
Glu Val Ile Glu Ile Arg Ala Val Ser Ser Thr Ser Val Met Val Asn>
 b   b   b   b   b   b   b   b   b   b   b   b   b   b   b   b    ORF 2

2330        2340        2350        2360        2370
    *           *           *           *           *
GCT TGT TAT GAT CTT CTT AGT GAA GGT TTA GGT GTT GTC CCT TAT GCT
Ala Cys Tyr Asp Leu Leu Ser Glu Gly Leu Gly Val Val Pro Tyr Ala>
 b   b   b   b   b   b   b   b   b   b   b   b   b   b   b   b    ORF 2

2380        2390        2400        2410        2420
      *           *           *           *           *
TGT GTT GGT CTC GGT GGT AAC TTC GTG GGC GTG GTT GAT GGA ATT CAT
Cys Val Gly Leu Gly Gly Asn Phe Val Gly Val Val Asp Gly Ile His>
 b   b   b   b   b   b   b   b   b   b   b   b   b   b   b   b    ORF 2

2430        2440        2450        2460        2470
    *           *           *           *           *
TAC ACA AAC CAT CTT TAA CTCTGAATAC CCTAGTTAAG GTAAGTGAAG
Tyr Thr Asn His Leu>                                             (SEQ ID NO:30)
 b   ORF 2            >

FIG. 30L
```

```
           2480       2490       2500       2510       2520       2530
             *          *          *          *          *          *
      TAACTAGGCA AATTAGTGCT GCACCACTCG TGAAACAAAC TACGATCAGC GATTCACCAT 2540       2550       2560       2570       2580       2590
             *          *          *          *          *          *
      ACTTAGTAAG TCCGTACAGT GGCTTTACGC TCTTACCCAT CATGAAAAAT ACTTGCTATC 2600       2610       2620       2630       2640       2650
             *          *          *          *          *          *
      TAGGAATCTC CTCTAAAACT TTACAGAGGT TATCTGTACT TCGAGAGGAA GCTAATCTGT 2660       2670       2680       2690       2700       2710
             *          *          *          *          *          *
      GGCTCATGAG GATGGTATTT AGCGTATCAC AGGTTCCAGC TGTCTTACAG TCTCTGGAGA 2720       2730       2740       2750       2760       2770
             *          *          *          *          *          *
      TGTTATAAGG GTGCACATAT AAAACTATGC AATATTCGC TGCAATACGA TTCCGATTCG 2780       2790       2800       2810       2820       2830
             *          *          *          *          *          *
      AAAACACTGA AAAGTATTCC CATTATCTAT GAATCTCTGT GTAGATATAA ATAAGGGTAT 2840       2850       2860       2870       2880       2890
             *          *          *          *          *          *
      ACGCAGTAAC TCTTACTTGT TAAAACAAG ACCAATGGTA TAAGGAAAAA GCCTCAGTGT 2900       2910       2920       2930       2940       2950
             *          *          *          *          *          *
      TGTTCCTCAT GCTTGCAGCT TACCCGATGC ACTCTTATTT AATAAGGTTG AATGTTAATC 2960       2970       2980       2990       3000       3010
             *          *          *          *          *          *
      AGTGTTTCTG GGAAGGGAAT ATCTTATTGC AAAACCTCA GCAGCTGCTT AGATATTGAA
```

FIG. 30M

```
                3020       3030       3040       3050       3060       3070
                  *          *          *          *          *          *
            ACAAATGCGA TCATGCCGTC AGCACAATTA TGACATCTCT TAAGGCTCTG TAGTGCGCTT 3080       3090       3100       3110       3120       3130
                  *          *          *          *          *          *
            ATTTAGTCTA ACAGTGGTA AAGCTTGCC AGTTCTTTAC CACATGTTCA CCATCAGTTA 3140       3150       3160       3170
                       *          *          *          *
            ATT GAA AGC AAA TCT TGC TCC TAT GTT GAA GCC GTA ACT AGC TAT ATT
           <Asn Phe Ala Phe Arg Ala Gly Ile Asn Phe Gly Tyr Ser Ala Ile Asn
            v    c   c   c   c   c   c   c   c   c ORF 3 c   c   c   c   c 3180       3190       3200       3210       3220
              *          *          *          *          *
            TGC CTT TAC CTT GGC TGC AGC ACC TGC TAT GTT TAC ACG GTT ACT
           <Ala Lys Val Lys Ala Ala Ala Gly Gly Ala Ile Asn Val Arg Asn Ser
            v    c   c   c   c   c   c   c   c   c ORF 3 c   c   c   c   c 3230       3240       3250       3260       3270
              *          *          *          *          *
            AGC GGG AAT ACC TGC ATA CTG TTC ATC GAA AAT TCC GTG GTA AAA ACC
           <Ala Pro Ile Gly Ala Tyr Gln Glu Asp Phe Ile Gly His Tyr Phe Gly
            v    c   c   c   c   c   c   c   c   c ORF 3 c   c   c   c   c
```

FIG. 30N

```
          3280                3290                3300                3310                3320
            *                   *                   *                   *                   *
         TCC AGC TAT TAA AGA TAT TTC AGG AGT AAG CTT GTA ACT TAC GCC TAC
        <Gly Ala Ile Leu Ser Ile Glu Pro Thr Leu Lys Tyr Ser Val Gly Val
        <   c   c   c   c   c   c   ORF 3   c   c   c   c   c   c   c   c 3330                3340                3350                3360                3370
            *                   *                   *                   *                   *
         CTT TCC TCT ATA AGC CAA CTT ACT TGT AAC GTG ATC GGC GAT ATT AAT
        <Lys Gly Arg Tyr Ala Leu Lys Ser Thr Val His Asp Ala Ile Asn Ile
        <   c   c   c   c   c   c   ORF 3   c   c   c   c   c   c   c   c 3380                3390                3400                3410
                               *                   *                   *                   *
                          AAA GCT CGC CCC TAA CCC AGC ACA CAT GTA AGG AGG GAA TTC GAT ATC
                         <Phe Ser Ala Gly Leu Gly Ala Cys Met Tyr Pro Pro Phe Glu Ile Asp
                         <   c   c   c   c   c   ORF 3   c   c   c   c   c   c   c   c   c 3420                3430
            *                   *
         AAG CTT ATC GAT ACC GT            (SEQ ID NO:28)
        <Leu Lys Asp Ile Gly
        <   c   ORF 3   c
```

FIG. 30O

```
                    10         20         30         40         50         60       (SEQ ID
                                                                                      NO:27)
GE MSP-2A    mr kgKIiILGisVMMSMAivMAgndvrahddvSaleTGG..........AGvFYvGLDYSP
GE MSP-2B                                                                    (SEQ ID
                                                                              NO:30)
GE MSP-2C    mrsrsKLfLGsVMMSLAivMAgndvrahddvSaldTGG..........AGyFYVGLDYSP
AM msp2      msavsnrKLpLGgVLMAlAaaVApihsllaapaAgaAGGeglfsgagAGsFYiGLDYSP      (SEQ ID
                                                                              NO:31)

70         80         90        100        110        120
GE MSP-2A    AFskIRDFsIRESNGeTKaVYPYlKDgk.sVklesHKFDWnTPDPRIgFKDnMLVAMEGS
GE MSP-2B                                                          MLVAMEGS  (SEQ ID
                                                                              NO:29)
GE MSP-2C    AFskIRDFsIRESNGeTKaVYPYlKDgk.sVklesHKFDWnTPDPRIsFKDnMLVAMEGS
AM msp2      AFgsIKDFKVQEAGGtIRgVFPYkRDaagrVdfkvHnFDWsAPEPKIsFKDsMLtALEGS 130        140        150        160        170        180
GE MSP-2A    VGYGIGGARVELEIGYERFKTKGIRDSGSKEDEADTVYLLAKELAYDVVTGQTDNLAAAL
GE MSP-2B    VGYGIGGARVELEIGYERFKTKGIRDSGSKEDEADTVYLLAKELAYDVVTGQTDNLAAAL
GE MSP-2C    VGYGIGGARVEIEIGYERFKTKGIRDSGSKEDEADTVYLLAKELAYDVVTGQTDNLAAAL
AM msp2      IGYsIGGARVEVEvGYERFviKGgKKS..nED.TaSVFLIgKELAYhtarGgVDFLAfAL
```

FIG. 31A

```
              190          200          210          220          230         240
GE MSP-2A  AKTSGKD VQFA KAVIsVSh PgIDkKVC dgghargkksgdngsIAdyTdggaSqtnk TAQC
GE MSP-2B  AKTSGKD VQFA NAVklSyPkIDeQVCnknhtvInt...gkgTtfNpdpkTTedn TAQC
GE MSP-2C  AKTSGKD FVQFA kAVgV Sh PsIDgKVC ktkadsskk... fplySdeThtkgASeGr TslC
AM msp2    gKmTksEakKwgnA fesAt

PEPTIDE #23

\*-E-L-\*-\*-V-V-\*-G-E-N-T-L  (SEQ ID NO:36)

PEPTIDE #24

\*-\*-P-F-H-M-Y-P-G-L-Y-S-E-N-L-F-R-S-T-R-D-L-R-G-V-S-G-V (SEQ ID NO:34)

PRIMER 5F: CCNTTYCAYATGTAYCCNGG (SEQ ID NO:32)

PEPTIDE #25

F-R-L-S-L-A-G-E-Y-A-R-P-K (SEQ ID NO:35)

PEPTIDE #26

\*-\*-E-D-T-V-R-D-G-L-A-G-F-D-S-L  (SEQ ID NO:37)

PRIMER 6R: GGNCKNGCRTAYTCNCCNGC (SEQ ID NO:33)

FIG. 34

```
   1  GAATTCCTAGCAACAAGGGTGGATATTTCACGCTTGCTAGCTGAGTGATTAGGACTGA
  61  GGGTGAGCTATGAGATGTATAGGGGGAGAGTATGCCGCTTGCCGTCGTGCCTTTTACTCAGCTTC
 121  ATAAGATAGCGGCGAGCTACAGCTTGCTACGGGTTCGTAGAAAAGCGTTATGTCGCT
 181  ATAACACTCGTGATGTATATCATCGTGATCTCGGTTATCAGTCGATCATGATGTGCTATGG
 241  TTAAGCCTTTGAAGTATGACTTTGGCTTGATGGTCTTTAGGTGTGAAGCTGGTCTTCTAAG
 301  AAGAGTGTGGGTGTTGTGGATTTTGAAGTTTTGTATGAGAGTTCTCGTAGTTGT
                                        M  R  G  S  L  V  V  V
 421  GAGTATGGCGATGCTTCTCCTGGGGTCCTCGTGTGCTAGTGCTGCATCTTCTGGAGG
         S  M  A  M  L  L  G  S  S  G  G  V  V  A  A  S  S  G  G
 481  GGGGTTTGAAGGAGAGCCGTCGGTAACGGGTAAGGTGTATCTTATGCCTGGTTGTT
         G  F  E  G  E  R  A  S  V  T  G  K  V  L  S  Y  A  W  L  L
 541  GAGTCGATCGGGCTGTAAAAGGGCAAGTAACAGTGAAGCTCAGAAGCTCGCGCTGAAAT
         S  D  R  A  V  K  G  Q  N  S  E  G  Q  K  L  A  L  E  M
 601  GTATGGCGCAAAGTTGGGCTATAAGGGTTATCGATTCTTGATTCCAGGAGTTGGAGATGTCTTTC
         Y  G  A  K  L  G  Y  K  G  Y  P  G  V  G  D  V  F  S
 661  TTCGCCGTTGGAGCATGTCCTTGATTCTTGGGAGCTAGCTATGATGCGATGTATCTCT
         S  P  L  E  H  G  L  D  S  W  G  A  S  Y  D  A  M  L  S  L
 721  TGGATTGCGCTACGGCTCGTGATGCTAGTACCAATATGGGCAAATTTTCCCTTAT
         G  L  R  T  G  R  D  V  L  G  T  Q  Y  G  A  N  F  S  L  M
 781  GGTTCCTCGCGGGTTCTCGGTGGATCTATGGTGTTCATGGTGCCGCTGGTATAGAGAGCAG
         V  P  A  G  S  G  G  S  M  V  F  H  G  A  P  G  I  E  S  R
 841  GGTTTTGCTGATACTTCCTTGGGAATTCTGTGGTTACCAGGAAGGTGTCGAGTC
         V  F  A  D  T  S  L  G  N  F  S  V  G  Y  Q  E  G  V  E  S
 901  AAAAATGAAGGTGGATGTCTTCCGTGGCTTATCAGTGAAATGGAAGCGCTTGGGGTCG
         K  M  K  V  D  V  F  G  G  L  S  G  E  N  G  S  A  W  G  R
 961  GTACTTGCGTGGCTTTTAAAGTATGCGAAGGGTGTACCTTTTCACATGTATCCAGGGCT
         Y  L  R  G  F  L  K  Y  A  K  G  V  P  F  H  M  Y  P  G  L
1021  TTACAGTGAGAATTTATTCCGGTCTACAAGAGACTTACGGGGTGTTAGTGGTGTTTCTGC
         Y  S  E  N  L  F  R  S  T  R  D  L  R  G  V  S  G  V  S  A
```

FIG. 36A

```
1081 GAAGACAAAGGATGTCTTAAATTCTATGCCGCTGAGGTTTTCTTTTGAGTCTGCTAGGTT
       K  T  K  D  V  L  N  S  M  P  L  R  F  S  F  E  S  A  R  L
1141 GGGTGGCTTGTCTGTTGTGGTTTAGTTACTCTCCAACGGGATATCGGGATGATATGTACAA
       G  G  L  S  V  G  F  S  Y  S  P  T  G  Y  R  D  D  M  Y  K
1201 GGGTGGAGAGTTTACTGTACGGGATGGGGGTTAAGTTTGGCAAAATGATTGCCTTGGTGTCCTCCTCGTTT
       G  G  E  F  T  V  R  D  G  I  A  G  F  D  S  L  G  T  V  N
1261 TTTATTCGCGAAGACGGGGGTTAAGTTTGGCAAAATGATTGCCGTGGTGCCTCCTCGTTT
       L  F  A  K  T  G  V  K  F  G  K  M  I  A  V  V  P  P  R  F
1321 TGATTCTGGTCCGGTATATAAAACATAGTAAGCGGTCTGCGAATTACGAGTACGAGTT
       D  S  G  P  V  Y  K  N  I  V  S  G  A  A  N  Y  E  Y  E  L
1381 AGCCGATATATGCTAAGTTGCTTAGGTTTATCGCTTGCTGGTGAGTATGCAAGACCGAAGAAGGC
       A  D  I  A  K  E  R  L  S  L  A  G  E  Y  A  R  P  K  K  A
1441 TAGGGATATAGTGCCAGAGTGCCTTAGAAGAAGAAATTTATGTAGCTGATTACAATGA
       R  D  I  V  P  E  G  R  R  K  E  E  I  Y  V  A  D  Y  N  D
1501 TTTGTCCGGTTTTCCAGTGGCTTAGAATAGACTTGGGTAGGTTGCCGGTTTGCTGTTGG
       L  S  A  F  S  S  G  L  E  O  D  L  G  R  L  R  F  A  V  G
1561 CGGTGGAGATACCTTGGGAAGTCTGTAGTCCTAAAATGTACATATTAAGGATGTAAGACA
       G  G  Y  L  G  K  S  G  S  P  K  M  Y  I  L  K  D  V  R  H
1621 TAAGGTACCTTATGTGAAAAGAAGGGTTTGCCGTCCTTATTATGTGACTTCAGCGGTTTC
       K  V  P  Y  V  K  K  K  G  L  P  S  H  Y  V  T  S  A  V  S
1681 CTATACGATTGGTTCTTCTCTGCTACAGTTGCTTACTTTATGAGTAGGTTAACGCACAT
       Y  T  I  G  S  F  S  A  T  V  A  Y  F  M  S  R  L  T  H  I
1741 TCCGCCTGCTACGGTATCTCATAAGATCCCAGGAAGTATGGATTCCGTTGTGGA
       P  P  A  T  V  S  H  K  I  P  G  K  Y  E  L  D  S  V  V  D
1801 TGGGGAGAATACGTTGAAGGATTGGTTGTTGGAGTCGGTTATAACCTTTTTAGTAAGG
       G  E  N  L  L  K  D  L  V  V  G  V  G  Y  N  L  F  S  K  G
```

FIG. 36B

```
1861  AAGTACGAGCTTAGAAGTATTTCTAAATTGTCACATGTTCTCTGTGCAACATAAATTCAA
         S  T  S  L  E  V  F  L  N  C  H  M  F  S  V  Q  H  K  F  N
1921  CATCCATGAGTACAAATCTACTGAGAGTAGTGGGTTTGTATTGAAAGAAGGTGGAGAGCG
         I  H  E  Y  K  S  T  E  S  S  G  F  V  L  K  E  G  G  E  R
1981  TGCAAATACTAATAATGGGCCTGTGGCCGTTATTAGGAATGAAGTTTGCGTTTAATAACA
         A  N  T  N  N  G  A  V  A  L  L  G  M  K  F  A  F      (SEQ ID NO:39)
2041  AGGGGTTGTTGCAAGAATACTCTTGTGGTTTATTTAGCCAAGTCTTCTTATTGGGGCGTG
2101  TACTGAGGTACGGCGCCCCCTTTTTTGTGGAGAGTCTAAGGTTTGTTATGTTGTGTAGA (SEQ ID NO:38)
```

FIG. 36C

CHARACTERIZATION OF GRANULOCYTIC EHRLICHIA AND METHODS OF USE

RELATED APPLICATIONS

This Application claims the benefit under 35 U.S.C. §120 of U.S. application Ser. No. 13/346,088, entitled "CHARACTERIZATION OF GRANULOCYTIC EHRLICHIA AND METHODS OF USE" filed on Jan. 9, 2012, which is herein incorporated by reference in its entirety. application Ser. No. 13/346,088 claims the benefit under 35 U.S.C. §120 of U.S. application Ser. No. 12/859,236, now U.S. Pat. No. 8,093,008, entitled "CHARACTERIZATION OF GRANULOCYTIC EHRLICHIA AND METHODS OF USE" filed on Aug. 18, 2010, which is herein incorporated by reference in its entirety. application Ser. No. 12/859,236 claims the benefit under 35 U.S.C. §120 of U.S. application Ser. No. 09/792,957, entitled "CHARACTERIZATION OF GRANULOCYTIC EHRLICHIA AND METHODS OF USE" filed on Feb. 26, 2001, now U.S. Pat. No. 7,863,434, which is herein incorporated by reference in its entirety. application Ser. No. 09/792,957 claims the benefit under 35 U.S.C. §120 of U.S. application Ser. No. 09/066,046, entitled "CHARACTERIZATION OF GRANULOCYTIC EHRLICHIA AND METHODS OF USE" filed on Apr. 24, 1998, which is herein incorporated by reference in its entirety. application Ser. No. 09/066,046 claims priority under 35 U.S.C. §119(e) to U.S. Provisional Application Ser. No. 60/044,933, entitled "GRANULOCYTIC EHRLICHIA NUCLEIC ACIDS, PROTEINS, AND METHODS OF USE" filed on Apr. 25, 1997, which is herein incorporated by reference in its entirety.

BACKGROUND OF THE INVENTION

1. Field of the Invention

The present invention relates, in general, to granulocytic Ehrlichia (GE) proteins. In particular, the present invention relates to nucleic acid molecules coding for GE S2, S7, S22, S23, C6.1, C6.2, S11, E8, E46#1, and E46#2 proteins; purified GE S2, S7, S22, S23, C6.1, C6.2, S11, E8, E46#1, and E46#2 proteins and polypeptides; recombinant nucleic acid molecules; cells containing the recombinant nucleic acid molecules; antibodies having binding affinity specifically to GE S2, S7, S22, S23, C6.1, C6.2, S11, E8, E46#1, and E46#2 proteins and polypeptides; hybridomas containing the antibodies; nucleic acid probes for the detection of nucleic acids encoding GE S2, S7, S22, S23, C6.1, C6.2, S11, E8, E46#1, and E46#2 proteins; a method of detecting nucleic acids encoding GE S2, S7, S22, S23, C6.1, C6.2, S11, E8, E46#1, and E46#2 proteins or polypeptides in a sample; kits containing nucleic acid probes or antibodies; bioassays using the nucleic acid sequence, protein or antibodies of this invention to diagnose, assess, or prognose a mammal afflicted with ehrlichiosis; therapeutic uses, specifically vaccines comprising GE S2, S7, S22, S23, C6.1, C6.2, S11, E8, E46#1, and E46#2 proteins or polypeptides; and methods of preventing ehrlichiosis in an animal.

2. Related Art

Granulocytic ehrlichiosis is an acute, potentially fatal tick-borne infection. The causative agent, granulocytic Ehrlichia (GE), has been identified by the polymerase chain reaction (PCR) using universal primers for eubacterial 16S ribosomal RNA (rRNA) to amplify the DNA of infected patients' blood (Chen et al., J. Clin. Micro. 32:589-595 (1994)). Comparison of the 16S rRNA gene sequence of GE to other known 16S rDNA sequences revealed a nearly identical match to the 16S genes of Ehrlichia phagocytophila and Ehrlichia equi (Chen et al., 1994). Two other groups of Ehrlichia species have also been categorized according to their 16S rRNA gene sequences, the Ehrlichia canis and Ehrlichia sennetsu groups. The E. canis and E. sennetsu species predominantly infect mononuclear phagocytes (Dumler et al., N. Eng. J. Med. 325:1109-1110 (1991)), whereas members of the E. phagocytophila group including GE are tropic for granulocytes (Ristic et al., in Bergey's Manual of Systemic Bacteriology, Krieg et al., eds., (1984), pp. 704-709). The near identity of the 16S rRNA gene sequences and the sharing of significant antigenicity by IFA and immunoblot (Dumler et al., J. Clin. Micro. 33:1098-1103 (1995)) indicate that E. phagocytophila, E. equi, and GE are closely related.

Full classification of the E. phagocytophila species including antigenic relationships among the individual isolates has been impeded by the inability to cultivate these organisms in cell culture. It has been shown that GE can be successfully cultivated in HL60 cells, a human promyelocytic leukemia cell line (Coughlin et al., PCT Application No. PCT/US96/10117; Goodman et al., N. Eng. J. Med. 334:209-215 (1996)). Walker et al., PCT Application No. PCT/US97/09147 teaches an isolated gene encoding a 120 kDa immunodominant antigen of E. chaffeensis that stimulates production of specific antibodies in infected humans.

The present invention describes GE specific genes encoding ten proteins (S2, S7, S22, S23, C6.1, C6.2, S11, E8, E46#1, and E46#2) which can be used as diagnostic reagents and vaccines.

SUMMARY OF INVENTION

The invention provides isolated nucleic acid molecules coding for polypeptides comprising amino acid sequences corresponding to GE S2, S7, S22, S23, C6.1, C6.2, S11, E8, E46#1, and E46#2 proteins.

The invention further provides purified polypeptides comprising amino acid sequences corresponding to GE S2, S7, S22, S23, C6.1, C6.2, S11, E8, E46#1, and E46#2 proteins.

The invention also provides nucleic acid probes for the specific detection of the presence of GE S2, S7, S22, S23, C6.1, C6.2, S11, E8, E46#1, and E46#2 proteins or polypeptides in a sample.

The invention further provides a method of detecting nucleic acid encoding GE S2, S7, S22, S23, C6.1, C6.2, S11, E8, E46#1, or E46#2 protein in a sample.

The invention also provides a kit for detecting the presence of nucleic acid encoding GE S2, S7, S22, S23, C6.1, C6.2, S11, E8, E46#1, or E46#2 protein in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides a recombinant nucleic acid molecule comprising a sequence complimentary to an RNA sequence encoding an amino acid sequence corresponding to the above-described polypeptide.

The invention also provides a cell that contains the above-described recombinant nucleic acid molecule.

The invention further provides a non-human organism that contains the above-described recombinant nucleic acid molecule.

The invention also provides an antibody having binding affinity specifically to a GE S2, S7, S22, S23, C6.1, C6.2, S11, E8, E46#1, or E46#2 protein or polypeptide.

The invention further provides a method of detecting GE S2, S7, S22, S23, C6.1, C6.2, S11, E8, E46#1, or E46#2 protein or polypeptide in a sample.

The invention also provides a method of measuring the amount of GE S2, S7, S22, S23, C6.1, C6.2, S11, E8, E46#1, or E46#2 protein or polypeptide in a sample.

The invention further provides a method of detecting antibodies having binding affinity specifically to a GE S2, S7, S22, S23, C6.1, C6.2, S11, E8, E46#1, or E46#2 protein or polypeptide.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for ehrlichiosis. More specifically, the invention further provides a method for identifying granulocytic Ehrlichia in an animal comprising analyzing tissue or body fluid from the animal for a S2, S7, S22, S23, C6.1, C6.2, S11, E8, E46#1, or E46#2 nucleic acid, protein, polysaccharide, or antibody.

The invention also provides methods for therapeutic uses involving all or part of the GE S2, S7, S22, S23, C6.1, C6.2, S11, E46#1, or E46#2 nucleic acid or protein. More specifically, the invention further provides a vaccine comprising a GE S2, S7, S22, S23, C6.1, C6.2, S11, E46#1, or E46#2 protein or nucleic acid together with a pharmaceutically acceptable diluent, carrier, or excipient, wherein the protein or nucleic acid is present in an amount effective to elicit a beneficial immune response in an animal to the protein.

The invention also provides a method of preventing or inhibiting ehrlichiosis in an animal comprising administering to the animal the above-described vaccine.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA.

Recombinant DNA. Any DNA molecule formed by joining DNA segments from different sources and produced using recombinant DNA technology (i.e., molecular genetic engineering).

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length to sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Open Reading Frame ("orf"). The property of some nucleic acid sequences to encode for more than one peptide within the same sequence, which is possible because these sequences contain a series of triplets coding for amino acids without any termination codons interrupting the relevant reading frames.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the base sequence GAATTC/CTTAAG.

Restriction Fragment. The DNA molecules produced by digestion with a restriction endonuclease are referred to as restriction fragments. Any given genome can be digested by a particular restriction endonuclease into a discrete set of restriction fragments.

Agarose Gel Electrophoresis. To determine the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action or electrophoretic transfer.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter as by the Southern hybridization transfer procedures. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., *Current Protocols in Molecular Biology*, John Wily & Sons, Inc., New York, N.Y. (1989). For example, a nitrocellulose filter is incubated overnight at 68° C. with labeled probe in a solution containing 50% formamide, high salt (either 5×SSC [20×: 3M NaCl/0.3M trisodium citrate] or 5×SSPE [20×: 3.6M NaCl/0.2M $NaH_2PO_4$/0.02M EDTA, pH 7.7]), 5×Denhardt's solution, 1% SDS, and 100 µg/ml denatured salmon sperm DNA. This is followed by several washes in 0.2× SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional to derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Purified. A "purified" protein or nucleic acid is a protein or nucleic acid that has been separated from a cellular component. "Purified" proteins or nucleic acids have been purified to a level of purity not found in nature.

BRIEF DESCRIPTION OF FIGURES

FIG. 4. DNA sequence of S22 (SEQ ID NO:1). The complete DNA sequence of the S22 insert in Lambda Zap II is shown. The nucleotide number is indicated in the left margin.

FIG. 5. FIG. 5A shows the amino acid sequence of S22 (SEQ ID NO:2). This sequence constitutes the translated amino acid sequence for the open reading frame of S22 beginning at nucleotide 500 and ending with the stop codon at nucleotide 2359 of SEQ ID NO:1 (See, FIG. 4). FIG. 5B shows the nucleic acid sequence of the 130 kDa protein, corresponding to nucleotides 451-2379 of SEQ ID NO:1. Nucleotide numbers are indicated at the left. The ATG start codon and TAA stop codon are shown in bold type. The translated amino acid sequence for the open reading frame is displayed underneath the DNA sequence using the single-letter amino acid code (SEQ ID NO:2).

FIG. 6. DNA sequence of S2 (SEQ ID NO:3). The complete DNA sequence of the S2 insert in Lambda Zap II is shown in FIG. 6A and continued in FIGS. 6B and 6C. The nucleotide number is indicated in the left margin.

FIG. 7. FIG. 7A shows the amino acid sequence of S2 (SEQ ID NO:4) for the open reading frame beginning at nucleotide 1576 and ending with the stop codon at nucleotide 3801 (See, FIG. 6). FIG. 7B shows the nucleic acid sequence of the 160 kDa protein gene (nucleotides 1501-3850 of SEQ ID NO:3). Nucleotide numbers are indicated at the left. The ATG start codon and TAA stop codon are shown in bold type. The translated amino acid sequence for the open reading frame is displayed underneath the DNA sequence using the single-letter amino acid code (SEQ ID NO:4).

FIG. 8. DNA sequence of S7 (SEQ ID NO:5). The complete DNA sequence of the S7 insert in Lambda Zap II is shown in FIG. 8A and continued in FIGS. 8B and 8C. The nucleotide number is indicated in the left margin.

FIG. 9. FIG. 9A shows the amino acid sequence of S7 (SEQ ID NO:6) for the open reading frame beginning at nucleotide 233 and ending with the stop codon at nucleotide 1969 (See, FIG. 8). FIG. 9B also shows the nucleic acid sequence of the 100 kDa protein gene (nucleotide 172-2001 of SEQ ID NO:5). Nucleotide numbers are indicated at the left. The ATG start codon and TAA stop codon are shown in bold type. The translated amino acid sequence for the open reading frame is displayed underneath the DNA sequence using the single-letter amino acid code (SEQ ID NO:6).

FIG. 10. DNA sequence of S23 (SEQ ID NO:7). The complete DNA sequence of the S23 insert in Lambda Zap II is shown in FIG. 10A and continued in FIGS. 10B, 10C and 10D. The nucleotide number is indicated in the left margin.

FIG. 11 Amino acid sequence of S23 for the open reading frame which begins at nucleotide 254 and ends at nucleotide 1708 of SEQ ID NO:7 (See, FIG. 10) is shown (SEQ ID NO:8). Two smaller open reading frames are found at nucleotides 2656-2997 (complementary strand) and nucleotides 3904-4248 (See, FIG. 10).

FIG. 12. Schematic diagram of S22 and S23 proteins. The boxes represent amino acid repeat regions. Lighter boxes: 28 amino acid repeats; Darker boxes: 59 amino acid repeats. Note: the 28 amino acid repeats are also contained within the 59 amino acid repeat regions. The approximate size and location of the S22 deletion which results in S23 is indicated.

FIG. 13. Schematic diagrams of S2 (top) and S7 (bottom) proteins. Repeat regions are indicated by the boxes.

FIG. 14. Schematic diagram of GE 160 kDa protein. Repeat regions are indicated by the boxes. Sequences of proposed ankyrin repeats, numbered 1-8 (SEQ ID NOS:9-16), are aligned using the consensus sequence (SEQ ID NO:17) at the top: h, hydrophobic; t, turn-like or polar; S/T, serine or threonine; capitals, conserved amino acids.

FIG. 15. Amino acid sequence alignments of selected regions of GE 130 kDa and *E. chaffeensis* 120 kDa proteins (A) (SEQ ID NOS:73-77) and GE 100 kDa (SEQ ID NOS: 78-81) and *E. chaffeensis* 120 kDa proteins (SEQ ID NOS: 82-83) (B). Each protein is shown as a linear amino acid sequence and amino acids are numbered in hundreds. Boxed regions on the linear sequence represent repeated amino acids.

FIG. 18. Western blot analysis of GE proteins. Three different human serum samples were used to probe Western blots containing SDS-disrupted USG3 (GE lanes), GE160, GE100, and GE130. A pBluescript library clone containing no insert was used as a negative control (NEG). Origin of sera is indicated at the bottom of each panel (WI, Wisconsin; NY, New York). Molecular weight markers (in kilodaltons) are shown to the left of each panel.

FIG. 21. Amino acid sequence (SEQ ID NO:21) which is the translated amino acid sequence for the open reading frame of the C6.1 gene, which begins at nucleotide 312 and ends at nucleotide 1532 of SEQ ID NO:23 (See, FIG. 23).

FIG. 22. Amino acid sequence (SEQ ID NO:22) which is the translated amino acid sequence for the open reading frame of the C6.2 gene, which begins at nucleotide 1542 and ends at nucleotide 2336 of SEQ ID NO:23 (See, FIG. 23).

FIG. 23. DNA sequence of C6 (SEQ ID NO:23). The complete double strand DNA sequence of the C6 insert in Lambda Zap II is shown.

FIG. 26. ClustalW alignment of amino acids encoded by the 550 bp PCR product (SEQ ID NO:24) and the MSP-2 protein of A. marginate (GenBank accession number U07862) (SEQ ID NO:25). Identical amino acids are enclosed by boxes Amino acids which represent conservative codon changes are shown in capital letters.

FIG. 29. Sequence of the GE E8 msp2 gene (SEQ ID NO:26). Nucleotide numbers are indicated at the left. The ATG start codon and TAA stop codon are shown in bold type. The translated amino acid sequence for the open reading frame is displayed underneath the DNA sequence using the single letter amino acid code (SEQ ID NO:27). A possible ribosome binding site upstream of the ATG codon is also underlined.

FIG. 30. Complete sequence of E46. The nucleotide number is indicated above the sequences. The complete DNA sequence of the E46 insert in Lambda Zap II is shown (SEQ ID NO:28). The translated amino acid sequences for the open reading frames are displayed underneath the DNA sequences. The amino acid sequence of E46#1 which begins at nucleotide 305 and ends at nucleotide 1282, is shown (SEQ ID NO:29). The amino acid sequence of E46#2 which begins at nucleotide 1346 and ends at nucleotide 2437, is shown (SEQ ID NO:30). The amino acid sequence of ORF3 corresponds to SEQ ID NO: 84. The amino acid sequence of ORF4 corresponds to SEQ ID NO: 85.

FIG. 31. ClustalW alignment of GE MSP-2 and A. marginale MSP-2 (U07862) protein sequences (SEQ ID NOS:27, 29-31). Identical amino acids are enclosed by boxes. Amino acids which represent conservative codon changes are indicated by capital letters. The symbol—denotes a gap used to achieve optimal alignment between the sequences.

FIG. 34 Amino acid sequence of 64 kDa protein degenerate primer sequences derived therefrom (SEQ ID NOS:32-33) are listed for SEQ ID NOS:34 and 35 (peptides 24 and 25, respectively) Amino Acids from which the primer sequences were generated are underlined. Two other peptides are listed: peptide #23 (SEQ ID NO:36) and peptide #26 (SEQ ID NO:37). Undetermined positions of the peptide sequences are designated with an asterisk (*).

FIG. 36. Nucleic acid sequence (SEQ ID NO:38) and amino acid sequence (SEQ ID NO:39) of S11/GE 59 kDa. Start and stop codons are in bold type. Sequenced peptides are underlined in FIG. 36.

DETAILED DESCRIPTION OF THE PREFERRED EMBODIMENTS

Figure 1:
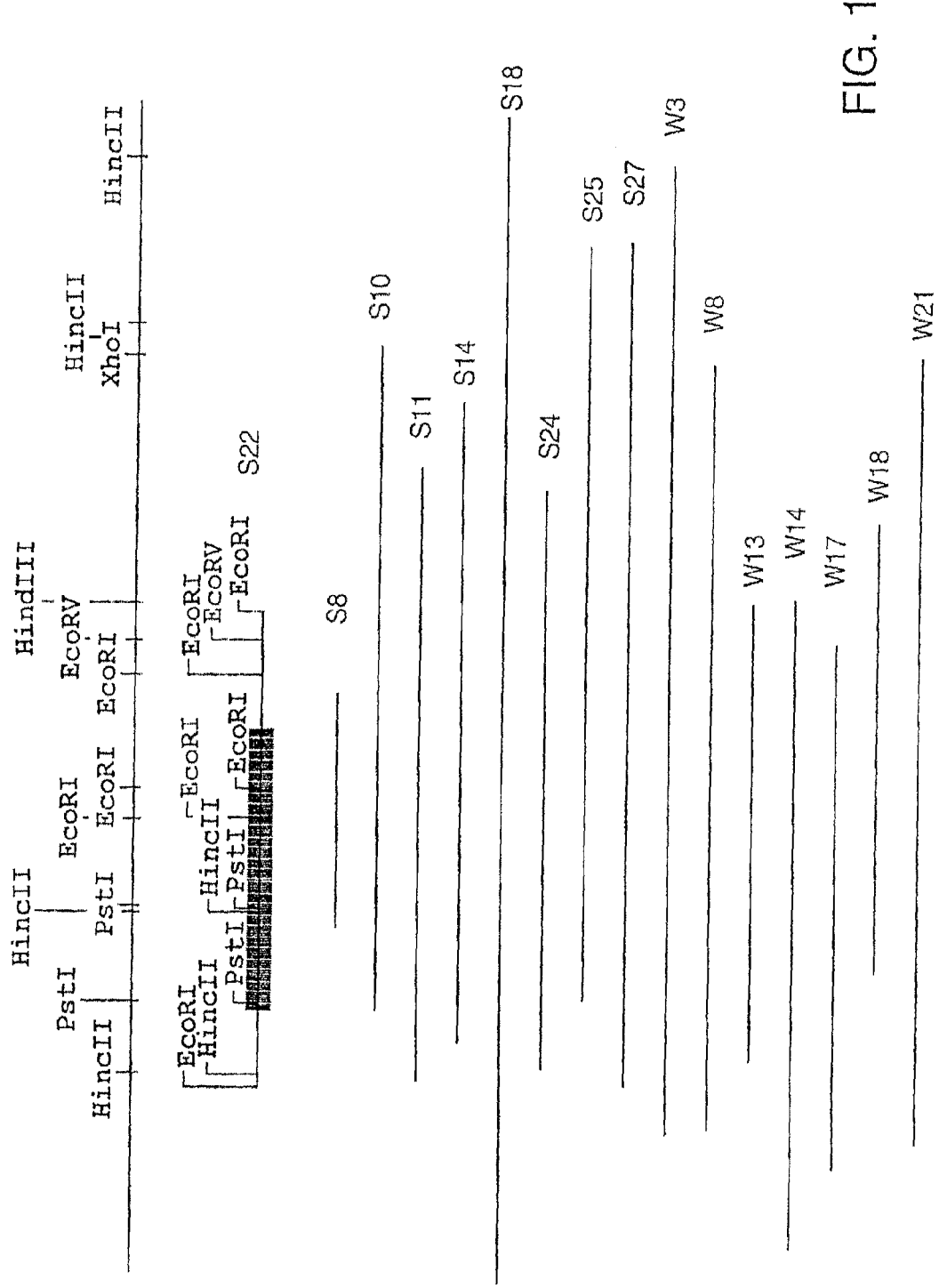
FIG. 1. Restriction enzyme map of group I clones. The top line represents a composite map of all the group I clones and contains the recognition sites for selected enzymes. Each group I clone is listed individually below this map and the relative length of the DNA insert is indicated by the line next to the clone name. A more detailed map of S22 is shown with the open reading frame indicated by the black box.

The sequencing and protein analysis of nine recombinant clones (S2, S7, S22, S23, C6, S11, E8, E46#1, and E46#2) identified by immunological screening of a GE genomic library is described. Two of these clones, S22 and S23, encode identical proteins which differ only by the loss of a repeated region in S23. One clone, C6, contains two open reading frames encoding polypeptides C6.1, C6.2. Clones E8, E46#1, and E46#2 contain conserved amino- and carboxy-terminus regions. These genomic DNA isolates were proven to be specific to GE based on PCR analysis of GE DNA and HL60 DNA.

Of the hundreds of phage plaques that came up positive using either convalescent dog sera or vaccinated mouse sera, the vast majority were identified as either group I (e.g., S22 or S23), group II (e.g., S2), group III (e.g., S7). The genes described herein most likely encode immunodominant GE antigens which may also be present in more than one copy in the GE genome. Other immunodominant rickettsial antigens have been shown to be important diagnostic reagents and vaccine targets including the outer membrane polypeptides of *Anaplasma marginale* (Tebele et al., *Infect. Immun.* 59:3199-3204 (1991)), immunogenic proteins of *Cowdria rumantiun* (Mahan et al., *Microbiology* 140:2135-2142 (1994); van Vliet et al., *Infect. Immun.* 62:1451-1456 (1994)), the 120 kDa immunodominant protein of *E. chaffeensis* (Yu et al., *J. Clin. Micro.* 34:2853-2855 (1996)), the immuno-dominant surface protein antigen of *Rickettsia prowazekii* (Dasch et al., in *Microbiology*, D. Schlessinger (ed.), American Society for Microbiology, Washington, D.C., (1984), pp. 251-256,1) and two *Rickettsia rickettsii* surface proteins (Anacker et al., *Infect. Immun.* 55:825-827 (1987); Sumner et al., *Vaccine* 13:29-35 (1995)). Many of these proteins contain highly repeated regions similar to those found for GE proteins. Repetitive protein domains have been shown to function in ligand binding—(Wren, *Mol. Microbiol.* 5:797-803 (1991)) and may function to facilitate rickettsial uptake by host cell membranes.

For purposes of clarity of disclosure, and not by way of limitation, the detailed description of the invention is divided into the following subsections:

I. Isolated Nucleic Acid Molecules Coding for S2, S7, S22, S23, C6.1, C6.2, S11, E8, E46#1, and E46#2 Polypeptides;

II. Recombinantly Produced S2, S7, S22, S23, C6.1, C6.2, S11, E8, E46#1, and E46#2 Polypeptides;

III. A Nucleic Acid Probe for the Specific Detection of S2, S7, S22, S23, C6.1, C6.2, S11, E8, E46#1, and E46#2;

IV. A Method of Detecting The Presence of S2, S7, S22, S23, C6.1, C6.2, S11, E8, E46#1, or E46#2 in a Sample;

V. A Kit for Detecting the Presence of S2, S7, S22, S23, C6.1, C6.2, S11, E8, E46#1, or E46#2 in a Sample;

VI. DNA Constructs Comprising S2, S7, S22, S23, C6.1, C6.2, S11, E8, E46#1, and E46#2 Nucleic Acid Molecule and Cells Containing These Constructs;

VII. An Antibody Having Binding Affinity to S2, S7, S22, S23, C6.1, C6.2, S11, E8, E46#1, or E46#2 Polypeptide and a Hybridoma Containing the Antibody;

VIII. A Method of Detecting a S2, S7, S22, S23, C6.1, C6.2, S11, E8, E46#1, or E46#2 Polypeptide or Antibody in a Sample;

IX. A Diagnostic Kit Comprising S2, S7, S22, S23, C6.1, C6.2, S11, E8, E46#1, or E46#2 Protein or Antibody;

X. Diagnostic Screening; and

XI. Vaccines

I. Isolated Nucleic Acid Molecules Coding for S2, S7, S22, S23, C6.1, C6.2, S11, E8, E46#1, and E46#2 Polypeptides In one embodiment, the present invention relates to isolated nucleic acid molecules comprising a polynucleotide sequence at least 90% identical (more preferably, 95%, 96%, 97%, 98%, 99%, or 100% identical) to a sequence selected from:

(a) a nucleotide sequence encoding the S2, S7, S22, S23, C6.1, C6.2, S11, E8, or E46#1, E46#2 polypeptide comprising the complete amino acid sequence in SEQ ID NOS:4, 6, 2, 8, 21, 22, 39, 27, 29, and 30, respectively;

(b) a nucleotide sequence encoding the S2, S7, S22, S23, C6.1, C6.2, S11, E8, E46#1, or E46#2 polypeptide comprising the complete amino acid sequence encoded by the polynucleotide clone contained in ATCC Deposit Nos. 97844, 97840, 97842, 97843, 97841, 97841, 209740, 209736, 209743, and 209743 respectively (note, C6.1 and C6.2, are encoded by the polynucleotide clone contained in ATCC Deposit No. 97841 and that E46#1 and E46#2 are encoded by the polynucleotide clone contained in ATCC Deposit No. 209743); and (c) a nucleotide sequence complementary to any of the nucleotide sequences in (a) or (b).

The S2, S7, S22, S23, and C6 (encoding C6.1 and C6.2) nucleic acids were deposited at the American Type Culture Collection (ATCC), 12301 Parklawn Drive, Rockville, Md. 20852, USA on Dec. 31, 1996 as ATCC Deposit Nos. 97844, 97840, 97842, 97843, and 97841, respectively. The S11, E8, and E46 (encoding E46#1 and E46#2) nucleic acids were deposited at the ATCC on Mar. 31, 1998 as ATCC Deposit Nos. 209740, 209736 and 209743, respectively.

In one preferred embodiment, the isolated nucleic acid molecule comprises a GE S2, S7, S22, S23, C6.1, C6.2, S11, E8, E46#1, or E46#2 nucleotide sequence with greater than 90% identity or similarity to the nucleotide sequence present in SEQ ID NOS:3, 5, 1, 7, 23, 23, 38, 26, 28 or 28 (preferably greater than 95%, 96%, 97%, 98%, 99% or 100%), respectively. In another preferred embodiment, the isolated nucleic acid molecule comprises the S2, S7, S22, S23, C6.1, C6.2, S11, E8, E46#1, or E46#2 nucleotide sequence present in SEQ ID NOS:3, 5, 1, 7, 23, 23, 38, 26, 28, or 28, respectively. In another embodiment, the isolated nucleic acid molecule encodes the S2, S7, S22, S23, C6.1, C6.2, S11, E8, E46#1, and E46#2 amino acid sequence present in SEQ ID NOS:4, 6, 2, 8, 21, 22, 39, 27, 29, or 30, respectively.

Also included within the scope of this invention are the functional equivalents of the herein-described isolated nucleic acid molecules and derivatives thereof. For example, the nucleic acid sequences depicted in SEQ ID NOS:3, 5, 1, 7, 23, 23, 38, 26, 28, or 28 can be altered by substitutions, additions or deletions that provide for functionally equivalent molecules. Due to the degeneracy of nucleotide coding sequences, other DNA sequences which encode substantially the same amino acid sequence as depicted in SEQ ID NOS:4, 6, 2, 8, 21, 22, 39, 27, 29, or 30 can be used in the practice of the present invention. These include but are not limited to nucleotide sequences comprising all or portions of S2, S7, S22, S23, C6.1, C6.2, S11, E8, E46#1, and E46#2 nucleic acid depicted in SEQ ID NOS:3, 5, 1, 7, 23, 23, 38, 26, or 28, respectively which are altered by the substitution of different codons that encode a functionally equivalent amino acid residue within the sequence.

In addition, the nucleic acid sequence can comprise a nucleotide sequence which results from the addition, deletion or substitution of at least one nucleotide to the 5'-end and/or the 3'-end of the nucleic acid formula shown in SEQ ID NOS:3, 5, 1, 7, 23, 23, 38, 26, 28, or 28 or a derivative thereof. Any nucleotide or polynucleotide can be used in this regard, provided that its addition, deletion or substitution does not substantially alter the amino acid sequence of SEQ ID NOS: 4, 6, 2, 8, 21, 22, 39, 27, 29, or 30 which is encoded by the nucleotide sequence. Moreover, the nucleic acid molecule of the present invention can, as necessary, have restriction endonuclease recognition sites added to its 5'-end and/or 3'-end. All variations of the nucleotide sequence of the S2, S7, S22, S23, C6.1, C6.2, S11, E8, E46#1, and E46#2 gene and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid

In one aspect of the present invention, isolated nucleic acid molecules coding for polypeptides having amino acid sequences corresponding to S2, S7, S22, S23, C6.1, C6.2, S11, E8, E46#1, and E46#2 are provided. In particular, the nucleic acid molecule can be isolated from a biological sample (preferably of mammalian or tick origin) containing GE RNA or DNA.

The nucleic acid molecule can be isolated from a biological sample containing GE RNA using the techniques of cDNA cloning and subtractive hybridization. The nucleic acid molecule can also be isolated from a cDNA library using a homologous probe.

The nucleic acid molecule can be isolated from a biological sample containing genomic DNA or from a genomic library. Suitable biological samples include, but are not limited to, whole organisms, organs, tissues, blood and cells. The method of obtaining the biological sample will vary depending upon the nature of the sample.

One skilled in the art will realize that genomes can be subject to slight allelic variations between individuals. Therefore, the isolated nucleic acid molecule is also intended to include to allelic variations, so long as the sequence is a functional derivative of the S2, S7, S22, S23, C6.1, C6.2, S11, E8, E46#1, and E46#2 coding sequence. When an S2, S7, S22, S23, C6.1, C6.2, S11, E8, E46#1, or E46#2, allele does not encode the identical sequence to that found in SEQ ID NOS:3, 5, 1, 7, 23, 23, 38, 26, 28 or 28 it can be isolated and identified as S2, S7, S22, S23, C6.1, C6.2, S11, E8, E46#1, or E46#2 using the same techniques used herein, and especially PCR techniques to amplify the appropriate gene with primers based on the sequences disclosed herein.

One skilled in the art will realize that organisms other than GE will also contain S2, S7, S22, S23, C6.1, C6.2, S11, E8, E46#1, and E46#2 genes. The invention is intended to include, but not be limited to, S2, S7, S22, S23, C6.1, C6.2, S11, E8, E46#1, and E46#2 nucleic acid molecules isolated from the above-described organisms. Also, infected eukaryotes (for example, mammals, birds, fish and humans) may contain the S2, S7, S22, S23, C6.1, C6.2, S11, E8, E46#1, and E46#2 genes.

B. Synthesis of Nucleic Acid

Isolated nucleic acid molecules of the present invention are also meant to include those chemically synthesized. For example, a nucleic acid molecule with the nucleotide sequence which codes for the expression product of S2, S7, S22, S23, C6.1, C6.2, S11, E8, E46#1, or E46#2 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185-3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

II. Recombinantly Produced S2, S7, S22, S23, C6.1, C6.2, S11, E8, E46#1, and E46#2 Polypeptides In another embodiment, the present invention relates to a purified polypeptide (preferably, substantially pure) having an amino acid sequence corresponding to S2, S7, S22, S23, C6.1, C6.2, S11, E8, E46#1, or E46#2 or a functional derivative thereof. In a preferred embodiment, the polypeptide has the amino acid sequence set forth in SEQ ID NOS:4, 6, 2, 8, 21, 22, 39, 27, 29, or 30, respectively, or mutant or species variation thereof, or at least 60% identity or at least 70% similarity thereof (preferably, at least 85%, 90%, 95%, 96%, 97%, 98%, or 99% identity or at least 95%, 96%, 97%, 98%, or 99% similarity thereof), or at least 6 contiguous amino acids thereof (preferably, at least 10, 15, 20, 25, or 50 contiguous amino acids thereof).

In a preferred embodiment, the invention relates to S2, S7, S22, S23, C6.1, C6.2, S11, E8, E46#1, or E46#2 epitopes. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art. (Sutcliffe et al., *Science* 219:660-666 (1983)). Antigenic epitope-bearing peptides and polypeptides of the invention are useful to raise an immune response that specifically recognizes the polypeptides. Antigenic epitope-bearing peptides and polypeptides of the invention comprise at least 7 amino acids (preferably, 9, 10, 12, 15, or 20 amino acids) of the proteins of the invention. Non-limiting examples of antigenic polypeptides or peptides include those listed in Table 1, below.

TABLE 1

Antigenic Epitopes

| | Size[1] | Amino Acids[2] |
|---|---|---|
| S2 | 10 | 181-190 |
| | 22 | 411-432 |
| | 15 | 636-650 |
| S7 | 16 | 13-28 |
| | 10 | 73-82 |
| | 11 | 496-506 |
| S22 | 13 | 41-53 |
| | 17 | 168-184 |
| | 19 | 317-335 |
| S23 | 15 | 6-20 |
| | 11 | 78-88 |
| | 18 | 387-404 |
| C6.1 | 9 | 110-118 |
| | 9 | 338-346 |
| | 11 | 353-363 |
| C6.2 | 12 | 65-76 |
| | 9 | 104-112 |
| | 9 | 170-178 |
| S11 | 12 | 90-101 |
| | 17 | 144-160 |
| | 9 | 334-342 |
| E8 | 10 | 40-49 |
| | 12 | 132-143 |
| | 15 | 261-275 |
| E46.#1 | 9 | 32-41 |
| | 12 | 125-136 |
| | 20 | 222-241 |
| E46#2 | 12 | 55-66 |
| | 14 | 177-190 |
| | 10 | 291-300 |

[1]Number of amino acids.
[2]See FIGS. 7, (S2), 9 (S7), 5 (S22), 11 (S23), 17 (C6.1), 18 (C6.2) and 23 (S11) for amino acid numbering.

Amino acid sequence variants of S2, S7, S22, S23, C6.1, C6.2, S11, E8, E46#1, and E46#2 can be prepared by mutations in the DNA. Such variants include, for example, deletions from, or insertions or substitutions of, residues within the amino acid sequence shown in SEQ ID NOS:4, 6, 2, 8, 21, 22, 39, 27, 29, or 30. Any combination of deletion, insertion, and substitution can also be made to arrive at the final construct, provided that the final construct possesses the desired activity.

While the site for introducing an amino acid sequence variation is predetermined, the mutation per se need not be predetermined. For example, to optimize the performance of a mutation at a given site, random mutagenesis can be conducted at the target codon or region and the expressed S2, S7, S22, S23, C6.1, C6.2, S11, E8, E46#1, and E46#2 variants screened for the optimal combination of desired activity. Techniques for making substitution mutations at predetermined sites in DNA having a known sequence are well known, for example, site-specific mutagenesis.

Preparation of an S2, S7, S22, S23, C6.1, C6.2, S11, E8, E46#1, or E46#2 variant in accordance herewith is preferably achieved by site-specific mutagenesis of DNA that encodes an earlier prepared variant or a nonvariant version of the protein. Site-specific mutagenesis allows the production of S2, S7, S22, S23, C6.1, C6.2, S11, E8, E46#1, and E46#2 variants through the use of specific oligonucleotide sequences that encode the DNA sequence of the desired mutation. In general, the technique of site-specific mutagenesis is well known in the art, as exemplified by publications such as Adelman et al., *DNA* 2:183 (1983) and Ausubel et al., "Current Protocols in Molecular Biology", J. Wiley & Sons, New York, N.Y., 1996.

As will be appreciated, the site-specific mutagenesis technique can employ a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton (ed.), Elsevier, Amsterdam (1981). These phage are readily commercially available and their use is generally well known to those skilled in the art. Alternatively, plasmid vectors that contain a single-stranded phage origin of replication (Vieira et al., *Meth. Enzymol.* 153:3 (1987)) can be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. (USA)* 75:5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells and clones are selected that include recombinant vectors bearing the mutated sequence arrangement.

After such a clone is selected, the mutated protein region can be removed and placed in an appropriate vector for protein production, generally an expression vector of the type that can be employed for transformation of an appropriate host.

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the complete S2, S7, S22, S23, C6.1, C6.2, S11, E8, E46#1, or E46#2 sequence) can range generally from about 1 to 10 residues, more preferably 1 to 5.

The third group of variants are those in which at least one amino acid residue in the S2, S7, S22, S23, C6.1, C6.2, S11, E8, E46#1, or E46#2 molecule, and preferably, only one, has to been removed and a different residue inserted in its place. Such substitutions preferably are made in accordance with the following Table 2 when it is desired to modulate finely the characteristics of S2, S7, S22, S23, C6.1, C6.2, S11, E8, E46#1, or E46#2.

TABLE 2

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |

TABLE 2-continued

| Original Residue | Exemplary Substitutions |
|---|---|
| Thr | ser |
| Trp | tyr |
| Tyr | trp; phe |
| Val | ile; leu |

Substantial changes in functional or immunological identity are made by selecting substitutions that are less conservative than those in Table 2, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of S2, S7, S22, S23, C6.1, C6.2, S11, E8, E46#1, or E46#2. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native S2, S7, S22, S23, C6.1, C6.2, S11, E8, E46#1, or E46#2, encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified S2, S7, S22, S23, C6.1, C6.2, S11, E8, E46#1, or E46#2 molecule variant is then screened in a suitable screening assay for the desired characteristic. For example, a change in the immunological character of the S2, S7, S22, S23, C6.1, C6.2, S11, E8, E46#1, or E46#2 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments can be used to express the S2, S7, S22, S23, C6.1, C6.2, S11, E8, E46#1, or E46#2 protein in any organism. The samples of the present invention include cells, protein extracts or membrane extracts of cells, or biological fluids. The sample will vary based on the assay format, the detection method and the nature of the tissues, cells or extracts used as the sample.

Any prokaryotic (preferably, a granulocytic ehrlichia) organism can be used as a source for the peptide of the invention, as long as the source organism naturally contains such a peptide. A eukaryotic organism infected with granulocytic ehrlichia can also be used as the source organism. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants These include, but are not limited to: immunochromotography, size-exclusion chromatography, HPLC, ion-exchange chromatography, and immuno-affinity chromatography.

III. A Nucleic Acid Probe for the Specific Detection of S2, S7, S22, S23, C6.1, C6.2, S11, E8, E46#1 and E46#2

In another embodiment, the present invention relates to a nucleic acid probe for the specific detection of the presence of S2, S7, S22, S23, C6.1, C6.2, S11, E8, E46#1, or E46#2 nucleic acid in a sample comprising the above-described nucleic acid molecules or at least a fragment thereof which binds under stringent conditions to S2, S7, S22, S23, C6.1, C6.2, S11, E8, E46#1, or E46#2 nucleic acid.

In one preferred embodiment, the present invention relates to an isolated nucleic acid probe consisting of 10 to 1000 nucleotides (preferably, 10 to 500, 10 to 100, 10 to 50, 10 to 35, 20 to 1000, 20 to 500, 20 to 100, 20 to 50, or 20 to 35) which hybridizes preferentially to RNA or DNA of granulocytic ehrlichia but not to RNA or DNA of non-granulocytic ehrlichia organisms (example, humans), wherein said nucleic acid probe is or is complementary to a nucleotide sequence consisting of at least 10 consecutive nucleotides (preferably, 15, 20, 25, or 30) from the nucleic acid molecule comprising a polynucleotide sequence at least 90% identical to a sequence selected from:

(a) a nucleotide sequence encoding the S2, S7, S22, S23, C6.1, C6.2, S11, E8, E46#1, or E46#2 polypeptide comprising the complete amino acid sequence in SEQ ID NOS:4, 6, 2, 8, 21, 22, 39, 27, 29, or 30, respectively;

(b) a nucleotide sequence encoding the S2, S7, S22, S23, C6.1, C6.2, S11, E8, E46#1, E46#2 polypeptide comprising the complete amino acid sequence encoded by the polynucleotide clone contained in ATCC Deposit Nos. 97844, 97840, 97842, 97843, 97841, 97841, 209740, 209736, 209743 or 209743 respectively (note, C6.1 and C6.2 are encoded by the polynucleotide clone contained in ATCC Deposit No. 97841 and E46#1 and E46#2 are encoded by the polynucleotide clone contained in ATCC Deposit No. 209743);

(c) a nucleotide sequence complementary to any of the nucleotide sequences in (a) or (b); and (d) a nucleotide sequence as previously described above.

Examples of specific nucleic acid probes which can be used in the present invention are set forth in Table 3, below.

TABLE 3

| | Nucleic Acid Probes | |
|---|---|---|
| | Size[3] | Nucleotides[4] |
| S2 | 20 | 2660-2679 |
| | 37 | 2643-2679 |
| | 75 | 1820-1894 |
| | 450 | 2150-2599 |
| S7 | 20 | 489-508 |
| | 35 | 321-355 |
| | 75 | 420-494 |
| | 450 | 300-749 |
| S22 | 23 | 1220-1242 |
| | 36 | 1187-1222 |

TABLE 3-continued

Nucleic Acid Probes

| | Size[3] | Nucleotides[4] |
|---|---|---|
| | 75 | 1220-1294 |
| | 450 | 570-1019 |
| S23 | 23 | 974-996 |
| | 35 | 962-996 |
| | 75 | 720-794 |
| | 450 | 600-1049 |
| C6 | 19 | 530-548 |
| | 35 | 1097-1131 |
| | 75 | 1710-1784 |
| | 450 | 1850-2299 |
| S11 | 20 | 570-589 |
| | 35 | 1045-1079 |
| | 75 | 1600-1674 |
| | 450 | 500-949 |
| E8 | 20 | 520-539 |
| | 35 | 650-684 |
| | 75 | 900-974 |
| | 450 | 700-1149 |
| E46 | 20 | 1450-1469 |
| | 35 | 1800-1834 |
| | 75 | 1030-1104 |
| | 450 | 400-849 |

[3]Number of bases
[4]See FIGS. 6 (S2), 8 (S7), 4 (S22), 10 (S23), 16 (C6) and 23 (S11) for nucleotide numbering.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf. *Molecular Cloning: A Laboratory Manual, 2nd edition*, edited by Sambrook, Fritsch, & Maniatis, Cold Spring Harbor Laboratory, 1989).

In the alternative, chemical synthesis is carried out in order to obtain nucleic acid probes having nucleotide sequences which correspond to amino-terminal and carboxy-terminal portions of the S2, S7, S22, S23, C6.1, C6.2, S11 amino acid sequence (See, Table 3) or E8, E46#1, or to E46#2 amino acid sequence. Thus, the synthesized nucleic acid probes can be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal, cDNA or cell line library to obtain the fragment of the present invention.

One skilled in the art can readily design such probes based on the sequence disclosed herein using methods of computer alignment and sequence analysis known in the art (cf. *Molecular Cloning: A Laboratory Manual, 2nd edition*, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting The Presence of S2, S7, S22, S23, C6.1, C6.2, S11, E8, E46#1, or E46#2 in a Sample In another embodiment, the present invention relates to a method of detecting the presence of S2, S7, S22, S23, C6.1, C6.2, S11, E8, E46#1, or E46#2 nucleic acid in a sample comprising a) contacting the sample with the above-described nucleic acid probe, under specific hybridization conditions such that hybridization occurs, and b) detecting the presence of the probe bound to the nucleic acid molecule. Alternatively, in another preferred embodiment, the method of detecting the presence of S2, S7, S22, S23, C6.1, C6.2, S11, E8, E46#1, or E46#2 nucleic acid in a sample may comprise a) amplifying the nucleic acid in the sample with the nucleic acid probe wherein the amplification uses PCR techniques and b) detecting the presence of the amplified nucleic acid molecules. One skilled in the art would select the nucleic acid probe according to techniques known in the art as described above. Samples to be tested include but should not be limited to RNA samples from human tissue.

V. A Kit for Detecting the Presence of S2, S7, S22, S23, C6.1, C6.2, S11, E8, E46#1, or E46#2 in a Sample In another embodiment, the present invention relates to a kit for detecting the presence of S2, S7, S22, S23, C6.1, C6.2, S11, E8, E46#1, or E46#2 nucleic acid in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or streptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers to which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising an S2, S7, S22, S23, C6.1, C6.2, S11, E8, E46#1, or E46#2 Nucleic Acid Molecule and Cells Containing These Constructs In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the S2, S7, S22, S23, C6.1, C6.2, S11, E8, E46#1, or E46#2 coding sequence can be obtained by the above-described methods. This region can be retained for its transcriptional termination regulatory sequences, such as termination and polyadenylation. Thus, by retaining the 3'-region naturally contiguous to the DNA sequence encoding a S2, S7, S22, S23, C6.1, C6.2, S11, E8, E46#1, or E46#2 gene, the transcriptional termination signals can be provided. Where the transcriptional termination signals are not satisfactorily functional in the expression host cell, then a 3' region functional in the host cell can be substituted. Two DNA sequences (such as a promoter region sequence and a S2, S7, S22, S23, C6.1, C6.2, S11, E8, E46#1, or E46#2 coding sequence) are said to be operably linked if the nature of the linkage between the two DNA sequences does not (1) result in the introduction of a frame-shift mutation, (2) interfere with the ability of the promoter region sequence to direct the transcription of a S2, S7, S22, S23, C6.1, C6.2, S11, E8, E46#1, or E46#2 coding sequence, or (3) interfere with the ability of the S2, S7, S22, S23, C6.1, C6.2, S11, E8, E46#1, or E46#2 coding sequence to be transcribed by the promoter region sequence. Thus, a promoter region would be operably linked to a DNA sequence if the promoter were capable of effecting transcription of that DNA sequence.

The present invention encompasses the expression of the S2, S7, S22, S23, C6.1, C6.2, S11, E8, E46#1, or E46#2 coding sequence (or a functional derivative thereof) in either prokaryotic or eukaryotic cells. Prokaryotic hosts are, generally, the most efficient and convenient for the production of recombinant proteins and, therefore, are preferred for the expression of the S2, S7, S22, S23, C6.1, C6.2, S11, E8, E46#1, or E46#2 coding sequence.

Prokaryotes most frequently are represented by various strains of *E. coli*. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC18, pUC19, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as *E. coli, Bacillus, Streptomyces, Pseudomonas, Salmonella, Serratia*, and the like. However, under such conditions, the peptide will not be glycosylated. The prokaryotic host must be compatible with the replicon and control sequences in the expression plasmid.

To express S2, S7, S22, S23, C6.1, C6.2, S11, E8, E46#1, or E46#2 in a prokaryotic cell, it is necessary to operably link the S2, S7, S22, S23, C6.1, C6.2, S11, E8, E46#1, or E46#2 coding sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage X, ($P_L$ and $P_R$), the trp, recA, lacZ, lacI, and gal promoters of *E. coli*, the α-amylase (Ulmanen et al., *J. Bacteriol.* 162:176-182 (1985)) and the ç-28-specific promoters of *B. subtilis* (Gilman et al., *Gene sequence* 32:11-20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468-478 (1986)). Prokaryotic promoters are reviewed by Click (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the gene sequence-encoding sequence. Such ribosome binding sites are disclosed, for example, by Gold et al., (*Ann. Rev. Microbiol.* 35:365-404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny cannot be precisely identical in DNA content, due to deliberate or inadvertent mutations. However, as defined, mutant progeny have the same functionality as that of the originally transformed cell. Host cells which can be used in the expression systems of the present invention are not strictly limited, provided that they are suitable for use in the expression of the S2, S7, S22, S23, C6.1, C6.2, S11, E8, E46#1, or E46#2 peptide of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example Drosophila larvae. Using insect cells as hosts, the *Drosophila* alcohol dehydrogenase promoter can be used, (Rubin, *Science* 240:1453-1459 (1988)). Alternatively, baculovirus vectors can be engineered to express large amounts of S2, S7, S22, S23, C6.1, C6.2, S11, E8, E46#1, or E46#2 in insect cells (Jasny, *Science* 238:1653 (1987); Miller et al., In: *Genetic Engineering* (1986), Setlow, J. K., et al., eds., *Plenum, Vol.* 8, pp. 277-297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of S2, S7, S22, S23, C6.1, C6.2, S11, E8, E46#1, or E46#2.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of S2, S7, S22, S23, C6.1, C6.2, S11, E8, E46#1, or E46#2 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature* (London) 290:304-310 (1981)); the yeast gal4 gene sequence promoter (Johnston et al., *Proc. Natl. Acad. Sci.* (*USA*) 79:6971-6975 (1982)); Silver et al., *Proc. Natl. Acad. Sci.* (*USA*) 81:5951-5955 (1984)) and the CMV immediate-early gene promoter (Thomsen et al., *Proc. Natl. Acad. Sci.* (*USA*) 81:659-663 (1984)).

As is widely known, translation of eukaryotic mRNA is initiated at the codon which encodes the first methionine. For this reason, it is preferable to ensure that the linkage between a eukaryotic promoter and a S2, S7, S22, S23, C6.1, C6.2, S11, E8, E46#1, or E46#2 coding sequence does not contain any intervening codons which are capable of encoding a methionine (i.e., AUG). The presence of such codons results either in a formation of a fusion protein (if the AUG codon is in the same reading frame as the S2, S7, S22, S23, C6.1, C6.2, S11, E8, E46#1, or E46#2 coding sequence) or a frame-shift mutation (if the AUG codon is not in the same reading frame as the S2, S7, S22, S23, C6.1, C6.2, S11, E8, E46#1, or E46#2 coding sequence).

A S2, S7, S22, S23, C6.1, C6.2, S11, E8, E46#1, or E46#2 nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancer signal sequences, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πEVX). Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable *Streptomyces* plasmids include pIJ101 (Kendall et al., *J. Bacteriol.* 169:4177-4183 (1987)), and *streptomyces* bacteriophages such as ΦC31 (Chater et al., In: *Sixth International Symposium on Actinomycetales Biology*, Akademiai Kaido, Budapest, Hungary (1986), pp. 45-54). *Pseudomonas* plasmids are reviewed by John et al., (*Rev. Infect. Dis.* 8:693-704 (1986)), and Izaki (*Jpn. J. Bacteriol.* 33:729-742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 28:203-204 (1982); Bolton et al., *J. Clin. Hematol. Oncol.* 10:39-48 (1980); Maniatis, In: *Cell Biology: A Comprehensive Treatise*, Vol. 3, Gene Sequence Expression, Academic Press, NY, pp. 563-608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of S2, S7, S22, S23, C6.1, C6.2, S11, E8, E46#1, or E46#2. This can take place in the transformed cells as such, or following the induction of these cells to differentiate (for example, by administration of bromodeoxyuracil to neuroblastoma cells or the like).

VII. An Antibody Having Binding Affinity to an S2, S7, S22, S23, C6.1, C6.2, S11, E8, E46#1, or E46#2 Polypeptide and a Hybridoma Containing the Antibody In another embodiment, the present invention relates to an antibody having binding affinity specifically to an S2, S7, S22, S23, C6.1, C6.2, S11, E8, E46#1, or E46#2 polypeptide as described above or specifically to an S2, S7, S22, S23, C6.1, C6.2, S11, E8, E46#1, or E46#2 polypeptide binding fragment thereof. An antibody binds specifically to a S2, S7, S22, S23, C6.1, C6.2, S11, E8, E46#1, or E46#2 polypeptide or to consensus sequences described herein corresponding to the amino- and/or carboxy-terminus regions shared by E8, E46#1, and E46#2, or binding fragment thereof if it does not bind to non-S2, S7, S22, S23, C6.1, C6.2, S11, E8, to E46#1, or E46#2 polypeptides. Those which bind selectively to S2, S7, S22, S23, C6.1, C6.2, S11, E8, E46#1, or E46#2 or to consensus sequences described herein corresponding to the amino- and/or carboxy-terminus regions shared by E8, E46#1, and E46#2, would be chosen for use in methods which could include, but should not be limited to, the analysis of altered S2, S7, S22, S23, C6.1, C6.2, S11, E8, E46#1, or E46#2 expression in tissue containing S2, S7, S22, S23, C6.1, C6.2, S11, E8, E46#1, or E46#2.

The S2, S7, S22, S23, C6.1, C6.2, S11, E8, E46#1, or E46#2 proteins, or proteins including the consensus sequences corresponding to the amino- and/or carboxy-terminus regions shared by E8, E46#1, and E46#2 of the present invention can be used in a variety of procedures and methods, such as for the generation of antibodies, for use in identifying pharmaceutical compositions, and for studying DNA/protein interaction.

The S2, S7, S22, S23, C6.1, C6.2, S11, E8, E46#1, or E46#2 proteins, or proteins including the consensus sequences corresponding to the amino and/or carboxy terminus regions shared by E8, E46#1, and E46#2 of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the F(ab')$_2$ fragment; the Fab' fragments, Fab fragments, and Fv fragments.

Of special interest to the present invention are antibodies to S2, S7, S22, S23, C6.1, C6.2, S11, E8, E46#1, E46#2 or to proteins, or proteins including the consensus sequences corresponding to the amino- and/or carboxy-terminus regions shared by E8, E46#1, and E46#2 which are produced in humans, or are "humanized" (i.e.; non-immunogenic in a human) by recombinant or other technology. Humanized antibodies can be produced, for example by replacing an immunogenic portion of an antibody with a corresponding, but non-immunogenic portion (i.e., chimeric antibodies) (Robinson et al., PCT Application No. PCT/US86/02269; Akira et al., European Patent No. 184,187; Taniguchi, European Patent No. 171,496; Morrison et al., European Patent No. 173,494; Neuberger et al., PCT Application WO 86/01533; Cabilly et al., European Patent No. 125,023; Better, et al., *Science* 240:1041-1043 (1988); Liu et al., *Proc. Natl. Acad. Sci. USA* 84:3439-3443 (1987); Liu et al., *J. Immunol.* 139:3521-3526 (1987); Sun, et al., *Proc. Natl. Acad. Sci. USA* 84:214-218 (1987); Nishimura et al., *Canc. Res.* 47:999-1005 (1987); Wood et al., *Nature* 314:446-449 (1985)); Shaw et al., *J. Natl. Cancer Inst.* 80:1553-1559 (1988). General reviews of "humanized" chimeric antibodies are provided by Morrison (*Science,* 229:1202-1207 (1985)) and by Oi et al., *BioTechniques* 4:214 (1986)). Suitable "humanized" antibodies can be alternatively produced by CDR or CEA substitution (Jones et al., *Nature* 321:552-525 (1986); Verhoeyan et al., *Science* 239:1534 (1988); Beidler et al., *J. Immunol.* 141:4053-4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1-21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109-124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horseradish peroxidase, alkaline phosphatase, and the like), fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention, the above-described antibodies are immobilized on a solid support. Examples of such solid supports include plastics such as polycarbonate, complex carbohydrates such as agarose and sepharose, and acrylic resins such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, NY, pp. 289-307 (1992), and Kaspczak et al., *Biochemistry* 28:9230-8 (1989).

Anti-peptide peptides can be generated in one of two fashions. First, the anti-peptide peptides can be generated by replacing the basic amino acid residues found in the S2, S7, S22, S23, C6.1, C6.2, S11, E8, E46#1, and E46#2 peptide sequence or consensus sequences described herein with acidic residues, while maintaining hydrophobic and uncharged polar groups. For example, lysine, arginine, and/or histidine residues are replaced with aspartic acid to or glutamic acid and glutamic acid residues are replaced by lysine, arginine or histidine.

VIII. A Method of Detecting an S2, S7, S22, S23, C6.1, C6.2, S11, E8, E46#1, or E46#2 Polypeptide or Antibody in a Sample In another embodiment, the present invention relates to a method of detecting a S2, S7, S22, S23, C6.1, C6.2, S11, E8, E46#1, or E46#2 polypeptide including the consensus sequence corresponding to the amino- and/or carboxy-terminus regions shared by E8, E46#1, and E46#2 polypeptide in a sample, comprising: a) contacting the sample with an above-described antibody (or protein), under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of peptides S2, S7, S22, S23, C6.1, C6.2, S11, E8, E46#1, or E46#2, or in a sample as compared to normal levels can indicate a specific disease.

In a further embodiment, the present invention relates to a method of detecting a S2, S7, S22, S23, C6.1, C6.2, S11, E8, E46#1, or E46#2 antibody in a sample, comprising: a) contacting the sample with an above-described S2, S7, S22, S23, C6.1, C6.2, S11, E8, E46#1, or E46#2 polypeptide, including the consensus sequence corresponding to the amino- and/or carboxy-terminus regions shared by E8, E46#1, and E46#2 polypeptide under conditions such that immunocomplexes form, and b) detecting the presence of the protein bound to the antibody or antibody bound to the protein. In detail, the methods comprise incubating a test sample with one or more of the proteins of the present invention and assaying whether the antibody binds to the test sample. The presence of antibodies to S2, S7, S22, S23, C6.1, C6.2, S11, E8, E46#1, or E46#2 may indicate exposure to GE, the potential need for therapy of the affected individual, or GE contamination of a biological sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier to Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising S2, S7, S22, S23, C6.1, C6.2, S11, E8, E46#1, or E46#2 Protein or Antibody In another embodiment of the present invention, a kit is provided which contains all the necessary reagents to carry out the previously described methods of detection.

The kit can comprise: i) a first container means containing an above-described antibody, and ii) second container means containing a conjugate comprising a binding partner of the antibody and a label.

The kit can comprise: i) a first container means containing an above-described protein, and preferably, ii) second container means containing a conjugate comprising a binding partner of the protein and a label. More specifically, a diagnostic kit comprises S2, S7, S22, S23, C6.1, C6.2, S11, E8, E46#1, E46#2, or a peptide having consensus sequences corresponding to the amino and/or carboxy terminus regions shared by E8, E46#1, and E46#2 protein as described above, to detect antibodies in the serum of potentially infected animals or humans.

In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

X. Diagnostic Screening

It is to be understood that although the following discussion is specifically directed to human patients, the teachings are also applicable to any animal which can be infected with GE.

The diagnostic and screening methods of the invention are especially useful for a patient suspected of being at risk for developing ehrlichiosis.

According to the invention, a pre- and post-symptomatic screening of an individual in need of such screening is now possible using DNA encoding the S2, S7, S22, S23, C6.1, C6.2, S11, E8, E46#1, or E46#2 protein or fragment thereof, or a protein having consensus sequences corresponding to the amino and/or carboxy terminus regions shared by E8, E46#1, and E46#2 of the invention. The screening method of the invention allows a presymptomatic diagnosis of the presence of S2, S7, S22, S23, C6.1, C6.2, S11, E8, E46#1, or E46#2 protein or DNA in individuals, and thus an opinion concerning the likelihood that such individual would develop or has developed ehrlichiosis. Early diagnosis is desired to maximize appropriate timely intervention.

In one preferred embodiment of the method of screening, a tissue sample would be taken from an individual, and screened for (1) the presence of the S2, S7, S22, S23, C6.1, C6.2, S11, E8, E46#1, or E46#2 DNA coding sequence; (2) the presence of S2, S7, S22, S23, C6.1, C6.2, S11, E8, E46#1, or E46#2 mRNA; (3) the presence of S2, S7, S22, S23, C6.1, C6.2, S11, E8, E46#1, or E46#2 protein; and/or (4) the presence of antibody to S2, S7, S22, S23, C6.1, C6,2, S11, E8, E46#1, or E46#2 protein.

A preferred method of detecting the presence of S2, S7, S22, S23, C6.1, C6.2, S11, E8, E46#1, or E46#2 protein and/or the presence of antibody to S2, S7, S22, S23, C6.1, C6.2, S11, E8, E46#1, or E46#2 protein comprises: a) contacting the sample with a polypeptide or antibody to a polypeptide having the amino acid sequence of S2, S7, S22, S23, C6.1, C6.2, S11, E8, E46#1, or E46#2, or a fragment thereof under conditions such that immunocomplexes form; and b) detecting the presence of the immunocomplexed antibody and polypeptide.

Individuals not infected with GE do not have GE S2, S7, S22, S23, C6.1, C6.2, S11, E8, to E46#1, or E46#2 DNA, mRNA, or protein.

The screening and diagnostic methods of the invention do not require that the entire S2, S7, S22, S23, C6.1, C6.2, S11, E8, E46#1, or E46#2 coding sequence be used for the probe. Rather, it is only necessary to use a fragment or length of nucleic acid that is sufficient to detect the presence of the S2, S7, S22, S23, C6.1, C6.2, S11, E8, E46#1, or E46#2 nucleic acid in a DNA preparation from an individual.

Analysis of nucleic acid specific to GE can be by PCR techniques or hybridization techniques (cf. *Molecular Cloning: A Laboratory Manual,* 2nd edition, edited by Sambrook, Fritsch, & Maniatis, Cold Spring Harbor Laboratory, 1989; Eremeeva et al., *J. Clin. Microbiol.* 32:803-810 (1994) which describes differentiation among spotted fever group *Rickettsiae* species by analysis of restriction fragment length polymorphism of PCR-amplified DNA). Nucleic acid probes used to analyze GE genomic DNA via PCR analysis have been described in Chen et al., *J. Clin. Microbiol.* 32:589-595 (1994).

XI. Vaccines

In another embodiment, the present invention relates to a vaccine comprising a GE S2, S7, S22, S23, C6.1, C6.2, S11, E8, E46#1, or E46#2 protein or a fragment thereof, or a protein having consensus sequences corresponding to the amino and/or carboxy terminus regions shared by E8, E46#1, and E46#2 (preferably, an immunologically active fragment) together with a pharmaceutically acceptable diluent, carrier, or excipient, wherein the protein is present in an amount effective to elicit a beneficial immune response in an animal to GE. S2, S7, S22, S23, C6.1, C6.2, S11, E8, E46#1, or E46#2 protein, or a protein having consensus sequences corresponding to the amino- and/or carboxy-terminus regions shared by E8, E46#1, and E46#2 may be obtained as described above and using methods well known in the art. An immunologically active fragment comprises an epitope-bearing portion of the protein.

In a further preferred embodiment, the present invention relates to a composition comprising a GE S2, S7, S22, S23, C6.1, C6.2, S11, E8, E46#1, or E46#2 protein or fragment thereof, or a protein having consensus sequences corresponding to the amino- and/or carboxy-terminus regions shared by E8, E46#1, and E46#2 (preferably, an immunologically reactive fragment-antigenic epitope, examples are listed in Table 1) and a carrier.

In another embodiment, the present invention relates to a vaccine comprising a GE S2, S7, S22, S23, C6.1, C6.2, S11, E8, E46#1, or E46#2 nucleic acid (preferably, DNA) or a to fragment thereof (preferably, a fragment encoding an immunologically active protein or peptide), or nucleic acid coding for a polypeptide, or a protein having consensus sequences corresponding to the amino- and/or carboxy-terminus regions shared by E8, E46#1, and E46#2 together with a pharmaceutically acceptable diluent, carrier, or excipient, wherein the nucleic acid is present in an amount effective to elicit a beneficial immune response in an animal to GE. S2, S7, S22, S23, C6.1, C6.2, S11, E8, E46#1, or E46#2 nucleic acid may be obtained as described above and using methods well known in the art. An immunologically active fragment comprises an epitope-bearing portion of the nucleic acid.

In a further preferred embodiment, the present invention relates to a composition comprising a GE S2, S7, S22, S23, C6.1, C6.2, S11, E8, E46#1, or E46#2 nucleic acid (preferably, DNA) or fragment thereof (preferably, encoding an immunologically reactive protein or fragment-antigenic epitope) and a carrier.

In a further preferred embodiment, the present invention relates to a method of producing an immune response which recognizes GE in a host comprising administering to the host the above-described composition.

In a preferred embodiment, the animal to be protected is selected from humans, horses, deer, cattle, pigs, sheep, dogs, and chickens. In a more preferred embodiment, the animal is a human or a dog.

In a further embodiment, the present invention relates to a method of preventing ehrlichiosis in an animal comprising administering to the animal the above-described vaccine, wherein the vaccine is administered in an amount effective to prevent or inhibit Ehrlichiosis. The vaccine of the invention is used in an amount effective depending on the route of administration. Although intranasal, subcutaneous or intramuscular routes of administration are preferred, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 μg of the S2, S7, S22, S23, C6.1, C6.2, S11, E8, E46#1, E46#2 protein, or a protein having consensus sequences corresponding to the amino and/or carboxy terminus regions shared by E8, E46#1, and E46#2 per kg body weight to 100 μg per kg body weight (preferably, 2 μg to 50 μg, 2 μg to 25 μg, 5 μg to 50 μg, or 5 μg to 10 μg).

Examples of vaccine formulations including antigen amounts, route of administration to and addition of adjuvants can be found in Kensil, *Therapeutic Drug Carrier Systems* 13:1-55 (1996), Livingston et al., *Vaccine* 12:1275 (1994), and Powell et al., *AIDS RES, Human Retroviruses* 10:5105 (1994).

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the vaccine has suitable solubility properties. The vaccines may be in the form of single dose preparations or in multi-dose flasks which can be used for mass vaccination programs. Reference is made to Remington's *Pharmaceutical Sciences*, Mack Publishing Co., Easton, Pa., Osol (ed.) (1980); and *New Trends and Developments in Vaccines*, Voller et al. (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (e.g., QS-21, U.S. Pat. No. 5,047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

The present invention is described in further detail in the following non-limiting examples.

EXAMPLES

The following Protocols A-G and experimental details are referenced in the non-limiting examples, Examples 1-16.

Protocol A: Cultivation of GE in HL60 Cells

The GE-infected HL60 cell line, USG3, was obtained by co-culturing HL60 cells (ATCC CCL 240) with blood cells from dogs challenged with field collected *Ixodes scapularis* ticks. After degenerative cell morphology became noticeable, the infected cells were passed over fresh to uninfected HL60 cells to maintain the culture. USG3 was grown in RPMI 1640 containing 10-20% heat-inactivated fetal bovine serum, 2 mM l-glutamine, 1 mM sodium pyruvate, 0.1 mM MEM non-essential amino acids and was split into fresh HL60 cells two to three times per week. This procedure is also outlined in Coughlin et al., PCT Application No. PCT/US96/10117 and has also been demonstrated by Goodman et al., *N. Eng. J. Med.* 334:209-215 (1996).

Protocol B: DNA Isolation

USG3 cultures at approximately 80% cell lysis (monitored microscopically) were centrifuged at 840×g for 15 min at 4° C. to remove host HL60 cell debris. The supernatant was filtered through a Poretics (Livermore, Calif.) 5 μm polycarbonate membrane, 47 mm in diameter, followed by a Poretics 3 μm filter under negative pressure. The USG3 filtrate was centrifuged at 9460×g in a Sorvall centrifuge for 30 min at 4° C. Following centrifugation, the GE pellet was resuspended in 5 ml 25 mM Tris, pH 8.0, 10 mM MgCl, and 0.9% NaCl. DNase I (Life Technologies, Gaithersburg, Md.) was added to a final concentration of 9 μg per ml and the solution was incubated for 15 min at 37° C. Following incubation, the DNase was inactivated by the addition of 0.5 ml of 0.5M EDTA and the GE was pelleted at 14,000×g in a Sorvall centrifuge for 30 min at 4° C.

Protocol C: Construction of the GE Genomic Library

Genomic DNA was isolated from purified GE using the QIAamp Genomic DNA kit (Qiagen, Chatsworth, Calif.) for library preparation (Stratagene, La Jolla, Calif.). The DNA was mechanically sheared to a 4-10 kb size range and ligated to EcoRI linkers. Linkered fragments were ligated into the EcoRI site of Lambda Zap II and the library was amplified in *E. coli* strain XL1-Blue MER' to a titer of $10^{10}$ Pfu/ml.

Protocol D: Preparation of the Screening Sera

Dog sera: Adult *Ixodes scapularis* ticks collected from regions of the eastern United States having a high incidence of human Lyme disease were applied to dogs as described (Coughlin et al., *J. Infect. Dis.* 171:1049-1052 (1995)). Sera from the dogs was tested for immunoreactivity to *E. equi* by an immunofluorescence assay. Positive sera from infected dogs was pooled and used for immuno screening of the GE genomic library.

Mouse sera: Proteins contained in SDS-disrupted whole GE were separated by SDS-PAGE and forty-six individual bands were excised from each of two gels, 10% and 15% acrylamide. Each gel fragment was mashed, added to buffer and Ribi adjuvant and used to immunize two mice. Sera with similar immuno reactivity patterns against GE antigen as determined by Western blot were pooled into 4 groups: A, B, C, and D.

Goat sera: Mixtures of 100 μg of purified heat-inactivated USG3 antigen were used to immunize goats. Goats received three subcutaneous doses of antigen at bi-weekly intervals. Serum was collected two weeks following the third immunization and used for immunoscreening of the GE genomic DNA library.

Protocol E: Screening of the GE Genomic DNA Library

Bacteriophage were diluted and plated with XL1-Blue MRF cells on NZY agar plates. Plates were prepared giving approximately 50,000 plaques per plate. Phages were induced to express cloned protein with 10 mM IPTG (Sigma, St. Louis, Mo.) and transferred to nitrocellulose filters. For immuno screening, filters were blocked in TBS (25 mM Tris HCl, pH 7.5, 0.5 M NaCl) containing 0.1% polyoxyethylene 20 cetyl ether (Brij 58) and incubated with pooled dog sera, pooled mouse sera, or pooled goat sera. The filters were washed and then reacted with anti-dog HRP conjugated antibody, anti-mouse HRP conjugated antibody, or anti-goat HRP conjugated antibody. The filters were washed again and developed with 4-chloronapthol (Bio-Rad).

Positive plaques were isolated, replated and rescreened twice to achieve purity. Plasmid DNA containing the putative recombinant clones was obtained by plasmid rescue (Strategene, La Jolla, Calif.).

Protocol F: DNA Analysis

Restriction enzyme analysis: Standard techniques were followed according to the protocols of Sambrook et al., *Molecular Cloning* (2nd ed.), Cold Spring Harbor Laboratory Press, New York (1989)).

DNA sequencing and sequencing analysis: DNA sequencing of recombinant clones was performed using the primer walking method and an ABI 373A DNA sequencer (ACGT, Northbrook, Ill.; Lark Technologies, Houston, Tex.; and Sequegen, Shrewsbury, Mass.). Sequences were analyzed by using the MacVector (Oxford Molecular Group) sequence analysis program, version 6.0. The BLAST algorithm, D version 1.4, was used to search for homologous nucleic acid and protein sequences available on the National Center for Biotechnology Information (NCBI) server.

PCR amplification of target sequences: DNA oligonucleotide primer sets were designed based on sequencing information from each individual clone. PCR primers were synthesized by Life Technologies (Gaithersburg, Md.). Templates for PCR were either purified plasmid DNA, purified GE or HL60 genomic DNA, or phage lysates. All reactions were performed using a GeneAmp 9600 thermal cycler (Perkin-Elmer, Conn.), GenAmp reagents from Perkin-Elmer, and TaqStart antibody (Clontech, Calif.). The cycling program consisted of 30 cycles, each of 30 s at 94° C., 30 s at 48° C. to 55° C., and 1 min at 72° C., and an additional cycle of 10 min at 72° C. PCR products were analyzed on 4% Nusieve 3:1 agarose gels (FMC Bioproducts, Rockland, Me.).

Protocol G: Protein Isolation and Analysis

Overnight cultures of individual clones were diluted 1:25 into TP broth (per liter: 20 g bactotryptone, 2 g Na$_2$HPO$_4$, 1 g KH$_2$PO$_4$, 8 g NaCl, 15 g yeast extract) and grown at 37° C. until an OD$_{600}$ of 0.5 to 1 was reached. A 1.5 ml aliquot of culture was harvested. IPTG was added to a concentration of 5 mM and growth was continued for 3 hours at 37° C. The OD$_{600}$ was read and each culture was pelleted. Pellets were resuspended in 5× Laemmli buffer (12% glycerol, 0.2M Tris-HCl, pH 6.8, 5% SDS, 5% (β-mercaptoethanol) at 200 μl per 1 OD unit. In the alternative, harvested GE protein preparations were pelleted and resuspended in 0.4% SDS, 12.5 mM Tris, pH 6.8 and heated at 90-100° C. for 20 min. For cell lysis, 50 μl of a cocktail consisting of RNase (33 μg/ml) and aprotinin (0.2 mg/ml) and 9 μl of DNase (0.17 mg/ml) was added per 5 mg of GE. 20 μl of 25× Boehringer/Mannheim protease inhibitor cocktail (Cat. #1697498) was added per 0.5 ml cell suspension and 2 μl of a PMSF solution (1M in DMSO) was added just prior to cell disruption. Cells were disrupted in 30 second intervals for a total of 3 min in a mini-beadbeater cell disrupter, Type BX-4 (BioSpec), agitated at room temperature for 30 min and centrifuged at 15,000×g for 10 min. The pellet was suspended in Laemmli sample buffer and adjusted to 1.4 mg SDS/mg protein. Samples were boiled and 10 μl of each were electrophoresed on SDS-PAGE gels.

For Western blot analysis, gels were transferred to nitrocellulose filters, the filters were blocked in TBS/Brij 58 and the blots were probed with antisera. Blots were then washed and incubated with HRP conjugated secondary antibody. After a final washing step, blots were to developed with 4-chloronapthol (Bio-Rad, Hercules, Calif.) or detected using enhanced chemiluminescence (Pierce, Rockford, Ill.).

Example 1

PCR Amplification and Cloning of GE 16S rDNA

GE was cultivated in HL60 cells as described in Protocol A (supra). Cell extracts were prepared by lysis protocols as described supra, PCR primers (specific for the 16S ribosomal DNA of the genogroup comprising *E. equi, E. phagocytophila*, and the HGE agent used to amplify DNA from the cell extracts) were modified to include restriction enzyme recognition sites as follows:

```
forward primer,
                                        (SEQ ID NO: 40)
5'-CTGCAGGTTTGATCCTGG-3' (PstI site);

reverse primer,
                                        (SEQ ID NO: 41)
5'-GGATCCTACCTTGTTACGACTT-3' (BamHI site),
```

These primers (0.5 μM) were added to a 100 μl reaction mixture containing IX PCR buffer II (Perkin-Elmer Corp), 1.5 mM MgCl$_2$ (Perkin-Elmer Corp.), 200 μM each dATP, dGTP, dCTP and dTTP, 2.5 U of Amplitaq DNA polymerase and 20 μl of USG3 DNA. Amplification was performed as described in Protocol F. The amplified 1500 bp fragment was digested with Pst I and Bam HI and ligated to pUC19 linearized with the same enzymes. The resulting clone, pUCHGE16S, was sequenced.

Example 2

Isolation of Clones Using Canine Sera

Figure 2:
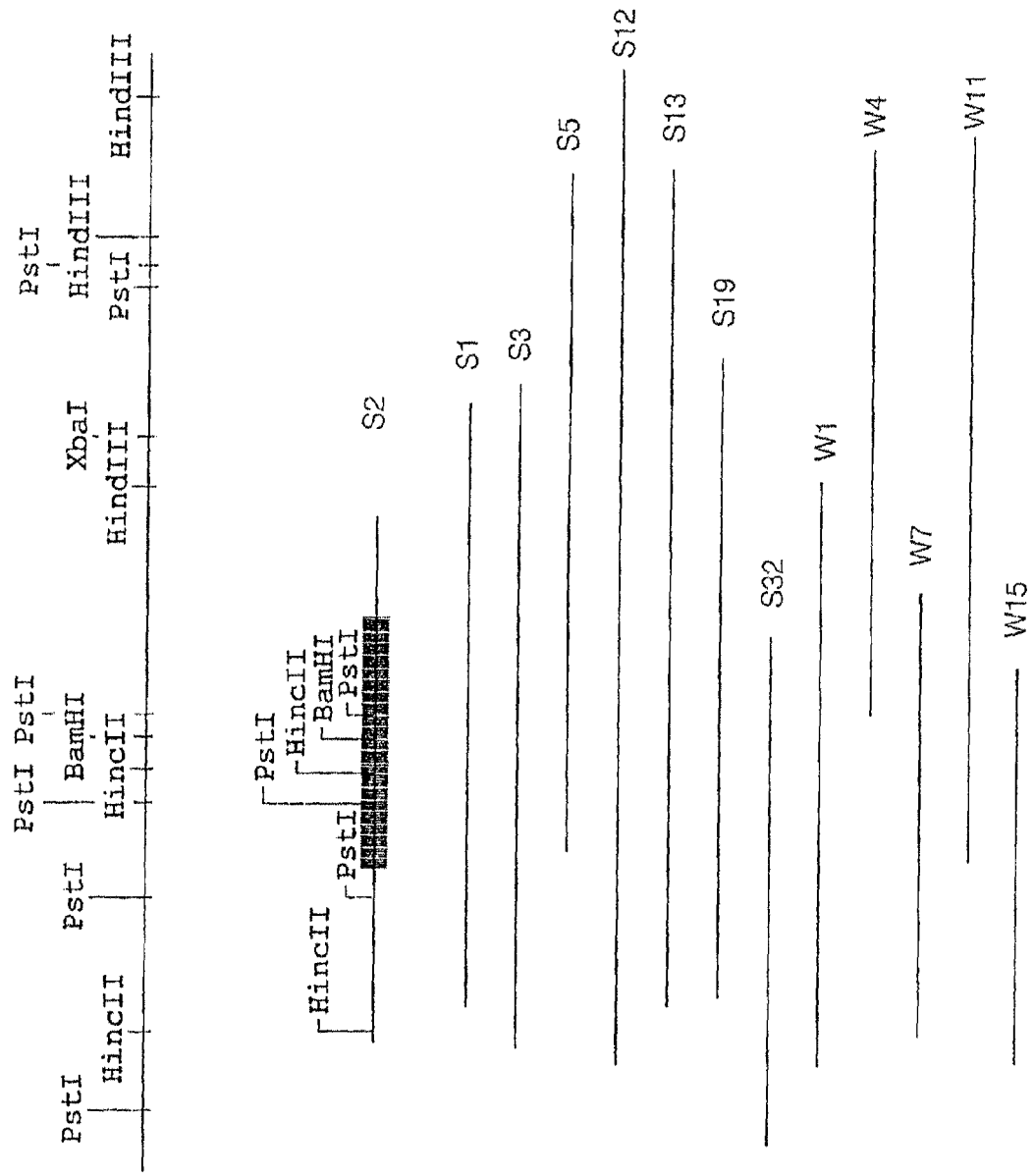
FIG. 2. Restriction enzyme map of group II clones. Individual group II clones are depicted as described in the legend for FIG. 1. S2 is the representative clone for this group and the open reading frame is indicated by the black box.
Figure 3:
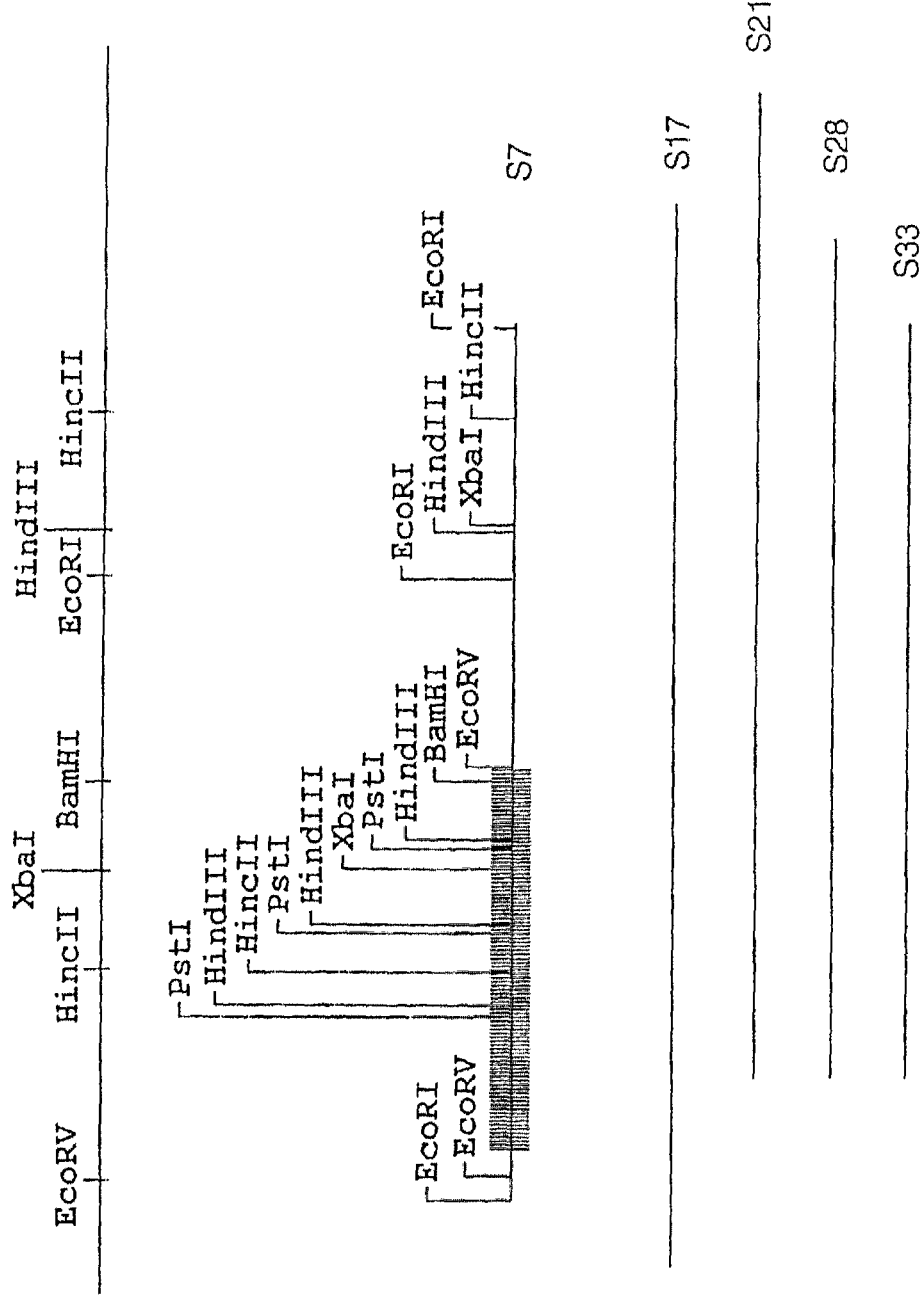
FIG. 3. Restriction enzyme map of group III clones. Individual group III clones are depicted as described in the legend for FIG. 1. S7 is the representative clone for this group and the open reading frame is indicated by the black box.

Western blot analysis of the individual recombinant plasmid was performed as described in Protocol G using canine sera prepared as described in Protocol D or a 1:1000 dilution of human sera prepared from two convalescent-phase sera from patients (No. 2 and 3, New York, kindly provided by Dr. Aguero-Rosenfeld) and from an individual in Wisconsin who was part of a seroprevalence study (No. 1, kindly provided by Dr. Bakken). Blots were washed and incubated with biotin-labeled goat anti-dog IgG (Kirkegaard & Perry Laboratories, Inc., Gaithersburg, Md.) followed by peroxidase labeled streptavidin (Kirkegaard & Perry Laboratories, Inc., Gaithersburg, Md.) or HRP conjugated anti-human IgG (Bio-Rad, Hercules, Calif.). After several additional washes, the dog sera blots were developed with 4-chloronapthol to (Bio-Rad, Hercules, Calif.). Over 1000 positive clones were identified. Three hundred of these clones (both strong (S) and weak (W) immunoreactivity) were further purified by a secondary screen of the library. From this group, 48 clones were purified as single plaques by a third immunoscreening. Plasmids were rescued according to the Stratagene protocol and DNA was purified using Qiagen plasmid purification kits. Of the original forty-eight clones, seven were not able to be analyzed due to lack of sufficient DNA. A number of restriction digests were performed on each clone to assess their relatedness. Single enzyme digests were performed with EcoRI, IlindIII, BamIII, IIincII, XbaI, PstI and A1w26I and in some cases a number of double digests were done. Based on these digests restriction maps were generated and most of the clones could be placed into one of three groups—designated groups I, II and III. FIGS. 1-3 show the structures of the three groups based on the restriction enzyme analysis. Another five clones had lost the insert during the plasmid rescue and were not grouped.

Example 3

Characterization of Representative Clones S2, S7, S22, and S23

A representative clone was chosen for further characterization from each of the three groups (see Example 2, supra). These clones, S2, S7, and S22, were sequenced according to Protocol F. S23 was also sequenced since it did not appear to fall into one of these groups. The complete nucleic acid sequence of each of these clones is shown as follows: FIG. 4, group I (S22); FIG. 6, group II (S2); FIG. 8, group III (S7); FIG. 10, (S23). Sequence analysis (Mac Vector, Oxford Molecular Group) showed that each clone contained a single large open reading frame encoded by the plus strand of the insert and each one appeared to be a complete gene. The amino acid sequences encoded by each clone are shown in FIG. 5 (S22), FIG. 7, (S2), and FIG. 9 (S7), and FIG. 11 (S23). There are also two additional small open reading frames in the S23 DNA insert, one on the negative strand and the other on the positive strand. A comparison of the DNA sequences of the 4 clones revealed that S23 is a group I clone which is missing a stretch of nucleotides in S22 containing two EcoRI sites. The nucleotide sequences of the genes described here have been assigned the following GenBank accession numbers: GE ank (GE 160), AF020521; GE rea (GE 130), AF020522; GE gra (GE 100), AF020523. Further sequence analysis of the four clones showed that all of them contain regions of repeated amino acids.

FIG. 12 represents a schematic diagram of the S22 and S23 proteins and the repeat to regions within those proteins. Similarly, FIG. 13 shows the repeat regions of the S2 and S7 proteins in a schematic diagram Amino acid sequence analysis of the proteins encoded by the three gene clones S22, S2, and S7, showed that all contain regions of repeated amino acids. A schematic version of these repeat structures is shown in FIGS. 14 and 15. The S2 encoded protein (160 kDa) has three groups of repeats. The first set consists of a number of ankyrin-like repeat units of 33 amino acids, the second consists of repeat units of 27 amino acids, and the third consists of repeat units of 11 amino acids. The ankyrin repeats were revealed by a BLAST database search for protein homologies. Ankyrin repeats occur in at least four consecutive copies and are present in yeast, plants, bacteria, and mammals. FIG. 14 shows a multiple alignment of the S2 encoded protein (160 kDa) ankyrin repeats under a consensus sequence derived from the analysis of several hundred similar ankyrin-like motifs. The eighth repeat sequence holds to the consensus only through the first half of the repeat unit and may not represent a full ankyrin-like repeat.

Figure 15A:
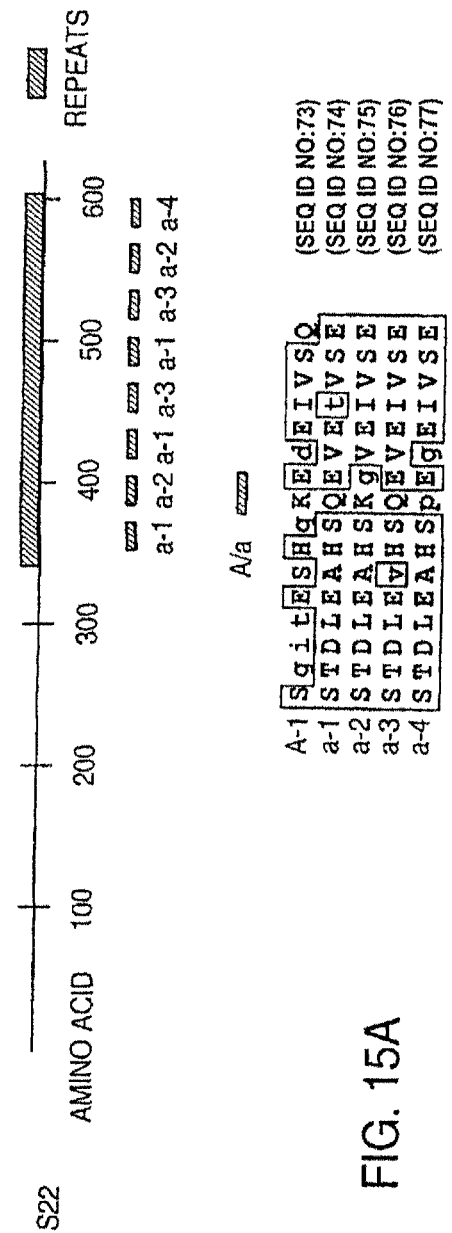
FIG. 15A shows the amino acid alignments of a sequence which occurs 4 times in the *E. chaffeensis* protein (top line of alignment, A-I) and 8 times in the GE 130 kDa protein (a-1 to a-4). Sequence a-1 is repeated 3 times, related sequences a-2 and a-3 are each repeated twice, and related sequence a-4 is found once. The position of these sequences in the proteins is indicated by the small bold lines.

The S22 encoded protein (130 kDa) has a repeat unit of 26 to 34 amino acids which occurs eight times in the carboxy-terminal half of the protein (See FIG. 15). The sequence varies somewhat from repeat to repeat. A database homology search with the NCBI BLAST algorithm revealed that the S22 encoded protein has limited homology to the *E. chaffeensis* 120 kDa protein. An amino acid sequence alignment of a motif common to both proteins is shown in FIG. 15A. This motif is represented by a bold line and occurs four times in an identical fashion in the *E. chaffeensis* protein (designated A-1) and eight times with four variations in the 130 kDa protein (a-1, a-2, a-3, and a-4).

Figure 15B:
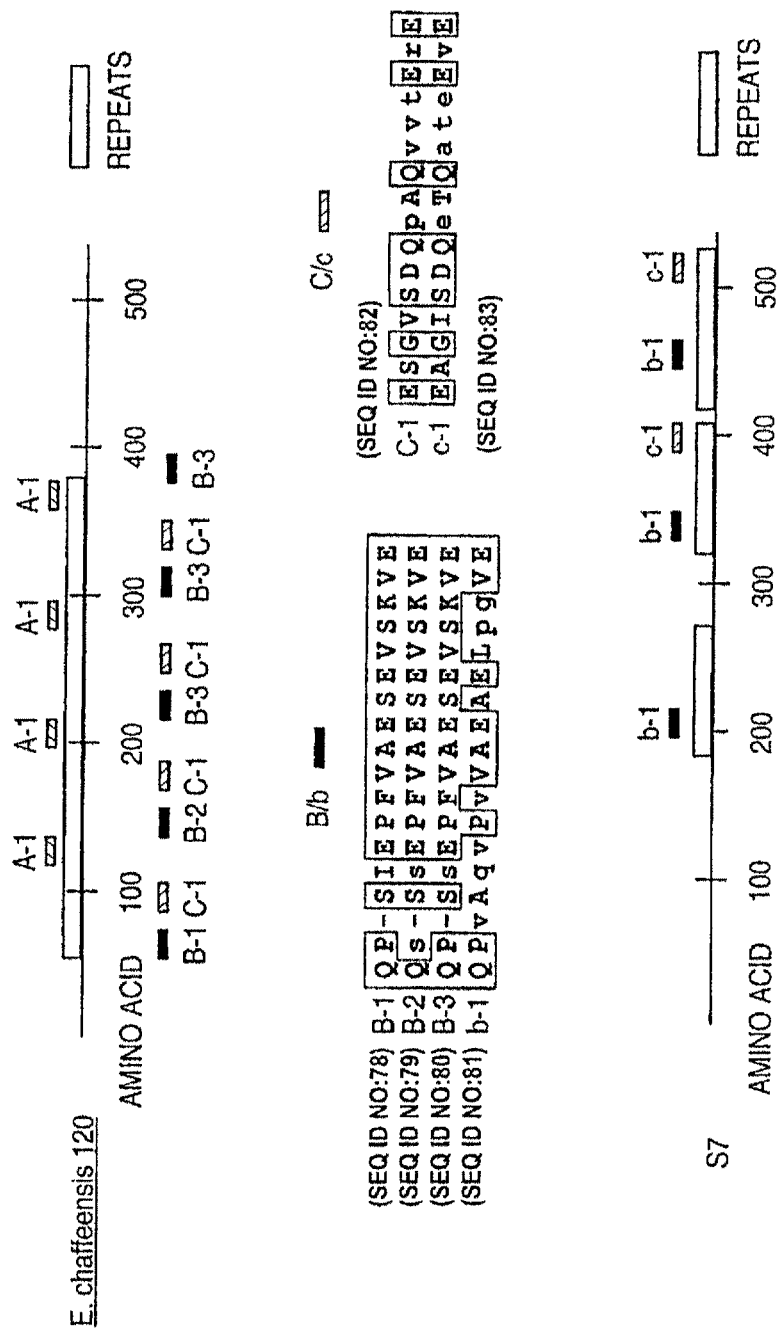
FIG. 15B shows the amino acid alignments of two different sequence motifs which occur in the *E. chaffeensis* 120 kDa protein (B-1 to B-3 and C-1) and the GE 100 kDa protein (b-1 and c-1). Bold and cross-hatched boxes indicate the position of these sequences in the proteins. Identical amino acids are surrounded by boxes and conserved amino acids are in capital letters.

The S7 encoded protein (100 kDa) has three large repeat units, which differ somewhat in length (See FIG. 15). A database search revealed that it is similar to the 120 kDa *E. chaffeensis* protein, which contains four repeats of 80 amino acids each. Both proteins contain large amounts of glutamic acid: 18% for the 100 kDa protein and 17% for the 120 kDa protein. When the two protein sequences are aligned, most of the homology occurs in the repeat regions. FIG. 15B shows alignments for two homologous groups of amino acid motifs from the two proteins (designated B/b and C/c) found with the BLAST algorithm. These are not the only possible alignments of the two proteins but do provide an example of their similarities. The locations of the homologous sequences are indicated by bold or hatched lines above (S7 encoded 100 kDa protein) or below (*E. chaffeensis* 120 kDa protein) the respective proteins. The B sequence represented by the bold line varies slightly in the *E. chaffeensis* protein (shown as B-1, to B-2, and B-3) and occurs a total of five times. The S7 encoded protein equivalent, b-1, is invariant and occurs three times. The sequence represented by the hatched line occurs four times in *E. chaffeensis* 120 kDa (C-1) and two times in S7 (C-1).

Figure 16A:
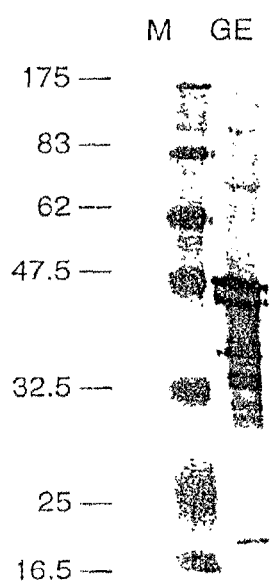
FIG. 16. Western blot analysis of: A) Purified USG3 disrupted in SDS (lane GE). B) Individual recombinant clones of GE 100 kDa (S7), GE 160 kDa (S2), GE 130 kDa (S22), and a negative control (NEG, no insert), were grown and incubated with IPTG to induce protein expression according to Materials and Methods. Samples of each were electrophoresed on SDS-PAGE gels and transferred to nitrocellulose for Western blotting. Blots were probed with convalescent dog sera. Molecular weight markers (in kilodaltons) are shown to the left of each figure.
Figure 16B:
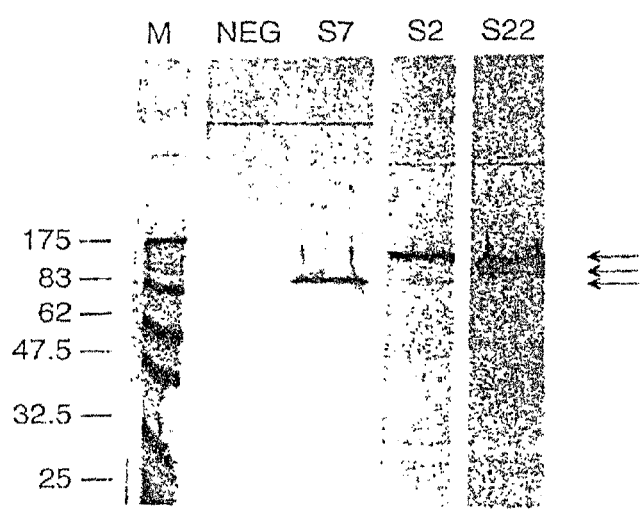
Figure 17:
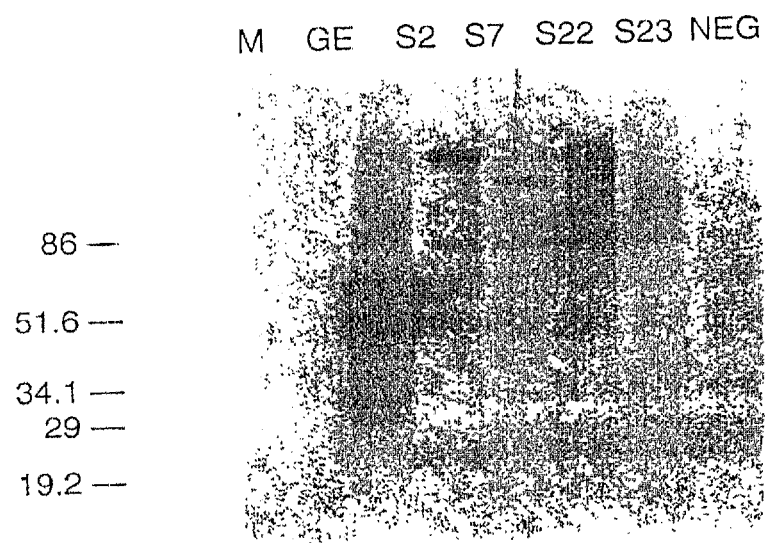
FIG. 17. Western blot analysis of S2, S7, S22, and S23 proteins. Individual recombinant clones of S2, S7, S22, S23, and a negative control were grown and induced by IPTG to induce protein expression. Samples of each were electrophoresed on a SDS-PAGE gel and transferred to nitrocellulose for Western blotting. SDS-disrupted GE was used as a positive control. The blot probed with convalescent dog sera and samples are indicated at the top of the gel. Molecular weight markers (in kilodaltons) are shown to the left of each figure.

Samples of recombinant clones were induced to express the encoded protein and bacterial extracts were prepared for SDS-PAGE as outlined in Protocol G. FIG. 16 shows a Western blot containing samples of S2, S7, S22, and FIG. 17 shows a western blot also containing a sample of S23. SDS-disrupted whole GE was used as a positive control and a non-protein expressing clone was run as a negative control Immunoreactive proteins for all 4 clones were detected by the dog sera. The same proteins were also detected when the blots were probed with sera obtained from a human patient with GE, as evident in FIG. 18. The blots were probed with human antisera. Based on the amino acid sequences of these proteins, the calculated molecular weights are significantly lower than the apparent molecular weights by SDS-PAGE. The calculated (based on the amino acid sequence) and apparent (based on mobility in SDS-PAGE) molecular weights of each protein encoded by the open reading frames of the listed clones are compared in Table 4. This phenomenon has been observed in other proteins (see Barbet et al., *Infect. Immun.* 59:971-976 (1991); Hollingshead et al., *J. Biol. Chem.* 267:1677-1686 (1986); Yu et al., *Gene* 184:149-154 (1997)).

TABLE 4

| Clone | Calculated Molecular Weight | Apparent Molecular Weight |
|---|---|---|
| S2 | 78 kDa | 160 kDa |
| S7 | 61 kDa | 100 kDa |
| S22 | 66 kDa | 130 kDa |
| S23 | 52 kDa | 90 kDa |

Example 4

Verification that Clones S2, S7, S22, and S23 are GE Derived by PCR Analysis PCR primer sets were designed based on the sequences of each of the three GE clones and are as described in Table 5. The sequences of each primer set indicated in Table 5 were used to amplify regions of the listed clones (SEQ ID NOS: 47-52). Each oligonucleotide sequence is shown in the 5' to 3' orientation. Each 50 µl reaction contained 0.5 µM of each primer, IX PCR Supermix (Life Technologies, Gaithersburg, Md.) and either 100 ng USG3 DNA, 100 ng HL60 DNA or 200 ng plasmid DNA. PCR amplification was performed as to described in Protocol F.

TABLE 5

| Clone | Forward Primer | Reverse Primer |
|---|---|---|
| S22 | CACGCCTTCTTCTAC (SEQ ID NO: 42) | CTCTGTTGCTATAGGGGC (SEQ ID NO: 43) |
| S7 | GATGTTGCTTCGGGTATGC (SEQ ID NO: 44) | CAGAGATTACTTCTTTTTGCGG (SEQ ID NO: 45) |
| S2 | GCGTCTCCAGAACCAG (SEQ ID NO: 46) | CCTATATAGCTTACCG (SEQ ID NO: 47) |

Figure 19A:
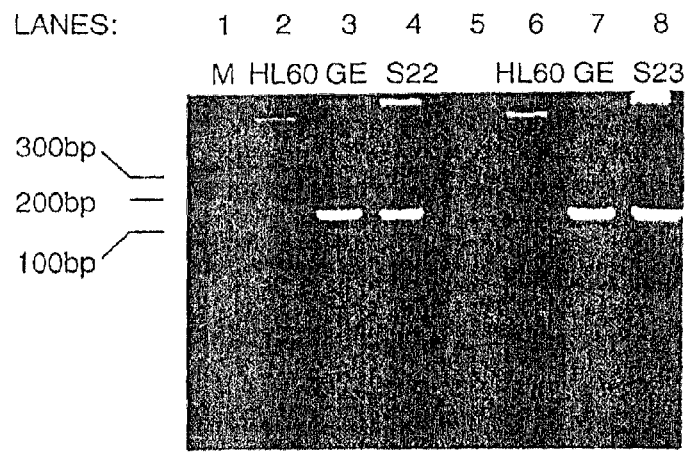
FIG. 19. PCR analysis of groups I, II and III. PCR reactions were performed and the products analyzed using 4% Nusieve gels. Primer sequences are listed in Table 5. A) S22 primers were used to amplify a 159 bp region of S22 DNA using as templates: S22 plasmid DNA (lane 4), S23 plasmid DNA (lane 8), HL60 DNA (lanes 2 and 6) and GE DNA (lanes 3 and 7). B) S2 primers were used to amplify a 395 bp region of S2 DNA using as templates: S2 plasmid DNA (lanes 4 and 5), HL60 DNA (lane 2) and GE DNA (lane 3). C) S7 primers were used to amplify a 643 bp region of S7 DNA using as templates: S7 plasmid DNA (lane 3), HL60 DNA (lane 4) and GE DNA (lane 2). DNA molecular weight markers (50-1000 bp, FMC) are present in lane 1 of each figure.
Figure 19B:
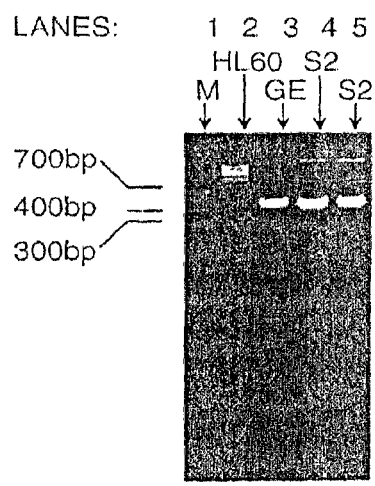
Figure 19C:
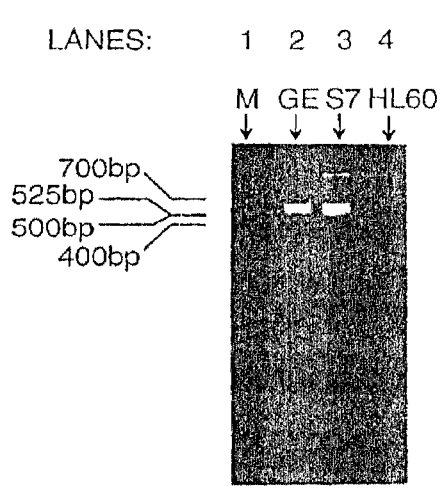
Figure 20:
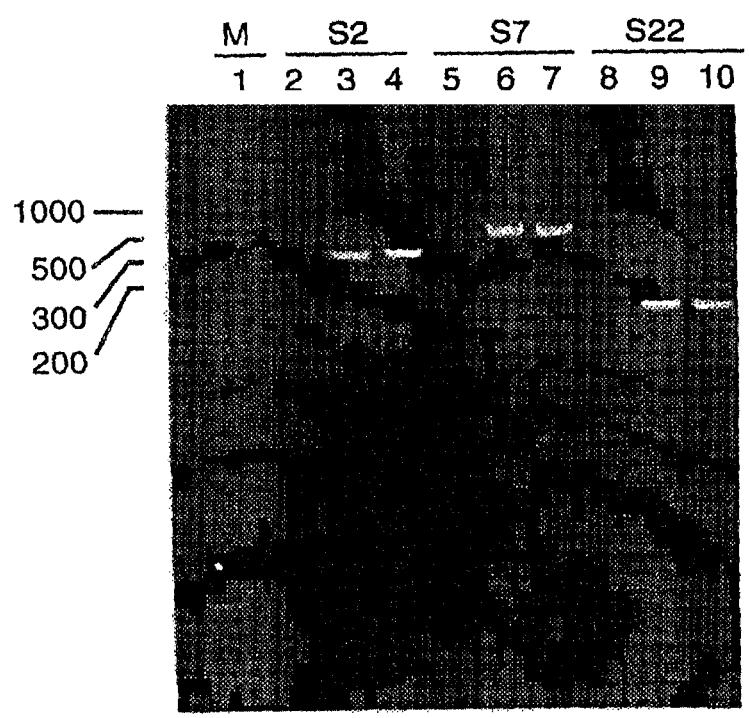
FIG. 20. PCR analysis of GE genes. PCR reactions were performed as described in Materials and Methods and the products analyzed using 4% Nusieve gels. S2 primers were used to amplify a 395 bp region of S2 DNA using as templates: HL60 DNA (lane 2), S2 plasmid DNA (lane 3), and USG3 DNA (lane 4). S7 primers were used to amplify a 643 bp region of S7 DNA using as templates: HL60 DNA (lane 5), S7 plasmid DNA (lane 6), and USG3 DNA (lane 7). S22 primers were used to amplify a 159 bp region of S22 DNA using as templates: HL60 DNA (lane 8), S22 plasmid DNA (lane 9), and USG3 DNA (lane 10). DNA molecular weight markers (50-1000 bp, FMC, Rockland, Me.) are present in lane 1.

These experiments established that the sequenced genes were derived from GE DNA and not HL60 DNA, and allowed the elimination of duplicate clones prior to plasmid rescue and DNA isolation by using them in PCR of phage lysates. Primer pairs specific for S22/S23, S2 and S7 were used in separate PCR reactions to amplify three different templates: GE DNA, HL60 DNA, or the purified plasmid DNA of each clone. FIGS. 19 and 20 show the results obtained for primers of S22, S23, S2, and S7 using the PCR conditions outlined above. All three clones were specific to GE and were not present in HL60 DNA. In each case the size of the PCR product using genomic DNA as a template was the same as that generated by purified plasmid DNA.

Example 5

Further Characterization of Isolated GE Clones

The same primer pairs (supra) were also used to confirm or establish the identity of each purified phage stock from all 48 clones derived from the library screening with the dog sera. Every isolate, with one exception (W20), was either a group I, II, or III clone, as evident in Table 6 below. Clones were isolated by immunoscreening with convalescent dog sera. Each clone is classified as a group I, II or III clone based on PCR with primers specific for the group I, II or III DNA sequences. Clone W20 was the only clone different from the other 3 groups.

TABLE 6

| Clone Name | Group |
|---|---|
| S1 | II |
| S2 | II |
| S3 | II |
| S5 | II |
| S6 | III |
| S7 | III |
| S8 | I |
| S9 | I |
| S10 | I |
| S11 | I |
| S12 | II |
| S13 | II |
| S14 | I |
| S19 | II |
| S22 | I |
| S23 | I |
| S24 | I |
| S25 | I |
| S27 | I |
| S32 | II |
| W1 | II |
| W2 | I |
| W3 | I |
| W4 | I |
| S16 | III |
| S17 | III |
| S18 | I |
| S20 | III |
| S21 | III |
| S28 | III |
| S30 | II |
| S33 | III |
| W5 | II |
| W7 | II |
| W8 | I |
| W9 | III |
| W10 | III |
| W11 | I |
| W13 | I |
| W14 | I |
| W15 | II |
| W16 | III |
| W17 | I |
| W18 | I |
| W19 | III |
| W20 | — |
| W21 | I |
| W22 | III |

Example 6

Isolation of Clones Using Murine Sera

Four different pools of sera (designated A, B, C, and D) obtained from mice immunized with gel band samples of GE protein (Protocol D) were used to screen the GE genomic DNA library. Twenty-six clones were plaque purified and used for further analysis. These were designated A1, A2, A8, A11, A14, A16; B1, B3, B6, B8, B9, B12; C1, C3, C5, C6, C7, C10, C11; D1, D2, D7, D8, D9, D11, and D14. Plasmid DNA was rescued from each clone and restriction analyses were performed. Several of the clones (A14, B12, C3, C5, D1, D2, D9 and to D11) had no insert. Of the remaining clones, nine could be placed into one of two groups due to similarities in their restriction enzyme patterns. The first group included all of the C clones and the second group consisted of all of the D clones plus B3. Some of the other clones were not grouped at this stage due to lack of sufficient DNA.

Example 7

Characterization of Representative Clone C6

One representative clone from the C group (C6) was selected for DNA sequencing. The insert of 2.7 kb contained two open reading frames (designated C6.1, C6.2, and whose amino acid sequences are given in FIGS. 21 and 22, respectively) on the plus strand which were separated by 9 nucleotides (FIG. 23). A search of the protein/nucleotide databases revealed that the first amino acid sequence (C6.1) has significant homology to dihydrolipoamide succinyltransferase, an enzyme involved in the oxidative decarboxylation of pyruvate and 2-oxoglutarate (Spencer et al., *Eur. J. Biochem.* 141:361-374 (1984)). The second amino acid sequence (C6.2) is homologous to a methionine aminopeptidase found in several types of bacterial species.

Figure 24:
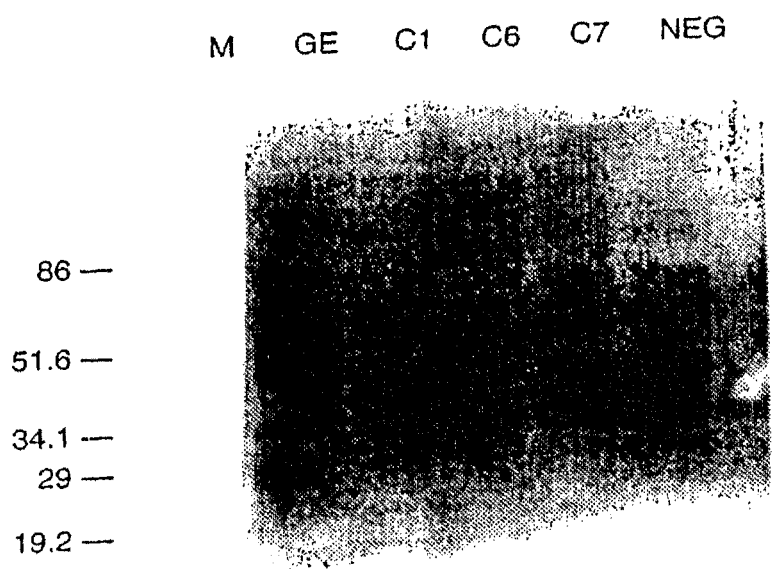
FIG. 24. Western blot analysis of three C clones. Individual recombinant clones of C1, C6, and C7 were grown and induced by IPTG to induce protein expression according to Materials and Methods. Samples of each were electrophoresed on SDS-PAGE gels and transferred to nitrocellulose for Western blotting. SDS-disrupted GE was used as a positive control. The blot was probed with vaccinated mouse "C" sera. Samples are indicated at the top of the gel. Molecular weight markers (in kilodaltons) are shown to the left of the figure.

Clones, C1, C6, and C7, were induced to express the encoded protein and bacterial extracts were prepared for SDS-PAGE. FIG. 24 shows a Western blot of these samples electrophoresed next to SDS-disrupted whole GE. The immune mouse serum designated "C" was used to probe the blot. All three recombinant clones expressed a protein of the same molecular weight, about 50 kDa. The calculated molecular weights of C6.1 and C6.2 are 44 kDa and 29 kDa, respectively. Thus, based on size, C6.1 is more likely to be the expressed recombinant protein detected by immunoscreening.

DNA sequencing also revealed that the group of clones consisting of all of the D clones and the B3 clone contained an open reading frame for a protein with homology to the heat shock protein hsp70.

Based on the DNA sequences of each clone, PCR primers were designed to amplify specific regions of each open reading frame contained in C6. The primers used were as follows:

```
forward primer for C6.1:
                                        (SEQ ID NO: 48)
5'-CAGGCAGTGAGCACTCAAAAACC-3';

reverse primer for C6.1:
                                        (SEQ ID NO: 49)
5'-GCGACTCCAATGTTACAATAGTCCC-3';

forward primer for C6.2:
                                        (SEQ ID NO: 50)
5'-TGTGATCCTCGATGGTTGGC-3';

reverse primer for C6.2:
                                        (SEQ ID NO: 51)
5'-CCCTCCTGAATCGTAACATCATCC-3'.
```

Figure 25:
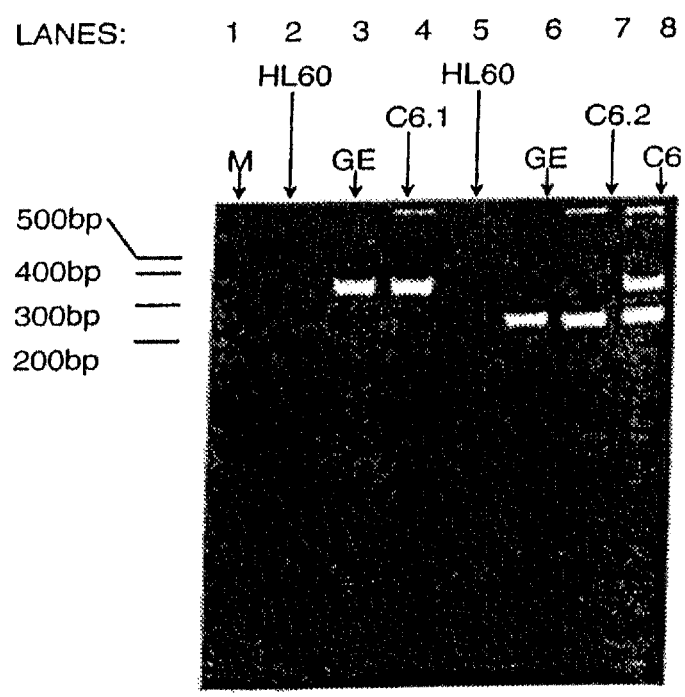
FIG. 25. PCR analysis of C6. PCR reactions were performed and the products analyzed using 4% Nusieve gels. Primer sequences are listed in Table 5. C6.1 primers (from the first open reading frame, lanes 2, 3, 4) were used to amplify a 500 bp region of C6 DNA using as templates: C6 plasmid DNA (lane 4), HL60 DNA (lane 2) and GE DNA (lane 3). C6.2 primers (from the second open reading frame, lanes 5, 6, 7) were used to amplify a 300 bp region of C6 DNA using as templates: C6 plasmid DNA (lane 7), HL60 DNA (lane 5) and GE DNA (lane 6). Both primer sets were also used together in the same PCR reaction using C6 plasmid DNA as template (lane 8). DNA molecular weight markers (50-1000 bp, FMC) are present in lane 1.

FIG. 25 shows the results obtained with each primer pair using GE DNA, HL60 DNA or the C6 plasmid DNA as templates in a PCR reaction. Both primer sets amplified a region of the expected size using GE or plasmid templates but not the HL60 template. Thus both C6 genes are GE specific.

The C6 primers were also used to amplify phage lysates from each of the other twenty-five clones isolated using the immune mouse sera. In addition to all of the C clones, the C6.1 and C6.2 genes were also found in A1, A11, A14 and A16.

The following examples (Examples 8-15) all relate to the characterization of the GE immunoreactive protein in the 42-45 kDa molecular mass range.

Example 8

SDS-PAGE and Peptide Sequencing of Immunoreactive Proteins

To characterize the GE proteins in the 42 to 45 kDa range, a 50 µl of a cocktail consisting of RNase (33 µg/ml) and aprotinin (0.2 mg/ml) and 9 µl of DNase (0.17 mg/ml) was added per 5 mg of USG3 pellet in 2 mM $MgCl_2$, 50 mM Tris-HCl, pH 7.5 buffer. Twenty µl of 25× Boehringer/Mannheim protease inhibitor cocktail was added per 0.5 ml cell suspension and 2 µl of a PMSF solution (1M in DMSO) was added just prior to USG3 disruption. Cells were disrupted in 30 second intervals for a total of 3 min in a mini-beadbeater cell disrupter, Type BX-4 (BioSpec), agitated at room temperature for 30 min and centrifuged at 15,000×g for 10 min. The pellet was suspended in Laemmli sample buffer and adjusted to 1.4 mg SDS per mg protein, and heated at 90-100° C. for 5 min. The protein concentration was determined by BCA to assay (Pierce Chemical Co., Rockford, Ill.). Electrophoresis was performed on a 15% SDS-PAGE gel and proteins were transferred onto a 0.2 µm PVDF membrane. Half of the blot was probed with anti-GE dog sera (6) and the other half was stained with Ponceau S. Two protein bands which matched the molecular mass of the two most immunoreactive bands on the Western blot (43 and 45 kDa) were excised. A portion of each band was used for direct N-terminal sequencing. The remaining material was digested with trypsin in situ and individual peptides were separated by RP-HPLC on a ZORBAX C18 (1 mm×150 mm) column The peptides were analyzed and screened by MALDI-TOF mass spectrometry. Sequencing of peptides was performed by Edman degradation (Harvard Microchemistry, Cambridge, Mass.). An N-terminal peptide and two internal peptides were obtained for each protein (Table 7).

TABLE 7

| Peptide Sequences from Transblotted GE Proteins | | | |
|---|---|---|---|
| | N-terminal (N) Or Internal (I) | Homology to A. marginale MSP-2 | Location |
| 45 kDa | | | |
| HDDVSALETGGAGYF[a] (SEQ ID NO: 66) | N | no | MSP-2A, MSP-2C (1)[b] |
| SGDNGSLADYTDGGASQTNK (SEQ ID NO: 67) | I | no | MSP-2A |
| AVGVSHPGIDK (SEQ ID NO: 68) | I | no | MSP-2A, MSP-2C(2) |

TABLE 7-continued

Peptide Sequences from Transblotted GE Proteins

| | N-terminal (N) Or Internal (I) | Homology to A. marginale MSP-2 | Location |
|---|---|---|---|
| 43 kDa | | | |
| HDDVSALETGGAGYF (SEQ ID NO: 66) | N | no | MSP-2A, MSP-2C(1) |
| FDWNTPDPR (SEQ ID NO: 69) | I | yes | MSP-2A, MSP-2C |
| LSYQLSPVISAFAGGFYH (SEQ ID NO: 70) | I | yes | MSP-2A, MSP-2B(1) |

<sup>a</sup>Amino acids are shown using the single letter code
<sup>b</sup>Numbers in parentheses indicate the number of amino acid changes from the sequence shown.

The results show that the amino-terminal peptides from the two proteins are identical. A BLAST homology search showed that two of the internal peptides from the 43 kDa protein were homologous to the MSP-2 proteins of *Anaplasma marginale*, a rickettsial hemoparasite of livestock (Palmer et al., *Infect. Immun.* 62:3808-3816 (1994)) which is phylogenetically closely related to the GE (Dumler et al., *J. Clin. Microbiol.* 33:1098-1103(1995)).

Example 9

PCR Amplification of USG3 Genomic DNA

To obtain additional sequence information for these proteins, degenerate pools of oligonucleotides were synthesized based on the reverse translation of the peptide sequences and used to amplify DNA from USG3. The reverse complement of each oligonucleotide was also synthesized with the exception of the one corresponding to the amino-terminal peptide. PCR amplifications were performed using one forward and one reverse primer set using USG3 genomic DNA as template and an annealing temperature of 55° C. Primer pairs either gave no PCR product or a single band. The primer pair that resulted in generating the longest product, 550 bp, consisted of the forward primer 5'-ACNGGNGGNGCWGGNTAY-TTY-3' (SEQ ID NO:71) (amino-terminal peptide HDDVSALETGGAGYF (SEQ ID NO:66)) and the reverse primer 5'-CCNCCRTCNGTRTARTCNGC-3' (SEQ ID NO:72) (peptide SGDNGSLADYTDGGASQTNK (SEQ ID NO:67)). This DNA was sequenced and found to contain an open reading frame with homology to the MSP-2 protein of *A. marginale* (FIG. 26). Two other peptides, one from the 45 kDa protein and one from the 43 kDa protein, were also contained within this sequence. The similarity in protein sequence between the two immunoreactive 43 and 45 kDa proteins may indicate that they are differentially modified or processed versions of the same protein or they may represent proteins expressed from two different members of a gene family.

Example 10

Isolation of Clones Using Goat Sera

Figure 27A:
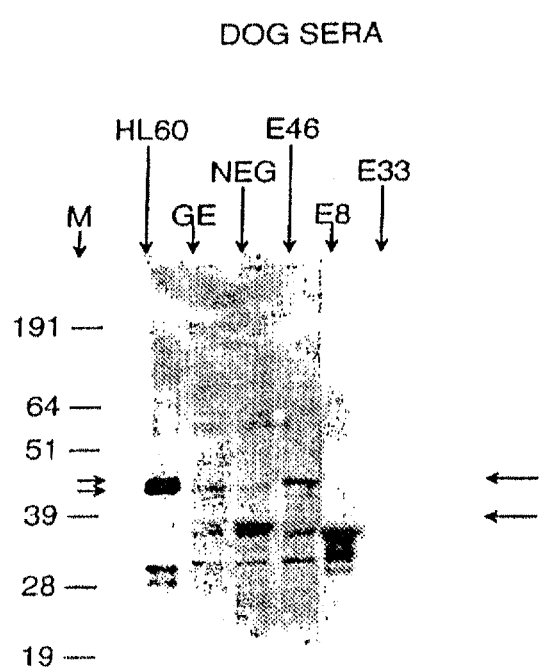
FIG. 27. Western blot of GE proteins. Samples containing purified USG3 antigen (GE lanes), uninfected HL60 cell proteins (HL60), a pBluescript library clone with no insert (NEG), E46, E8, or E33 were analyzed by SDS-PAGE and transferred to nitrocellulose blots. Blots were probed with either dog (FIG. 27A) or goat (FIG. 27B) sera. Molecular size markers are indicated on the left of each blot. Positions of expressed proteins are indicated by arrows at the right side of each blot. The double arrow on the left indicates the proteins that were excised for peptide sequencing.
Figure 27B:
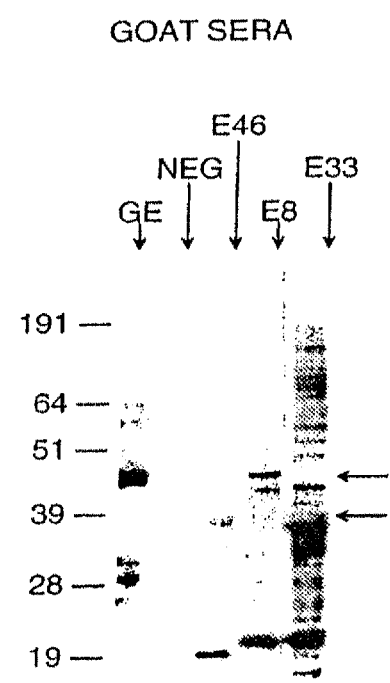

A goat serum reactive against proteins of the HGE agent was obtained by immunizing animals 3 times with purified USG3 antigen. Western blot analysis showed that many proteins of various molecular mass were recognized by this serum including the 43 and 45 kDa proteins (FIG. 27, GE lanes). The USG3 genomic expression library (prepared as described in Protocol C) was screened with immune goat serum and several immunoreactive plaques were identified for further analysis. To eliminate clones previously isolated using immune dog sera, phage supernatants from the plaques were screened by PCR using primers based on the sequences of those previously identified clones. Bacteriophage were plated with XL1-Blue MRF and induced to express protein with 10 mM IPTG (Sigma, St. Louis, Mo.). Proteins were transferred to nitrocellulose filters and the filters were washed with TBS (25 mM Tris HCl, pH 7.5, 0.5 M NaCl). Washed filters were blocked in TBS containing 0.1% polyoxyethylene 20 cetyl ether (Brij 58) and incubated with a 1:1000 dilution of goat serum depleted of anti-*E. coli* antibodies. The filters were washed and incubated with rabbit anti-goat Ig HRP conjugated antibody to (1:2000 dilution), rewashed and developed with 4-chloronapthol. Positive plaques were isolated, replated and screened again. Plasmid DNA containing the putative recombinant clones was obtained by plasmid rescue (Stratagene, La Jolla, Calif.). pBluescript plasmids were rescued from the remaining clones and they were assessed for relatedness by restriction enzyme analysis. Two clones, E8 and E33, appeared to contain the same insert in opposite orientation from the lacZ promoter. Two other clones, E46 and E80, shared restriction enzyme fragments in common but E46 contained a larger insert than E80.

Example 11

DNA Sequencing and Sequence Analysis

Figure 28:
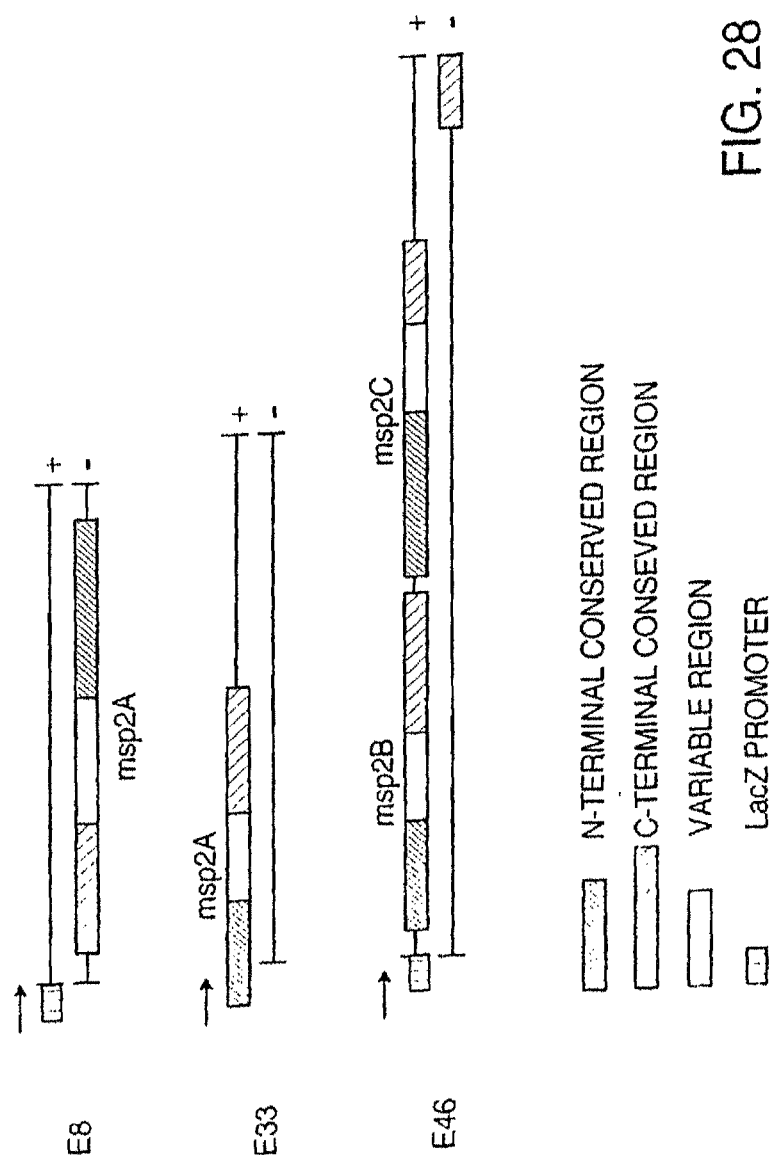
FIG. 28. Schematic diagram of E8, E33 and E46 pBluescript inserts. Each strand of the DNA insert is shown as a line; +) plus strand of DNA; −) minus strand of DNA. Boxed regions indicate related open reading frames. The position and orientation (arrows) of the lacZ promoter is indicated.

Three clones, E8, E33, and E46, were sequenced by the primer walking method. Both strands of each insert were sequenced as described in Protocol F. The sequences of the three clones shared considerable homology. The E8 clone contained a larger version of the E33 insert but in opposite orientation with respect to the lacZ promoter (FIG. 28). Both clones contained the same open reading frame but E33 was missing 420 nucleotides from the 5' end of the gene. The deduced amino acid sequence of the E33 open reading frame was in frame with the partial β-galactosidase amino acid sequence encoded by the vector (data not shown). The nucleotide and deduced amino acid sequences of the pBluescript E8 insert (which did contain the entire gene) are shown in FIG. 29. The predicted molecular mass of the protein encoded by this gene was 45.9 kDa. The nucleotide and deduced amino acid sequences for E46 clone is shown in FIG. 30. The E46 insert contained one partial and two complete open reading frames which all shared considerable homology with the protein encoded by the E8 gene. FIG. 28 shows how the DNA sequences (+ and − strands) and deduced amino acid sequences from E46 compare with those from E8 and E33. The boxed regions represent the open reading frames and shaded areas indicate homologous sequences. As shown in FIG. 31, all three of the complete genes showed a similar pattern for the encoded proteins: a variable domain flanked by conserved regions having a consensus amino-terminal sequence as set forth in SEQ ID NOS:41-43, and/or a carboxy terminus having a consensus sequence as set forth in SEQ ID NOS:41-43. (See FIG. 31). The length of the conserved regions varied among the encoded proteins, with the longest amino and carboxy-terminal conserved regions present in the E8 protein. The sequences present in the E8, E33 and E46 pBluescript plasmids were confirmed to be derived from USG3 genomic DNA and not HL60 DNA by PCR analysis using the primers described herein. When to the sequences of the three full length genes isolated by expression library cloning were compared with the sequence of the PCR product derived from the peptide analysis, it was found that the PCR fragment was contained within the E8 sequence, by 232 to 760 (FIG. 29). In fact, the amino-terminal peptide and all four internal peptides sequenced from the 43 kDa and 45 kDa proteins could be found within the amino acid sequence of the E8 protein. The sequenced peptides are underlined in FIG. 29. The amino-terminal peptide (HDDVSALE . . . ) was found beginning at amino acid 27 and this may indicate that the first 26 amino acids are part of a signal peptide which is cleaved to produce the mature protein. Since the PCR product had both nucleotide and amino acid homology to the *A. marginale* msp2 gene family, a BLAST homology search was performed to assess the relatedness of the E8 and E46 gene products to this family as well. Strong matches were observed for all of the GE proteins described here to the *A. marginals* MSP-2 proteins. A ClustalW amino acid alignment of the GE proteins (designated GE MSP-2A (E8), MSP-2B (E46#1), and MSP-2C (E46#2)) with one of the *A. marginale* MSP-2 proteins (GenBank accession number U07862) is shown in FIG. 31. The homology of the GE MSP-2 proteins with *A. marginale* MSP-2 occurred primarily in the conserved regions shown in FIG. 28. Amino acid identity ranged from 40 to 50% between the proteins of the two species and amino acid similarity was close to 60%. The *A. marginale* MSP-2 proteins contain signal peptides (data not shown) and the data indicating that GE MSP-2A has a signal peptide is consistent with the homology observed between the MSP-2 proteins of the two species. The nucleotide sequences of the genes described here have been assigned the following GenBank accession numbers: GE msp2A (E8):AF029322; GE msp2B (E46#1) and GE msp2C (E46#2):AF029323.

The three GE clones E8, E33, and E46 thus appear to be part of a multigene family encoding proteins containing highly homologous amino- and carboxy-terminal regions related to the MSP-2 proteins of *A. marginale*. In addition to the three full length and one truncated msp2-like genes reported here, there are likely to be others present in the GE genome. Hybridization studies (infra) using probes from either the 5' or 3' end of the E8 msp2 gene identified multiple copies of homologous msp2 genes in the genome of USG3. Sequencing of several other GE library clones has revealed short (100 to 300 nucleotides) stretches of DNA homologous to msp2. Several different MSP-2 proteins ranging in size from 33 to 41 kDa have been reported for *A. marginale* and >1% of its genome may consist of msp2. The function of the GE MSP-2 to proteins is unknown. Zhi et al., supra, demonstrated that the antigens are present in outer membrane fractions of purified granulocytic ehrlichiae. Thus, they may play a role in the interaction between the pathogen and the host cell. In *A. marginale*, expression of antigenically unique MSP-2 variants by individual organisms during acute rickettsemia in cattle suggests that the multiple msp-2 gene copies may provide a mechanism for evasion of the beneficial immune response directed against these antigens. This may explain the observation that the GE MSP-2A protein is present in purified USG3 but the MSP-2B and MSP-2C are not.

Example 12

Southern Blot Analysis

Figures 32A, 32B:
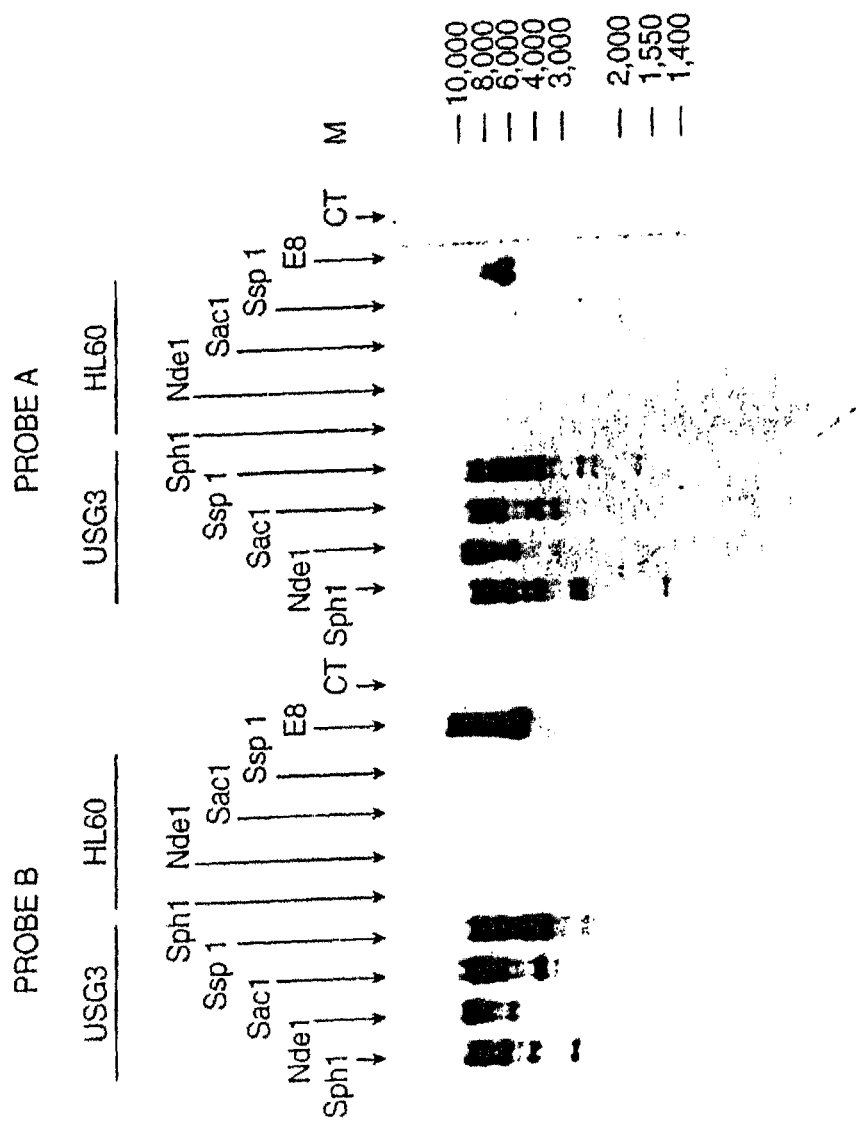
FIG. 32. Southern blot analysis of USG3 genomic DNA. Genomic DNA from USG3 or HL60 cells was digested with the restriction enzymes indicated above the lanes and Southern blotted. Eco RI-digested E8 plasmid DNA was used as a positive control for probe hybridization and calf thymus DNA (CT) as a negative control. The blots were hybridized with digoxigenin-labeled probe A (5'end of E8 msp-2A) (FIG. 32B) or probe B (3' end of E8 msp-2A) (FIG. 32A).

To determine whether additional copies of msp-2 were present in the genome, genomic DNA was isolated from USG3 and digested with restriction enzymes. Digoxigenin-labeled probes were prepared by PCR using the PCR Dig Probe Synthesis kit (Boehringer Mannheim). Two sets of primers were used to generate a 240 bp product (probe A) from the 5' end of the E8 gene:
(forward primer: 5'-CATGCTTGTAGCTATG-3' (SEQ ID NO:52);
reverse primer: 5'-GCAAACTGAACAATATC-3' (SEQ ID NO:53)) and a 238 bp product (probe B) from the 3'-end of the E8 gene;
(forward primer: 5'-GACCTAGTACAGGAGC-3' (SEQ ID NO:54);
reverse primer: 5'-CTATAAGCAAGCTTAG-3' (SEQ ID NO:55) including the consensus sequence corresponding to the amino- and/or carboxy-terminus regions shared by E8, E46#1, and E46#2 polypeptide). Genomic DNA was prepared from USG3 or HL6O cells as described above and aliquots of 1 μg of DNA were digested with SphI, NdeI, SacI, or SspI (New England Biolabs, Beverly, Mass.). These restriction endonucleases do not cut within the sequence of E8 msp2A. Calf thymus DNA was digested identically as a control. Recombinant pBluescript E8 plasmid DNA was digested with EcoRI and used as a positive control for probe hybridization. Digested fragments were separated by gel electrophoresis in a 1% agarose gel. Southern blotting was performed under prehybridization and hybridization conditions of 65° C. in Dig Easy Hyb (Boehringer Mannheim) and hybridization was performed overnight. Two membrane washes in 2×SSC/0.1% SDS were performed at room temp for 5 min each followed by two washes in 0.5×SSC/0.1% SDS at 65° C. for 15 min each. Bound probe was detected by chemiluminescence using anti-digoxigenin alkaline phospate conjugated antibody (Boehringer to Mannheim). FIG. 32 shows that multiple bands were present on the Southern blots using both probes, indicating the presence of multiple msp-2 copies. The exact number of genes cannot be determined since sequence differences may generate additional restriction enzyme sites in some of the msp-2 copies, resulting in more than one band from a single copy. Also, more than one msp-2 gene could be present on a single restriction fragment, an event which does occur with the msp-2B and msp-2C genes.

Example 13

Western Blot Analysis of Proteins Encoded by GE Clones

Bacterial lysates from the genomic library clones, E8, E33, and E46, were analyzed by SDS-PAGE and Western blotting.

Individual recombinant plasmid containing cultures were induced to express protein with 5 mM IPTG. Bacterial cells were pelleted by centrifugation and resuspended in 5× Laemmli buffer (12% glycerol, 0.2M Tris-HCl, pH 6.8, 5% SDS, 5% p-mercaptoethanol) at 200 μl per 1 OD unit of culture. Samples were boiled and 10 μl of each were analyzed on NuPage gels (Novex, San Diego, Calif.). Proteins were transferred to nitrocellulose filters, the filters were blocked in TBS/Brij 58 and the blots were probed with either a 1:500 dilution of pooled sera from dogs that were infected with GE by tick exposure, a 1:500 dilution of the goat serum described above, or a 1:1000 dilution of human serum. Preimmune dog and goat sera were also used at a 1:500 dilution. Blots were washed and incubated with HRP conjugated secondary antibody (Bio-Rad, Hercules, Calif.). After several additional washes, the blots were developed using the Pierce (Rockford, Ill.) Super Signal Chemiluminescence kit and viewed by autoradiography. FIG. 27 shows that a protein of approximately 37 kDa from the E46 clone and a 45 kDa protein from the E8 clone were specifically detected by dog and goat sera (indicated by arrows on the right side of each blot). The reactivity of the sera differed somewhat in that the dog sera reacted much better than the goat sera with the E46 protein and the goat sera had better reactivity to the E8 protein. Whether the 37 kDa/E46 protein is encoded by the first or second E46 gene is unknown and the reason for the expression of two closely sized immunoreactive E33 proteins is also unclear. Preimmune sera did not detect these proteins and expression was observed in the absence of IPTG induction. The molecular mass of the proteins is consistent with the coding capacity of the msp-2 genes found in the library clones. The negative control (NEG lane) was a pBluescript library clone without an insert. FIG. 27 also shows a couple of proteins of smaller molecular mass from to E46 and E8 that react specifically with the goat serum. It is not known whether they are breakdown products of the full length MSP-2 proteins or whether they are produced by internal initiation within the msp-2 genes.

Example 14

PCR Amplification of Isolated Clones

PCR primer sets were designed based on the sequences of each GE clone and are as follows:

```
                                          (SEQ ID NO: 56)
E8 (forward 5'-GCGTCACAGACGAATAAGACGG-3';

(SEQ ID NO: 57)
reverse 5'-AGCGGAGATTACAGGAGAGAGCTG-3');

(SEQ ID NO: 58)
E46.1 (forward 5'-TGTTGAATACGGGGAAAGGGAC-3';

(SEQ ID NO: 59)
reverse 5' AGCGGAGATTTCAGGAGAGAGCTG 3';)

(SEQ ID NO: 60)
E46.2 (forward 5'-TGGTTTGGATTACAGTCCAGCG 3';

(SEQ ID NO: 61)
reverse 5' ACCTGCCCAGTTTCACTTACATTC 3'.
```

Each 50 μl reaction contained 0.5 μM of each primer, 1×PCR Supermix (Life Technologies, Gaithersburg, Md.) and either 100 ng USG3 DNA, 100 ng HL60 DNA or 250 ng plasmid DNA. PCR amplification was performed using the following conditions: 94° C. for 30 s, 61° C. for 30 s, and 72° C. for 1 min After 30 cycles, a single 10 min extension at 72° C. was done. PCR products were analyzed on 4% Nusieve 3:1 agarose gels (FMC Bioproducts, Rockland, Me.).

Example 15

Recognition of MSP-2A and MSP-2B by GE-Positive Human Sera

PCR amplification of the first gene in pBluescript clone E46 was performed to generate an insert for subcloning in *E. coli*. Primer sets were designed to contain restriction sites for cloning, a translation termination codon and a six residue histidine sequence for expressed protein purification

```
                                          (SEQ ID NO: 62)
(forward 5-CCGGCATATGCTTGTAGCTATGGAAGGC-3';

(SEQ ID NO: 63)
reverse.5'-CCGGCTCGAGCTAGTGGTGGTGGTGGTGAAAAGCA

AACCTAACACCAAATTCCCC-3').
```

The 100 μl reaction contained 500 ng of each primer, 500 ng of E46 template, and 1×PCR to Supermix (Life Technologies, Gaithersburg, Md.). Amplification was performed using the following conditions: 94° C. for 30 s, 58° C. for 30 s, 72° C. for 1 min. After 37 cycles a single 10 min extension at 72° C. was performed. Following analysis on a 1% TBE agarose gel, amplified product was purified using a QIAEX II gel extraction kit (QIAGEN Inc, Chatsworth, Calif.) and digested with restriction enzymes NdeI and XhoI (New England Biolabs, Beverly, Mass.) using the manufacturer's recommended conditions. The 1004 bp fragment was ligated into NdeI and XhoI digested pXA and transformed into *E. coli* strain MZ-1(19). Expression vector pXA is a pBR322-based vector containing the bacteriophage lambda pL promoter, a ribosome binding site, ATG initiation codon and transcription and translation termination signals. Recombinant MSP-2B was induced by growing the Mz-1 transformed clone to an $A_{550}$=1.0 at 30° C. and then shifting the temperature to 38° C. for an additional 2 hr. Aliquots (1.5 ml) of pre-induced and induced cells were pelleted by centrifugation and resuspended in 5× Laemmli buffer.

Figures 33A, 33B:
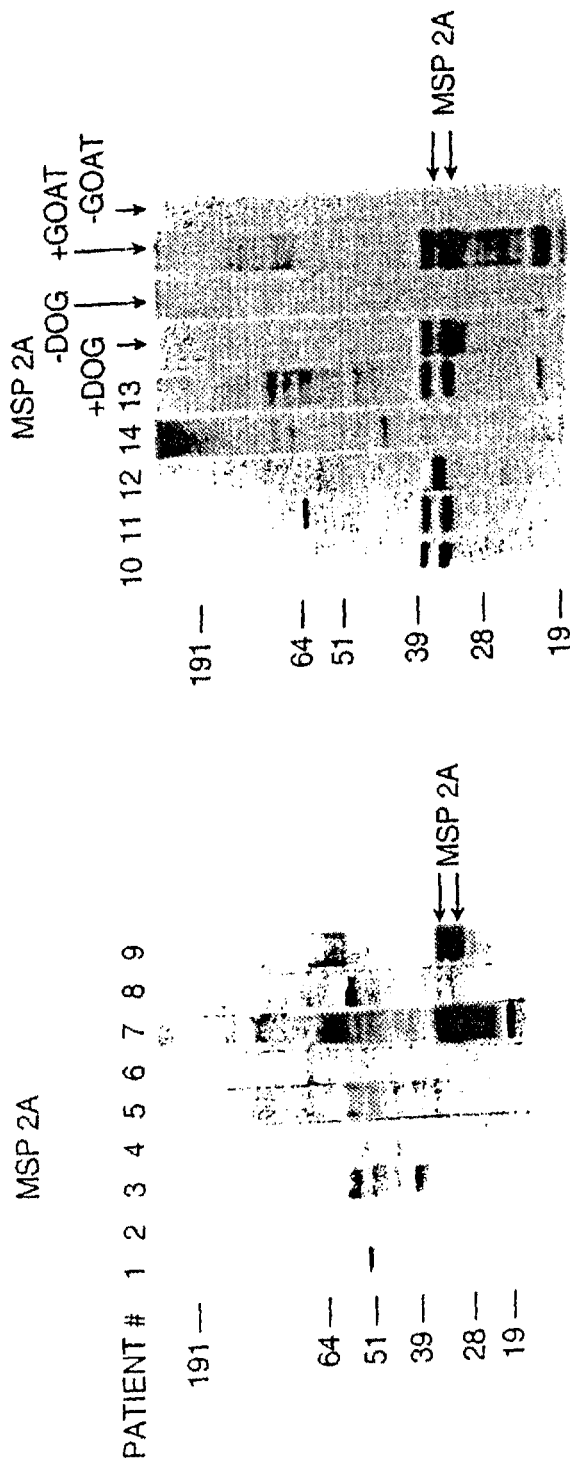
FIG. 33. Western blot analysis of E33 bacterial cultures expressing MSP-2A and MSP-2B probed with HGE patient sera. Bacterial cultures of E33 MSP-2A (top) and MSP-2B (bottom) were analyzed by SDS-PAGE and the proteins transferred to nitrocellulose blots. The blots were cut into strips and probed with patient sera #1-14 as indicated above the lanes. These numbers correspond to the patient numbers shown in Table 7 Immune(+) and preimmune(−) dog and goat sera were also used as positive and negative controls. Molecular size markers are indicated on the left side of each blot. The arrows show the positions of the MSP-2 proteins.
Figures 33C, 33D:
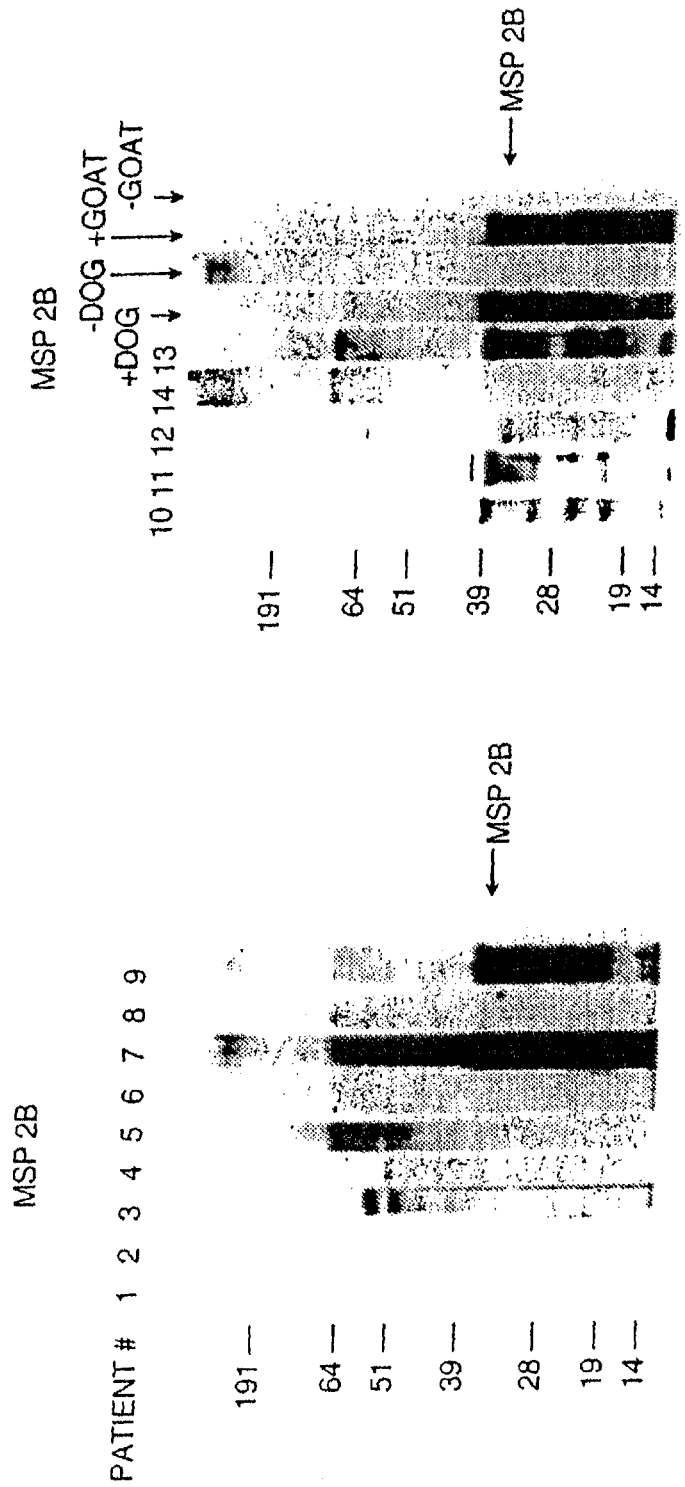

The coding regions for MSP-2A and MSP-2B were recloned using a heat inducible *E. coli* expression system as outlined above. The expression of the MSP2-A protein using this system remained low. However, the recombinant MSP-2B protein was expressed and could be detected with both dog and goat GE-positive sera (FIG. 32). The recombinant MSP-2B protein and the E33 MSP-2A protein were then tested for reactivity with human serum samples which had previously been shown to be positive for granulocytic *Ehrlichia* by immunofluorescence assay (IFA). Table 8 shows the patient profiles and diagnostic laboratory results from fourteen individuals. Ten of these individuals were clinically diagnosed with HGE (#1-9, 13), three of them participated in a seroprevalence study (#10-12), and one was a negative control (#14) Immune and preimmune dog and goat sera were also used as positive and negative controls in the Western blots. FIG. 33 shows the reactivity of each human serum sample with MSP-2A (top) and MSP-2B (bottom). All of the human samples with IFA titers of 512 or more (#7,9,10,11,13) reacted with the MSP-2 proteins as did the positive dog and goat sera. Human serum #8 also reacted faintly with both proteins. In addition, these same sera all reacted with purified GE on Western blots (data not shown). Human serum #12 reacted with an *E. coli* protein which migrates in between the two E33 MSP-2 proteins. This reactivity was seen with all of the library clones we have tested, including those which do not express any GE related proteins (data not shown). From these data it appears that the IFA assay is more sensitive than the Western blot for diagnosis of HGE.

TABLE 8

HE Patient Profiles and Diagnostic Laboratory Test Results

| Patient | Gender | Age | Loc'n (state) | Conval. Stage (months) | Morulae | PCR[1] | IFA[2] | Peak IFA[3] |
|---|---|---|---|---|---|---|---|---|
| 1 | F | 57 | MN | .05 | + | ND | 320 | >2560 |
| 2 | M | 56 | WI | 12 | + | + | 160 | 640 |
| 3 | M | 59 | MN | 6 | + | ND | 320 | 320 |
| 4 | M | 74 | WI | 12 | + | + | 160 | >2560 |
| 5 | M | 40 | WI | 12 | + | + | 320 | 5120 |
| 6 | M | 71 | WI | 24 | + | + | 320 | 1280 |
| 7 | M | 80 | WI | 36 | + | − | >2560 | >2560 |
| 8 | M | 60 | MN | 6 | − | ND | 320 | >2560 |
| 9 | F | 44 | MN | 42 | − | − | >2560 | 5120 |
| 10 | M | 50 | WI | random | ND | ND | >2560 | ND |
| 11 | F | 50 | WI | random | ND | ND | >2560 | ND |
| 12 | M | 64 | WI | random | ND | ND | 60 | ND |
| 13[3] | F | 65 | RI | 1 | − | + | 512 | 1024 |
| 14 | F | 29 | MA | NA | − | ND | <32 | <32 |

[1]PCR with GE9F and GE1 OR primers (6).
[2]Polylonal IFA assay with *E. equi* antigen.
[3]Data taken from reference 27.
+ Positive,
− negative,
ND not done,
NA not applicable.

Example 16

Characterization of Representative Clone S11

Purified GE protein preparations were obtained as described in Protocol G. Aliquots were run on four lanes to allow the staining of three lanes with Ponceau S (0.1% in 1 N acetic acid) and one lane with Coomassie blue staining. Molecular weight markers were also run in two lanes. Electrophoresis was performed on a 10% SDS-PAGE preparative gel and proteins were transferred onto a 0.2 μm PVDF membrane. The Ponceau S bands with the same molecular weight as the bands stained with Coomassie blue (five total) were cut out for sequencing. N-terminal sequence was obtained for one of the five bands. The proteins in the other four bands were digested with trypsin in situ for internal peptide sequencing. Peptides were separated by RP-HPLC on a ZORBAX C18 (1 mm×150 mm) column Potential candidates for sequencing were screened for molecular mass by MALDI-TOF Mass Spectrometry on a Finnigan Lasermet 2000 (Hemel, UK). Protein sequencing was performed by Edman degradation.

Four of the five gel bands contained either serum proteins (probably from the fetal to bovine serum used to culture the cells) or heat shock proteins. The other band appeared to contain a unique protein. Four internal peptide sequences were obtained from this gel band, representing a protein of approximately 64 kDa, that did not match any protein sequences in the database. The sequences of these peptides are shown in FIG. 34. (SEQ ID NOS:34-37). Based on these sequences, degenerate DNA oligonucleotides were designed for each peptide (both forward and reverse/complement orientation) and used in all possible combinations for PCR using GE DNA as template. One combination, primers 5F (SEQ ID NO:32) and 6R (SEQ ID NO:33) (shown in FIG. 34), produced a PCR fragment of 450 base pairs. The DNA was cloned into pCR Script SK(+) and the insert was sequenced.

When the insert DNA was translated, both peptides (#24 and 25) (SEQ ID NOS:34-35) were found in the sequence, one at each end as expected.

To obtain a clone containing the entire gene represented by the PCR fragment, two primers were designed based on the DNA sequence of the PCR fragment. These primers were used in PCR reactions to screen sublibraries of the GE genomic library.

```
Forward primer (250F2):
                                        (SEQ ID NO: 64)
5' CCCCGGGCTTTACAGT 3'

Reverse primer (250R2):
                                        (SEQ ID NO: 65)
5' CCAGCAAGCGATAACC 3'
```

The sublibraries were generated by the initial screening of the genomic library with convalescent dog sera.

Figure 35:
FIG. 35. Linear map of pBluescript S11. Boxes on either end represent vector sequences and the solid center line denotes the insert. The T3 and T7 promoter sequences are positioned as indicated and the S11 gene is shown as a bold line.

When a positive phage stock was found by PCR screening, the lysate was serially diluted twice and replated with bacterial stock XL1-Blue MRF to obtain isolated plaques. Forty-eight of these plaques were picked and lysates screened by PCR with primers 250F2 and 250R2. A positive clone was obtained which was designated S11. The plasmid DNA was rescued and restriction enzyme analysis performed to determine the size of the insert DNA and the approximate location of the gene within the insert. Results indicated that the insert size was about 8 kb and that the gene of interest was located at the T7 end of the insert relative to the pBluescript vector (FIG. 35). A 2 kb portion of the S11 insert was sequenced and found to contain an open reading frame of 545 amino acids. The complete sequence is shown in FIG. 36 (SEQ ID NO:39).

When the amino acid sequence of S11 (SEQ ID NO:39) was compared to the peptide sequences obtained from the excised gel band representing a protein of 64 kDa, all four peptide sequences were found. These are shown underlined in FIG. 36. The only difference between to the nucleic acid sequence and the peptide sequences was the presence of phenylalanine (F) instead of aspartic acid (D) in position 4 of peptide #26 (SEQ ID NO:37). The reason for this difference is unknown. The calculated molecular weight of the protein encoded by the S11 gene was 58.5 kDa. A search of the nucleic acid and protein databases did not reveal any significant homology between it and other proteins in the database. There were, however, some minor similarities to outer surface proteins of some bacterial species.

All publications mentioned hereinabove are hereby incorporated in their entirety by reference. While the foregoing invention has been described in some detail for purposes of clarity and understanding, it will be appreciated by one skilled in the art from a reading of this disclosure that various changes in form and detail can be made without departing from the true scope of the invention and appended claims.

SEQUENCE LISTING

<160> NUMBER OF SEQ ID NOS: 85

<210> SEQ ID NO 1
<211> LENGTH: 3147
<212> TYPE: DNA
<213> ORGANISM: Granulocytic Ehrlichia
<220> FEATURE:
<223> OTHER INFORMATION: S22 of Granulocytic Ehrlichia

<400> SEQUENCE: 1

```
gaattcctta cctccctata tttcgtacag gttatttcgc agtctagcta tgatgcttta      60
ccaggatacg ttaaacgttg acgttctacg ctgtcatagc cttttattct gcaaaaatag     120
cttaactgtg tcacttcctg agaaagtaag atacatattt agtttttgca cagccaaaaa     180
acttctagtg aactgtggtt tctctggaat caataacctg ttttatattc gtgcgttcta     240
taacaatcta cagctgtggt tattaggcgt ggtttcgcct gataataaag atactttaga     300
gggtataaac ttggaaaaaa taatgaaaaa ccctccttag tgcctccccg tttttgacaa     360
catactctta tggaaaagcg ttagggagtt gcttcgcttg tcacgcgtgc gttaggtttt     420
acgtatacgt gtctgggact tcacgaaaac tcgacgcagg cggattttgt actatgtttc     480
acttaacaag gtattataaa tgtttgaaca caatattcct gatacataca caggaacaac     540
tgcagaaggt tctcctggct tagcaggcgg ggattttagc ttaagttcta ttgactttac     600
aagggacttt acaattgaat cacatagagg aagctcagct gatgacccag gttacatcag     660
ctttagggat caagacggaa acgtcatgtc acgttttctt gatgtgtacg tagctaattt     720
cagcttgcga tgcaagcatt ctccctataa caacgacaga atggaaacag ctgcgttctc     780
tctaactccc gacataatag agccttctgc tttattgcaa gaatcacata gtacacaaaa     840
caatgtagaa gaggcagtac aagttacagc tcttgagtgc cctccatgta atccagtccc     900
tgccgaggaa gtagctcctc aaccgtcttt tctaagcaga ataattcagg cgttcttgtg     960
gttattcacg ccttcttcta ctaccgacac tgctgaagac agcaagtgta atagtagcga    1020
tacttcaaaa tgtacctctg ctagcagtga gtcattagag cagcaacaag aatcagtgga    1080
agtgcaacca tctgtactta tgtctactgc ccctatagca acagagcctc aaaatgcggt    1140
tgttaaccaa gtaaacacta ctgcagtaca agtagaatca tccattattg tgccagaatc    1200
gcaacacact gacgttaccg tgctcgaaga tactactgag acgataactg ttgatgggga    1260
atatggacat tttagtgaca ttgcttcagg tgaacacaat aacgatctgc ctgccatgtt    1320
gttagatgaa gcagacttca ctatgttatt agcgaacgag gagtcaaaga ccctggagtc    1380
tatgccttct gatagcctag aagacaatgt tcaggaacta ggtacattgc ctttacaaga    1440
aggtgaaaca gttctgaggg gcaacacacg agagtcacta cccactgacg tttcacaaga    1500
ctcagttggt gtaagtacag atcttgaagc tcattctcaa gaagttgaaa cagtttctga    1560
```

-continued

```
ggtcagcaca caagattcac tatccactaa catttcacaa gactcagttg gtgtaagtac      1620
agatcttgaa gctcattcta aaggagttga aatagtttct gagggcggca cacaagattc      1680
actatccgct gattttccaa taaacacagt tgaaagtgaa agtacagatc ttgaagctca      1740
ttctcaagaa gttgaaactg tttctgaatt cacacaagat tcactatcca ctaacatttc      1800
acaagactca gttggtgtaa gtacagatct tgaagttcat tctcaagaag ttgaaatagt      1860
ttctgagggc ggcacacaag attcactatc cactaacatt tcacaagact cagttggtgt      1920
aagtacagat cttgaagctc attctcaaga agttgaaact gtttctgaat tcacacaaga      1980
ttcactatcc actaacattt cacaagactc agttggtgta agtacagatc ttgaagttca      2040
ttctcaagaa gttgaaatag tttctgaggg cggcacacaa gattcactat ccactaacat      2100
ttcacaagac tcagttggtg taagtacaga tcttgaagct cattctaaag gagttgaaat      2160
agtttctgag gcggcacac aagattcact atccgctgat tttccaataa acacagttga      2220
aagtgaaagt acagatcttg aagctcattc cccagaaggt gaaatagttt ctgaggtcag      2280
cacacaagat gcgccatcca ctggagtaga gatcagattt atggatcgtg attctgatga      2340
tgacgtgctc gcgttgtcaa gtgatcatgg taggggaaac agttatgcg taaagacatc      2400 tttgatgact tgtcttgcgt gaataagtag tgcaagtttt ttatgcattg atgtgcatga      2460
tcattgcccc taaggaaagc agtactaatg gtagtctaag atcttataca gggtttcgga      2520
ctaccacttt tggtgtttta aaacgtctta ttcgcgttgg gtgcttgctt acaatgtacc      2580
tgtacgtgcc caacactaaa aatggtcagt attacttagg ggagttcgta gacgaggcat      2640
ctcgatttac tctaagtaag ctacaaataa ctcagtcata tcaaggtagt tcaagatgaa      2700
agcagtgcta tgcttatcat ggagaattcc tgcggttctc ttcaaaattc tcttttcccg      2760
caagggcaga ctcttatttg ttaaaataac aaaatttctc tacaggaagc gacatttcat      2820
atcaaagctg attgtgaaat aatggcattg agtattttc tcgccctaga agataatcat      2880
ttcggcacta tcaaagcatt tacgatattc tccattatct tgtaatcaga tggctatctt      2940
gaaagcaacc aaggatatcc gtacatggta gcttacatac tgctatcaat ctcctatacg      3000
accttcaatg aaacggtaac tgttgctgac agcttgcaca tgctgtgatt caattcctgg      3060
ttcctagatg ttctactacg tttatccggt actaatatta ttctttggcg ctctattatc      3120
tagcaactca gagtccatta ggaattc                                          3147
```

<210> SEQ ID NO 2
<211> LENGTH: 619
<212> TYPE: PRT
<213> ORGANISM: Granulocytic Ehrlichia
<220> FEATURE:
<223> OTHER INFORMATION: S22 of Granulocytic Ehrlichia

<400> SEQUENCE: 2

```
Met Phe Glu His Asn Ile Pro Asp Thr Tyr Thr Gly Thr Thr Ala Glu
 1               5                  10                  15

Gly Ser Pro Gly Leu Ala Gly Gly Asp Phe Ser Leu Ser Ser Ile Asp
            20                  25                  30

Phe Thr Arg Asp Phe Thr Ile Glu Ser His Arg Gly Ser Ser Ala Asp
        35                  40                  45

Asp Pro Gly Tyr Ile Ser Phe Arg Asp Gln Asp Gly Asn Val Met Ser
    50                  55                  60

Arg Phe Leu Asp Val Tyr Val Ala Asn Phe Ser Leu Arg Cys Lys His
65                  70                  75                  80

Ser Pro Tyr Asn Asn Asp Arg Met Glu Thr Ala Ala Phe Ser Leu Thr
```

```
                    85                  90                  95
Pro Asp Ile Ile Glu Pro Ser Ala Leu Leu Gln Glu Ser His Ser Thr
                100                 105                 110

Gln Asn Asn Val Glu Glu Ala Val Gln Val Thr Ala Leu Glu Cys Pro
            115                 120                 125

Pro Cys Asn Pro Val Pro Ala Glu Glu Val Ala Pro Gln Pro Ser Phe
        130                 135                 140

Leu Ser Arg Ile Ile Gln Ala Phe Leu Trp Leu Phe Thr Pro Ser Ser
145                 150                 155                 160

Thr Thr Asp Thr Ala Glu Asp Ser Lys Cys Asn Ser Ser Asp Thr Ser
                165                 170                 175

Lys Cys Thr Ser Ala Ser Ser Glu Ser Leu Glu Gln Gln Gln Glu Ser
            180                 185                 190

Val Glu Val Gln Pro Ser Val Leu Met Ser Thr Ala Pro Ile Ala Thr
        195                 200                 205

Glu Pro Gln Asn Ala Val Val Asn Gln Val Asn Thr Thr Ala Val Gln
    210                 215                 220

Val Glu Ser Ser Ile Ile Val Pro Glu Ser Gln His Thr Asp Val Thr
225                 230                 235                 240

Val Leu Glu Asp Thr Thr Glu Thr Ile Thr Val Asp Gly Glu Tyr Gly
                245                 250                 255

His Phe Ser Asp Ile Ala Ser Gly Glu His Asn Asn Asp Leu Pro Ala
            260                 265                 270

Met Leu Leu Asp Glu Ala Asp Phe Thr Met Leu Leu Ala Asn Glu Glu
        275                 280                 285

Ser Lys Thr Leu Glu Ser Met Pro Ser Asp Ser Leu Glu Asp Asn Val
    290                 295                 300

Gln Glu Leu Gly Thr Leu Pro Leu Gln Glu Gly Glu Thr Val Ser Glu
305                 310                 315                 320

Gly Asn Thr Arg Glu Ser Leu Pro Thr Asp Val Ser Asn Asp Ser Val
                325                 330                 335

Gly Val Ser Thr Asp Leu Glu Ala His Ser Gln Glu Val Glu Thr Val
            340                 345                 350

Ser Glu Val Ser Thr Gln Asp Ser Leu Ser Thr Asn Ile Ser Gln Asp
        355                 360                 365

Ser Val Gly Val Ser Thr Asp Leu Glu Ala His Ser Lys Gly Val Glu
    370                 375                 380

Ile Val Ser Glu Gly Gly Thr Gln Asp Ser Leu Ser Ala Asp Phe Pro
385                 390                 395                 400

Ile Asn Thr Val Glu Ser Glu Ser Thr Asp Leu Glu Ala His Ser Gln
                405                 410                 415

Glu Val Glu Thr Val Ser Glu Phe Thr Gln Asp Ser Leu Ser Thr Asn
            420                 425                 430

Ile Ser Gln Asp Ser Val Gly Val Ser Thr Asp Leu Glu Val His Ser
        435                 440                 445

Gln Glu Val Glu Ile Val Ser Glu Gly Gly Thr Gln Asp Ser Leu Ser
    450                 455                 460

Thr Asn Ile Ser Gln Asp Ser Val Gly Val Ser Thr Asp Leu Glu Ala
465                 470                 475                 480

His Ser Gln Glu Val Glu Thr Val Ser Glu Phe Thr Gln Asp Ser Leu
                485                 490                 495

Ser Thr Asn Ile Ser Gln Asp Ser Val Gly Val Ser Thr Asp Leu Glu
            500                 505                 510
```

```
Val His Ser Gln Glu Val Glu Ile Val Ser Glu Gly Gly Thr Gln Asp
        515                 520                 525

Ser Leu Ser Thr Asn Ile Ser Gln Asp Ser Val Gly Val Ser Thr Asp
        530                 535                 540

Leu Glu Ala His Ser Lys Gly Val Glu Ile Val Ser Glu Gly Gly Thr
545                 550                 555                 560

Gln Asp Ser Leu Ser Ala Asp Phe Pro Ile Asn Thr Val Glu Ser Glu
            565                 570                 575

Ser Thr Asp Leu Glu Ala His Ser Pro Glu Gly Glu Ile Val Ser Glu
        580                 585                 590

Val Ser Thr Gln Asp Ala Pro Ser Thr Gly Val Glu Ile Arg Phe Met
        595                 600                 605

Asp Arg Asp Ser Asp Asp Val Leu Ala Leu
    610                 615

<210> SEQ ID NO 3
<211> LENGTH: 4724
<212> TYPE: DNA
<213> ORGANISM: Granulocytic Ehrlichia
<220> FEATURE:
<223> OTHER INFORMATION: S2 of Granulocytic Ehrlichia

<400> SEQUENCE: 3 ggatccccg  ggctgcagga  attcctaaaa  agatctggcg  cctgagcgtc  tgctacaggc     60
agattgtgcg  cgctaagata  ggtttagtaa  gacgtgtttt  ttattgaata  aaggccccaa    120
caatgttgac  agaagaagaa  aagaaaaaga  gcgccggtgc  tctgcaagcc  attatcacag    180
gagattacga  gagtgttcag  gcgtccgttc  agggaatttc  ttccgaagac  ttaatactcc    240
cgttgattat  gagggagaa   cactactgca  ctatgcagct  tcatcccgta  atggtaattt    300
ctatggcatt  ctggttgaaa  gaggatgtgt  tactaatatc  agagatgctt  atggatttac    360
tccagaacaa  gcacgtgaga  aggcagggta  tgcacgcaca  cagtggtatg  agcagatgt    420 aaatgaccct  ggtgtatcta  ggcagttaat  gacgcaagct  gttcagcagt  ctgcgaaagg    480
taacatgtat  gctgctctcg  ctatattaga  ccttgtgcgt  aatgacgatg  caaaacattc    540
aggtcaatga  ggaaaggggc  atagtgtttt  gcatctagca  tgtattgaag  gcagtaatcc    600
atctttcact  tcatccctca  tgctaaaggg  ttgttcttta  aacattaagg  atgtagatgg    660
taatacgcca  ttacatacag  ctgcgttttc  agtaggcaaa  aatgctttag  gcaatcttga    720
tgtactatgc  gacaagctct  tatagcagat  gttaatgcta  agggaccggg  tggaaacact    780
ccgcttcata  ttgctacgga  gcgtatggct  caccagaaag  tagagcatct  tctctcaagg    840
ttaagtgata  ttagcgttgc  aaatcgatgc  tggtgaaacc  gtttgccaca  ttgttgcaaa    900
gcaatggcca  aggcgggatg  ttttaccata  cattgacaag  atgcaagaag  cggtgtcgtc    960
aaatattgag  ggcaatcgcg  agtgtgcaga  ggcactaata  ttcccggata  aaaaagggat   1020
gagtgcagta  cagtatgcta  ttagaaggca  ataccggag   ctgagaagat  cttcgagaag   1080
gccattaaca  ttgcagataa  agtgtatggc  ttagcttctt  cagaagtaga  atctctcttt   1140
acatgtccta  atccagagga  cgcatcaacg  ctggtgcatt  ttgtatcttc  taatgggacc   1200
ccaaattttg  attctcttgc  gaaaagggta  ttggaggaag  catatcatag  gtatggagag   1260 aaaccttta   ctaatttaga  tgttgcaggt  aatgcaccta  acatgctgc   agcacaaaaa   1320 tcaacagtgg  gggttttga   gcaggtggta  agatacactc  ctgagtctgt  tgtaaactca   1380
attagcaccg  aatggcaaag  cgcctattca  catgatagtt  gaggatgagc  caagccataa   1440
aagcgtaagc  attaaattgc  agatgttgat  tgggaatgtg  cgtaatattc  catcaatcaa   1500
```

```
tgtaccatcc ccagtgacag gtgaaacgct gcggtagctg cgtataaagg gggcaacact    1560
gaggatgtta agactatgtt acgctgtaat agcatggacg tagatgctcg gtcacatgat    1620
ggtagaacta taatacatta cgcagcaaag gatggaaatt tagagatatt gcagcaggct    1680
cttggaagga agagtagtta ttctaagttt cctgtaaagg atggtgttcc tactccaggt    1740
gtatatgcga ttcgtgaagc aagtggtgta aaagtatcgc tacaagcact tgacatgtta    1800
atgagatatg agcctcaccc gcagcatgtt gctgtcgagg cagtaagaac aggtgcagta    1860
ggtgtattgg agcaccttat taccactgaa gtgattagtg taaatgaaga aattacaact    1920
cctgaaggaa aaagacaac tttgaccgct gaagcactaa ctagtggtaa atatggtgta    1980
gtgaaggcgt taattaaaaa cagtgctgat gtaaatgcgt ctccagaacc agctattact    2040
ttgggtatac aaggaaggtg ctttcagggg agtaaagcta taaagcattt aaagcgtgtt    2100
gtagaagctg ggcacatat aaatactcct accggatcta tgagccctt agctgctgca    2160 gttcaagcgg caaatgaggc aagtaacctt aaagaggcta ataagattgt aaatttcctt    2220
ttacataggg gtgcagatct ttcgtctacg gaacacactg gaactccagc cttgcattta    2280
gcaacagctg ctggcaacca taggactgct atgttgctct tggataaagg ggctccagca    2340
acgcagagag atgctagggg taggacggct ttacatatag cagctgctaa tggtgacggt    2400
aagctatata ggatgattgc gaaaaaatgc ccagatagct gtcaaccact ctgttctgat    2460
atgggagata cagcgttaca tgaggctta tattctgata atgttacaga aaaatgcttt    2520
ttaaagatgc ttaaagagtc tcgaaagcat ttgtcaaact catcttttt cggagacttg    2580 cttaatactc ctcaagaagc aaatggtgac acgttactgc atctggctgc atcgcgtggt    2640
ttcggtaaag catgtaaaat actactaaag gctggggcgt cagtatcagt cgtgaatgta    2700
gagggaaaaa caccggtaga tgttgcggat ccatcattga aaactcgtcc gtggtttttt    2760
ggaaagtccg ttgtcacaat gatggctgaa cgtgttcaag ttcctgaagg gggattccca    2820
ccatatctgc cgcctgaaag tccaactcct tctttaggat ctatttcaag ttttgcgagt    2880
gtctctgcgc tatcatcctt gggtagtggc ctagatactg caggagctga ggagtctatc    2940
tacgaagaaa ttaaggatac agcaaaaggt acaacggaag ttgaaagcac atatacaact    3000
gtaggagctg aggagtctat ctacgaagaa attaaggata cagcaaaagg tacaacggaa    3060
gttgaaagca catatacaac tgtaggagct gaaggtccga gaacaccaga aggtgaagat    3120
ctgtatgcta ctgtgggagc tgcaattact ccgaggcgc aagcatcaga tgcggcgtca    3180
tctaagggag aaaggccgga atccatttat gctgatccat ttgatatagt gaaacctagg    3240
caggaaaggc ctgaatctat ctatgctgac ccatttgctg cggaacgaac atcttctgga    3300
gtaacgacat ttggccctaa ggaagagccg atttatgcaa cagtgaaaaa gggtcctaag    3360
aagagtgata cttctcaaaa agaaggaaca gcttctgaaa aagtctgctc aacaataact    3420
gtgattaaga agaaagtgaa acctcaggtt ccagctagga caagtagttt gcctactaaa    3480
gaaggtatag gttctgataa agacctgagt tcaggaacta gtagctcttt tgcagctgag    3540
ctgcaagcac aaagggtaa attgcgtcct gtgaagggag gtgctccgga ttctaccaaa    3600
gacaaaacag ctacttctat attctccagt aaagagttca aaaggaact aacaaaagct    3660 gccgaaggat tacagggagc agttgaagaa gctcagaagg gtgatggagg agctgcaaag    3720
gcaaagcaag atcttggcat ggaatctggt gccccaggat ctcaaccaga agctcctcaa    3780
agtgaaggcc ctagtctgt aaaaggaggt cgcggtaggg agaattatac cgaaaaatcg    3840
ctgaggtact tgatcaata taattcgcgc ttctgagtat ttaggcgatg atctcgccac    3900
```

```
tttaataata ccccttttag agtacataac gctctaaagg gggcagatta tttaagtag    3960 tagggttttg attctgagat cttttgagta caactattcc ttagtgtttt tttggaatgc    4020
tatgtgcttg ataaagaaaa aacttgctct ggggtgggat gcactcttga gtactttccg    4080
cgctctgtat attcctttt ttgcatctgc ataatctgct gcatatgtga ttatgtgata     4140
atgacggaat tacccagaaa agccttagcg tgtgaggcct atcattctca gaaagtcaca    4200
gtaggaaact tgcattttca tcttgtattt ttgtaagttg gctaagagca ctagctataa    4260
caaatgcatc tatggcattt tttgagagtt ataataatga gagcaacaaa gggtggtact    4320
attgttcaaa atttgtttat gtgctttgtc tcacaatgga gtttaaagtc atctccgagt    4380
agtactacga ctttaagtag agaatacttt gtattttctt tatagagctc agagatatac    4440
ttcagtatgt gtcggaggtt gttcccttgg gaaaagggc attttatcaa ctgtgaacta     4500
tcgctactat ggctgaggaa aagtagatag caacaaagat agtattctgg tttataatc     4560 aaaccgtaat ctttcaacat gttcgaagat cgctttcact ttataatcct ttttgactgc    4620
cctgctgaaa gggcttttt gttatgaaac tatcctcgct cgattttctt atctttggat     4680
tctattacca cggataatgt ttgttggaat tattttagaa gaag                     4724
```

<210> SEQ ID NO 4
<211> LENGTH: 748
<212> TYPE: PRT
<213> ORGANISM: Granulocytic Ehrlichia
<220> FEATURE:
<223> OTHER INFORMATION: S22 of Granulocytic Ehrlichia

<400> SEQUENCE: 4

```
Met Leu Arg Cys Asn Ser Met Asp Val Asp Ala Arg Ser His Asp Gly
 1               5                  10                  15

Arg Thr Ile Ile His Tyr Ala Ala Lys Asp Gly Asn Leu Glu Ile Leu
            20                  25                  30

Gln Gln Ala Leu Gly Arg Lys Ser Ser Tyr Ser Lys Phe Pro Val Lys
        35                  40                  45

Asp Gly Val Pro Thr Pro Gly Val Tyr Ala Ile Arg Glu Ala Ser Gly
    50                  55                  60

Gly Lys Val Ser Leu Gln Ala Leu Asp Met Leu Met Arg Tyr Glu Pro
65                  70                  75                  80

His Pro Gln His Val Ala Val Glu Ala Val Arg Thr Gly Ala Val Gly
                85                  90                  95

Val Leu Glu His Leu Ile Thr Thr Glu Val Ile Ser Val Asn Glu Glu
            100                 105                 110

Ile Thr Thr Pro Glu Gly Lys Lys Thr Thr Leu Thr Ala Glu Ala Leu
        115                 120                 125

Thr Ser Gly Lys Tyr Gly Val Val Lys Ala Leu Ile Lys Asn Ser Ala
    130                 135                 140

Asp Val Asn Ala Ser Pro Glu Pro Ala Ile Thr Leu Gly Ile Gln Gly
145                 150                 155                 160

Arg Cys Phe Gln Gly Ser Lys Ala Ile Lys His Leu Lys Arg Val Val
                165                 170                 175

Glu Ala Gly Ala His Ile Asn Thr Pro Thr Gly Ser Met Ser Pro Leu
            180                 185                 190

Ala Ala Ala Val Gln Ala Ala Asn Glu Ala Ser Asn Leu Lys Glu Ala
        195                 200                 205

Asn Lys Ile Val Asn Phe Leu Leu His Arg Gly Ala Asp Leu Ser Ser
    210                 215                 220
```

```
Thr Glu His Thr Gly Thr Pro Ala Leu His Leu Ala Thr Ala Ala Gly
225                 230                 235                 240

Asn His Arg Thr Ala Met Leu Leu Leu Asp Lys Gly Ala Pro Ala Thr
            245                 250                 255

Gln Arg Asp Ala Arg Gly Arg Thr Leu His Ile Ala Ala Ala Asn
        260                 265                 270

Gly Asp Gly Lys Leu Tyr Arg Met Ile Ala Lys Lys Cys Pro Asp Ser
        275                 280                 285

Cys Gln Pro Leu Cys Ser Asp Met Gly Asp Thr Ala Leu His Glu Ala
        290                 295                 300

Leu Tyr Ser Asp Asn Val Thr Glu Lys Cys Phe Leu Lys Met Leu Lys
305                 310                 315                 320

Glu Ser Arg Lys His Leu Ser Asn Ser Ser Phe Phe Gly Asp Leu Leu
            325                 330                 335

Asn Thr Pro Gln Glu Ala Asn Gly Asp Thr Leu Leu His Leu Ala Ala
        340                 345                 350

Ser Arg Gly Phe Gly Lys Ala Cys Lys Ile Leu Leu Lys Ala Gly Ala
        355                 360                 365

Ser Val Ser Val Val Asn Val Glu Gly Lys Thr Pro Val Asp Val Ala
370                 375                 380

Asp Pro Ser Leu Lys Thr Arg Pro Trp Phe Phe Gly Lys Ser Val Val
385                 390                 395                 400

Thr Met Met Ala Glu Arg Val Gln Val Pro Glu Gly Gly Phe Pro Pro
            405                 410                 415

Tyr Leu Pro Pro Glu Ser Pro Thr Pro Ser Leu Gly Ser Ile Ser Ser
        420                 425                 430

Phe Glu Ser Val Ser Ala Leu Ser Ser Leu Gly Ser Gly Leu Asp Thr
        435                 440                 445

Ala Gly Ala Glu Glu Ser Ile Tyr Glu Glu Ile Lys Asp Thr Ala Lys
450                 455                 460

Gly Thr Thr Glu Val Glu Ser Thr Tyr Thr Thr Val Gly Ala Glu Glu
465                 470                 475                 480

Ser Ile Tyr Glu Glu Ile Lys Asp Thr Ala Lys Gly Thr Thr Glu Val
            485                 490                 495

Glu Ser Thr Tyr Thr Thr Val Gly Ala Glu Gly Pro Arg Thr Pro Glu
        500                 505                 510

Gly Glu Asp Leu Tyr Ala Thr Val Gly Ala Ala Ile Thr Ser Glu Ala
        515                 520                 525

Gln Ala Ser Asp Ala Ala Ser Ser Lys Gly Glu Arg Pro Glu Ser Ile
        530                 535                 540

Tyr Ala Asp Pro Phe Asp Ile Val Lys Pro Arg Gln Glu Arg Pro Glu
545                 550                 555                 560

Ser Ile Tyr Ala Asp Pro Phe Ala Ala Glu Arg Thr Ser Ser Gly Val
            565                 570                 575

Thr Thr Phe Gly Pro Lys Glu Glu Pro Ile Tyr Ala Thr Val Lys Lys
        580                 585                 590

Gly Pro Lys Lys Ser Asp Thr Ser Gln Lys Glu Gly Thr Ala Ser Glu
        595                 600                 605

Lys Val Cys Ser Thr Ile Thr Val Ile Lys Lys Val Lys Pro Gln
610                 615                 620

Val Pro Ala Arg Thr Ser Ser Leu Pro Thr Lys Glu Gly Ile Gly Ser
625                 630                 635                 640

Asp Lys Asp Leu Ser Ser Gly Thr Ser Ser Phe Ala Ala Glu Leu
```

```
                645                 650                 655

Gln Ala Gln Arg Gly Lys Leu Arg Pro Val Lys Gly Gly Ala Pro Asp
            660                 665                 670

Ser Thr Lys Asp Lys Thr Ala Thr Ser Ile Phe Ser Ser Lys Glu Phe
        675                 680                 685

Lys Lys Glu Leu Thr Lys Ala Ala Glu Gly Leu Gln Gly Ala Val Glu
    690                 695                 700

Glu Ala Gln Lys Gly Asp Gly Gly Ala Ala Lys Ala Lys Gln Asp Leu
705                 710                 715                 720

Gly Met Glu Ser Gly Ala Pro Gly Ser Gln Pro Glu Ala Pro Gln Ser
                725                 730                 735

Glu Gly Pro Lys Ser Val Lys Gly Gly Arg Gly Arg
            740                 745
```

<210> SEQ ID NO 5
<211> LENGTH: 3998
<212> TYPE: DNA
<213> ORGANISM: Granulocytic Ehrlichia
<220> FEATURE:
<223> OTHER INFORMATION: S7 of Granulocytic Ehrlichia

<400> SEQUENCE: 5

```
gaattcctga tagtatttta gaggatagta ggcaatatgg tttaggggat ttcttcgcat     60
acttgttatc atcgtcctta tttgtgctta gttggtcgga tatttgtgca agttgttgta    120
aaatatgcat attgtatgta taggtgtgca agatatcatc tctttaggtg tatcgtgtag    180
cacttaaaca aatgctggtg aacgtagagg gattaaagga ggatttgcgt atatgtatgg    240
tatagatata gagctaagtg attacagaat tggtagtgaa accatttcca gtggagatga    300
tggctactac gaaggatgtg cttgtgacaa agatgccagc actaatgcgt actcgtatga    360
caagtgtagg gtagtacggg gaacgtggag accgagcgaa ctggttttat atgttggtga    420
tgagcatgtg gcatgtagag atgttgcttc gggtatgcat catggtaatt tgccagggaa    480
ggtgtatttt atagaggcag aagcgggcag agctgctact gctgaaggtg gtgtttatac    540
taccgttgtg gaggcattat cgctggtgca agaggaagag ggtacaggta tgtacttgat    600
aaacgcacca gaaaaagcgg tcgtaaggtt tttcaagata gaaaagagtg cagcagagga    660
acctcaaaca gtagatccta gtgtagttga gtcagcaaca gggtcgggtg tagatacgca    720
agaagaacaa gaaatagatc aagaagcacc agcaattgaa gaagttgaga cagaagagca    780
agaagttatt ctggaagaag gtactttgat agatcttgag caacctgtag cgcaagtacc    840
tgtagtagct gaagcagaat tacctggtgt tgaagctgca gaagcgattg taccatcact    900
agaagaaaat aagcttcaag aagtggtagt tgctccagaa gcgcaacaac tagaatcagc    960
tcctgaagtt tctgcgccag cacaacctga gtctacagtt cttggtgttg ctgaaggtga   1020
tctaaagtct gaagtatctg tagaagctaa tgctgatgta ccgcaaaaag aagtaatctc   1080
tggtcaacaa gagcaagaaa ttgcagaagc actagaggga actgaagctc ctgtagaagt   1140
aaaagaagaa acagaagttc ttctaaagga agatactttg atagatcttg agcaacctgt   1200
agcacaagta cctgtagtag ctgaagcaga attacctggt gttgaagctg cagaagcgat   1260
tgtaccatca ctagaagaaa ataagcttca agaagtggta gttgctccag aagcgcaaca   1320
actagaatca gctcctgaag tttctgcgcc agcacaacct gagtctacag ttcttggtgt   1380
tactgaaggt gatctgaagt ctgaagtatc tgtagaagct gatgctggta tgcagcaaga   1440
agcaggaatc tctgatcaag agacacaagc aactgaagaa gttgaaaagg ttgaagtatc   1500
```

```
tgtagaaaca aaaacggaag agccagaagt tattctagaa gaaggtactt tgatagatct    1560
tgagcaacct gtagcgcaag tacctgtagt agctgaagca gaattacctg gtgttgaagc    1620
tgcagaagcg attgtaccat cactagaaga aaataagctt caagaagtgg tagttgctcc    1680
agaagcggaa caactagaat cagctcctga agtttctgcg ccagtacaac ctgagtctac    1740
agttcttggt gttactgaag gtgatctgaa gtctgaagta tctgtagaag ctgatgctgg    1800
tatgcagcaa gaagcaggaa tctctgatca agagacacaa gcaactgaag aagttgagaa    1860
ggttgaagta tctgtagaac ctgatcctgg tatgcagcaa gagttagtag atgttccgac    1920
tgctttgccg ttaaaggatc ctgacgatga agatgttcta agttattagg atatctttct    1980
cgtgaaaagt atggggaagg ttcgatgtgt tgaaccgtgc cccatgcttt ttctttaaga    2040
tttcttcaaa aagaggtaaa actctcctat gttttttgtg agcagtaatt tcttgcagtt    2100
ttgcgactga gttgtgtgtt attgcgaagt ttttcttctg attattggac gaaggtggtg    2160
cttgtcatgt ctgtggtgcg tgcttttcat gcttgataga gctcctgatt attttcttta    2220
tacgcaagcc aggtaaatcg tgtatgtggc gacttttcga atcagtgttt agattacata    2280
gaagtaattg tggcttatac gctgttaatt gcgctgcaat ctgtcaaaag tgatgcagta    2340
acttcctcta tatgtcctaa tgctgttaca tgacatgggt aatgcatagc attatcaatg    2400
gtcatggtgt ctttagtagg cataccagcg gttttatata ccagtgatgc gcgagccttg    2460
ttctccgctt tcataaaaga tttattactc aagatattgg tatacctagc gattcacgtg    2520
taatttgagt acttacctgc gtatttcgaa ggtaacgtac taatagcgta tggtaaaact    2580
atctattatc ccaatcccta agaataacta tgctgttttg gagctgttgc atgctgaaag    2640
atgtcttata gcatcgcggt tatatatttt cacattttag agattttaag agtataactt    2700
tctagcatct tagagaacta tactcaaagt taaacacaat aaaaacatga agcattaaaa    2760
ctcaagtata ctaaaccagc cttagacctt aaaggaaagt aaggaatgct tatctatgtt    2820
caattgtgcc attacttaaa aagcgaacct aacaccgaat tccccaccga cataagccat    2880
ggagaaatta gcaatagcag tatccttagt acgacccgcc ggactagtat catctacaag    2940
acgttgagcc ggcagatcat cataaacgcc atctccaaca acgcgatgat agaatccacc    3000
cgcaaaagcg gagatttcag gtgagagctg ataactcaag ccagccttta acctcaagct    3060
taggagtgat gttctagaca ccatccgtat tagtcacaga ttagcttcct ctcgaagtac    3120
agataacctc tggaaagttt tagaaaggac ggaatgtgta acgccgctcc gtgccatcaa    3180
ccacgccaac gaagttaccg cctaaaccaa cacaagcata aggaacaaca cctaaacctt    3240
cactaagaag atcataacaa gcattaacca ttacagatgt agaagaaaca gctctgatct    3300
caacaacctc tcccccttca atagttttag caagtaatcc tgctactatg gttttttcat    3360
cacgattaag acctaatagg tctttagcca tagcgtttgc attactatta ggttctccct    3420
cgacgttttg actgctgcca ttactccctc gtccccctagg ccagttttta ccttcaccga    3480
ctttcacagt attaacaaaa ccactcaacg tctttggtcc tgtcgccccc gtcgtatttc    3540
ccaaaccgct acactgtgtt gtctcctcgt tgccgtgtgt cgtcgacaac tccgcaacat    3600
acttcttccc cttagcctta gttatagcag catgatcccc actacaaacc ttcccatcaa    3660
tttcagggct ggaaattttc acagcattgg caaactgaac gatgtctttc ccagaggttt    3720
tggcaagagc agcggcaagg ttatcagtct gcccagtaac aacatcataa gctaactcct    3780
tagctagtag atatactgta tcagcttcat cttccttact accactatct ctaataccct    3840
tggtcttcct tttaataata agagttattg cataggatat tgatatacct atcgatttat    3900
```

-continued aggcagttga gccggaagat catcttaaac accatctccc acaacacgat ggtaaaagcc 3960
acccgcagga attccggaat tccggaattc cggaattc 3998


<210> SEQ ID NO 6
<211> LENGTH: 578
<212> TYPE: PRT
<213> ORGANISM: Granulocytic Ehrlichia
<220> FEATURE:
<223> OTHER INFORMATION: S7 of Granulocytic Ehrlichia

<400> SEQUENCE: 6

```
Met Tyr Gly Ile Asp Ile Glu Leu Ser Asp Tyr Arg Ile Gly Ser Glu
 1               5                  10                  15

Thr Ile Ser Ser Gly Asp Asp Gly Tyr Tyr Glu Gly Cys Ala Cys Asp
            20                  25                  30

Lys Asp Ala Ser Thr Asn Ala Tyr Ser Tyr Asp Lys Cys Arg Val Val
        35                  40                  45

Arg Gly Thr Trp Arg Pro Ser Glu Leu Val Leu Tyr Val Gly Asp Glu
    50                  55                  60

His Val Ala Cys Arg Asp Val Ala Ser Gly Met His His Gly Asn Leu
65                  70                  75                  80

Pro Gly Lys Val Tyr Phe Ile Glu Ala Glu Ala Gly Arg Ala Ala Thr
                85                  90                  95

Ala Glu Gly Gly Val Tyr Thr Thr Val Val Glu Ala Leu Ser Leu Val
            100                 105                 110

Gln Glu Glu Glu Gly Thr Gly Met Tyr Leu Ile Asn Ala Pro Glu Lys
        115                 120                 125

Ala Val Val Arg Phe Phe Lys Ile Glu Lys Ser Ala Ala Glu Glu Pro
    130                 135                 140

Gln Thr Val Asp Pro Ser Val Val Glu Ser Ala Thr Gly Ser Gly Val
145                 150                 155                 160

Asp Thr Gln Glu Glu Gln Glu Ile Asp Gln Glu Ala Pro Ala Ile Glu
                165                 170                 175

Glu Val Glu Thr Glu Glu Gln Glu Val Ile Leu Glu Glu Gly Thr Leu
            180                 185                 190

Ile Asp Leu Glu Gln Pro Val Ala Gln Val Pro Val Val Ala Glu Ala
        195                 200                 205

Glu Leu Pro Gly Val Glu Ala Ala Glu Ala Ile Val Pro Ser Leu Glu
    210                 215                 220

Glu Asn Lys Leu Gln Glu Val Val Val Ala Pro Glu Ala Gln Gln Leu
225                 230                 235                 240

Glu Ser Ala Pro Glu Val Ser Ala Pro Ala Gln Pro Glu Ser Thr Val
                245                 250                 255

Leu Gly Val Ala Glu Gly Asp Leu Lys Ser Glu Val Ser Val Glu Ala
            260                 265                 270

Asn Ala Asp Val Pro Gln Lys Glu Val Ile Ser Gly Gln Gln Glu Gln
        275                 280                 285

Glu Ile Ala Glu Ala Leu Glu Gly Thr Glu Ala Pro Val Glu Val Lys
    290                 295                 300

Glu Glu Thr Glu Val Leu Leu Lys Glu Asp Thr Leu Ile Asp Leu Glu
305                 310                 315                 320

Gln Pro Val Ala Gln Val Pro Val Val Ala Glu Ala Glu Leu Pro Gly
                325                 330                 335

Val Glu Ala Ala Glu Ala Ile Val Pro Ser Leu Glu Glu Asn Lys Leu
            340                 345                 350

-continued

```
Gln Glu Val Val Ala Pro Glu Ala Gln Gln Leu Glu Ser Ala Pro
        355                 360                 365
Glu Val Ser Ala Pro Ala Gln Pro Glu Ser Thr Val Leu Gly Val Thr
370                 375                 380
Glu Gly Asp Leu Lys Ser Glu Val Ser Val Glu Ala Asp Ala Gly Met
385                 390                 395                 400
Gln Gln Glu Ala Gly Ile Ser Asp Gln Glu Thr Gln Ala Thr Glu Glu
                405                 410                 415
Val Glu Lys Val Glu Val Ser Val Glu Thr Lys Thr Glu Glu Pro Glu
            420                 425                 430
Val Ile Leu Glu Glu Gly Thr Leu Ile Asp Leu Glu Gln Pro Val Ala
        435                 440                 445
Gln Val Pro Val Ala Glu Ala Glu Leu Pro Gly Val Glu Ala Ala
    450                 455                 460
Glu Ala Ile Val Pro Ser Leu Glu Glu Asn Lys Leu Gln Glu Val Val
465                 470                 475                 480
Val Ala Pro Glu Ala Gln Leu Glu Ser Ala Pro Glu Val Ser Ala
                485                 490                 495
Pro Val Gln Pro Glu Ser Thr Val Leu Gly Val Thr Glu Gly Asp Leu
            500                 505                 510
Lys Ser Glu Val Ser Val Glu Ala Asp Ala Gly Met Gln Gln Glu Ala
        515                 520                 525
Gly Ile Ser Asp Gln Glu Thr Gln Ala Thr Glu Glu Val Lys Val
    530                 535                 540
Glu Val Ser Val Glu Ala Asp Ala Gly Met Gln Gln Glu Leu Val Asp
545                 550                 555                 560
Val Pro Thr Ala Leu Pro Leu Lys Asp Pro Asp Asp Glu Asp Val Leu
                565                 570                 575
Ser Tyr

<210> SEQ ID NO 7
<211> LENGTH: 5570
<212> TYPE: DNA
<213> ORGANISM: Granulocytic Ehrlichia
<220> FEATURE:
<223> OTHER INFORMATION: S23 of Granulocytic Ehrlichia

<400> SEQUENCE: 7
gaattccctg tggttattag gcgtggtttc gcctgataat aaagatactt tagagggtat      60
aaacttggaa aaataatga aaacccctcc ttagtgcctc cccgttttg acaacatact       120 cttatggaaa agcgttaggg agttgcttcg cttgtcacgc gtgcgttagg ttttacgtat     180
acgtgtctgg gacttcacga aaactcgacg caggcggatt ttgtactatg tttcacttaa     240
caaggtatta taattgtttg aacacaatat tcctgataca tacacaggaa caactgcaga     300
aggttctcct ggcttagcag gcggggattt tagtttaagt tctattgact ttacaaggga     360
ctttacaatt gaatcacata gaggaagctc agctgatgac ccaggttaca tcagctttag     420
ggatcaagac ggaaacgtca tgtcacgttt tcttgatgtg tacgtagcta atttcagctt     480
gcgatgcaag cattctccct ataacaacga cagaatggaa acagctgcgt tctctctaac     540
tcccgacata atagagcctt ctgctttatt gcaagaatca catagtacac aaaacaatgt     600
agaagaggca gtacaagtta cagctcttga gtgccctcca tgtaatccag tccctgccga     660
ggaagtagct cctcaaccgt cttttctaag cagaataatt caggcgttct gtggttatt      720 cacgccttct tctactaccg acactgctga agacagcaag tgtaatagta gcgatacttc     780
```

```
aaaatgtacc tctgctagca gtgagtcatt agagcagcaa caagaatcag tggaagtgca    840
accatctgta cttatgtcta ctgcccctat agcaacagag cctcaaaatg cggttgttaa    900
ccaagtaaac actactgcag tacaagtaga atcatccatt attgtgccag aatcgcaaca    960
cactgacgtt accgtgctcg aagatactac tgagacgata actgttgatg gggaatatgg   1020
acattttagt gacattgctt caggtgaaca caataacgat ctgcctgcca tgttgttaga   1080
tgaagcagac ttcactatgt tattagcgaa cgaggagtca aagaccctgg agtctatgcc   1140
ttctgatagc ctagaagaca atgttcagga actaggtaca ttgcctttac aagaaggtga   1200
aacagtttct gagggcaaca cacgagagtc actacccact gacgtttcac aagactcagt   1260
tggtgtaagt acagatcttg aagctcattc tcaagaagtt gaaacagttt ctgaggtcag   1320
cacacaagat tcactatcca ctaacatttc acaagactca gttggtgtaa gtacagatct   1380
tgaagttcat tctcaagaag ttgaaatagt ttctgagggc ggcacacaag attcactatc   1440
cactaacatt tcacaagact cagttggtgt aagtacagat cttgaagctc attctaaagg   1500
agttgaaata gtttctgagg gcggcacaca aaattcacta tccgctgatt ttccaataaa   1560
cacagttgaa agtgaaagta cagatcttga agctcattcc ccagaaggtg aaatagtttc   1620
tgaggtcagc acacaagatg cgccatccac tggagtagag atcagattta tggatcgtga   1680
ttttgatgat gacgtgctcg cgttgtgaag tgatcatggt aggggaaaca gttatggcgt   1740
aaagacatct ttgatgactt gtcttgcgtg aataagtagt gcaagttttt tatgcattga   1800
tgtgcatgat cattgcccct aaggaaagca gtactaatgg tagtctaaga tcttatacag   1860
ggtttcggac taccactttt ggtgttttaa aacgtcttat tcgcgttggg tgcttgctta   1920
caatgtacct gtacgtgccc aacactaaaa atggtcagta ttacttaggg gagttcgtag   1980
acgaggcatc tcgatttact cttggtaagc tacaaataac tcagtcatat caaggtagtt   2040
caagatgaaa gcagtcctat gcttatcatg gagaattcct gcggttctct tcaaaattct   2100
cttttcccgc aagggcagac tcttatttgt taaaataaca aaatttctct acaggaagcg   2160
acatttcata tcaaagctga ttgtgaaata atggcattga gtattttttct cgccctagaa   2220 gataatcatt tcggcactat caaagcattt acgatattct ccattatctt gtaatcagat   2280
ggctatcttg aaagcaacca aggatatccg tacatggtag cttacatact gctatcaatc   2340
tcctatacga ccttcaatga aacggtaact gttgctgaca gcttgcacat gctgtgattc   2400
aattcctggt tcctagatgt tctactacgt ttatccggta ctaatattat tctttggcgc   2460
tctattatct agcaactcag agtccattat tggatctcta ataccaaggg tataagggaa   2520
agtggaagag tattattaga gagaagaagc aaatacagta tatctactag ctaaggagtt   2580
agcttatgat gttgttactg gacagactga taagcttgct gctgctcttg ccaagacctc   2640
cgggaaagat atcgttcagt ttgctaaggc agttgagatt tcggctccta agatcgataa   2700
gcaagtttgt gtgactaata agaatgggga tagcggaaca agatatgcta agtacctcga   2760
agaagctgga acgtctagca atgctggcac gtcgttgtgt ggtggtaaaa acctaaagac   2820
gactgactcc aacacaggag tagagaaagg acaggtgtta catgactttg tttctggaac   2880
gttgagtggg ggtactaaga actggccgac atctagtgaa agtactaaag aaaataacga   2940
caacgcaggg aaggtagcta aagacctgac aaaaactaacc cctgaggaaa aaccatagt   3000 agcagggtta ctagctaaga ctattgaagg gggtgaagtt gttgagatca gggcggtttc   3060
ttctacttct gtgatggtta atgcttgtta tgatcttctt agtgaaggtt taggtgtcgt   3120
tccttacgct tgtgttggtc ttgggggtaa cttcgtgggg ggttgttgat ggcacggcgc   3180
```

```
agcgttacac aatccgtcct tgacctgaat actctagtta agcactaggc aaaattagtg   3240
ctggatcact tacgcaacat actacggtca gcgattttcc atactgagca ggtacgtaca   3300
gtggctttat actcttaccc agcatgaaat tacttgttat ctaagaatct ccacagctga   3360
ccttagaaag gttatctgtc cttcgagaga aagctaatct gtgtcttatg cggatggcgt   3420
tgaacgtatt acaggtccca agctgtcttg caagtttcta aggatattat aagggcacac   3480
ctataaaact gcgcaatata tcacctgcaa tacggtcccg attcgaaaac actgggaagt   3540
gcgctcatta tctatgaatc gctagctagg cataaataag agtatacgca ataacgctta   3600
ttattaaaaa caagaccaag ggtattagag atagtggtag taaggaagat gaagctgata   3660
cagtatatct actagctaag gagttagctt atgatgttgt tactgggcag actgataacc   3720
ttgctgctgc tcttgccaag acttctggta agatattgt tcagtttgct aagactctta   3780
atatttctca ctctaatatc gatgggaagg tttgtaggag ggaaaagcat gggagtcaag   3840
gtttgactgg aaccaaagca ggttcgtgtg atagtcagcc acaaacggcg ggtttcgatt   3900
ccatgaaaca aggtttgatg gcagctttag gcgaacaagg cgctgaaaag tggcccaaaa   3960
ttaacaatgg tggccacgca acaatttata gtagtagcgc aggtccagga atgcgtatg    4020
ctagagatgc atctactacg gtagctacag acctaacaaa gctcactact gaagaaaaaa   4080
ccatagtagc agggttacta gctagaacta ttgaaggggg tgaagttgtt gagattaggg   4140
cagtttcttc tacttctgtg atggttaatg cttgttatga tcttctgaag ggaaacgcat   4200
cacattattt atctggttgc tgtaatctga tcttcccgtt gctatgatcg catctccccc   4260
tcacttctct cgcaaactct ggattaacct ctggatgcga ataatgttta tcagctttga   4320
gaaaaacata ttagagtttt atacagcacc aatgataagc gtgggcactt aaataaaggt   4380
tcatatccct agaaatttat cccactagct aaaattattg aaggggggtga ggtcgttgag   4440
ataagggcag tttcttctac ttctgtgatg gttaatgctt gttatgatct tcttagtgaa   4500
ggtttaggcg ttgttcctta tgcttgcgtg ggtcttggtg ggaacttcgt gggcgtggtt   4560
gatgggcata tcacaaacca ctccatctct gaccctgtat gcactagcaa gtaactaggc   4620
aaaattattg ctgcatcact ttgaaacaaa ctacgatcag caatgttcaa tacttagcag   4680
gtctgtacag tggctttaca ctcttaccca gcatgaaata cttgctatct aagaatctcc   4740
tctaaaactt tccagaggtt atctgtactt tgagggaagc taatctgtgg ctaatgagga   4800
tggtgtctag aatatcactc ctaagcttgc ttataggtta aaggctgggt tgagttatca   4860
gctttctcct gaaatctctg cttttgtagg tggtttctat cattggtttg ttggttatgg   4920
tgtttatgat gatcttccgg ctcaacgtct tgtagatgat actagtccgg cgggtcgtac   4980
taaggatact gctattgcta acttctccat ggcctatgtt ggtgcatcat ttcagccata   5040
ttacgcagtt cttctagtag aactgtatga gtatcgataa aaagatatac gacgcagcat   5100
gctctgaaaa agtgacaggg tgaacagcag tgcagcatac attagcctgt ctgtatcagt   5160
gtgcaatctg ttacaaaact actaggatca ttctttttaac acctatcggg ttcatcaaga   5220
aaatgagtgc atacgtgacg gcaagcgcta aaacgctaaa gctgatgcat cacattaaaa   5280
tgtgttgacg ttagaccttc caagcactgt aaagtgtggc gattcccccg catacgttct   5340
tatgcgtgat tttgaaaaac ccggcgtctg caacttcgga agagaattgt ttttgtgtgg   5400
gaaaagctct tatgctttca actaagtagg aatatgcatc aatatccccg gctactattt   5460
tgccaatttt cggtataaca aagaaagaat acaggtcata agctgttttg aatgcactgt   5520
cttcgagtat aggagaaaac tccaagcata aaaacctacc acatggtttc                5570
```

-continued

<210> SEQ ID NO 8
<211> LENGTH: 484
<212> TYPE: PRT
<213> ORGANISM: Granulocytic Ehrlichia
<220> FEATURE:
<223> OTHER INFORMATION: S23 of Granulocytic Ehrlichia

<400> SEQUENCE: 8

```
Met Phe Glu His Asn Ile Pro Asp Thr Tyr Thr Gly Thr Thr Ala Glu
 1               5                  10                  15

Gly Ser Pro Gly Leu Ala Gly Gly Asp Phe Ser Leu Ser Ser Ile Asp
            20                  25                  30

Phe Thr Arg Asp Phe Thr Ile Glu Ser His Arg Gly Ser Ser Ala Asp
        35                  40                  45

Asp Pro Gly Tyr Ile Ser Phe Arg Asp Gln Asp Gly Asn Val Met Ser
    50                  55                  60

Arg Phe Leu Asp Val Tyr Val Ala Asn Phe Ser Leu Arg Cys Lys His
65                  70                  75                  80

Ser Pro Tyr Asn Asn Asp Arg Met Glu Thr Ala Ala Phe Ser Leu Thr
                85                  90                  95

Pro Asp Ile Ile Glu Pro Ser Ala Leu Leu Gln Glu Ser His Ser Thr
            100                 105                 110

Gln Asn Asn Val Glu Glu Ala Val Gln Val Thr Ala Leu Glu Cys Pro
        115                 120                 125

Pro Cys Asn Pro Val Pro Ala Glu Glu Val Ala Pro Gln Pro Ser Phe
    130                 135                 140

Leu Ser Arg Ile Ile Gln Ala Phe Leu Trp Leu Phe Thr Pro Ser Ser
145                 150                 155                 160

Thr Thr Asp Thr Ala Glu Asp Ser Lys Cys Asn Ser Ser Asp Thr Ser
                165                 170                 175

Lys Cys Thr Ser Ala Ser Ser Glu Ser Leu Glu Gln Gln Gln Glu Ser
            180                 185                 190

Val Glu Val Gln Pro Ser Val Leu Met Ser Thr Ala Pro Ile Ala Thr
        195                 200                 205

Glu Pro Gln Asn Ala Val Val Asn Gln Val Asn Thr Thr Ala Val Gln
    210                 215                 220

Val Glu Ser Ser Ile Ile Val Pro Glu Ser Gln His Thr Asp Val Thr
225                 230                 235                 240

Val Leu Glu Asp Thr Thr Glu Thr Ile Thr Val Asp Gly Glu Tyr Gly
                245                 250                 255

His Phe Ser Asp Ile Ala Ser Gly Glu His Asn Asn Asp Leu Pro Ala
            260                 265                 270

Met Leu Leu Asp Glu Ala Asp Phe Thr Met Leu Leu Ala Asn Glu Glu
        275                 280                 285

Ser Lys Thr Leu Glu Ser Met Pro Ser Asp Ser Leu Glu Asp Asn Val
    290                 295                 300

Gln Glu Leu Gly Thr Leu Pro Leu Gln Glu Gly Glu Thr Val Ser Glu
305                 310                 315                 320

Gly Asn Thr Arg Glu Ser Leu Pro Thr Asp Val Ser Gln Asp Ser Val
                325                 330                 335

Gly Val Ser Thr Asp Leu Glu Ala His Ser Gln Glu Val Glu Thr Val
            340                 345                 350

Ser Glu Val Ser Thr Gln Asp Ser Leu Ser Thr Asn Ile Ser Gln Asp
        355                 360                 365

Ser Val Gly Val Ser Thr Asp Leu Glu Val His Ser Gln Glu Val Glu
```

```
            370                 375                 380
Ile Val Ser Glu Gly Gly Thr Gln Asp Ser Leu Ser Thr Asn Ile Ser
385                 390                 395                 400

Gln Asp Ser Val Gly Val Ser Thr Asp Leu Glu Ala His Ser Lys Gly
                405                 410                 415

Val Glu Ile Val Ser Glu Gly Gly Thr Gln Asp Ser Leu Ser Ala Asp
                420                 425                 430

Phe Pro Ile Asn Thr Val Glu Ser Glu Ser Thr Asp Leu Glu Ala His
                435                 440                 445

Ser Pro Glu Gly Glu Ile Val Ser Glu Val Ser Thr Gln Asp Ala Pro
                450                 455                 460

Ser Thr Gly Val Glu Ile Arg Phe Met Asp Arg Asp Ser Asp Ser Asp
465                 470                 475                 480

Val Leu Ala Leu

<210> SEQ ID NO 9
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 9

Asp Gly Arg Thr Ile Ile His Tyr Ala Ala Lys Asp Gly Asn Leu Glu
1               5                   10                  15

Ile Leu Gln Gln Ala Leu Gly Arg Lys Ser Ser Tyr Ser Lys Phe Pro
                20                  25                  30

Val

<210> SEQ ID NO 10
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 10

Lys Lys Thr Thr Leu Thr Ala Glu Ala Leu Thr Ser Gly Lys Tyr Gly
1               5                   10                  15

Val Val Lys Ala Leu Ile Lys Asn Ser Ala Asp Val Asn Ala Ser Pro
                20                  25                  30

Glu

<210> SEQ ID NO 11
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 11

Ala Val Gln Ala Ala Asn Glu Ala Ser Asn Leu Lys Glu Ala Asn Lys
1               5                   10                  15

Ile Val Asn Phe Leu Leu His Arg Gly Ala Asp Leu Ser Ser Thr Glu
                20                  25                  30

His

<210> SEQ ID NO 12
<211> LENGTH: 33
<212> TYPE: PRT
```

```
<213> ORGANISM: Granulocytic Ehrlichia
<220> FEATURE:
<223> OTHER INFORMATION: proposed ankyrin repeat

<400> SEQUENCE: 12

Thr Gly Thr Pro Ala Leu His Leu Ala Thr Ala Ala Gly Asn His Arg
 1               5                  10                  15

Thr Ala Met Leu Leu Leu Asp Lys Gly Ala Pro Ala Thr Gln Arg Asp
                20                  25                  30

Ala

<210> SEQ ID NO 13
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 13

Arg Gly Arg Thr Ala Leu His Ile Ala Ala Ala Asn Gly Asp Gly Lys
 1               5                  10                  15

Leu Tyr Arg Met Ile Ala Lys Lys Cys Pro Asp Ser Cys Gln Pro Leu
                20                  25                  30

Cys

<210> SEQ ID NO 14
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 14

Met Gly Asp Thr Ala Leu His Glu Ala Leu Tyr Ser Asp Asn Val Thr
 1               5                  10                  15

Glu Lys Cys Phe Leu Lys Met Leu Lys Glu Ser Arg Lys Arg Leu Ser
                20                  25                  30

Asn

<210> SEQ ID NO 15
<211> LENGTH: 35
<212> TYPE: PRT
<213> ORGANISM: Granulocytic Ehrlichia
<220> FEATURE:
<223> OTHER INFORMATION: proposed ankyrin repeat

<400> SEQUENCE: 15

Asn Gly Asp Thr Leu Leu His Leu Ala Ala Ser Arg Gly Phe Gly Lys
 1               5                  10                  15

Ala Cys Lys Ile Leu Leu Lys Ala Gly Ala Ser Val Ser Val Val Ala
                20                  25                  30

Ser Asn Val
        35

<210> SEQ ID NO 16
<211> LENGTH: 33
<212> TYPE: PRT
<213> ORGANISM: Granulocytic Ehrlichia
<220> FEATURE:
<223> OTHER INFORMATION: proposed ankyrin repeat

<400> SEQUENCE: 16

Glu Gly Lys Thr Pro Val Asp Val Ala Asp Pro Ser Leu Lys Thr Arg
```

```
                    1               5                  10                  15
Pro Trp Phe Phe Gly Lys Ser Val Val Thr Met Met Ala Glu Arg Val
                    20                  25                  30
Gln

<210> SEQ ID NO 17
<211> LENGTH: 33
<212> TYPE: PRT
<213> ORGANISM: Artificial Sequence
<220> FEATURE:
<221> NAME/KEY: VARIANT
<222> LOCATION: 1, 3, 9, 12, 13, 16, 21, 25, 27, 29, 30, 31, 32, 33
<223> OTHER INFORMATION: Xaa = Any Amino Acid
<220> FEATURE:
<223> OTHER INFORMATION: Consensus sequence of ankyrin repeats

<400> SEQUENCE: 17

Xaa Thr Xaa Ser Thr Pro Leu His Xaa Ala His Xaa Xaa Thr Thr Xaa
 1               5                  10                  15
Thr His His Thr Xaa Leu Leu Thr Xaa Thr Xaa Thr Xaa Xaa Xaa Xaa
                    20                  25                  30
Xaa

<210> SEQ ID NO 18
<211> LENGTH: 29
<212> TYPE: PRT
<213> ORGANISM: E. chaffeensis

<400> SEQUENCE: 18

Ser Gly Thr Asp Leu Thr Leu Glu Ser Ala Val His Ser Gln Lys Gln
 1               5                  10                  15
Pro Glu Gly Val Asp Gly Glu Ile Thr Val Ser Glu Gln
                    20                  25

<210> SEQ ID NO 19
<211> LENGTH: 28
<212> TYPE: PRT
<213> ORGANISM: Granulocytic Ehrlichia

<400> SEQUENCE: 19

Gln Pro Ser Val Ser Ala Leu Ser Gln Glu Val Pro Phe Val Val Ala
 1               5                  10                  15
Glu Ser Ala Glu Val Leu Ser Pro Lys Gly Val Glu
                    20                  25

<210> SEQ ID NO 20
<211> LENGTH: 24
<212> TYPE: PRT
<213> ORGANISM: E. chaffeensis

<400> SEQUENCE: 20

Glu Ser Ala Gly Val Ile Ser Asp Gln Pro Gly Ala Thr Gln Val Ala
 1               5                  10                  15
Val Thr Thr Glu Glu Arg Val Glu
                    20

<210> SEQ ID NO 21
<211> LENGTH: 406
<212> TYPE: PRT
<213> ORGANISM: Granulocytic Ehrlichia
<220> FEATURE:
<223> OTHER INFORMATION: C6.1 of Granulocytic Ehrlichia

<400> SEQUENCE: 21
```

```
Met Gly Asp Ala Val Glu Val Arg Ala Glu Asn Leu Gly Gly Glu Ser
  1               5                  10                  15

Ile Leu Glu Ala Pro Ile Arg Val Met Lys Lys Val Gly Asp Thr Val
             20                  25                  30

Ser Ala Glu Asp Val Leu Phe Ile Val Glu Thr Asp Lys Thr Ser Leu
         35                  40                  45

Glu Ile Ser Ala Pro Val Ala Gly Val Leu Thr Glu Leu Arg Val Ala
     50                  55                  60

Asp Glu Glu Val Ile Thr Lys Gly Gln Val Leu Ala Ile Ile Arg Pro
 65                  70                  75                  80

Gln Gly Glu Ala Thr Ala Glu Gly Val Asn Lys Glu Pro Glu Ser Lys
                 85                  90                  95

Glu Glu Val Pro Ala Gln Pro Val Ala Gln Ala Val Ser Thr Gln
            100                 105                 110

Lys Pro Gln Glu Lys Thr Ile Ile Glu Gly Lys Gly Leu Val Thr Pro
            115                 120                 125

Thr Val Glu Asp Phe Val Ala Gly Ile Asn Thr Thr Pro Thr Ser Arg
        130                 135                 140

Ala Leu Gly Met Ser Ala Lys Ser Glu Gln Asp Lys Lys Ile Val Ala
145                 150                 155                 160

Ser Gln Pro Ser Lys Asp Leu Met Ser Cys His Gly Asp Val Val Gly
            165                 170                 175

Glu Arg Arg Val Lys Met Ser Lys Ile Arg Gln Val Ile Ala Ala Arg
        180                 185                 190

Leu Lys Glu Ser Gln Asn Thr Ser Ala Thr Leu Ser Thr Phe Asn Glu
    195                 200                 205

Val Asp Met Ser Lys Val Met Glu Leu Arg Ala Lys Tyr Lys Asp Ala
    210                 215                 220

Phe Val Lys Arg Tyr Asp Val Lys Leu Gly Phe Met Ser Phe Phe Ile
225                 230                 235                 240

Arg Ala Val Val Leu Val Leu Ser Glu Ile Pro Val Leu Asn Ala Glu
            245                 250                 255

Ile Ser Gly Asp Asp Ile Val Tyr Arg Asp Tyr Cys Asn Ile Gly Val
            260                 265                 270

Ala Val Gly Thr Asp Lys Gly Leu Val Val Pro Val Ile Arg Arg Ala
            275                 280                 285

Glu Thr Met Ser Leu Ala Glu Met Glu Gln Ala Leu Val Asp Leu Ser
    290                 295                 300

Thr Lys Ala Arg Ser Gly Lys Leu Ser Val Ser Asp Met Ser Gly Ala
305                 310                 315                 320

Thr Phe Thr Ile Thr Asn Gly Gly Val Tyr Gly Ser Leu Leu Ser Thr
            325                 330                 335

Pro Ile Ile Asn Pro Pro Gln Ser Gly Ile Leu Gly Met His Ala Ile
            340                 345                 350

Gln Gln Arg Pro Val Ala Val Asp Gly Lys Val Glu Ile Arg Pro Met
            355                 360                 365

Met Tyr Leu Ala Leu Ser Tyr Asp His Arg Ile Val Asp Gly Gln Gly
    370                 375                 380

Ala Val Thr Phe Leu Val Arg Val Lys Gln Tyr Ile Glu Asp Pro Asn
385                 390                 395                 400

Arg Leu Ala Leu Gly Ile
                405
```

<210> SEQ ID NO 22
<211> LENGTH: 264
<212> TYPE: PRT
<213> ORGANISM: Granulocytic Ehrlichia
<220> FEATURE:
<223> OTHER INFORMATION: C6.2 of Granulocytic Ehrlichia

<400> SEQUENCE: 22

```
Met Gly Arg Gly Thr Ile Thr Ile His Ser Lys Glu Asp Phe Ala Cys
  1               5                  10                  15

Met Arg Arg Ala Gly Met Leu Ala Ala Lys Val Leu Asp Phe Ile Thr
             20                  25                  30

Pro His Val Val Pro Gly Val Thr Thr Asn Ala Leu Asn Asp Leu Cys
         35                  40                  45

His Asp Phe Ile Ile Ser Ala Gly Ala Ile Pro Ala Pro Leu Gly Tyr
     50                  55                  60

Arg Gly Tyr Pro Lys Ser Ile Cys Thr Ser Lys Asn Phe Val Val Cys
 65                  70                  75                  80

His Gly Ile Pro Asp Asp Ile Ala Leu Lys Asn Gly Asp Ile Val Asn
                 85                  90                  95

Ile Asp Val Thr Val Ile Leu Asp Gly Trp His Gly Asp Thr Ser Arg
            100                 105                 110

Met Tyr Trp Val Gly Asp Asn Val Ser Ile Lys Ala Lys Arg Ile Cys
        115                 120                 125

Glu Ala Ser Tyr Lys Ala Leu Met Ala Ala Ile Gly Val Ile Gln Pro
    130                 135                 140

Gly Lys Lys Leu Asn Ser Ile Gly Leu Ala Ile Glu Glu Glu Ile Arg
145                 150                 155                 160

Gly Tyr Gly Tyr Ser Ile Val Arg Asp Tyr Cys Gly His Gly Ile Gly
                165                 170                 175

Arg Glu Phe His Ala Ala Pro Asn Ile Val His Tyr Tyr Asp Glu Glu
            180                 185                 190

Asp Asp Val Thr Ile Gln Glu Gly Met Phe Phe Thr Val Glu Pro Met
        195                 200                 205

Ile Asn Ala Gly Lys Tyr His Thr Val Leu Asp Lys Lys Asp Gly Trp
    210                 215                 220

Thr Val Thr Thr Arg Asp Phe Ser Leu Ser Ala Gln Phe Glu His Thr
225                 230                 235                 240

Leu Gly Val Thr Glu Thr Gly Val Glu Ile Phe Thr Met Ser Pro Lys
                245                 250                 255

Asn Trp His Cys Pro Pro Tyr Leu
            260
```

<210> SEQ ID NO 23
<211> LENGTH: 2706
<212> TYPE: DNA
<213> ORGANISM: Granulocytic Ehrlichia
<220> FEATURE:
<223> OTHER INFORMATION: C6 of Granulocytic Ehrlichia

<400> SEQUENCE: 23

```
gaattccgga attccggaat tcctatggat cgtgcagtga tggaagaggg cagcatgtta    60
gctgcaggtt cactgctcac tagggtaag attgtaaaat ctggagagtt atgggcaggt   120
aggcctgcaa aatttctacg tatgatgact gaagaggaga ttttatacct acaaaaatct   180
gctgaaaatt acatagcgtt atcgcgtgga tacttataac aaggtattca tctatggttt   240
gacattagtg tctttggtg attacactgc ctttcaatct gtgttttttg ttttagttct   300
```

```
ggtttgtatt tatgggtgat gctgtagaag ttagggctga gaatcttggt ggcgaatcca    360
ttctagaagc tccgattcgg gtaatgaaaa aggtgggaga tactgtatct gcagaagatg    420
tgctcttcat tgttgaaaca gacaagactt ctcttgaaat atcagcccct gttgctggtg    480
ttctcacaga gttgagagtt gcagatgaag aagtgattac caaggggcag gtcttggcta    540
tcatacggcc acagggtgag gctactgcag agggtgttaa taaggagcca gagagcaagg    600
aggaggtgcc tgctcaaccc gttgttgcac aggcagtgag cactcaaaaa ccgcaggaaa    660
agacaattat tgaaggcaaa ggtctagtaa ctcctactgt agaagatttt gttgcaggaa    720
tcaacacaac tcctacttct agagctttgg gtatgagtgc taagagtgaa caagacaaga    780
agatagttgc tagccagccg tctaaggatc tgatgagttg ccatggcgac gtggtgggtg    840
aaagacgcgt gaagatgagc aaaatccgcc aagtttatag ctgctaggctt aaggagtcac    900 aaaatacctc tgctacactc agcacccttta atgaagttga tatgagcaaa gtgatggagc    960
tcagagctaa gtacaaagat gcctttgtga agaggtatga tgttaagctt gggtttatgt   1020
ccttctttat cagagcggtt gtgctagtcc tttccgaaat tcctgtgctg aatgcggaga   1080
tttcaggcga tgatatagtc tacagggact attgtaacat tggagtcgcg gtaggtaccg   1140
ataaggggtt agtggtgcct gttatcagaa gagcggaaac tatgtcactt gctgaaatgg   1200
agcaagcact tgttgactta agtacaaaag caagaagtgg caagctctct gtttctgata   1260
tgtctggtgc aacctttact attaccaatg gtggtgtgta tgggtcgcta ttgtctaccc   1320
ctataatcaa ccctcctcaa tctggaatct tgggtatgca tgctatacag cagcgtcctg   1380
tggcagtaga tggtaaggta gagataaggc ctatgatgta tttggcgcta tcatatgatc   1440
atagaatagt tgacgggcaa ggtgctgtga cgttttttggt aagagtgaag cagtacatag   1500
aagatcctaa cagattggct ctaggaattt agggggtttt tatggggcgg ggtacaataa   1560
ccatccactc caaagaggat tttgcctgta tgagaagggc tgggatgctt gcagctaagg   1620
tgcttgattt tataacgccg catgttgttc ctggtgtgac tactaatgct ctgaatgatc   1680
tatgtcacga tttcatcatt tctgccgggg ctattccagc gcctttgggc tatagagggt   1740
atcctaagtc tatttgtact tcgaagaatt ttgtggtttg ccatggcatt ccagatgata   1800
ttgcattaaa aaacggcgat atagttaaca tagacgttac tgtgatcctc gatggttggc   1860
acggggatac tagtaggatg tattgggttg gtgataacgt ctctattaag gctaagcgca   1920
tttgtgaggc aagttataag gcattgatgg cggcgattgg tgtaatacag ccaggtaaga   1980
agctcaatag catagggtta gctatagagg aagaaatcag aggttatgga tactccattg   2040
ttagagatta ctgcggacat gggataggtc gcgaatttca tgctgctcct aacatagttc   2100
actactatga cgaagaggat gatgttacga ttcaggaggg aatgttttttc actgttgagc   2160 caatgatcaa tgctggaaag tatcatactg tgctagataa gaaagacgga tggacagtta   2220
caacgagaga cttttccctt tcagcgcagt ttgaacatac cttgggtgta actgaaactg   2280
gcgttgagat ttttactatg tcgccaaaaa attggcattg tccgccatac ctttaagtag   2340 gatattttttg ttatgtgtaa agcgtgtggc agggtaatgt taggtgcatg ttctgttgac   2400
gatgtgtgct gataagaaat tgtacaatca tactgcgttg gaagttagga atatgtactt   2460
atgagtgcta ataagcttgc tgtgttatta agcgaagccg cttcagtttt gaaaagagta   2520
ggaatagata caccggggtt agacgctcga ctaattgcgg gacatgtttt gggtttaagt   2580
gagcatgagg tgctaataaa tccagattta gttgttactg ctgctaaaac aaaagaattt   2640
tttgaagtta ttgcaagacg tttagccggg gtaccagttt cgcatatttt acgcagacga   2700
``` gaattc 2706

<210> SEQ ID NO 24
<211> LENGTH: 176
<212> TYPE: PRT
<213> ORGANISM: Artificial Sequence
<220> FEATURE:
<223> OTHER INFORMATION: amino acid sequence encoded by 550 bp PCR product

<400> SEQUENCE: 24

Thr Gly Gly Ala Gly Tyr Phe Tyr Val Gly Leu Asp Tyr Ser Pro Ala
1               5                   10                  15

Phe Ser Lys Ile Arg Asp Phe Ser Ile Arg Glu Ser Asn Gly Glu Thr
            20                  25                  30

Lys Ala Val Tyr Pro Tyr Leu Lys Asp Gly Lys Ser Val Lys Leu Glu
        35                  40                  45

Ser His Lys Phe Asp Trp Asn Thr Pro Asp Pro Arg Ile Gly Phe Lys
    50                  55                  60

Asp Asn Met Leu Val Ala Met Glu Gly Ser Val Gly Tyr Gly Ile Gly
65                  70                  75                  80

Gly Ala Arg Val Glu Leu Glu Ile Gly Tyr Gln Arg Phe Lys Thr Lys
                85                  90                  95

Gly Ile Arg Asp Ser Gly Ser Lys Glu Asp Glu Ala Asp Thr Val Tyr
            100                 105                 110

Leu Leu Ala Lys Glu Leu Ala Tyr Asp Val Val Thr Gly Gln Thr Asp
        115                 120                 125

Asn Leu Ala Ala Ala Leu Ala Lys Thr Ser Gly Lys Asp Ile Val Gln
    130                 135                 140

Phe Ala Lys Ala Val Gly Val Ser His Pro Gly Ile Asp Lys Lys Val
145                 150                 155                 160

Cys Asp Gly Gly His Ala Arg Gly Lys Lys Ser Gly Asp Asn Gly Ser
                165                 170                 175

<210> SEQ ID NO 25
<211> LENGTH: 181
<212> TYPE: PRT
<213> ORGANISM: A. marginale
<220> FEATURE:
<223> OTHER INFORMATION: Genbank accession number U07862

<400> SEQUENCE: 25

Gly Ala Gly Ala Gly Ser Phe Tyr Ile Gly Leu Asp Tyr Ser Pro Ala
1               5                   10                  15

Phe Gly Ser Ile Lys Asp Phe Lys Val Gln Glu Ala Gly Gly Thr Thr
            20                  25                  30

Arg Gly Val Phe Pro Tyr Lys Arg Asp Ala Ala Gly Arg Val Asp Phe
        35                  40                  45

Lys Val His Asn Phe Asp Trp Ser Ala Pro Glu Pro Lys Ile Ser Phe
    50                  55                  60

Lys Asp Ser Met Leu Thr Ala Leu Glu Gly Ser Ile Gly Tyr Ser Ile
65                  70                  75                  80

Gly Gly Ala Arg Val Glu Val Glu Val Gly Tyr Glu Arg Phe Val Ile
                85                  90                  95

Lys Gly Gly Lys Lys Ser Asn Glu Asp Thr Ala Ser Val Phe Leu Leu
            100                 105                 110

Gly Lys Glu Leu Ala Tyr His Thr Ala Arg Gly Gln Val Asp Arg Leu
        115                 120                 125

```
Ala Thr Ala Leu Gly Lys Met Thr Lys Ser Glu Ala Lys Lys Trp Gly
        130                 135                 140

Asn Ala Ile Glu Ser Ala Thr Gly Thr Thr Ser Gly Asp Glu Leu Ser
145                 150                 155                 160

Lys Lys Val Cys Gly Lys Gly Thr Thr Ser Gly Ser Thr Asn Gln Cys
                165                 170                 175

Gly Thr Thr Asp Ser
            180

<210> SEQ ID NO 26
<211> LENGTH: 1840
<212> TYPE: DNA
<213> ORGANISM: Granulocytic Ehrlichia
<220> FEATURE:
<223> OTHER INFORMATION: E8 msp2 gene

<400> SEQUENCE: 26
gaggtcgacg gtatcgataa gcttgatatc gaattcctgg ctggagatgt tagaggggt      60 tagcccttga gtggaccggc tgaagtgagg agacgaagaa aaagaaggaa tttggagaag    120
ttgaaaagta tgagaaaagg aaagataatc ttaggaagcg taatgatgtc gatggctata    180
gtcatggctg ggaatgatgt cagggctcat gatgacgtta gcgctttgga gactggtggt    240
gcgggatatt tctatgttgg cttggattac agtccagcgt ttagcaagat aagagatttt    300
agtataaggg agagtaacgg agagactaag gcagtatatc catacttaaa ggatggaaag    360
agtgtaaagc tagagtcaca caagtttgac tggaacactc ctgatcctcg gattgggttt    420
aaggacaaca tgcttgtagc tatggaaggt agtgttggtt atggtattgg tggtgccagg    480
gttgagcttg agattggtta cgagcgcttc aagaccaagg gtattagaga tagtggtagt    540
aaggaagatg aagctgatac agtatatcta ctagctaagg agttagctta tgatgttgtt    600
actgggcaga ctgataaccct tgctgctgct cttgccaaga cctctggtaa agatattgtt    660
cagtttgcta aggcggttgg ggtttctcat cccggtattg ataagaaggt ttgtgatggg    720
ggtcatgcac ggggaaaaaa gagtggagat aatggctcgc tggccgacta tacggatggt    780
ggcgcgtcac agacgaataa gacggctcag tgtagtggta tgggaaccgg caaagccggc    840
aagagaggat tgggcttgac tgagtttgtt aacaaaacaa aggttggaga aggtaagaat    900
tggccaacgg ggtacgttaa tgatggcgac aacgttaatg tgctcggcga tacgaatggt    960
aacgccgaag ccgtagctaa agacctagta caggagctaa ccctgaaga aaaaaccata   1020 gtagcagggt tactagctaa gactattgaa ggggtgaag ttgttgagat cagggcggtt    1080
tcttctactt ccgtaatggt caatgcttgt tatgatcttc ttagtgaagg tttaggtgtt    1140
gttccttatg cttgtgttgg tcttggcggt aacttcgtgg gcgtggttga tggccatatc    1200
actcctaagc ttgcttatag attaaaggct gggttgagtt atcagctctc tcctgtaatc    1260
tccgcttttg cgggtggatt ctaccatcgc gttgtgggag atggcgttta tgatgatctg    1320
ccggctcaac gtcttgtaga tgatactagt ccggcgggtc gtactaagga tactgctatt    1380
gctaacttct ccatggctta tgtcggtggg gaatttggtg ttaggttttgc ttttttaagct    1440 tgcttatcta aagagggggg ctaagggctc ccctttctcta ctttaattct acttcctgcg    1500
gtacttcacc ctcttcctga cttcttctgg ttctgctacc attaattatt actccgtgac    1560
cgttcctatt atttattttc ttgctgctca ggttagaagg tttctatcag tgcttgatgg    1620
ggatttggcg tgtttttata gtgcaaatcg catcgctccc atttgtacaa atcttgacac    1680
ttttggcttc aatgtctatt gttgagcagt taaaattctt gtgataccc atggttgaaa    1740
```

```
tgctattggt cagattgaac tgaaggactc cccctctgat aagcagcggg ctgttgatgc   1800
gcgcttttgg gcgtggatct attatgaggc tgcagaatag                        1840
```

<210> SEQ ID NO 27
<211> LENGTH: 435
<212> TYPE: PRT
<213> ORGANISM: Granulocytic Ehrlichia
<220> FEATURE:
<223> OTHER INFORMATION: E8 msp2 gene

<400> SEQUENCE: 27

```
Met Arg Lys Gly Lys Ile Ile Leu Gly Ser Val Met Met Ser Met Ala
 1               5                  10                  15

Ile Val Met Ala Gly Asn Asp Val Arg Ala His Asp Val Ser Ala
            20                  25                  30

Leu Glu Thr Gly Gly Ala Gly Tyr Phe Tyr Val Gly Leu Asp Tyr Ser
        35                  40                  45

Pro Ala Phe Ser Lys Ile Arg Asp Phe Ser Ile Arg Glu Ser Asn Gly
    50                  55                  60

Glu Thr Lys Ala Val Tyr Pro Tyr Leu Lys Asp Gly Lys Ser Val Lys
65                  70                  75                  80

Leu Glu Ser His Lys Phe Asp Trp Asn Thr Pro Asp Pro Arg Ile Gly
                85                  90                  95

Phe Lys Asp Asn Met Leu Val Ala Met Glu Gly Ser Val Gly Tyr Gly
            100                 105                 110

Ile Gly Gly Ala Arg Val Glu Leu Glu Ile Gly Tyr Glu Arg Phe Lys
        115                 120                 125

Thr Lys Gly Ile Arg Asp Ser Gly Ser Lys Glu Asp Glu Ala Asp Thr
    130                 135                 140

Val Tyr Leu Leu Ala Lys Glu Leu Ala Tyr Asp Val Val Thr Gly Gln
145                 150                 155                 160

Thr Asp Asn Leu Ala Ala Ala Leu Ala Lys Thr Ser Gly Lys Asp Ile
                165                 170                 175

Val Gln Phe Ala Lys Ala Val Gly Val Ser His Pro Gly Ile Asp Lys
            180                 185                 190

Lys Val Cys Asp Gly Gly His Ala Arg Gly Lys Lys Ser Gly Asp Asn
        195                 200                 205

Gly Ser Leu Ala Asp Tyr Thr Asp Gly Gly Ala Ser Gln Thr Asn Lys
    210                 215                 220

Thr Ala Gln Cys Ser Gly Met Gly Thr Gly Lys Ala Gly Lys Arg Gly
225                 230                 235                 240

Leu Gly Leu Thr Glu Phe Val Asn Lys Thr Lys Val Gly Glu Gly Lys
                245                 250                 255

Asn Trp Pro Thr Gly Tyr Val Asn Asp Gly Asp Asn Val Asn Val Leu
            260                 265                 270

Gly Asp Thr Asn Gly Asn Ala Glu Ala Val Ala Lys Asp Leu Val Gln
        275                 280                 285

Glu Leu Thr Pro Glu Glu Lys Thr Ile Val Ala Gly Leu Leu Ala Lys
    290                 295                 300

Thr Ile Glu Gly Gly Glu Val Val Glu Ile Arg Ala Val Ser Ser Thr
305                 310                 315                 320

Ser Val Met Val Asn Ala Cys Tyr Asp Leu Leu Ser Glu Gly Leu Gly
                325                 330                 335

Val Val Pro Tyr Ala Cys Val Gly Leu Gly Gly Asn Phe Val Gly Val
            340                 345                 350
```

Val Asp Gly His Ile Thr Pro Lys Leu Ala Tyr Arg Leu Lys Ala Gly
        355                 360                 365

Leu Ser Tyr Gln Leu Ser Pro Val Ile Ser Ala Phe Ala Gly Gly Phe
        370                 375                 380

Tyr His Arg Val Val Gly Asp Gly Val Tyr Asp Asp Leu Pro Ala Gln
385                 390                 395                 400

Arg Leu Val Asp Asp Thr Ser Pro Ala Gly Arg Thr Lys Asp Thr Ala
                405                 410                 415

Ile Ala Asn Phe Ser Met Ala Tyr Val Gly Gly Glu Phe Gly Val Arg
                420                 425                 430

Phe Ala Phe
        435

<210> SEQ ID NO 28
<211> LENGTH: 3435
<212> TYPE: DNA
<213> ORGANISM: Artificial Sequence
<220> FEATURE:
<223> OTHER INFORMATION: E46 gene inset in Lambda Zap II

<400> SEQUENCE: 28

| | | | | | |
|---|---|---|---|---|---|
| tttttatatc | tggagctctt | gtactgtgtt | taccacggga | tttattattg | ggtaggcttg | 60 |
| atattcaggc | tctatcaacg | cagctattca | tggcattatt | acagataaat | ttggcatttt | 120 |
| ggagataggc | gatctagggt | tctattatta | ggaatctatt | atttagatat | ataggggatat | 180 |
| aagggagagt | aacggagaga | ctaaggcagt | atatccatac | ttaaaggatg | gaaagagtgt | 240 |
| aaagctagag | tcacacaagt | ttgactggaa | cactcctgat | cctcggattg | ggtttaagga | 300 |
| caacatgctt | gtagctatgg | aaggcagtgt | tggttatggt | attggtggtg | ccagggttga | 360 |
| gcttgagatt | ggttacgagc | gcttcaagac | caagggtatt | agagatagtg | gtagtaagga | 420 |
| agatgaagca | gatacagtat | atctactagc | taaggagtta | gcttatgatg | ttgttactgg | 480 |
| acagactgat | aaccttgccg | ctgctcttgc | caaaacctcg | ggaaggaca | tcgttcagtt | 540 |
| tgccaatgct | gtgaaaattt | cttaccctaa | aattgatgag | caggtttgta | ataaaaatca | 600 |
| tacagtgttg | aatacgggga | aagggacaac | ctttaatcca | gatcccaaga | caaccgaaga | 660 |
| taatacagcg | cagtgcagtg | ggttgaacac | gaagggaacg | aataagttta | gcgattttgc | 720 |
| tgaaggtgta | ggtttgaaag | ataataagaa | ttggcctact | ggtcaggctg | ggaagagcag | 780 |
| tggtggtcct | gtggtgggtg | catctaatag | taatgccaac | gctatggcta | gagacctagt | 840 |
| agatcttaat | cgagacgaaa | aaaccatagt | agcaggggta | ctagctaaaa | ctattgaagg | 900 |
| tggtgaggtt | gttgagatta | gggcggtttc | ttctacttct | gtaatggtca | atgcttgtta | 960 |
| tgatcttctt | agtgaaggtc | taggcgttgt | tccttacgct | tgtgtcggtc | ttggaggtaa | 1020 |
| cttcgtgggc | gttgttgatg | ggcatatcac | tcctaagctt | gcttatagat | aaaggctgg | 1080 |
| gttgagttat | cagctctctc | ctgaaatctc | cgcttttgct | gggggattct | atcatcgcgt | 1140 |
| tgtgggagat | ggtgtctatg | atgatcttcc | agctcaacgt | cttgtagatg | atactagtcc | 1200 |
| ggcgggtcgt | actaaggata | ctgctattgc | taacttctcc | atggcttatg | tcggtgggga | 1260 |
| atttggtgtt | aggtttgctt | tttaaggtgg | tttgttggaa | gcggggtaag | tcaaacttac | 1320 |
| cccgcttcta | ttagggagtt | agtatatgag | atctagaagt | aagctatttt | taggaagcgt | 1380 |
| aatgatgtcg | ttggctatag | taatggctgg | gaatgatgtc | agggctcatg | atgacgttag | 1440 |
| cgctttggat | actggtggtg | cgggatattt | ctatgttggt | ttggattaca | gtccagcgtt | 1500 |
| tagcaagata | agagatttta | gtataaggga | gagtaacgga | gagactaagg | cagtatatcc | 1560 |

```
atacttaaag gatggaaaga gtgtaaagct agagtcacac aagtttgact ggaacactcc    1620
tgatcctcgg attgggttta aggacaacat gcttgtagct atggaaggta gtgttggtta    1680
tggtattggt ggtgccaggg ttgagcttga gattggttac gagcgcttca agaccaaggg    1740
tattagagat agtggtagta aggaagatga agctgataca gtatatctac tagctaagga    1800
gttggcttat gatgttgtta ctgggcagac tgataacctt gccgctgctc tggccaaaac    1860
ctccggtaaa gactttgtcc agtttgctaa ggcggttggg gtttctcatc ctagtattga    1920
tgggaaggtt tgtaagacga aggcggatag ctcgaagaaa tttccgttat atagtgacga    1980
aacgcacacg aaggggggcaa gtgaggggag aacgtctttg tgcggtgaca atggtagttc    2040
tacgataaca aacagtggtg cgaatgtaag tgaaactggg caggttttta gggatttat     2100
cagggcaacg ctgaaagagg atggtagtaa aaactggcca acttcaagcg gcacgggaac    2160
tccaaaacct gtcacgaacg acaacgccaa agccgtagct aaagacctag tacaggagct    2220
aaccccctgaa gaaaaaacca tagtagcagg gttactagct aaaactattg aaggtggtga    2280
ggttattgaa atcagggcgg tttcttctac ttctgtgatg gtcaatgctt gttatgatct    2340
tcttagtgaa ggtttaggtg ttgtccctta tgcttgtgtt ggtctcggtg gtaacttcgt    2400
gggcgtggtt gatggaattc attacacaaa ccatctttaa ctctgaatac cctagttaag    2460
gtaagtgaag taactaggca aattagtgct gcaccactcg tgaaacaaac tacgatcagc    2520
gattcaccat acttagtaag tccgtacagt ggctttacgc tcttacccat catgaaaaat    2580
acttgctatc taggaatctc ctctaaaact ttacagaggt tatctgtact tcgagaggaa    2640
gctaatctgt ggctcatgag gatggtattt agcgtatcac aggttccagc tgtcttacag    2700
tctctggaga tgtttataagg gtgcacatat aaaactatgc aatatttcgc tgcaatacga    2760
ttccgattcg aaaacactga aaagtattcc cattatctat gaatctctgt gtagatataa    2820
ataagggtat acgcagtaac tcttacttgt taaaaacaag accaatggta taggaaaaaa    2880
gcctcagtgt tgttcctcat gcttgcagct tacccgatgc actcttattt aataaggttg    2940
aatgttaatc agtgtttctg ggaagggaat atcttattgc aaaaccctca gcagctgctt    3000
agatattgaa acaaatgcga tcatgccgtc agcacaatta tgcatctct  taaggctctg    3060
tagtgcgctt atttagtcta acatgtggta aagctttgcc agttctttac cacatgttca    3120
ccatcagtta attgaaagca aatcttgctc ctatgttgaa gccgtaacta gctatatttg    3180
cctttacctt ggctgcagca ccacctgcta tgtttacacg gttactagcg ggaatacctg    3240
catactgttc atcgaaaatt ccgtggtaaa aacctccagc tattaaagat atttcaggag    3300
taagcttgta acttacgcct accttcctc tataagccaa cttacttgta acgtgatcgg     3360
cgatattaat aaagctcgcc cctaacccag cacacatgta aggagggaat tcgatatcaa    3420
gcttatcgat accgt                                                     3435
```

<210> SEQ ID NO 29
<211> LENGTH: 326
<212> TYPE: PRT
<213> ORGANISM: Granulocytic Ehrlichia
<220> FEATURE:
<223> OTHER INFORMATION: E46#1

<400> SEQUENCE: 29

Met Leu Val Ala Met Glu Gly Ser Val Gly Tyr Gly Ile Gly Gly Ala
1               5                   10                  15

Arg Val Glu Leu Glu Ile Gly Tyr Glu Arg Phe Lys Thr Lys Gly Ile
            20                  25                  30

Arg Asp Ser Gly Ser Lys Glu Asp Glu Ala Asp Thr Val Tyr Leu Leu
35                  40                  45

Ala Lys Glu Leu Ala Tyr Asp Val Val Thr Gly Gln Thr Asp Asn Leu
50                  55                  60

Ala Ala Ala Leu Ala Lys Thr Ser Gly Lys Asp Ile Val Gln Phe Ala
65                  70                  75                  80

Asn Ala Val Lys Ile Ser Tyr Pro Lys Ile Asp Glu Gln Val Cys Asn
                85                  90                  95

Lys Asn His Thr Val Leu Asn Thr Gly Lys Gly Thr Thr Phe Asn Pro
            100                 105                 110

Asp Pro Lys Thr Thr Glu Asp Asn Thr Ala Gln Cys Ser Gly Leu Asn
            115                 120                 125

Thr Lys Gly Thr Asn Lys Phe Ser Asp Phe Ala Glu Gly Val Gly Leu
130                 135                 140

Lys Asp Asn Lys Asn Trp Pro Thr Gly Gln Ala Gly Lys Ser Ser Gly
145                 150                 155                 160

Gly Pro Val Val Gly Ala Ser Asn Ser Asn Ala Asn Ala Met Ala Arg
                165                 170                 175

Asp Leu Val Asp Leu Asn Arg Asp Glu Lys Thr Ile Val Ala Gly Leu
            180                 185                 190

Leu Ala Lys Thr Ile Glu Gly Gly Glu Val Val Glu Ile Arg Ala Val
            195                 200                 205

Ser Ser Thr Ser Val Met Val Asn Ala Cys Tyr Asp Leu Leu Ser Glu
210                 215                 220

Gly Leu Gly Val Val Pro Tyr Ala Cys Val Gly Leu Gly Gly Asn Phe
225                 230                 235                 240

Val Gly Val Val Asp Gly His Ile Thr Pro Lys Leu Ala Tyr Arg Leu
                245                 250                 255

Lys Ala Gly Leu Ser Tyr Gln Leu Ser Pro Glu Ile Ser Ala Phe Ala
            260                 265                 270

Gly Gly Phe Tyr His Arg Val Gly Asp Gly Val Tyr Asp Asp Leu
            275                 280                 285

Pro Ala Gly Arg Leu Val Asp Asp Thr Ser Pro Ala Gly Arg Thr Lys
290                 295                 300

Asp Thr Ala Ile Ala Asn Phe Ser Met Ala Tyr Val Gly Gly Glu Phe
305                 310                 315                 320

Gly Val Arg Phe Ala Phe
                325

<210> SEQ ID NO 30
<211> LENGTH: 364
<212> TYPE: PRT
<213> ORGANISM: Granulocytic Ehrlichia
<220> FEATURE:
<223> OTHER INFORMATION: E46#2

<400> SEQUENCE: 30

Met Arg Ser Arg Ser Lys Leu Phe Leu Gly Ser Val Met Met Ser Leu
1               5                   10                  15

Ala Ile Val Met Ala Gly Asn Asp Val Arg Ala His Asp Asp Val Ser
                20                  25                  30

Ala Leu Asp Thr Gly Gly Ala Gly Tyr Phe Tyr Val Gly Leu Asp Tyr
            35                  40                  45

Ser Pro Ala Phe Ser Lys Ile Arg Asp Phe Ser Ile Arg Glu Ser Asn
50                  55                  60

Gly Glu Thr Lys Ala Val Tyr Pro Tyr Leu Lys Asp Gly Lys Ser Val

```
                65                  70                  75                  80
Lys Leu Glu Ser His Lys Phe Asp Trp Asn Thr Pro Asp Pro Arg Ile
                    85                  90                  95
Gly Phe Lys Asp Asn Met Leu Val Ala Met Glu Gly Ser Val Gly Tyr
                100                 105                 110
Gly Ile Gly Gly Ala Arg Val Glu Leu Glu Ile Gly Tyr Glu Arg Phe
                115                 120                 125
Lys Thr Lys Gly Ile Arg Asp Ser Gly Ser Lys Glu Asp Glu Ala Asp
                130                 135                 140
Thr Val Tyr Leu Leu Ala Lys Glu Leu Ala Tyr Asp Val Val Thr Gly
145                 150                 155                 160
Gln Thr Asp Asn Leu Ala Ala Ala Leu Ala Lys Thr Ser Gly Lys Asp
                165                 170                 175
Phe Val Gln Phe Ala Lys Ala Val Gly Val Ser His Pro Ser Ile Asp
                180                 185                 190
Gly Lys Val Cys Lys Thr Lys Ala Asp Ser Ser Lys Lys Phe Pro Leu
                195                 200                 205
Tyr Ser Asp Glu Thr His Thr Lys Gly Ala Ser Glu Gly Arg Thr Ser
                210                 215                 220
Leu Cys Gly Asp Asn Gly Ser Ser Thr Ile Thr Asn Ser Gly Ala Asn
225                 230                 235                 240
Val Ser Glu Thr Gly Gln Val Phe Arg Asp Phe Ile Arg Ala Thr Leu
                245                 250                 255
Lys Glu Asp Gly Ser Lys Asn Trp Pro Thr Ser Ser Gly Thr Gly Thr
                260                 265                 270
Pro Lys Pro Val Thr Asn Asp Asn Ala Lys Ala Val Ala Lys Asp Leu
                275                 280                 285
Val Gln Glu Leu Thr Pro Glu Glu Lys Thr Ile Val Ala Gly Leu Leu
                290                 295                 300
Ala Lys Thr Ile Glu Gly Gly Glu Val Ile Glu Ile Arg Ala Val Ser
305                 310                 315                 320
Ser Thr Ser Val Met Val Asn Ala Cys Tyr Asp Leu Leu Ser Glu Gly
                325                 330                 335
Leu Gly Val Val Pro Tyr Ala Cys Val Gly Leu Gly Gly Asn Phe Val
                340                 345                 350
Gly Val Val Asp Gly Ile His Tyr Thr Asn His Leu
                355                 360

<210> SEQ ID NO 31
<211> LENGTH: 409
<212> TYPE: PRT
<213> ORGANISM: A. marginale
<220> FEATURE:
<223> OTHER INFORMATION: msp-2 gene

<400> SEQUENCE: 31

Met Ser Ala Val Ser Asn Arg Lys Leu Pro Leu Gly Gly Val Leu Met
1               5                   10                  15
Ala Leu Ala Ala Ala Val Ala Pro Ile His Ser Leu Leu Ala Ala Pro
                20                  25                  30
Ala Ala Gly Ala Gly Ala Gly Gly Glu Gly Leu Phe Ser Gly Ala Gly
                35                  40                  45
Ala Gly Ser Phe Tyr Ile Gly Leu Asp Tyr Ser Pro Ala Phe Gly Ser
                50                  55                  60
Ile Lys Asp Phe Lys Val Gln Glu Ala Gly Gly Thr Thr Arg Gly Val
65                  70                  75                  80
```

Phe Pro Tyr Lys Arg Asp Ala Ala Gly Arg Val Asp Phe Lys Val His
                85                  90                  95

Asn Phe Asp Trp Ser Ala Pro Glu Pro Lys Ile Ser Phe Lys Asp Ser
            100                 105                 110

Met Leu Thr Ala Leu Glu Gly Ser Ile Gly Tyr Ser Ile Gly Gly Ala
        115                 120                 125

Arg Val Glu Val Glu Val Gly Tyr Glu Arg Phe Val Ile Lys Gly Gly
    130                 135                 140

Lys Lys Ser Asn Glu Asp Thr Ala Ser Val Phe Leu Leu Gly Lys Glu
145                 150                 155                 160

Leu Ala Tyr His Thr Ala Arg Gly Gln Val Asp Arg Leu Ala Thr Ala
                165                 170                 175

Leu Gly Lys Met Thr Lys Ser Glu Ala Lys Lys Trp Gly Asn Ala Ile
            180                 185                 190

Glu Ser Ala Thr Gly Thr Thr Ser Gly Asp Glu Leu Ser Lys Lys Val
        195                 200                 205

Cys Gly Lys Gly Thr Thr Ser Gly Ser Thr Asn Gln Cys Gly Thr Thr
    210                 215                 220

Asp Ser Thr Ala Thr Thr Lys Ile Ser Ala Val Phe Thr Glu Asp Ala
225                 230                 235                 240

Ala Ala Gln Leu Ser Thr Met Asp Asn Thr Thr Ile Asn Thr Thr Gly
                245                 250                 255

Met Ala Asn Asn Ile Asn Ser Leu Thr Lys Asp Glu Lys Ala Ile Val
            260                 265                 270

Ala Gly Ala Phe Ala Arg Ala Val Glu Gly Ala Glu Val Ile Glu Val
        275                 280                 285

Arg Ala Ile Gly Ser Thr Ser Val Met Leu Asn Ala Cys Tyr Asp Leu
    290                 295                 300

Leu Thr Asp Gly Ile Gly Val Val Pro Tyr Ala Cys Ala Gly Ile Gly
305                 310                 315                 320

Gly Asn Phe Val Ser Val Val Asp Gly His Ile Asn Pro Lys Phe Ala
                325                 330                 335

Tyr Arg Val Lys Ala Gly Leu Ser Tyr Ala Leu Thr Pro Glu Ile Ser
            340                 345                 350

Ala Phe Ala Gly Ala Phe Tyr His Lys Val Leu Gly Asp Gly Asp Tyr
        355                 360                 365

Asp Glu Leu Pro Leu Ser His Ile Ser Asp Tyr Thr Gly Thr Ala Gly
    370                 375                 380

Lys Asn Lys Asp Thr Gly Ile Ala Ser Phe Asn Phe Ala Tyr Phe Gly
385                 390                 395                 400

Gly Glu Leu Gly Val Arg Phe Ala Phe
            405

<210> SEQ ID NO 32
<211> LENGTH: 20
<212> TYPE: DNA
<213> ORGANISM: Artificial Sequence
<220> FEATURE:
<221> NAME/KEY: misc_feature
<222> LOCATION: 3, 18
<223> OTHER INFORMATION: n = A,T,C or G
<220> FEATURE:
<223> OTHER INFORMATION: Synthetic nucleotide - degenerate primer

<400> SEQUENCE: 32
ccnttycaya tgtayccngg                                              20

```
<210> SEQ ID NO 33
<211> LENGTH: 20
<212> TYPE: DNA
<213> ORGANISM: Artificial Sequence
<220> FEATURE:
<221> NAME/KEY: misc_feature
<222> LOCATION: 3, 6, 15, 18
<223> OTHER INFORMATION: n = A,T,C or G
<220> FEATURE:
<223> OTHER INFORMATION: Synthetic nucleotide - degenerate primer

<400> SEQUENCE: 33
ggnckngcrt aytcnccngc                                             20

<210> SEQ ID NO 34
<211> LENGTH: 24
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 34

Pro Phe His Met Tyr Pro Gly Ser Glu Asn Leu Phe Arg Ser Thr Arg
 1               5                  10                  15

Asp Leu Arg Gly Val Ser Gly Val
            20

<210> SEQ ID NO 35
<211> LENGTH: 13
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 35

Phe Arg Leu Ser Leu Ala Gly Glu Tyr Ala Arg Pro Lys
 1               5                  10

<210> SEQ ID NO 36
<211> LENGTH: 9
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 36

Glu Leu Val Val Gly Glu Asn Thr Leu
 1               5

<210> SEQ ID NO 37
<211> LENGTH: 14
<212> TYPE: PRT
<213> ORGANISM: Artificial Sequence
<220> FEATURE:
<223> OTHER INFORMATION: amino acid sequence of 64 kDa protein generated
      by using degenerate primers

<400> SEQUENCE: 37

Glu Asp Thr Val Arg Asp Gly Ile Ala Gly Phe Asp Ser Leu
 1               5                  10

<210> SEQ ID NO 38
<211> LENGTH: 2097
<212> TYPE: DNA
<213> ORGANISM: Granulocytic Ehrlichia
```

<220> FEATURE:
<221> NAME/KEY: CDS
<222> LOCATION: (338)...(1972)
<223> OTHER INFORMATION: S11 of Granulocytic Ehrlichia

<400> SEQUENCE: 38

```
gaattcctag caacaagggt ggatatttca cgcttgctag gctgagtgat ttaggactga      60
gggtgagcta tgagatgtat aggggggaga gtatgcgctg cgtgcttttt actcagcttc     120
ataagatagc ggcgagctac agctttgcta cggggttcgt agaaaagcgt tattgtcgct     180
ataacactcg tgatgtatat catcgtgatg tcggttataa ggatcatgga tgtgctatgg     240
ttaagccttt gaagtatgac tttggcttga tggctttagg tgtgaagctg gtcttctaag     300
aagagtgtgg gtgtttgtgg attttttgaag gttttgt atg aga ggt tct ctg gta    355
                                       Met Arg Gly Ser Leu Val
                                         1               5
```

| | | | |
|---|---|---|---|
| gtt gtg agt atg gcg atg ctt ctc ctg ggg tcc tct ggt ggt gta gtt<br>Val Val Ser Met Ala Met Leu Leu Leu Gly Ser Ser Gly Gly Val Val<br>          10                 15                20 | | | 403 |
| gct gca tct tct gga ggg ggg ttt gaa gga gag cgt gcg tcg gta acg<br>Ala Ala Ser Ser Gly Gly Gly Phe Glu Gly Glu Arg Ala Ser Val Thr<br>        25                  30                    35 | | | 451 |
| ggt aag gtg tta tct tat gcc tgg ttg ttg agt gat cgg gct gta aaa<br>Gly Lys Val Leu Ser Tyr Ala Trp Leu Leu Ser Asp Arg Ala Val Lys<br>40                    45                    50 | | | 499 |
| ggg caa ggt aac agt gaa ggt cag aag ctc gcg ctg gaa atg tat ggc<br>Gly Gln Gly Asn Ser Glu Gly Gln Lys Leu Ala Leu Glu Met Tyr Gly<br>55                    60                    65                    70 | | | 547 |
| gca aag ttg ggc tat aag ggt tat ggt tat cca gga gtt gga gat gtc<br>Ala Lys Leu Gly Tyr Lys Gly Tyr Gly Tyr Pro Gly Val Gly Asp Val<br>                 75                    80                    85 | | | 595 |
| ttt tct tcg ccg ttg gag cat ggt ctt gat tct tgg gga gct agc tat<br>Phe Ser Ser Pro Leu Glu His Gly Leu Asp Ser Trp Gly Ala Ser Tyr<br>          90                    95                   100 | | | 643 |
| gat gcg atg tta tct ctt gga ttg cgt acg ggt cgt gat gtg cta ggt<br>Asp Ala Met Leu Ser Leu Gly Leu Arg Thr Gly Arg Asp Val Leu Gly<br>        105                   110                  115 | | | 691 |
| acc caa tat ggg gca aat ttt tcc ctt atg gtt cct gcg ggt tct ggt<br>Thr Gln Tyr Gly Ala Asn Phe Ser Leu Met Val Pro Ala Gly Ser Gly<br>120                   125                  130 | | | 739 |
| gga tct atg gtg ttt cat ggt gcg cct ggt ata gag agc agg gtt ttt<br>Gly Ser Met Val Phe His Gly Ala Pro Gly Ile Glu Ser Arg Val Phe<br>135                   140                  145                  150 | | | 787 |
| gct gat act tcc ttg gga aat ttt tct gtt ggt tac cag gaa ggt gtc<br>Ala Asp Thr Ser Leu Gly Asn Phe Ser Val Gly Tyr Gln Glu Gly Val<br>                155                  160                  165 | | | 835 |
| gag tca aaa atg aag gtg gat gtc ttc ggt ggc tta tca ggt gaa aat<br>Glu Ser Lys Met Lys Val Asp Val Phe Gly Gly Leu Ser Gly Glu Asn<br>              170                   175                  180 | | | 883 |
| gga agc gct tgg ggt cgg tac ttg cgt ggc ttt tta aag tat gcg aag<br>Gly Ser Ala Trp Gly Arg Tyr Leu Arg Gly Phe Leu Lys Tyr Ala Lys<br>        185                 190                  195 | | | 931 |
| ggt gta cct ttt cac atg tat cca ggg ctt tac agt gag aat tta ttc<br>Gly Val Pro Phe His Met Tyr Pro Gly Leu Tyr Ser Glu Asn Leu Phe<br>200                   205                  210 | | | 979 |
| cgg tct aca aga gac tta cgg ggt gtt agt ggt gtt tct gcg aag aca<br>Arg Ser Thr Arg Asp Leu Arg Gly Val Ser Gly Val Ser Ala Lys Thr<br>215                   220                  225                  230 | | | 1027 |
| aag gat gtc tta aat tct atg ccg ctg agg ttt tct ttt gag tct gct<br>Lys Asp Val Leu Asn Ser Met Pro Leu Arg Phe Ser Phe Glu Ser Ala<br>                235                  240                  245 | | | 1075 |

| | | |
|---|---|---|
| agg ttg ggt ggc ttg tct gtt ggt ttt agt tac tct cca acg gga tat<br>Arg Leu Gly Gly Leu Ser Val Gly Phe Ser Tyr Ser Pro Thr Gly Tyr<br>         250                           255                       260 | 1123 | |
| cgg gat gat atg tac aag ggt gga gag ttt act gta cgg gat ggt att<br>Arg Asp Asp Met Tyr Lys Gly Gly Glu Phe Thr Val Arg Asp Gly Ile<br>         265                           270                       275 | 1171 | |
| gct ggt ttc gat tcc ttg ggt aca gta aat tta ttc gcg aag acg ggg<br>Ala Gly Phe Asp Ser Leu Gly Thr Val Asn Leu Phe Ala Lys Thr Gly<br> 280                           285                       290 | 1219 | |
| gtt aag ttt ggc aaa atg att gcc gtg gtg cct cct cgt ttt gat tct<br>Val Lys Phe Gly Lys Met Ile Ala Val Val Pro Pro Arg Phe Asp Ser<br>295                       300                       305               310 | 1267 | |
| ggt ccg gta tat aaa aac ata gta agc ggt gct gcg aat tac gag tac<br>Gly Pro Val Tyr Lys Asn Ile Val Ser Gly Ala Ala Asn Tyr Glu Tyr<br>                      315                       320               325 | 1315 | |
| gag tta gcc gat att gct aag ttt agg tta tcg ctt gct ggt gag tat<br>Glu Leu Ala Asp Ile Ala Lys Phe Arg Leu Ser Leu Ala Gly Glu Tyr<br>         330                           335                       340 | 1363 | |
| gca aga ccg aag aag gct agg gat ata gtg cca gaa gga aga aga aag<br>Ala Arg Pro Lys Lys Ala Arg Asp Ile Val Pro Glu Gly Arg Arg Lys<br>345                       350                       355 | 1411 | |
| gaa gaa att tat gta gct gat tac aat gat ttg tcc gcg ttt tcc agt<br>Glu Glu Ile Tyr Val Ala Asp Tyr Asn Asp Leu Ser Ala Phe Ser Ser<br>         360                           365                       370 | 1459 | |
| ggc tta gaa ata gac ttg ggt agg ttg cgg ttt gct gtt ggc ggt gga<br>Gly Leu Glu Ile Asp Leu Gly Arg Leu Arg Phe Ala Val Gly Gly Gly<br>375                       380                       385               390 | 1507 | |
| tac ctt ggg aag tct ggt agt cct aaa atg tac ata tta aag gat gta<br>Tyr Leu Gly Lys Ser Gly Ser Pro Lys Met Tyr Ile Leu Lys Asp Val<br>                      395                       400               405 | 1555 | |
| aga cat aag gta cct tat gtg aaa aag aag ggt ttg ccg tct cat tat<br>Arg His Lys Val Pro Tyr Val Lys Lys Lys Gly Leu Pro Ser His Tyr<br>                     410                       415               420 | 1603 | |
| gtg act tca gcg gtt tcc tat acg att ggt tct ttc tct gct aca gtt<br>Val Thr Ser Ala Val Ser Tyr Thr Ile Gly Ser Phe Ser Ala Thr Val<br>         425                           430                       435 | 1651 | |
| gct tac ttt atg agt agg tta acg cac att ccg cct gct acg gta tct<br>Ala Tyr Phe Met Ser Arg Leu Thr His Ile Pro Pro Ala Thr Val Ser<br>440                       445                       450 | 1699 | |
| cat aag atc cca ggg aag tat gag ttg gat tcc gtt gtg gat ggg gag<br>His Lys Ile Pro Gly Lys Tyr Glu Leu Asp Ser Val Val Asp Gly Glu<br>455                       460                       465               470 | 1747 | |
| aat acg ttg aag gat ttg gtt gta gga gtc ggt tat aac ctt ttt agt<br>Asn Thr Leu Lys Asp Leu Val Val Gly Val Gly Tyr Asn Leu Phe Ser<br>                     475                       480               485 | 1795 | |
| aag gga agt acg agc tta gaa gta ttt cta aat tgt cac atg ttc tct<br>Lys Gly Ser Thr Ser Leu Glu Val Phe Leu Asn Cys His Met Phe Ser<br>         490                           495                       500 | 1843 | |
| gtg caa cat aaa ttc aac atc cat gag tac aaa tct act gag agt agt<br>Val Gln His Lys Phe Asn Ile His Glu Tyr Lys Ser Thr Glu Ser Ser<br>505                       510                       515 | 1891 | |
| ggg ttt gta ttg aaa gaa ggt gga gag cgt gca aat act aat aat ggc<br>Gly Phe Val Leu Lys Glu Gly Gly Glu Arg Ala Asn Thr Asn Asn Gly<br>         520                           525                       530 | 1939 | |
| gct gtg gcg tta tta gga atg aag ttt gcg ttt taataacaag gggttgttgc<br>Ala Val Ala Leu Leu Gly Met Lys Phe Ala Phe<br>535                     540                       545 | 1992 | |
| aagaatactc ttgtggttta tttagccaag tcttcttatt ggggcgtgta ctgaggtacg | 2052 | |
| gcgccccttt ttttgtggag agtctaaggt ttgttatgtt gtaga | 2097 | |

```
<210> SEQ ID NO 39
<211> LENGTH: 545
<212> TYPE: PRT
<213> ORGANISM: Granulocytic Ehrlichia
<220> FEATURE:
<223> OTHER INFORMATION: open reading frame of Granulocytic
      Ehrlichia S11

<400> SEQUENCE: 39

Met Arg Gly Ser Leu Val Val Val Ser Met Ala Met Leu Leu Leu Gly
 1               5                  10                  15

Ser Ser Gly Gly Val Val Ala Ala Ser Ser Gly Gly Gly Phe Glu Gly
            20                  25                  30

Glu Arg Ala Ser Val Thr Gly Lys Val Leu Ser Tyr Ala Trp Leu Leu
        35                  40                  45

Ser Asp Arg Ala Val Lys Gly Gln Gly Asn Ser Glu Gly Gln Lys Leu
    50                  55                  60

Ala Leu Glu Met Tyr Gly Ala Lys Leu Gly Tyr Lys Gly Tyr Gly Tyr
65                  70                  75                  80

Pro Gly Val Gly Asp Val Phe Ser Ser Pro Leu Glu His Gly Leu Asp
                85                  90                  95

Ser Trp Gly Ala Ser Tyr Asp Ala Met Leu Ser Leu Gly Leu Arg Thr
            100                 105                 110

Gly Arg Asp Val Leu Gly Thr Gln Tyr Gly Ala Asn Phe Ser Leu Met
        115                 120                 125

Val Pro Ala Gly Ser Gly Gly Ser Met Val Phe His Gly Ala Pro Gly
    130                 135                 140

Ile Glu Ser Arg Val Phe Ala Asp Thr Ser Leu Gly Asn Phe Ser Val
145                 150                 155                 160

Gly Tyr Gln Glu Gly Val Glu Ser Lys Met Lys Val Asp Val Phe Gly
                165                 170                 175

Gly Leu Ser Gly Glu Asn Gly Ser Ala Trp Gly Arg Tyr Leu Arg Gly
            180                 185                 190

Phe Leu Lys Tyr Ala Lys Gly Val Pro Phe His Met Tyr Pro Gly Leu
        195                 200                 205

Tyr Ser Glu Asn Leu Phe Arg Ser Thr Arg Asp Leu Arg Gly Val Ser
    210                 215                 220

Gly Val Ser Ala Lys Thr Lys Asp Val Leu Asn Ser Met Pro Leu Arg
225                 230                 235                 240

Phe Ser Phe Glu Ser Ala Arg Leu Gly Gly Leu Ser Val Gly Phe Ser
                245                 250                 255

Tyr Ser Pro Thr Gly Tyr Arg Asp Asp Met Tyr Lys Gly Gly Glu Phe
            260                 265                 270

Thr Val Arg Asp Gly Ile Ala Gly Phe Asp Ser Leu Gly Thr Val Asn
        275                 280                 285

Leu Phe Ala Lys Thr Gly Val Lys Phe Gly Lys Met Ile Ala Val Val
    290                 295                 300

Pro Pro Arg Phe Asp Ser Gly Pro Val Tyr Lys Asn Ile Val Ser Gly
305                 310                 315                 320

Ala Ala Asn Tyr Glu Tyr Glu Leu Ala Asp Ile Ala Lys Phe Arg Leu
                325                 330                 335

Ser Leu Ala Gly Glu Tyr Ala Arg Pro Lys Lys Ala Arg Asp Ile Val
            340                 345                 350

Pro Glu Gly Arg Arg Lys Glu Glu Ile Tyr Val Ala Asp Tyr Asn Asp
        355                 360                 365
```

```
Leu Ser Ala Phe Ser Ser Gly Leu Glu Ile Asp Leu Gly Arg Leu Arg
    370                 375                 380

Phe Ala Val Gly Gly Gly Tyr Leu Gly Lys Ser Gly Ser Pro Lys Met
385                 390                 395                 400

Tyr Ile Leu Lys Asp Val Arg His Lys Val Pro Tyr Val Lys Lys Lys
                405                 410                 415

Gly Leu Pro Ser His Tyr Val Thr Ser Ala Val Ser Tyr Thr Ile Gly
            420                 425                 430

Ser Phe Ser Ala Thr Val Ala Tyr Phe Met Ser Arg Leu Thr His Ile
        435                 440                 445

Pro Pro Ala Thr Val Ser His Lys Ile Pro Gly Lys Tyr Glu Leu Asp
    450                 455                 460

Ser Val Val Asp Gly Glu Asn Thr Leu Lys Asp Leu Val Gly Val
465                 470                 475                 480

Gly Tyr Asn Leu Phe Ser Lys Gly Ser Thr Ser Leu Glu Val Phe Leu
                485                 490                 495

Asn Cys His Met Phe Ser Val Gln His Lys Phe Asn Ile His Glu Tyr
            500                 505                 510

Lys Ser Thr Glu Ser Ser Gly Phe Val Leu Lys Glu Gly Glu Arg
        515                 520                 525

Ala Asn Thr Asn Asn Gly Ala Val Ala Leu Leu Gly Met Lys Phe Ala
    530                 535                 540

Phe
545

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
ctgcaggttt gatcctgg                                                   18

<210> SEQ ID NO 41
<211> LENGTH: 22
<212> TYPE: DNA
<213> ORGANISM: Artificial Sequence
<220> FEATURE:
<223> OTHER INFORMATION: Synthetic primer

<400> SEQUENCE: 41
ggatcctacc ttgttacgac tt                                              22

<210> SEQ ID NO 42
<211> LENGTH: 15
<212> TYPE: DNA
<213> ORGANISM: Artificial Sequence
<220> FEATURE:
<223> OTHER INFORMATION: Synthetic primer

<400> SEQUENCE: 42
cacgccttct tctac                                                      15

<210> SEQ ID NO 43
<211> LENGTH: 18
<212> TYPE: DNA
<213> ORGANISM: Artificial Sequence
<220> FEATURE:
<223> OTHER INFORMATION: Synthetic primer
```

```
<400> SEQUENCE: 43
ctctgttgct ataggggc                                                  18

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
gatgttgctt cgggtatgc                                                 19

<210> SEQ ID NO 45
<211> LENGTH: 22
<212> TYPE: DNA
<213> ORGANISM: Artificial Sequence
<220> FEATURE:
<223> OTHER INFORMATION: Synthetic primer

<400> SEQUENCE: 45
cagagattac ttcttttgc gg                                              22

<210> SEQ ID NO 46
<211> LENGTH: 16
<212> TYPE: DNA
<213> ORGANISM: Artificial Sequence
<220> FEATURE:
<223> OTHER INFORMATION: Synthetic primer

<400> SEQUENCE: 46
gcgtctccag aaccag                                                    16

<210> SEQ ID NO 47
<211> LENGTH: 16
<212> TYPE: DNA
<213> ORGANISM: Artificial Sequence
<220> FEATURE:
<223> OTHER INFORMATION: Synthetic primer

<400> SEQUENCE: 47
cctatatagc ttaccg                                                    16

<210> SEQ ID NO 48
<211> LENGTH: 23
<212> TYPE: DNA
<213> ORGANISM: Artificial Sequence
<220> FEATURE:
<223> OTHER INFORMATION: Synthetic primer

<400> SEQUENCE: 48
caggcagtga gcactcaaaa acc                                            23

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
gcgactccaa tgttacaata gtccc                                          25

<210> SEQ ID NO 50
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 50
tgtgatcctc gatggttggc                                               20

<210> SEQ ID NO 51
<211> LENGTH: 24
<212> TYPE: DNA
<213> ORGANISM: Artificial Sequence
<220> FEATURE:
<223> OTHER INFORMATION: Synthetic primer

<400> SEQUENCE: 51
ccctcctgaa tcgtaacatc atcc                                          24

<210> SEQ ID NO 52
<211> LENGTH: 16
<212> TYPE: DNA
<213> ORGANISM: Artificial Sequence
<220> FEATURE:
<223> OTHER INFORMATION: Synthetic primer

<400> SEQUENCE: 52
catgcttgta gctatg                                                   16

<210> SEQ ID NO 53
<211> LENGTH: 17
<212> TYPE: DNA
<213> ORGANISM: Artificial Sequence
<220> FEATURE:
<223> OTHER INFORMATION: Synthetic primer

<400> SEQUENCE: 53
gcaaactgaa caatatc                                                  17

<210> SEQ ID NO 54
<211> LENGTH: 16
<212> TYPE: DNA
<213> ORGANISM: Artificial Sequence
<220> FEATURE:
<223> OTHER INFORMATION: Synthetic primer

<400> SEQUENCE: 54
gacctagtac aggagc                                                   16

<210> SEQ ID NO 55
<211> LENGTH: 16
<212> TYPE: DNA
<213> ORGANISM: Artificial Sequence
<220> FEATURE:
<223> OTHER INFORMATION: Synthetic primer

<400> SEQUENCE: 55
ctataagcaa gcttag                                                   16

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
gcgtcacaga cgaataagac gg                                            22
```

<210> SEQ ID NO 57
<211> LENGTH: 24
<212> TYPE: DNA
<213> ORGANISM: Artificial Sequence
<220> FEATURE:
<223> OTHER INFORMATION: Synthetic primer

<400> SEQUENCE: 57
agcggagatt acaggagaga gctg                                          24

<210> SEQ ID NO 58
<211> LENGTH: 22
<212> TYPE: DNA
<213> ORGANISM: Artificial Sequence
<220> FEATURE:
<223> OTHER INFORMATION: Synthetic primer

<400> SEQUENCE: 58
tgttgaatac ggggaaaggg ac                                            22

<210> SEQ ID NO 59
<211> LENGTH: 24
<212> TYPE: DNA
<213> ORGANISM: Artificial Sequence
<220> FEATURE:
<223> OTHER INFORMATION: Synthetic primer

<400> SEQUENCE: 59
agcggagatt tcaggagaga gctg                                          24

<210> SEQ ID NO 60
<211> LENGTH: 22
<212> TYPE: DNA
<213> ORGANISM: Artificial Sequence
<220> FEATURE:
<223> OTHER INFORMATION: Synthetic primer

<400> SEQUENCE: 60
tggtttggat tacagtccag cg                                            22

<210> SEQ ID NO 61
<211> LENGTH: 24
<212> TYPE: DNA
<213> ORGANISM: Artificial Sequence
<220> FEATURE:
<223> OTHER INFORMATION: Synthetic primer

<400> SEQUENCE: 61
acctgcccag tttcacttac attc                                          24

<210> SEQ ID NO 62
<211> LENGTH: 28
<212> TYPE: DNA
<213> ORGANISM: Artificial Sequence
<220> FEATURE:
<223> OTHER INFORMATION: Synthetic primer

<400> SEQUENCE: 62
ccggcatatg cttgtagcta tggaaggc                                      28

<210> SEQ ID NO 63
<211> LENGTH: 58
<212> TYPE: DNA
<213> ORGANISM: Artificial Sequence
<220> FEATURE:
<223> OTHER INFORMATION: Synthetic primer

<400> SEQUENCE: 63
ccggctcgag ctagtggtgg tggtggtggt gaaaagcaaa cctaacacca aattcccc    58

<210> SEQ ID NO 64
<211> LENGTH: 16
<212> TYPE: DNA
<213> ORGANISM: Artificial Sequence
<220> FEATURE:
<223> OTHER INFORMATION: Synthetic primer

<400> SEQUENCE: 64
ccccgggctt tacagt    16

<210> SEQ ID NO 65
<211> LENGTH: 16
<212> TYPE: DNA
<213> ORGANISM: Artificial Sequence
<220> FEATURE:
<223> OTHER INFORMATION: Synthetic primer

<400> SEQUENCE: 65
ccagcaagcg ataacc    16

<210> SEQ ID NO 66
<211> LENGTH: 15
<212> TYPE: PRT
<213> ORGANISM: Granulocytic Ehrlichia

<400> SEQUENCE: 66

His Asp Asp Val Ser Ala Leu Glu Thr Gly Gly Ala Gly Tyr Phe
1               5                   10                  15

<210> SEQ ID NO 67
<211> LENGTH: 20
<212> TYPE: PRT
<213> ORGANISM: Granulocytic Ehrlichia

<400> SEQUENCE: 67

Ser Gly Asp Asn Gly Ser Leu Ala Asp Tyr Thr Asp Gly Gly Ala Ser
1               5                   10                  15

Gln Thr Asn Lys
            20

<210> SEQ ID NO 68
<211> LENGTH: 11
<212> TYPE: PRT
<213> ORGANISM: Granulocytic Ehrlichia

<400> SEQUENCE: 68

Ala Val Gly Val Ser His Pro Gly Ile Asp Lys
1               5                   10

<210> SEQ ID NO 69
<211> LENGTH: 9
<212> TYPE: PRT
<213> ORGANISM: Granulocytic Ehrlichia

<400> SEQUENCE: 69

Phe Asp Trp Asn Thr Pro Asp Pro Arg
1               5

<210> SEQ ID NO 70
<211> LENGTH: 18
<212> TYPE: PRT

<213> ORGANISM: Granulocytic Ehrlichia

<400> SEQUENCE: 70

Leu Ser Tyr Gln Leu Ser Pro Val Ile Ser Ala Phe Ala Gly Gly Phe
1 5 10 15

Tyr His

<210> SEQ ID NO 71
<211> LENGTH: 21
<212> TYPE: DNA
<213> ORGANISM: Artificial Sequence
<220> FEATURE:
<221> NAME/KEY: misc_feature
<222> LOCATION: 3, 6, 9, 15
<223> OTHER INFORMATION: n = A,T,C or G
<220> FEATURE:
<223> OTHER INFORMATION: Synthetic nucleotide - degenerate primer

<400> SEQUENCE: 71
acnggnggng cwggntaytt y 21

<210> SEQ ID NO 72
<211> LENGTH: 20
<212> TYPE: DNA
<213> ORGANISM: Artificial Sequence
<220> FEATURE:
<221> NAME/KEY: misc_feature
<222> LOCATION: 3, 9, 18
<223> OTHER INFORMATION: n = A,T,C or G
<220> FEATURE:
<223> OTHER INFORMATION: Synthetic nucleotide - degenerate primer

<400> SEQUENCE: 72
ccnccrtcng trtartcngc 20

<210> SEQ ID NO 73
<211> LENGTH: 16
<212> TYPE: PRT
<213> ORGANISM: E. chaffeensis

<400> SEQUENCE: 73

Ser Gly Ile Thr Glu Ser His Gly Lys Glu Asp Glu Ile Val Ser Gln
1 5 10 15

<210> SEQ ID NO 74
<211> LENGTH: 16
<212> TYPE: PRT
<213> ORGANISM: Granulocytic Ehrlichia

<400> SEQUENCE: 74

Ser Thr Asp Leu Glu Ala His Ser Gln Glu Val Glu Thr Val Ser Glu
1 5 10 15

<210> SEQ ID NO 75
<211> LENGTH: 16
<212> TYPE: PRT
<213> ORGANISM: Granulocytic Ehrlichia

<400> SEQUENCE: 75

Ser Thr Asp Leu Glu Ala His Ser Lys Gly Val Glu Ile Val Ser Glu
1 5 10 15

<210> SEQ ID NO 76
<211> LENGTH: 16
<212> TYPE: PRT
<213> ORGANISM: Granulocytic Ehrlichia

```
<400> SEQUENCE: 76

Ser Thr Asp Leu Glu Val His Ser Gln Glu Val Glu Ile Val Ser Glu
 1               5                  10                  15

<210> SEQ ID NO 77
<211> LENGTH: 16
<212> TYPE: PRT
<213> ORGANISM: Granulocytic Ehrlichia

<400> SEQUENCE: 77

Ser Thr Asp Leu Glu Ala His Ser Pro Glu Gly Glu Ile Val Ser Glu
 1               5                  10                  15

<210> SEQ ID NO 78
<211> LENGTH: 17
<212> TYPE: PRT
<213> ORGANISM: E. chaffeensis

<400> SEQUENCE: 78

Gln Pro Ser Ile Glu Pro Phe Val Ala Glu Ser Glu Val Ser Lys Val
 1               5                  10                  15

Glu

<210> SEQ ID NO 79
<211> LENGTH: 17
<212> TYPE: PRT
<213> ORGANISM: E. chaffeensis

<400> SEQUENCE: 79

Gln Ser Ser Ser Glu Pro Phe Val Ala Glu Ser Glu Val Ser Lys Val
 1               5                  10                  15

Glu

<210> SEQ ID NO 80
<211> LENGTH: 17
<212> TYPE: PRT
<213> ORGANISM: E. chaffeensis

<400> SEQUENCE: 80

Gln Pro Ser Ser Glu Pro Phe Val Ala Glu Ser Glu Val Ser Lys Val
 1               5                  10                  15

Glu

<210> SEQ ID NO 81
<211> LENGTH: 18
<212> TYPE: PRT
<213> ORGANISM: Granulocytic Ehrlichia

<400> SEQUENCE: 81

Gln Pro Val Ala Gln Val Pro Val Val Ala Glu Ala Glu Leu Pro Gly
 1               5                  10                  15

Val Glu

<210> SEQ ID NO 82
<211> LENGTH: 16
<212> TYPE: PRT
<213> ORGANISM: E. chaffeensis

<400> SEQUENCE: 82

Glu Ser Gly Val Ser Asp Gln Pro Ala Gln Val Val Thr Glu Arg Glu
 1               5                  10                  15
```

```
<210> SEQ ID NO 83
<211> LENGTH: 16
<212> TYPE: PRT
<213> ORGANISM: Granulocytic Ehrlichia

<400> SEQUENCE: 83

Glu Ala Gly Ile Ser Asp Gln Glu Thr Gln Ala Thr Glu Glu Val Glu
 1               5                  10                  15

<210> SEQ ID NO 84
<211> LENGTH: 101
<212> TYPE: PRT
<213> ORGANISM: Granulocytic Ehrlichia

<400> SEQUENCE: 84

Asn Phe Ala Phe Arg Ala Gly Ile Asn Phe Gly Tyr Ser Ala Ile Asn
 1               5                  10                  15

Ala Lys Val Lys Ala Ala Gly Gly Ala Ile Asn Val Arg Asn Ser
            20                  25                  30

Ala Pro Ile Gly Ala Tyr Gln Glu Asp Phe Ile Gly His Tyr Phe Gly
                35                  40                  45

Gly Ala Ile Leu Ser Ile Glu Pro Thr Leu Lys Tyr Ser Val Gly Val
        50                  55                  60

Lys Gly Arg Tyr Ala Leu Lys Ser Thr Val His Asp Ala Ile Asn Ile
65                  70                  75                  80

Phe Ser Ala Gly Leu Gly Ala Cys Met Tyr Pro Pro Phe Glu Ile Asp
                85                  90                  95

Leu Lys Asp Ile Gly
            100

<210> SEQ ID NO 85
<211> LENGTH: 111
<212> TYPE: PRT
<213> ORGANISM: Granulocytic Ehrlichia

<400> SEQUENCE: 85

Gly Leu Ile Ser Pro Phe Thr Gln Leu Val Phe Ala Ser Leu Glu Phe
 1               5                  10                  15

Phe Asn Gly Asn Tyr Leu Ser Ser Val Cys Val Phe Pro Ala Leu Ser
                20                  25                  30

Pro Leu Val Asp Lys His Pro Ser Leu Pro Leu Glu Val Ile Val Phe
                35                  40                  45

Leu Pro Ala Phe Thr Leu Ser Val Pro Cys Thr Lys Leu Ser Lys Ile
        50                  55                  60

Leu Ala Val Ser Phe Ser Ser Pro Leu Leu Phe Gln Gly Val Glu Leu
65                  70                  75                  80

Pro Val Pro Val Gly Phe Gly Thr Val Phe Ser Leu Ala Leu Ala Thr
                85                  90                  95

Ala Leu Ser Arg Thr Cys Ser Ser Val Gly Ser Ser Phe Val Met
                100                 105                 110
```

What is claimed is:

1. A method of screening a test sample obtained from a subject for antibodies relating to granulocytic Ehrlichiosis infection comprising:
   (a) providing one or more purified polypeptides that bind to an antibody that recognizes an immunologically reactive fragment of an amino acid sequence selected from the group consisting of SEQ ID NO: 4, 6, 2, 8, 21, 22, 39, 27, 29 and 30;
   (b) providing the test sample;
   (c) contacting the sample with said one or more polypeptides under conditions that allow immunocomplexes to form, wherein the immunocomplexes comprise said one or more purified polypeptides bound to the antibody; and
   (d) detecting the presence or absence of the immunocomplexes.

2. The method according to claim 1, wherein the test sample is obtained from a dog.

3. The method according to claim 1, wherein the test sample is a blood sample.

4. The method according to claim 3, wherein the blood sample is a serum sample.

5. The method according to claim 1, wherein the step of detecting is carried out using an immunofluorescence assay.

6. The method according to claim 1, wherein the antibody recognizes an immunologically reactive fragment of an amino acid sequence set forth as SEQ ID NO: 4.

7. The method according to claim 1, wherein the antibody recognizes an immunologically reactive fragment of an amino acid sequence set forth as SEQ ID NO: 6.

8. The method according to claim 1, wherein the antibody recognizes an immunologically reactive fragment of an amino acid sequence set forth as SEQ ID NO: 2.

9. The method according to claim 1, wherein the antibody recognizes an immunologically reactive fragment of an amino acid sequence set forth as SEQ ID NO: 8.

10. The method according to claim 1, wherein the antibody recognizes an immunologically reactive fragment of an amino acid sequence set forth as SEQ ID NO: 21.

11. The method according to claim 1, wherein the antibody recognizes an immunologically reactive fragment of an amino acid sequence set forth as SEQ ID NO: 22.

12. The method according to claim 1, wherein the antibody recognizes an immunologically reactive fragment of an amino acid sequence set forth as SEQ ID NO: 39.

13. The method according to claim 1, wherein the antibody recognizes an immunologically reactive fragment of an amino acid sequence set forth as SEQ ID NO: 27.

14. The method according to claim 1, wherein the antibody recognizes an immunologically reactive fragment of an amino acid sequence set forth as SEQ ID NO: 29.

15. The method according to claim 1, wherein the antibody recognizes an immunologically reactive fragment of an amino acid sequence set forth as SEQ ID NO: 30.

* * * * *